(12) United States Patent
Troukhan et al.

(10) Patent No.: US 7,989,676 B2
(45) Date of Patent: Aug. 2, 2011

(54) NUCLEOTIDE SEQUENCES AND CORRESPONDING POLYPEPTIDES CONFERRING MODULATED PLANT CHARACTERISTICS

(75) Inventors: Maxim Troukhan, Agoura Hills, CA (US); Gregory Nadzan, Woodland Hills, CA (US); Peter Mascia, Thousand Oaks, CA (US); Joel Rarang, Granada Hills, CA (US); James Burns, Valley Village, CA (US); Kyle Vos Strache, Mountain View, CA (US)

(73) Assignee: Ceres, Inc., Thousand Oaks, CA (US)

( * ) Notice: Subject to any disclaimer, the term of this patent is extended or adjusted under 35 U.S.C. 154(b) by 637 days.

(21) Appl. No.: 11/897,944

(22) Filed: Aug. 31, 2007

(65) Prior Publication Data

US 2008/0072340 A1    Mar. 20, 2008

Related U.S. Application Data

(60) Provisional application No. 60/841,779, filed on Aug. 31, 2006.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................. 800/278; 435/320.1; 435/419; 800/290; 800/298; 800/320.1; 800/287

(58) Field of Classification Search .................. None
See application file for complete search history.

(56) References Cited

OTHER PUBLICATIONS

Ralph et al (2004, NCBI Accession No. CV267710).*
Jaglo et al (2001, Plant Physiology 127:910-917).*
Bowie et al, Science 247:1306-1310, 1990.*
McConnell et al, Nature 411 (6838):709-713, 2001.*

* cited by examiner

*Primary Examiner* — Stuart F. Baum
(74) *Attorney, Agent, or Firm* — Birch, Stewart, Kolasch and Birch, LLP

(57) ABSTRACT

The present invention relates to isolated nucleic acid molecules and their corresponding encoded polypeptides able confer the trait of modulated plant size, vegetative growth, organ number, plant architecture, sterility or seedling lethality in plants. The present invention further relates to the use of these nucleic acid molecules and polypeptides in making transgenic plants, plant cells, plant materials or seeds of a plant having such modulated growth or phenotype characteristics that are altered with respect to wild type plants grown under similar conditions.

13 Claims, No Drawings

NUCLEOTIDE SEQUENCES AND CORRESPONDING POLYPEPTIDES CONFERRING MODULATED PLANT CHARACTERISTICS

CROSS-REFERENCE TO RELATED APPLICATIONS

This application claims priority under 35 USC §119(e) of provisional application 60/841,779, filed Aug. 31, 2006, the entire contents of which are hereby incorporated by reference.

INCORPORATION-BY-REFERENCE OF SEQUENCE LISTING OR TABLE

The material in the accompanying sequence listing is hereby incorporated by reference into this application. The accompanying file, named 2007-08-27 Sequence Listing 2750-1694PUS2.txt was created on Aug. 24, 2007 and is 13,263 KB. The file can be accessed using Microsoft Word on a computer that uses Windows OS.

FIELD OF THE INVENTION

The present invention relates to isolated nucleic acid molecules and their corresponding encoded polypeptides able to modulate plant characteristics. The present invention further relates to using the nucleic acid molecules and polypeptides to make transgenic plants, plant cells, plant materials or seeds of a plant having modulated phenotypic and growth characteristics as compared to wild-type plants grown under similar conditions.

BACKGROUND OF THE INVENTION

Plants specifically improved for agriculture, horticulture, biomass conversion, and other industries (e.g. paper industry, plants as production factories for proteins or other compounds) can be obtained using molecular technologies. As an example, great agronomic value can result from modulating the size of a plant as a whole or of any of its organs or the number of any of its organs.

Similarly, modulation of the size and stature of an entire plant, or a particular portion of a plant, allows production of plants better suited for a particular industry. For example, reductions in the height of specific crops and tree species can be beneficial by allowing easier harvesting. Alternatively, increasing height, thickness or organ number may be beneficial by providing more biomass useful for processing into food, feed, fuels and/or chemicals. Other examples of commercially desirable traits include increasing the length of the floral stems of cut flowers, increasing or altering leaf size and shape or enhancing the size of seeds and/or fruits. Changes in organ size, organ number and biomass also result in changes in the mass of constituent molecules such as secondary products and convert the plants into factories for these compounds.

Availability and maintenance of a reproducible stream of food and feed to feed people has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy for the population.

Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, great progress has been made in using molecular genetics approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (1).

Despite this progress, today there continues to be a great need for generally applicable processes that improve forest or agricultural plant growth to suit particular needs depending on specific environmental conditions. To this end, the present invention is directed to advantageously manipulating plant characteristics in traits such as appearance, architecture, biomass, composition, confinement, development, nitrogen use, nutrient uptake, phosphate use, photosynthetic capacity, shade avoidance, stress tolerance, vigor, flowering time and yield to maximize the benefits of various crops depending on the benefit sought and the particular environment in which the crop must grow, characterized by expression of recombinant DNA molecules in plants. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having modulated plant characteristics, with respect to wild-type plants grown under similar or identical conditions, in traits such as appearance, architecture, biomass, composition, confinement, development, nitrogen use, nutrient uptake, phosphate use, photosynthetic capacity, shade avoidance, stress tolerance, vigor, flowering time and yield. (sometimes hereinafter collectively referred to as modulated growth and phenotype characteristics).

Unless otherwise defined, all technical and scientific terms used herein have the same meaning as commonly understood by one of ordinary skill in the art to which this invention belongs.

DETAILED DESCRIPTION OF THE INVENTION

The present invention relates to isolated nucleic acid molecules and their corresponding encoded polypeptides able to confer the trait of modulated plant size, vegetative growth, organ number, plant architecture, sterility or seedling lethality in plants. The present invention further relates to the use of these nucleic acid molecules and polypeptides in making transgenic plants, plant cells, plant materials or seeds of a plant having such modulated growth or phenotype characteristics that are altered with respect to wild type plants grown under similar conditions.

1. DEFINITIONS

The following terms are utilized throughout this application:

Biomass refers to useful biological material including a product of interest, which material is to be collected and is intended for further processing to isolate or concentrate the product of interest. Biomass may comprise the fruit, or parts of it, or seeds, leaves, or stems or roots where these are the parts of the plant that are of particular interest for the industrial purpose. Biomass, as it refers to plant material, includes any structure or structures of a plant that contain or represent the product of interest.

Amino acid refers to one of the twenty biologically occurring amino acids and to synthetic amino acids, including D/L optical isomers.

Cell type-preferential promoter or tissue-preferential promoter refers to a promoter that drives expression preferentially in a target cell type or tissue, respectively, but may also lead to some transcription in other cell types or tissues as well.

Control plant refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

Domains are groups of substantially contiguous amino acids in a polypeptide that can be used to characterize protein families and/or parts of proteins. Such domains have a fingerprint or signature that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or to 55 amino acids, or 45 to 60 amino acids, or 200 to 300 amino acids, or 300 to 400 amino acids.

Down-regulation refers to regulation that decreases production of expression products (mRNA, polypeptide, or both) relative to basal or native states.

Exogenous with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression refers to the process of converting genetic information of a polynucleotide into RNA through transcription, which is catalyzed by an enzyme, RNA polymerase, and into protein, through translation of mRNA on ribosomes.

Functional Homologs are those proteins that have at least one functional characteristic in common. Such characteristics include sequence similarity, biochemical activity, transcriptional pattern similarity and phenotypic activity. Typically, the functionally comparable proteins share some sequence similarity or at least one biochemical. Within this definition, analogs are considered to be functionally comparable. In addition, functionally comparable proteins generally share at least one biochemical and/or phenotypic activity.

Heterologous sequences are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Heterologous polypeptide refers to a polypeptide that is not a naturally occurring polypeptide in a plant cell, e.g., a transgenic *Lycopersicon* plant transformed with and expressing the coding sequence for a kinase polypeptide from a *Glycine* plant.

Percentage of sequence identity refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gin, Glu, Arg, and Lys; residue-specific gap penalties: on. The output is a sequence alignment that reflects the relationship between sequences. ClustalW can be run, for example, at the Baylor College of Medicine Search Launcher site and at the European Bioinformatics Institute site on the World Wide Web.

In case of the functional homolog searches, to ensure a subject sequence having the same function as the query sequence, the alignment has to be along at least 80% of the length of the query sequence so that the majority of the query sequence is covered by the subject sequence. To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Isolated nucleic acid includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Misexpression refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene coding region from a different plant species or from a non-plant organism.

Modulation of the level of a compound or constituent refers to the change in the level of the indicated compound or constituent that is observed as a result of expression of, or transcription from, an exogenous nucleic acid in a plant cell. The change in level is measured relative to the corresponding level in control plants.

Nucleic acid and polynucleotide are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Polypeptide as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

Up-regulation refers to regulation that increases the level of an expression product (mRNA, polypeptide, or both) relative to basal or native states.

Vector refers to a replicon, such as a plasmid, phage, or cosmid, into which another DNA segment may be inserted so as to bring about the replication of the inserted segment. Generally, a vector is capable of replication when associated with the proper control elements. The term vector includes cloning and expression vectors, as well as viral vectors and integrating vectors. An expression vector is a vector that includes a regulatory region.

$T_0$ refers to the whole plant, explant or callus tissue, inoculated with the transformation medium.

$T_1$ refers to either the progeny of the $T_0$ plant, in the case of whole-plant transformation, or the regenerated seedling in the case of explant or callous tissue transformation.

$T_2$ refers to the progeny of the $T_1$ plant. $T_2$ progeny are the result of self-fertilization or cross-pollination of a $T_1$ plant.

$T_3$ refers to second generation progeny of the plant that is the direct result of a transformation experiment. $T_3$ progeny are the result of self-fertilization or cross-pollination of a $T_2$ plant.

2. THE INVENTION

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of the polypeptides in the sequence listing (SEQ ID Nos. 1-4084), (b) a nucleotide sequence encoding an amino acid sequence that is at least 85% identical to any one of the polypeptides from *Populus balsamifera* in the sequence listing (SEQ ID Nos. 1-4084), (c) a nucleotide sequence that is complementary to any one of the nucleotide sequences according to (a) and (b), (d) a nucleotide sequence according to any one of the nucleotides in the sequence listing SEQ ID Nos. 1-4084, (e) a nucleotide sequence able to interfere with any one of the nucleotide sequences according to (a) and (b), (f) a nucleotide sequence able to form a hybridized nucleic acid duplex with the nucleic acid according to any one of paragraphs (a)-(d) at a temperature from about 40° C. to about 48° C. below a melting temperature of the hybridized nucleic acid duplex, (g) a nucleotide sequence encoding any one of the polypeptide sequences from *Populus balsamifera* in the sequence listing, (h) a nucleotide sequence encoding any one of the polypeptide sequences given in the sequence listing.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of the polypeptides in the sequence listing.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth, increased organ number and/or increased biomass (sometimes hereinafter collectively referred to as increased biomass), lethality, sterility or ornamental characteristics as compared to a wild-type plant cultivated under identical conditions. Furthermore, the transgenic plant may comprise a first isolated nucleic acid molecule of the present invention, which encodes a protein involved in modulating growth and phenotype characteristics, and a second isolated nucleic acid molecule which encodes a promoter capable of driving expression in plants, wherein the growth and phenotype modulating component and the promoter are operably linked. More preferably, the first isolated nucleic acid may be mis-expressed in the transgenic plant of the present invention, and the transgenic plant exhibits modulated characteristics as compared to a progenitor plant devoid of the gene, when the transgenic plant and the progenitor plant are cultivated under identical environmental conditions. In another embodiment of the present invention the modulated growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the modulated growth and phenotype characteristics as compared to a wild-type plant cultivated under identical conditions.

Another embodiment of the present invention includes methods of modulating growth and phenotype characteristics in plants. More particularly, these methods comprise transforming a plant with an isolated nucleic acid molecule according to the present invention.

In yet another embodiment, lethality genes of the invention can be used to control transmission and expression of transgenic traits, thereby facilitating the cultivation of transgenic plants without the undesired transmission of transgenic traits to other plants. Such lethality genes can be also be utilized for selective lethality, by combining the lethal gene with appropriate promoter elements for selective expression, to thereby cause lethality of only certain cells or only under certain conditions.

3. Important Characteristics of the Polynucleotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit modulated growth and phenotype characteristics as compared to wild-type plants, as evidenced by the results of various experiments disclosed below. This trait can be used to exploit or maximize plant products. For example, the nucleic acid molecules and polypeptides of the present invention are used to increase the expression of genes that cause the plant to have modulated growth and phenotype characteristics.

Because some of the disclosed sequences and methods increase vegetative growth, the disclosed methods can be used to enhance biomass production. For example, plants that grow vegetatively have an increase biomass production, compared to a plant of the same species that is not genetically modified for substantial vegetative growth. Examples of increases in biomass production include increases of at least 5%, at least 10%, at least 20%, or even at least 50%, when compared to an amount of biomass production by a plant of the same species not growing vegetatively.

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase (12) where the floral organs are produced. If the appropriate environmental and developmental signals the plant switches to floral, or reproductive, growth are disrupted, the plant will not be able to enter reproductive growth, therefore maintaining vegetative growth.

As more and more transgenic plants are developed and introduced into the environment, it can be important to control the undesired spread of the transgenic triat(s) from transgenic plants to other traditional and transgenic cultivars, plant species and breeding lines, thereby preventing cross-contamination. The use of a conditionally lethal gene, i.e. one which results in plant cell death under certain conditions, has been suggested as a means to selectively kill plant cells containing a recombinant DNA (see e.g., WO 94/03619 and US patent publication 20050044596A1). The use of genes to control transmission and expression of transgenic traits is also described in U.S. application Ser. No. 10/667,295, filed on Sep. 17, 2003, which is hereby incorporated by reference. Some of the nucleotides of the invention are lethal genes, and can therefore be used as conditionally lethal genes, namely genes to be expressed in response to specific conditions, or in specific plant cells. For example, a gene that encodes a lethal trait can be placed under that control of a tissue specific promoter, or under the control of a promoter that is induced in response to specific conditions, for example, a specific chemical trigger, or specific environmental conditions.

Male or female sterile genes can also be used to control the spread of certain germplasm, such as by selective destruction of tissue, such as of the tapetum by fusing such a gene to a tapetum-specific promoter such as, TA29. Further examples of such promoters are described below.

The sequences of the invention can be applied to substrates for use in array applications such as, but not limited to, assays of global gene expression, under varying conditions of development, and growth conditions. The arrays are also used in diagnostic or forensic methods.

The polynucleotides of the invention are also used to create various types of genetic and physical maps of the genome of corn, *Arabidopsis*, soybean, rice, wheat, or other plants. Some are absolutely associated with particular phenotypic traits, allowing construction of gross genetic maps. Creation of such maps is based on differences or variants, generally referred to as polymorphisms, between different parents used in crosses. Common methods of detecting polymorphisms that can be used are restriction fragment length polymorphisms (RFLPs, single nucleotide polymorphisms (SNPs) or simple sequence repeats (SSRs).

The use of RFLPs and of recombinant inbred lines for such genetic mapping is described for *Arabidopsis* by Alonso-Blanco et al. (*Methods in Molecular Biology*, vol. 82, *Arabidopsis Protocols*, pp. 137-146, J. M. Martinez-Zapater and J. Salinas, eds., c. 1998 by Humana Press, Totowa, N.J.) and for corn by Burr (Mapping Genes with Recombinant Inbreds, pp. 249-254. In Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; Gardiner, J. et al., (1993) *Genetics* 134: 917). This procedure, however, is not limited to plants and is used for other organisms (such as yeast) or for individual cells.

The polynucleotides of the present invention are also used for simple sequence repeat (SSR) mapping. Rice SSR mapping is described by Morgante et al. (*The Plant Journal* (1993) 3: 165), Panaud et al. (*Genome* (1995) 38: 1170); Senior et al. (*Crop Science* (1996) 36: 1676), Taramino et al. (*Genome* (1996) 39: 277) and Ahn et al. (*Molecular and General Genetics* (1993) 241: 483-90). SSR mapping is achieved using various methods. In one instance, polymorphisms are identified when sequence specific probes contained within a polynucleotide flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms are identified by using the PCR fragment produced from the SSR-flanking sequence specific primer reaction as a probe against Southern blots representing different individuals (U. H. Refseth et al., (1997) *Electrophoresis* 18: 1519).

The polynucleotides of the invention can further be used to identify certain genes or genetic traits using, for example, known AFLP technologies, such as in EP0534858 and U.S. Pat. No. 5,878,215.

The polynucleotides of the present invention are also used for single nucleotide polymorphism (SNP) mapping.

The polynucleotides of the invention can be used with the various types of maps discussed above to identify Quantitative Trait Loci (QTLs). Many important crop traits, such as the solids content of tomatoes, are quantitative traits and result from the combined interactions of several genes. These genes reside at different loci in the genome, often times on different chromosomes, and generally exhibit multiple alleles at each locus. The polynucleotides of the invention are used to identify QTLs and isolate specific alleles as described by de Vicente and Tanksley (*Genetics* (1993) 134:585). Once a desired allele combination is identified, crop improvement is accomplished either through biotechnological means or by directed conventional breeding programs (for review see Tanksley and McCouch (1997) *Science* 277:1063). In addition to isolating QTL alleles in present crop species, the polynucleotides of the invention are also used to isolate alleles from the corresponding QTL of wild relatives.

In addition, the polynucleotides of the present invention can be used for marker assisted breeding. Marker assisted breeding uses genetic fingerprinting techniques to assist plant breeders in matching a molecular profile to the physical properties of a variety. This allows plant breeders to significantly accelerate the speed of natural plant breeding programs. Marker assisted breeding also allows better retention of sequences that participate in QTLs.

Following the procedures described above and using a plurality of the polynucleotides of the present invention, any individual can be genotyped. These individual genotypes are used for the identification of particular cultivars, varieties, lines, ecotypes and genetically modified plants or can serve as tools for subsequent genetic studies involving multiple phenotypic traits.

4. The Genes of the Invention

The polynucleotides of the present invention and the proteins expressed via translation of these polynucleotides are set forth in the Sequence Listing, specifically the polynucleotides described in any one of SEQ ID Nos. 1-4084. The Sequence Listing also consists of functionally comparable proteins that can be utilized for the purposes of the invention, namely to make transgenic plants with modulated growth and phenotype characteristics, including ornamental and compositional characteristics.

5. Use of the Genes to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, 16) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lamda phage vectors, T-DNA fusion vectors and plasmid vectors (see, 17-24).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorosulfuron or phosphinothricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To operably link a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *Plant Cell* 1:977-984.

A basal promoter is the minimal sequence necessary for assembly of a transcription complex required for transcription initiation. Basal promoters frequently include a TATA box element that may be located between about 15 and about 35 nucleotides upstream from the site of transcription initiation. Basal promoters also may include a CCAAT box element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucleus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al. (1989) *Plant Cell,* 1:855-866; Bustos, et al. (1989) *Plant Cell,* 1:839-854; Green, et al. (1988) *EMBO J.* 7, 4035-4044; Meier, et al. (1991) *Plant Cell,* 3, 309-316; and Zhang, et al. (1996) *Plant Physiology* 110: 1069-1079.

Examples of various classes of promoters are described below. Some of the promoters indicated below are described in more detail in U.S. Patent Application Ser. Nos. 60/505,689; 60/518,075; 60/544,771; 60/558,869; 60/583,691; 60/619,181; 60/637,140; Ser. Nos. 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation.

Examples of 3' UTRs include, but are not limited to, polyadenylation signals and transcription termination sequences, e.g., a nopaline synthase termination sequence.

Various promoters can be used to drive expression of the genes of the present invention. Nucleotide sequences of such promoters are set forth in SEQ ID NOs: 4085-4186 Some of them can be broadly expressing promoters, others may be more tissue preferential.

A promoter can be said to be broadly expressing when it promotes transcription in many, but not necessarily all, plant tissues or plant cells. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO: 4184), YP0144 (SEQ ID NO: 4163), YP0190 (SEQ ID NO: 4167), p13879 (SEQ ID NO: 4183), YP0050 (SEQ ID NO: 4143), p32449 (SEQ ID NO: 4185), 21876 (SEQ ID NO: 4109), YP0158 (SEQ ID NO: 4165), YP0214 (SEQ ID NO: 4169), YP0380 (SEQ ID NO: 4178), PT0848 (SEQ ID NO: 4134), and PT0633 (SEQ ID NO: 4115). Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root-active promoters drive transcription in root tissue, e.g., root endodermis, root epidermis, or root vascular tissues. In some embodiments, root-active promoters are root-preferential promoters, i.e., drive transcription only or predominantly in root tissue. Root-preferential promoters include the YP0128 (SEQ ID NO: 4160), YP0275 (SEQ ID NO: 4171), PT0625 (SEQ ID NO: 4114), PT0660 (SEQ ID NO: 4117), PT0683 (SEQ ID NO: 4122), and PT0758 (SEQ ID NO: 4130). Other root-preferential promoters include the PT0613 (SEQ ID NO: 4113), PT0672 (SEQ ID NO: 4119), PT0688 (SEQ ID NO: 4123), and PT0837 (SEQ ID NO: 4132), which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA* 86:7890-7894), root cell specific promoters reported by Conkling et al. (1990) *Plant Physiol.* 93:1203-1211), and the tobacco RD2 gene promoter.

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al. (1989) *Plant Cell* 1(9):839-853), the soybean trypsin inhibitor promoter (Riggs et al. (1989) *Plant Cell* 1(6):609-621), the ACP promoter (Baerson et al. (1993) *Plant Mol Biol,* 22(2):255-267), the stearoyl-ACP desaturase gene (Slocombe et al. (1994) *Plant Physiol* 104(4):167-176), the soybean α' subunit of β-conglycinin promoter (Chen et al. (1986) *Proc Natl Acad Sci USA* 83:8560-8564), the oleosin promoter (Hong et al. (1997) *Plant Mol Biol* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.* 13:5829-5842), the beta-amylase gene promoter, and the barley hordein gene promoter. Other maturing endosperm promoters include the YP0092 (SEQ ID NO: 4146), PT0676 (SEQ ID NO: 4120), and PT0708 (SEQ ID NO: 4125).

Promoters that drive transcription in ovary tissues such as the ovule wall and mesocarp can also be useful, e.g., a polygalacturonidase promoter, the banana TRX promoter, and the melon actin promoter. Other such promoters that drive gene expression preferentially in ovules are YP0007 (SEQ ID NO: 4138), YP0111 (SEQ ID NO: 4154), YP0092 (SEQ ID NO: 4146), YP0103 (SEQ ID NO: 4151), YP0028 (SEQ ID NO: 4141), YP0121 (SEQ ID NO: 4159), YP0008 (SEQ ID NO: 4139), YP0039 (SEQ ID NO: 4142), YP0115 (SEQ ID NO: 4155), YP0119 (SEQ ID NO: 4157), YP0120 (SEQ ID NO: 4158) and YP0374 (SEQ ID NO: 4176).

In some other embodiments of the present invention, embryo sac/early endosperm promoters can be used in order drive transcription of the sequence of interest in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.,* 32:571-57; Conceicao (1994) *Plant,* 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics,* 142:1009-1020); maize Cat3 (see, GenBank No. L05934; Abler (1993) *Plant Mol. Biol.,* 22:10131-1038). Other promoters include the following *Arabidopsis* promoters: YP0039 (SEQ ID NO: 4142), YP0101 (SEQ ID NO: 4149), YP0102 (SEQ ID NO: 4150), YP0110 (SEQ ID NO: 4153), YP0117 (SEQ ID NO: 4156), YP0119 (SEQ ID NO: 4157), YP0137 (SEQ ID NO: 4161), DME, YP0285 (SEQ ID NO: 4172), and YP0212 (SEQ ID NO: 4168). Other promoters that may be useful include the following rice promoters: p530c10 (SEQ ID NO: 4187), pOsFIE2-2 (SEQ ID NO: 4188), pOsMEA (SEQ ID NO: 4189), pOsYp102 (SEQ ID NO: 4190), and pOsYp285 (SEQ ID NO: 4191).

Promoters that preferentially drive transcription in zygotic cells following fertilization can provide embryo-preferential expression and may be useful for the present invention. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654, YP0097 (SEQ ID NO: 4148), YP0107 (SEQ ID NO: 4152), YP0088 (SEQ ID NO: 4145), YP0143 (SEQ ID NO: 4162), YP0156 (SEQ ID NO: 4164), PT0650 (SEQ ID NO: 4116), PT0695 (SEQ ID NO: 4124), PT0723 (SEQ ID NO: 4127), PT0838 (SEQ ID NO: 4133), PT0879 (SEQ ID NO: 4136) and PT0740 (SEQ ID NO: 4128).

Promoters active in photosynthetic tissue in order to drive transcription in green tissues such as leaves and stems are of particular interest for the present invention. Most suitable are promoters that drive expression only or predominantly such tissues. Examples of such promoters include the ribulose-1, 5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104: 997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad. Sci. USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab, rbcS. Other promoters that drive transcription in stems, leafs and green tissue are PT0535 (SEQ ID NO: 4111), PT0668 (SEQ ID NO: 4110), PT0886 (SEQ ID NO: 4137), PR0924 (SEQ ID NO: 4192), YP0144 (SEQ ID NO: 4163), YP0380 (SEQ ID NO: 4178) and PT0585 (SEQ ID NO: 4112).

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. Examples of drought inedible promoters are YP0380 (SEQ ID NO: 4178), PT0848 (SEQ ID NO: 4134), YP0381 (SEQ ID NO: 4179), YP0337 (SEQ ID NO: 4174), YP0337 (SEQ ID NO: 4174), PT0633 (SEQ ID NO: 4172), YP0374 (SEQ ID NO: 4176), PT0710 (SEQ ID NO: 4126), YP0356 (SEQ ID NO: 4175), YP0385 (SEQ ID NO: 4181), YP0396 (SEQ ID NO: 4182), YP0384 (SEQ ID NO: 4180), PT0688 (SEQ ID NO: 4123), YP0286 (SEQ ID NO: 4173), YP0377 (SEQ ID NO: 4177), and PD1367 (SEQ ID NO: 4186). Examples of promoters induced by nitrogen are PT0863 (SEQ ID NO: 4135), PT0829 (SEQ ID NO: 4131), PT0665 (SEQ ID NO: 4118) and PT0886 (SEQ ID NO: 4137). An example of a shade inducible promoter is PR0924 (SEQ ID NO: 4192).

Other Promoters: Other classes of promoters include, but are not limited to, leaf-preferential, stem/shoot-preferential, callus-preferential, guard cell-preferential, such as PT0678 (SEQ ID NO: 4121), and senescence-preferential promoters. Promoters designated YP0086 (SEQ ID NO: 4144), YP0188 (SEQ ID NO: 4166), YP0263 (SEQ ID NO: 4170), PT0758 (SEQ ID NO: 4130), PT0743 (SEQ ID NO: 4129), PT0829 (SEQ ID NO: 4131), YP0119 (SEQ ID NO: 4157), and YP0096 (SEQ ID NO: 4147), as described in the above-referenced patent applications, may also be useful. Other useful promoters include AtGGPS1 (SEQ ID NO: 4089), AtBASL (SEQ ID NO: 4090), AtBBE5 (SEQ ID NO: 4095), AtWDC (SEQ ID NO: 4106) and YP0019 (SEQ ID NO: 4140).

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

Another alternative consists in inhibiting expression of a growth or phenotype-modulating polypeptide in a plant species of interest. The term expression refers to the process of converting genetic information encoded in a polynucleotide into RNA through transcription of the polynucleotide (i.e., via the enzymatic action of an RNA polymerase), and into protein, through translation of mRNA. Up-regulation or activation refers to regulation that increases the production of expression products relative to basal or native states, while down-regulation or repression refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a biomass-modulating polypeptide. A nucleic acid that decreases the level of a transcription or translation product of a gene encoding a growth or phenotype-modulating polypeptide is transcribed into an antisense nucleic acid similar or identical to the sense coding sequence of the growth or phenotype-modulating polypeptide. Alternatively, the transcription product of an isolated nucleic acid can be similar or identical to the sense coding sequence of a growth or phenotype-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA,* 92(13):6175-6179; de Feyter and Gaudron, Methods in Molecular Biology, Vol. 74, Chapter 43, Expressing Ribozymes in Plants, Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the biomass-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.,* 7:187-195; Hyrup et al. (1996) *Bioorgan. Med. Chem.,* 4:5-23. In addition, the deoxyphosphate backbone can be replaced with, for example, a phosphorothioate or phosphorodithioate backbone, a phosphoroamidite, or an alkyl phosphotriester backbone.

Transformation

Nucleic acid molecules of the present invention may be introduced into the genome or the cell of the appropriate host plant by a variety of techniques. These techniques, able to transform a wide variety of higher plant species, are well known and described in the technical and scientific literature (see, e.g., 28-29).

A variety of techniques known in the art are available for the introduction of DNA into a plant host cell. These techniques include transformation of plant cells by injection (30), microinjection (31), electroporation of DNA (32), PEG (33), use of biolistics (34), fusion of cells or protoplasts (35), and via T-DNA using *Agrobacterium tumefaciens* (36-37) or *Agrobacterium rhizogenes* (38) or other bacterial hosts (39), for example.

In addition, a number of non-stable transformation methods that are well known to those skilled in the art may be desirable for the present invention. Such methods include, but are not limited to, transient expression (40) and viral transfection (41).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver,*

*Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea*.

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), Triticosecale (triticum-wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), Spinacea oleracea (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica., Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium*.

Suitable species also include *Parthenium argentatum* (guayule), *Hevea* spp. (rubber), *Mentha spicata* (mint), *Menthapiperita* (mint), *Bixa orellana,* and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus,* and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of the nucleotide sequences in the sequence listing due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and their Corresponding Nucleotide Sequences Some of the nucleic acid molecules, and nucleotide sequences thereof, of the present invention were identified by use of a variety of screens that are predictive of nucleotide sequences that provide plants with altered size, vegetative growth, organ number, plant architecture and/or biomass. One or more of the following screens were, therefore, utilized to identify the nucleotide (and amino acid) sequences of the present invention.

The present invention is further exemplified by the following examples. The examples are not intended to in any way limit the scope of the present application and its uses.

6. Analysis Indicating the Usefulness of the Polynucleotides and Polypeptides of the Invention

6.1 General Protocols

*Agrobacterium*-Mediated Transformation of *Arabidopsis*

Wild-type *Arabidopsis thaliana Wassilewskija* (WS) plants are transformed with Ti plasmids containing clones in the sense orientation relative to the 35S promoter. A Ti plasmid vector useful for these constructs, CRS 338, contains the Ceres-constructed, plant selectable marker gene phosphinothricin acetyltransferase (PAT), which confers herbicide resistance to transformed plants.

Ten independently transformed events are typically selected and evaluated for their qualitative phenotype in the $T_1$ generation.

Preparation of Soil Mixture: 24 L SunshineMix #5 soil (Sun Gro Horticulture, Ltd., Bellevue, Wash.) is mixed with 16 L Therm-O-Rock vermiculite (Therm-O-Rock West, Inc., Chandler, Ariz.) in a cement mixer to make a 60:40 soil mixture. To the soil mixture is added 2 Tbsp Marathon 1% granules (Hummert, Earth City, Mo.), 3 Tbsp OSMOCOTE® 14-14-14 (Hummert, Earth City, Mo.) and 1 Tbsp Peters fertilizer 20-20-20 (J.R. Peters, Inc., Allentown, Pa.), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µl 2 mg/ml benzylaminopurine to 900 ml water.

Dipping Infiltration: The pots are inverted and submerged for 5 minutes so that the aerial portion of the plants are in the *Agrobacterium* suspension. Plants are allowed to grow normally and seed is collected.

High-Throughput Phenotypic Screening of Misexpression Mutants:

Seed is evenly dispersed into water-saturated soil in pots and placed into a dark 4° C. cooler for two nights to promote uniform germination. Pots are then removed from the cooler and covered with 55% shade cloth for 4-5 days. Cotyledons are fully expanded at this stage. FINALE® (Sanofi Aventis, Paris, France) is sprayed on plants (3 ml FINALE® diluted into 48 oz. water) and repeated every 3-4 days until only transformants remain.

Screening is routinely performed at four stages: Seedling, Rosette, Flowering, and Senescence.

Seedling—the time after the cotyledons have emerged, but before the $3^{rd}$ true leaf begins to form.

Rosette—the time from the emergence of the $3^{rd}$ true leaf through just before the primary bolt begins to elongate.

Flowering—the time from the emergence of the primary bolt to the onset of senescence (with the exception of noting the flowering time itself, most observations should be made at the stage where approximately 50% of the flowers have opened).

Senescence—the time following the onset of senescence (with the exception of delayed senescence, most observations should be made after the plant has completely dried). Seeds are then collected.

Screens: Screening for increased size, vegetative growth, biomass, lethality, sterility and other modulated characteristics is performed by taking measurements, specifically $T_2$ measurements were taken as follows:

Days to Bolt=number of days between sowing of seed and emergence of first inflorescence.

Rosette Leaf Number at Bolt=number of rosette leaves present at time of emergence of first inflorescence.

Rosette Area=area of rosette at time of initial inflorescence emergence, using formula $((L \times W)*3.14)/4$.

Height=length of longest inflorescence from base to apex. This measurement was taken at the termination of flowering/onset of senescence.

Primary Inflorescence Thickness=diameter of primary inflorescence 2.5 cm up from base. This measurement was taken at the termination of flowering/onset of senescence.

Inflorescence Number=total number of unique inflorescences. This measurement was taken at the termination of flowering/onset of senescence.

PCR was used to amplify the cDNA insert in one randomly chosen $T_2$ plant. This PCR product was then sequenced to confirm the sequence in the plants.

Results

Plants transformed with the genes of interest were screened as described above for modulated growth and phenotype characteristics. The observations include those with respect to the entire plant, as well as parts of the plant, such as the roots and leaves. The observations for transformants with each polynucleotide sequence are noted in the Sequence listing and Table 1 for the corresponding encoded polypeptide.

Functional homologs/orthologs from *Populus balsamifera* for each gene of interest that gave a modulated growth and phenotype characteristic when transformed in plants were identified through the Determination of Functional Homolog/Ortholog Sequences process described below. Functional homologs/orthologs of a gene of interest are understood to possess the same phenotype(s) as was observed for the respective gene of interest when mis-expressed in plants. The modulated growth and phenotype characteristic(s) determined for the functional homologs/orthologs are noted in the Sequence Listing and Table 1.

Determination of Functional Homolog/Ortholog Sequences

A subject sequence was considered a functional homolog or ortholog of a query sequence if the subject and query sequences encoded proteins having a similar function and/or activity. A process known as Reciprocal BLAST (Rivera et al., *Proc. Natl. Acad. Sci. USA*, 95:6239-6244 (1998)) was used to identify potential functional homolog and/or ortholog sequences from a databases consisting of Ceres-Inc. proprietary peptide sequences from *Populus balsamifera* subsp. *trichocarpa*.

Before starting a Reciprocal BLAST process, a specific query polypeptide was searched against all peptides from its source species using BLAST in order to identify polypeptides having BLAST sequence identity of 80% or greater to the query polypeptide and an alignment length of 85% or greater along the shorter sequence in the alignment. The query polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e−5; 2) a word size of 5; and 3) the −postsw option. The BLAST sequence identity was calculated based on the alignment of the first BLAST HSP (High-scoring Segment Pairs) of the identified potential functional homolog and/or ortholog sequence with a specific query polypeptide. The number of identically matched residues in the BLAST HSP alignment was divided by the HSP length, and then multiplied by 100 to get the BLAST sequence identity. The HSP length typically included gaps in the alignment, but in some cases gaps can be excluded.

The main Reciprocal BLAST process consists of two rounds of BLAST searches; forward search and reverse search. In the forward search step, a query polypeptide sequence, polypeptide A, from source species SA was BLASTed against all Ceres-Inc. proprietary peptide sequences from *Populus balsamifera* subsp. *Trichocarpa*. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original query polypeptide was considered a potential functional homolog or ortholog as well.

In the reverse search round, the top hits identified in the forward search from *Populus balsamifera* subsp. *Trichocarpa* were BLASTed against all protein sequences from the source species SA. A top hit from the forward search that returned a polypeptide from the aforementioned cluster as its best hit was also considered as a potential functional homolog or ortholog.

Functional homologs and/or orthologs were identified by manual inspection of potential functional homolog and/or ortholog sequences. The BLAST percent identities and E-values of functional homologs and/or orthologs to the query sequences SEQ ID NO: X are shown in the sequence listing, respectively.

The BLAST sequence identity and E-value given in the sequence listing (in a miscellaneous feature section) was taken from the forward search round of the Reciprocal BLAST process.

Information in the Sequence Listing

The modulated growth and phenotype characteristics for each of the sequences of the invention are noted by an entry in the Phenotype field (in a miscellaneous feature section) for each respective nucleic acid and/or polypeptide sequence in the Sequence Listing. The Phenotype field in the Sequence Listing also gives the general location for which the noted modulated growth and phenotype characteristics occur. The Phenotype noted in the Sequence Listing for each relevant sequence further includes a valuable application of that sequence based on the observations and analysis.

Also, for each functional homolog, the E-value and the BLAST sequence identity relative to the respective query sequence is noted in a miscellaneous features field in the Sequence Listing.

For some of the polynucleotides/polypeptides of the invention, the sequence listing further includes (in a miscellaneous feature section) an indication of important identified dominant(s) and the corresponding function of the domain or identified by comparison to the publicly available pfam database.

For some of the polynucleotides/polypeptides of the invention, the sequence listing further includes (in a miscellaneous feature section) an indication of important identified characteristic(s) of a polypeptide sequence and the corresponding function of the polypeptide sequence identified by comparison to the publicly available Swiss-Prot database.

Table 1 correlates the Phenotype entries (in miscellaneous feature sections) in the sequence listing to the descriptions for each entry in the Phenotype Description column. Table 1 also gives the general location for where the modulated growth and phenotype characteristics are observed in the Tissue column. The Phenotype Category column in Table 1 groups the modulated growth and phenotype characteristics for possible Phenotype entries into the following plant trait categories: Appearance, Architecture, Biomass, Composition, Confinement, Development, Nitrogen use, Nutrient uptake, Phosphate use, Photosynthetic capacity, Shade, Stress tolerance, Vigor, and Yield. In addition to the use described for each phenotype in the Application column in Table 1, applications for modulated growth and phenotype that are given any one of the following designation in the Phenotype Category column in Table 1: Appearance, Architecture, Biomass, Composition, Confinement, Development, Nitrogen use, Nutrient uptake, Phosphate use, Photosynthetic capacity, Shade, Stress tolerance, Vigor, and Yield; are further discussed in preceding paragraphs.

Polypeptide sequences that are determined to be associated with a particular modulated growth and phenotype characteristic are listed in Table 1 by a Ceres internal identifier, given in the Ceres ID column in Table 1, and by their respective SEQ ID NOs.

TABLE 1

| Tissue | Phenotype Category | Phenotype | Phenotype Description | Applications | Ceres ID | SEQ ID NO |
|---|---|---|---|---|---|---|
| INFLORESCENCE | Appearance | Acauline Branching | The first branching is not subtended by a cauline leaf. | Useful for making ornamental plants with modified flowers | CLONE 3000; ANNOT 1518918; ANNOT 1518918; ANNOT 1535677; ANNOT 1535677; ANNOT 1482181; ANNOT 1482181; | 111; 112; 113; 114; 115; 116; 117; |
| INFLORESCENCE | Appearance | Asecondary Branching | The plant does not form secondary inflorescences. | Useful for making ornamental plants with modified flowers | CLONE 3000; ANNOT 1518918; ANNOT 1518918; ANNOT 1535677; ANNOT 1535677; ANNOT 1482181; ANNOT 1482181; CLONE 33232; ANNOT 1504045; ANNOT 1504045; ANNOT 1450983; ANNOT 1450983; CLONE 34412; ANNOT 1449739; ANNOT 1449739; ANNOT 1449738; ANNOT 1449738; ANNOT 1458830; ANNOT 1458830; CLONE 34783; ANNOT 1466952; ANNOT 1466952; ANNOT 1523551; ANNOT 1523551; ANNOT 1470164; ANNOT 1470164; CLONE 38973; ANNOT 1451899; ANNOT 1451899; ANNOT 1496367; ANNOT 1496367; CLONE 107731; ANNOT 1480518; ANNOT 1480518; ANNOT 1442194; ANNOT 1442194; ANNOT 1454127; ANNOT 1454127; ANNOT 1461414; ANNOT 1461414; ANNOT 1447424; ANNOT 1447424; ANNOT 1452873; ANNOT 1452873; ANNOT 1474708; ANNOT 1474708; CLONE 241379; ANNOT 1526950; ANNOT 1526950; ANNOT 1508362; ANNOT 1508362; ANNOT 1477361; CLONE 283597; ANNOT 1482074; ANNOT 1482074; ANNOT 1453923; ANNOT 1453923; | 111; 112; 113; 114; 115; 116; 117; 1263; 1264; 1265; 1266; 1267; 1376; 1377; 1378; 1379; 1380; 1381; 1382; 1423; 1424; 1425; 1426; 1427; 1428; 1429; 1818; 1819; 1820; 1821; 1822; 2263; 2264; 2265; 2266; 2267; 2268; 2269; 2270; 2271; 2272; 2273; 2274; 2275; 2276; 2277; 2718; 2719; 2720; 2721; 2722; 2723; 2724; 2833; 2834; 2835; 2836; 2837; |
| ROSETTE LEAVES | Appearance | Corkscrew | The leaves are completely curled/rolled up or down at the leaf margins, with the additional attribute of twisting like a corkscrew, instead of uniformly curling from both sides of the leaf. | Useful for making plants with altered leaf shape e.g. curled leaves | CLONE 32548; ANNOT 1450324; ANNOT 1450324; ANNOT 1460836; CLONE 96020; ANNOT 1450365; ANNOT 1460794; ANNOT 1460794; ANNOT 1471976; ANNOT 1471976; ANNOT 225200; CLONE 225200; ANNOT 1465507; ANNOT 1465507; | 1231; 1232; 1233; 1234; 1235; 2095; 2096; 2097; 2098; 2099; 2655; 2656; 2657; 2658; 2659; |
| CAULINE LEAVES | Appearance | Corkscrew | The leaves are completely curled/rolled up or down at the leaf margins, with the additional attribute of twisting like a corkscrew, | Useful for making ornamental plants with altered leaf shape | CLONE 9132; ANNOT 1458620; ANNOT 1458620; | 391; 392; 393; |

TABLE 1-continued

| Tissue | Phenotype Category | Phenotype | Phenotype Description | Applications | Ceres ID | SEQ ID NO |
|---|---|---|---|---|---|---|
| INFLORESCENCE | Appearance | Corkscrew Appearance | The inflorescence is twisted like a corkscrew, but somewhat more irregular. instead of uniformly curling from both sides of the leaf. | Useful for making ornamental plants with modified flowers | CLONE 123279; ANNOT 1508945; ANNOT 1531332; ANNOT 1482544; ANNOT 1478226; ANNOT 1478226; CLONE 225601; ANNOT 1457617; ANNOT 1465289; ANNOT 1453865; ANNOT 1465289; ANNOT 1478647; ANNOT 1453865; ANNOT 1438014; CLONE 627596; ANNOT 1500987; ANNOT 1500987; ANNOT 1490915; CDNA 2350103; ANNOT 1447690; ANNOT 1447690; ANNOT 149l278; ANNOT 1500987; ANNOT 1500987; ANNOT 1490915; | 2492; 2493; 2494; 2495; 2496; 2497; 2498; 2499; 2500; 2665; 2666; 2667; 2668; 2669; 2670; 2671; 2672; 2673; 2674; 2675; 3299; 3300; 3301; 3302; 3303; 3687; 3688; 3689; 3690; 3691; 3692; 3693; 3694; 3695; |
| ROSETTE LEAVES | Appearance | Cup-shaped | The leaves are curled up at the leaf margins such that they form a cup or bowl-like shape. | Useful for making ornamental plants with altered leaf shape | CLONE 8877; ANNOT 1507340; ANNOT 1507340; ANNOT 1529361; ANNOT 1529361; CLONE 13186; ANNOT 1464566; ANNOT 1458408; ANNOT 1458408; CLONE 26655; ANNOT 1477170; ANNOT 1477170; ANNOT 1508498; ANNOT 1530647; ANNOT 1530647; CLONE 37493; ANNOT 1494370; ANNOT 1494370; ANNOT 1441478; ANNOT 1441478; CLONE 41439; CLONE 42955; ANNOT 1505155; ANNOT 1505155; CLONE 262460; ANNOT 1530053; ANNOT 1530053; ANNOT 1493414; ANNOT 1493414; CLONE 382267; ANNOT 1456223; ANNOT 1456223; ANNOT 1467304; ANNOT 1467304; CDNA 36542397; ANNOT 1497958; ANNOT 1497958; ANNOT 1471743; ANNOT 1471743; ANNOT 1465272; ANNOT 1465272; ANNOT 1510814; ANNOT 1510814; | 383; 384; 385; 386; 387; 531; 532; 533; 534; 535; 1023; 1024; 1025; 1026; 1027; 1028; 1029; 1637; 1638; 1639; 1640; 1641; 1998; 2048; 2049; 2050; 2774; 2775; 2776; 2777; 2778; 2986; 2987; 2988; 2989; 2990; 3969; 3970; 3971; 3972; 3973; 4023; 4024; 4025; 4026; 4027; |
| CAULINE LEAVES | Appearance | Cup-shaped | The cauline leaves are curled up at the leaf margins such that they form a cup or bowl-like shape | Useful for making ornamental plants with altered leaf shape | CLONE 267564; ANNOT 1473933; ANNOT 1473933; ANNOT 1468704; ANNOT 1468704; | 2789; 2790; 2791; 2792; 2793; |
| ROSETTE LEAVES | Appearance | Curled 1 | The leaves are abnormally curled slightly up or down at the leaf margins. | Useful for making ornamental plants with altered leaf shape | CLONE 3000; ANNOT 1518918; ANNOT 1535677; ANNOT 1535677; ANNOT 1482181; CLONE 13757; ANNOT 1471425; ANNOT 1471425; CLONE 17409; ANNOT 1457617; ANNOT 1457617; ANNOT 1465289; ANNOT 1465289; ANNOT 1478647; ANNOT 1478647; ANNOT 1453865; ANNOT 1453865; CLONE 19486; ANNOT 1452204; ANNOT 1452204; ANNOT 1443204; ANNOT 1443204; CLONE 37493; ANNOT 1494370; ANNOT 1494370; ANNOT 1441478; ANNOT 1441478; CLONE 37663; ANNOT 1447659; ANNOT 1447659; ANNOT 1438478; ANNOT 1438478; CLONE 107731; ANNOT 1480518; ANNOT 1480518; ANNOT 1442194; ANNOT 1442194; ANNOT 1449026; CLONE 225601; ANNOT 1454127; ANNOT 1454127; ANNOT 1461414; ANNOT 1461414; ANNOT 1447424; ANNOT 1447424; ANNOT 1452873; ANNOT 1452873; ANNOT 1474708; ANNOT 1474708; CLONE 148943; CLONE 158333; ANNOT 1472949; ANNOT 1472949; CLONE 158333; ANNOT 1466505; ANNOT 1466505; ANNOT 1449026; CLONE 225601; ANNOT 1457617; ANNOT 1457617; ANNOT 1465289; ANNOT 1465289; ANNOT 1478647; ANNOT 1453865; ANNOT 1453865; ANNOT 1438014; ANNOT 1474923; ANNOT 1474923; CLONE 590462; ANNOT 1490788; ANNOT 1490788; ANNOT 1502230; ANNOT 1502230; CLONE 681088; ANNOT 1471330; ANNOT 1471330; ANNOT 1444437; ANNOT 1444437; | 111; 112; 113; 114; 115; 116; 117; 564; 565; 566; 678; 679; 680; 681; 682; 683; 684; 685; 686; 767; 768; 769; 770; 771; 1637; 1638; 1639; 1640; 1641; 1657; 1658; 1659; 1660; 1661; 2263; 2264; 2265; 2266; 2267; 2268; 2269; 2270; 2271; 2272; 2273; 2274; 2275; 2276; 2277; 2543; 2544; 2545; 2611; 2612; 2613; 2614; 2615; 2665; 2666; 2667; 2668; 2669; 2670; 2671; 2672; 2673; 2674; 2675; 3221; 3222; 3223; 3255; 3256; 3257; 3258; 3259; |

| Tissue | Phenotype Category | Phenotype | Phenotype Description | Applications | Ceres ID | SEQ ID NO |
|---|---|---|---|---|---|---|
| CAULINE LEAVES | Appearance | Curled 1 | The cauline leaves are curled slightly up or down at the leaf margins, but are not cup-shaped. | Useful for making ornamental plants with altered leaf shape | ANNOT 1444439; ANNOT 1444439; ANNOT 1486891; ANNOT 1486891; ANNOT 1479637; ANNOT 1479637; ANNOT 1446530; ANNOT 1446530; | 3345; 3346; 3347; 3348; 3349; 3350; 3351; 3352; 3353; 3354; 3355; 3356; 3357; |
| ROSETTE LEAVES | Appearance | Curled 2 | The leaves are abnormally curled up or down at the leaf margins, but do not form a cup or bowl-like shape. | Useful for making ornamental plants with altered leaf shape | CLONE 34552; ANNOT 1516449; ANNOT 1516449; ANNOT 1512976; ANNOT 1512976; CLONE 22560I; ANNOT 1457617; ANNOT 1457617; ANNOT 1465289; ANNOT 1465289; ANNOT 1478647; ANNOT 1478647; ANNOT 1453865; ANNOT 1453865; ANNOT 1438014; ANNOT 1438014; CLONE 241379; ANNOT 1526950; ANNOT 1526950; ANNOT 1508362; ANNOT 1508362; ANNOT 1477361; ANNOT 1477361; | 1406; 1407; 1408; 1409; 1410; 2665; 2666; 2667; 2668; 2669; 2670; 2671; 2672; 2673; 2674; 2675; 2718; 2719; 2720; 2721; 2722; 2723; 2724; |
| | | | | | CLONE 332; ANNOT 1474923; ANNOT 1474923; CLONE 5167; ANNOT 1465422; ANNOT 1465422; ANNOT 1457750; ANNOT 1457750; ANNOT 1513544; ANNOT 1513544; CLONE 6082; ANNOT 1443416; ANNOT 1505047; ANNOT 1505047; ANNOT 1488463; ANNOT 1496339; ANNOT 1496339; CLONE 6220; ANNOT 1488463; ANNOT 1541879; ANNOT 1541879; CLONE 8068; ANNOT 1510462; ANNOT 1510462; ANNOT 1471422; ANNOT 1471422; ANNOT 1497509; ANNOT 1497509; CLONE 11929; ANNOT 1518415; ANNOT 1518415; ANNOT 1475405; ANNOT 1475405; ANNOT 1457917; ANNOT 1457917; ANNOT 1515353; ANNOT 1515353; ANNOT 1484925; ANNOT 1484925; ANNOT 1484924; ANNOT 1484924; ANNOT 1462053; ANNOT 1462053; ANNOT 1450576; ANNOT 1450576; CLONE 12272; ANNOT 1506387; ANNOT 1506387; ANNOT 1474522; ANNOT 1474522; CLONE 17409; ANNOT 1457617; ANNOT 1457617; ANNOT 1478647; ANNOT 1478647; ANNOT 1453865; ANNOT 1453865; ANNOT 1465289; ANNOT 1465289; ANNOT 1541170; ANNOT 1541170; CLONE 25172; ANNOT 1457346; ANNOT 1457346; ANNOT 1450324; ANNOT 1450324; ANNOT 1460836; ANNOT 1460836; CLONE 32548; CLONE 32791; ANNOT 1540248; ANNOT 1540248; CLONE 37663; ANNOT 1447659; ANNOT 1447659; ANNOT 1438478; ANNOT 1438478; CLONE 38101; ANNOT 1454656; ANNOT 1454656; ANNOT 1528263; ANNOT 1528263; ANNOT 1458103; ANNOT 1458103; ANNOT 1464899; ANNOT 1464899; ANNOT 1482966; ANNOT 1482966; ANNOT 1441039; ANNOT 1441039; ANNOT 1520449; ANNOT 1520449; CLONE 38419; ANNOT 1542971; ANNOT 1542971; ANNOT 1521332; ANNOT 1521332; ANNOT 1467961; ANNOT 1467961; CLONE 38690; ANNOT 1525183; ANNOT 1525183; CLONE 97415; ANNOT 1481701; ANNOT 1481701; CLONE 103581; ANNOT 1486398; ANNOT 1486398; ANNOT 1496840; ANNOT 1496840; CLONE 104929; ANNOT 1449020; ANNOT 1449020; CLONE 107988; ANNOT 1459927; ANNOT 1459927; CLONE 115975; ANNOT 1507138; ANNOT 1507138; CLONE 117369; ANNOT 1499284; ANNOT 1499284; ANNOT 1499284; ANNOT 1481671; ANNOT 1481671; CLONE 147358; ANNOT 1493111; ANNOT 1493111; ANNOT 1461452; ANNOT 1461452; CLONE 241379; ANNOT 1526950; ANNOT 1526950; ANNOT 1508362; ANNOT 1508362; ANNOT 1477361; ANNOT 1477361; CLONE 645550; ANNOT 1479649; ANNOT 1479649; CLONE 681222; ANNOT 1456923; ANNOT 1456923; CLONE 1001432; ANNOT 1475043; ANNOT 1475043; ANNOT 1454586; ANNOT 1454586; ANNOT 1507756; ANNOT 1507756; ANNOT 1469708; CDNA 2355I244; ANNOT 1454030; ANNOT 1454030; ANNOT 1475651; ANNOT 1475651; CDNA 36542853; ANNOT 1524883; ANNOT 1524883; ANNOT 1497918; ANNOT 1497918; | 12; 13; 14; 223; 224; 225; 226; 227; 228; 229; 268; 269; 270; 271; 272; 273; 274; 275; 276; 277; 278; 279; 345; 346; 347; 348; 349; 350; 351; 480; 481; 482; 483; 484; 485; 486; 487; 488; 489; 490; 491; 492; 493; 494; 495; 496; 515; 516; 517; 518; 519; 678; 679; 680; 681; 682; 683; 684; 685; 686; 692; 693; 694; 952; 953; 954; 955; 956; 1231; 1232; 1233; 1234; 1235; 1255; 1256; 1257; 1657; 1658; 1659; 1660; 1661; 1682; 1683; 1684; 1685; 1686; 1687; 1688; 1689; 1690; 1691; 1692; 1693; 1694; 1695; 1696; 1747; 1748; 1749; 1750; 1751; 1752; 1753; 1774; 1775; 1776; 2100; 2101; 2102; 2232; 2233; 2234; 2235; 2236; 2237; 2238; 2239; 2278; 2279; 2280; 2373; 2374; 2375; 2407; 2408; 2409; 2410; 2411; 2528; 2529; 2530; 2531; 2532; 2718; 2719; 2720; 2721; 2722; 2723; 2724; 3311; 3312; 3313; 3358; 3359; 3360; 3419; 3420; 3421; 3422; 3423; 3424; 3425; 3426; 3427; 3821; 3822; 3823; 3824; 3825; 3974; 3975; 3976; 3977; 3978; |
| CAULINE LEAVES | Appearance | Curled 2 | The cauline leaves are | Useful for making | CLONE 32548; ANNOT 1450324; ANNOT 1450324; ANNOT 1460836; ANNOT 1460836; CLONE 22560I; ANNOT 1457617; ANNOT 1457617; ANNOT 1465289; ANNOT 1465289; | 1231; 1232; 1233; 1234; 1235; 2665; 2666; 2667; |

TABLE 1-continued

| Tissue | Phenotype Category | Phenotype | Phenotype Description | Applications | Ceres ID | SEQ ID NO |
|---|---|---|---|---|---|---|
| | | | abnormally curled up or down at the leaf margins, but are not cup-shaped. | ornamental plants with altered leaf shape | ANNOT 1465289; ANNOT 1478647; ANNOT 1478647; ANNOT 1453865; ANNOT 1453865; ANNOT 1438014; ANNOT 1438014; CLONE 645550; ANNOT 1479649; ANNOT 1479649; | 2668; 2669; 2670; 2671; 2672; 2673; 2674; 2675; 3311; 3312; 3313; |
| ROSETTE LEAVES | Appearance | Curled 3 | The leaves are abnormally curled up or down at the leaf margins, but do not form a cup or bowl-like shape. | Useful for making ornamental plants with altered leaf shape | CLONE 332; ANNOT 1474923; CLONE 3000; ANNOT 1518918; ANNOT 1518918; ANNOT 1535677; ANNOT 1535677; ANNOT 1482181; ANNOT 1482181; CLONE 3006; ANNOT 1472173; CLONE 3363; ANNOT 1445515; ANNOT 1445515; ANNOT 1461861; ANNOT 1449363; ANNOT 1449363; ANNOT 1465198; ANNOT 1518517; ANNOT 1518517; CLONE 6220; ANNOT 1488463; ANNOT 1488463; ANNOT 1541879; ANNOT 1541879; CLONE 8877; ANNOT 1507340; ANNOT 1507340; ANNOT 1529361; ANNOT 1529361; CLONE 9221; ANNOT 1535229; ANNOT 1535229; CLONE 11214; ANNOT 1501485; ANNOT 1501485; ANNOT 1490496; ANNOT 1490496; ANNOT 1448498; ANNOT 1448498; ANNOT 1474848; ANNOT 1474848; CLONE 11494; ANNOT 1438708; CLONE 1975; ANNOT 1460142; ANNOT 1460142; ANNOT 1483807; ANNOT 1483807; CLONE 12272; ANNOT 1506387; ANNOT 1506387; ANNOT 1474522; ANNOT 1474522; CLONE 13625; ANNOT 1455211; ANNOT 1455211; CLONE 13800; ANNOT 1458335; ANNOT 1458335; ANNOT 1464663; ANNOT 1464663; ANNOT 14105; ANNOT 1455669; ANNOT 1455669; ANNOT 1477732; ANNOT 1477732; ANNOT 1508866; ANNOT 1508866; CLONE 14555; ANNOT 1511392; ANNOT 1511392; ANNOT 1469356; ANNOT 1469356; ANNOT 1517500; ANNOT 1517500; ANNOT 1458151; ANNOT 1458151; ANNOT 1522757; ANNOT 1522757; ANNOT 25538; ANNOT 1480776; CLONE 28602; ANNOT 1461728; ANNOT 1461728; ANNOT 1488330; ANNOT 1488330; ANNOT 1460480; ANNOT 1460480; ANNOT 1461614; ANNOT 1461614; ANNOT 1479711; ANNOT 1479711; ANNOT 1479712; ANNOT 1479712; ANNOT 1488329; ANNOT 1460481; ANNOT 1460481; ANNOT 1461613; ANNOT 1461613; ANNOT 1458198; ANNOT 1458198; ANNOT 1488327; ANNOT 1488327; CLONE 32348; ANNOT 1470719; ANNOT 1470719; ANNOT 1543728; ANNOT 1543728; ANNOT 1482066; ANNOT 1482066; CLONE 32791; ANNOT 1540248; ANNOT 1540248; CLONE 37493; ANNOT 1494370; ANNOT 1494370; ANNOT 1441478; CLONE 38419; ANNOT 1542971; ANNOT 1542971; ANNOT 1521332; ANNOT 1521332; ANNOT 1467961; ANNOT 1467961; CLONE 103581; ANNOT 1486398; ANNOT 1486398; ANNOT 1496840; ANNOT 1496840; CLONE 109912; ANNOT 1451138; ANNOT 1451138; ANNOT 1456780; CLONE 156807; ANNOT 1464566; ANNOT 1464566; ANNOT 1458408; ANNOT 1458408; CLONE 222601; ANNOT 1457617; ANNOT 1457617; ANNOT 1465289; ANNOT 1465289; ANNOT 1478647; ANNOT 1478647; ANNOT 1453865; ANNOT 1453865; ANNOT 1438014; ANNOT 1438014; ANNOT 1139572; ANNOT 1139572; ANNOT 1139571; ANNOT 1139571; ANNOT 1519423; CLONE 304574; ANNOT 1481465; ANNOT 1481465; ANNOT 1482095; ANNOT 1482095; ANNOT 1482093; ANNOT 1482093; ANNOT 1440823; CLONE 537272; ANNOT 1518918; ANNOT 1518918; ANNOT 1535677; CLONE 557009; ANNOT 1474923; ANNOT 1474923; CLONE 645550; ANNOT 1479649; ANNOT 1479649; CDNA 3653561 8; ANNOT 1459998; ANNOT 1513263; ANNOT 1513263; CDNA 36567943; ANNOT 1467355; ANNOT 1467355; | 12; 13; 14; 111; 112; 113; 114; 115; 116; 117; 118; 119; 120; 129; 130; 131; 132; 133; 134; 135; 136; 137; 138; 139; 275; 276; 277; 278; 279; 383; 384; 385; 386; 387; 394; 395; 396; 448; 449; 450; 451; 452; 453; 454; 455; 456; 457; 458; 459; 502; 503; 504; 505; 506; 515; 516; 517; 518; 519; 544; 545; 546; 572; 573; 574; 575; 576; 587; 588; 589; 590; 591; 592; 593; 608; 609; 610; 611; 612; 613; 614; 615; 616; 617; 618; 967; 968; 969; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1219; 1220; 1221; 1222; 1223; 1224; 1225; 1255; 1256; 1257; 1637; 1638; 1639; 1640; 1641; 1747; 1748; 1749; 1750; 1751; 1752; 1753; 2232; 2233; 2234; 2235; 2236; 2303; 2304; 2305; 2306; 2307; 2583; 2584; 2585; 2586; 2587; 2665; 2666; 2667; 2668; 2669; 2670; 2671; 2672; 2673; 2674; 2675; 2690; 2691; 2692; 2693; 2694; 2695; 2696; 2884; 2885; 2886; 2887; 2888; 2889; 2890; 2891; 2892; 3163; 3164; 3165; 3166; 3167; 3221; 3222; 3223; 3311; 3312; 3313; 3951; 3952; 3953; 3954; 3955; 4028; 4029; 4030; |

TABLE 1-continued

| Tissue | Phenotype Category | Phenotype | Phenotype Description | Applications | Ceres ID | SEQ ID NO |
|---|---|---|---|---|---|---|
| CAULINE LEAVES | Appearance | Curled 3 | The cauline leaves are abnormally curled up or down at the leaf margins, but are not form a cup or bowl-like shape. | Useful for making ornamental plants with altered leaf shape | CLONE 14555; ANNOT 1511392; ANNOT 1469356; ANNOT 1469356; ANNOT 1517500; ANNOT 1458151; ANNOT 1458151; ANNOT 1522757; CLONE 32791; ANNOT 1540248; ANNOT 1540248; CLONE 34612; ANNOT 1479009; ANNOT 1469640; ANNOT 1469640; CLONE 105554; ANNOT 1451783; CLONE 156807; ANNOT 1464566; ANNOT 1458408; ANNOT 1458408; CLONE 645550; ANNOT 1479649; ANNOT 1479649; | 608; 609; 610; 611; 612; 613; 614; 615; 616; 617; 618; 1255; 1256; 1257; 1411; 1412; 1413; 1414; 1415; 2247; 2248; 2249; 2583; 2584; 2585; 2586; 2587; 3311; 3312; 3313; |
| ROSETTE LEAVES | Appearance | Curled 4 | The leaves are abnormally curled/rolled up or down at the leaf margins. | Useful for making ornamental plants with altered leaf shape | CLONE 3363; ANNOT 1445515; ANNOT 1445515; ANNOT 146186l; ANNOT 1461861; ANNOT 1449363; ANNOT 1449363; ANNOT 1465198; ANNOT 1465198; ANNOT 1518517; ANNOT 1518517; ANNOT 1464566; ANNOT 1464566; ANNOT 1458408; CLONE 13186; ANNOT 13745; ANNOT 1442604; ANNOT 1442604; ANNOT 1442612; ANNOT 1442608; ANNOT 1442608; ANNOT 1452827; CLONE 32791; ANNOT 1540248; ANNOT 1540248; CLONE 34412; ANNOT 1449739; ANNOT 1449738; ANNOT 1449738; CLONE 1458830; CLONE 37019; ANNOT 1517849; ANNOT 1511684; ANNOT 1511684; ANNOT 1464532; ANNOT 1458439; ANNOT 1540674; ANNOT 1540674; ANNOT 1494370; ANNOT 1494370 ANNOT 1441478; CLONE 38419; ANNOT 1542971; ANNOT 1542971; ANNOT 1521332; ANNOT 1489751; ANNOT 1467961; CLONE 38635; ANNOT 1489751; ANNOT 1446209; ANNOT 1446209; CLONE 40508; ANNOT 1453626; ANNOT 1453626; CLONE 96020; ANNOT 1450365; ANNOT 1508945; ANNOT 1460794; ANNOT 1460794; CLONE 123279; ANNOT 1482544; ANNOT 1482544; ANNOT 1478226; CLONE 228787; ANNOT 1139572; ANNOT 1139571; ANNOT 1139571; ANNOT 1519423; CLONE 608818; ANNOT 1528780; ANNOT 1518351; ANNOT 1518351; ANNOT 1525569; ANNOT 1453192; ANNOT 1441586; ANNOT 1441586; ANNOT 1509714; ANNOT 1509714; CLONE 681222; ANNOT 1456923; ANNOT 1456923; | 129; 130; 131; 132; 133; 134; 135; 136; 137; 138; 139; 531; 532; 533; 534; 535; 555; 556; 557; 558; 559; 560; 561; 562; 563; 1255; 1256; 1257; 1376; 1377; 1378; 1379; 1380; 1381; 1382; 1599; 1600; 1601; 1602; 1603; 1604; 1605; 1606; 1607; 1608; 1609; 1637; 1638; 1639; 1640; 1641; 1747; 1748; 1749; 1750; 1751; 1752; 1753; 1769; 1770; 1771; 1772; 1773; 1912; 1913; 1914; 2095; 2096; 2097; 2098; 2099; 2492; 2493; 2494; 2495; 2496; 2497; 2498; 2499; 2500; 2690; 2691; 2692; 2693; 2694; 2695; 2696; 3273; 3274; 3275; 3276; 3277; 3278; 3279; 3280; 3281; 3282; 3283; 3284; 3285; 3358; 3359; 3360; |
| CAULINE LEAVES | Appearance | Curled 4 | The cauline leaves are abnormally curled/rolled up or down at the leafmargins. | Useful for making ornamental plants with altered leaf shape | CLONE 32791; ANNOT 1540248; ANNOT 1540248; CLONE 34612; ANNOT 1479009; ANNOT 1479009; ANNOT 1469640; ANNOT 1469640; | 1255; 1256; 1257; 1411; 1412; 1413; 1414; 1415; |
| ROSETTE LEAVES | Appearance | Curled 5 | The leaves are completely curled/rolled up or down at the leaf margins. | Useful for making ornamental plants with altered leaf shape | CLONE 3000; ANNOT 1518918; ANNOT 1518918; ANNOT 1535677; ANNOT 1535677; ANNOT 1482181; ANNOT 1482181; CLONE 5055; ANNOT 1438157; ANNOT 1438157; ANNOT 1482181; ANNOT 1500936; CLONE 13186; ANNOT 1464566; ANNOT 1464566; ANNOT 1458408; ANNOT 1458408; CLONE 13263; ANNOT 1470919; CLONE 1470919; CLONE 32737; ANNOT 1536373; ANNOT 1536373; ANNOT 1536373; ANNOT 1482905; ANNOT 1482905; CLONE 32791; ANNOT 1540248; ANNOT 1540248; CLONE 34612; ANNOT 1479009; ANNOT 1479009; ANNOT 1469640; ANNOT 1469640; CLONE 37493; ANNOT 1494370; ANNOT 1494370; ANNOT 1441478; ANNOT 1441478; CLONE 123279; ANNOT 1508945; ANNOT 1508945; ANNOT 1531332; ANNOT 1531332; ANNOT 1482544; ANNOT 1482544; | 111; 112; 113; 114; 115; 116; 117; 215; 216; 217; 218; 219; 531; 532; 533; 534; 535; 536; 537; 538; 1242; 1243; 1244; 1245; 1246; 1255; 1256; 1257; 1411; 1412; 1413; 1414; 1415; 1637; 1638; 1639; 1640; 1641; 2492; 2493; 2494; 2495; 2496; 2497; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1478226; ANNOT 1478226; CLONE 148943; ANNOT 1472949; ANNOT 1472949; CLONE 228787; ANNOT 1139572; ANNOT 1139571; ANNOT 1139571; ANNOT 1519423; ANNOT 1519423; CLONE 331626; ANNOT 1479649; ANNOT 1479649; CLONE 608818; ANNOT 1528780; ANNOT 1518351; ANNOT 1518351; ANNOT 1522569; ANNOT 1525569; ANNOT 1453192; ANNOT 1453192; ANNOT 1441586; ANNOT 1509714; ANNOT 1509714; CDNA 36566773; ANNOT 1464046; ANNOT 1458861; ANNOT 1458861; | 2498; 2499; 2500; 2543; 2544; 2545; 2690; 2691; 2692; 2693; 2694; 2695; 2696; 2916; 2917; 2918; 3273; 3274; 3275; 3276; 3277; 3278; 3279; 3280; 3281; 3282; 3283; 3284; 3285; 4018; 4019; 4020; 4021; 4022; |
| CAULINE LEAVES | Appearance | Curled 5 | The cauline leaves are completely curled/rolled up or down at the leaf margins. | Useful for making ornamental plants with altered leaf shape | CLONE 13186; ANNOT 1464566; ANNOT 1464566; ANNOT 1458408; ANNOT 1458408; CLONE 32791; ANNOT 1540248; ANNOT 1540248; CLONE 37019; ANNOT 1517849; ANNOT 1517849; ANNOT 1511684; ANNOT 1511684; ANNOT 1464532; ANNOT 1464532; ANNOT 1458439; ANNOT 1540674; ANNOT 1540674; | 531; 532; 533; 534; 535; 1255; 1256; 1257; 1599; 1600; 1601; 1602; 1603; 1604; 1605; 1606; 1607; 1608; 1609; |
| ROSETTE LEAVES | Appearance | Interveinal Chlorosis | The leaf tissue is chlorotic between its veins. | Useful for making ornamental plants with modified color | CLONE 27464; ANNOT 1453044; ANNOT 1453044; ANNOT 1451171; ANNOT 1451171; CLONE 563522; ANNOT 1460321; ANNOT 1508144; ANNOT 1508144; ANNOT 1541886; ANNOT 1475178; ANNOT 1475178; | 1060; 1061; 1062; 1063; 1064; 3227; 3228; 3229; 3230; 3231; 3232; 3233; 3234; 3235; |
| ROSETTE LEAVES | Appearance | Lanceolate Shaped | The leaves are narrow and come to a dull point at the apex. | Useful for making ornamental plants with altered leaf shape | CLONE 332; ANNOT 1474923; ANNOT 1474923; CLONE 907; ANNOT 1502138; ANNOT 1502138; ANNOT 1449135; ANNOT 1449135; CLONE 3363; ANNOT 1445515; ANNOT 1445515; ANNOT 1461861; ANNOT 1449363; ANNOT 1449363; ANNOT 1465198; ANNOT 1465198; ANNOT 1518817; ANNOT 1518517; CLONE 4067; ANNOT 1514362; ANNOT 1494090; ANNOT 1494090; CLONE 5198; ANNOT 1472153; ANNOT 1472153; CLONE 5968; ANNOT 1450891; ANNOT 1450891; ANNOT 1456400; ANNOT 1456400; ANNOT 1450889; ANNOT 1450889; ANNOT 1456395; ANNOT 1456395; ANNOT 1447193; ANNOT 1447193; CLONE 13186; ANNOT 1464566; ANNOT 1464566; ANNOT 1458408; ANNOT 1458408; CLONE 13263; ANNOT 1470919; ANNOT 1470919; ANNOT 1470919; CLONE 13625; ANNOT 1455211; ANNOT 1455211; CLONE 13757; ANNOT 1471425; ANNOT 1471425; CLONE 14555; ANNOT 1511392; ANNOT 1511392; ANNOT 1469356; ANNOT 1469356; ANNOT 1460480; ANNOT 1517500; ANNOT 1517500; ANNOT 1458151; ANNOT 1458151; ANNOT 1522757; CLONE 18246; ANNOT 1489791; ANNOT 1489791; ANNOT 1470953; ANNOT 1470953; CLONE 20760; ANNOT 1462351; ANNOT 1462351; ANNOT 1488821; ANNOT 1488821; ANNOT 1469462; ANNOT 1469462; CLONE 21563; ANNOT 1438905; ANNOT 1438905; ANNOT 1483143; ANNOT 1483143; CLONE 25607; ANNOT 1450220; ANNOT 1450220; CLONE 28602; ANNOT 1461728; ANNOT 1461728; ANNOT 1488330; ANNOT 1488330; ANNOT 1460480; ANNOT 1461614; ANNOT 1461614; ANNOT 1461614; ANNOT 1479711; ANNOT 1479711; ANNOT 1479712; ANNOT 1479712; ANNOT 1488329; ANNOT 1460481; ANNOT 1460481; ANNOT 1461613; ANNOT 1461613; ANNOT 1458198; ANNOT 1458198; ANNOT 1488327; ANNOT 1488327; CLONE 32615; ANNOT 1471372; ANNOT 1471372; CLONE 33232; ANNOT 1504045; ANNOT 1504045; ANNOT 1450983; ANNOT 1450983; CLONE 34552; ANNOT 1516449; ANNOT 1516449; ANNOT 1512976; CLONE 37543; ANNOT 1539972; ANNOT 1539972; ANNOT 1486562; ANNOT 1486562; ANNOT 1496735; ANNOT 1443794; ANNOT 1443794; CLONE 37589; ANNOT 1440727; ANNOT 1440727; CLONE | 12; 13; 14; 30; 31; 32; 33; 34; 129; 130; 131; 132; 133; 134; 135; 136; 137; 138; 139; 196; 197; 198; 199; 200; 230; 231; 232; 250; 251; 252; 253; 254; 255; 256; 257; 258; 259; 260; 531; 532; 533; 534; 535; 536; 537; 538; 544; 545; 546; 564; 565; 566; 608; 609; 610; 611; 612; 613; 614; 615; 616; 617; 618; 715; 716; 717; 718; 719; 808; 809; 810; 811; 812; 813; 814; 842; 843; 844; 845; 846; 970; 971; 972; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1239; 1240; 1241; 1263; 1264; 1265; 1266; 1267; 1406; 1407; 1408; 1409; 1410; 1642; 1643; 1644; 1645; 1646; 1647; 1648; 1649; 1650; 1651; 1652; 1653; 1707; 1708; |

TABLE 1-continued

| Tissue | Phenotype Category | Phenotype | Phenotype Description | Applications | Ceres ID | SEQ ID NO |
|---|---|---|---|---|---|---|
| | | | | | 38214; ANNOT 1466779; ANNOT 1466779; ANNOT 1465769; ANNOT 1538318; ANNOT 1538318; CLONE 38690; ANNOT 1525183; ANNOT 1525183; CLONE 38757; ANNOT 1528846; ANNOT 1538329; ANNOT 1538329; CLONE 38843; ANNOT 1447896; ANNOT 1438197; ANNOT 1438197; CLONE 40436; ANNOT 1441645; ANNOT 1441645; CLONE 40729; ANNOT 1481678; ANNOT 1481678; CLONE 42533; ANNOT 1499810; ANNOT 1499810; ANNOT 1538733; ANNOT 1538733; ANNOT 1485323; ANNOT 1485323; CLONE 95453; ANNOT 1460836; ANNOT 1460836; ANNOT 1450324; ANNOT 1450324; CLONE 95677; ANNOT 1459723; ANNOT 1459723; ANNOT 1516455; ANNOT 1516455; CLONE 97415; ANNOT 1481701; ANNOT 1481701; CLONE 100319; ANNOT 1503141; ANNOT 1503141; ANNOT 1521524; ANNOT 1521524; CLONE 117369; ANNOT 1499284; ANNOT 1499284; ANNOT 1481671; ANNOT 1481671; CLONE 124720; ANNOT 1441430; ANNOT 1441430; CLONE 147358; ANNOT 1493111; ANNOT 1493111; ANNOT 1461452; ANNOT 1461452; CLONE 154718; ANNOT 1457453; ANNOT 1457453; CLONE 158734; ANNOT 1477956; CLONE 241379; ANNOT 1499284; ANNOT 1526950; ANNOT 1508362; ANNOT 1508362; ANNOT 1477361; ANNOT 1477361; CLONE 262460; ANNOT 1530053; ANNOT 1530053; ANNOT 1493414; ANNOT 1493414; CLONE 660003; ANNOT 1508184; ANNOT 1508184; ANNOT 1528645; ANNOT 1528645; CLONE 681088; ANNOT 1471330; ANNOT 1471330; ANNOT 1444437; ANNOT 1444437; ANNOT 1444439; ANNOT 1486891; ANNOT 1486891; ANNOT 1479637; ANNOT 1479637; ANNOT 1446530; ANNOT 1446530; CLONE 681222; ANNOT 1456923; ANNOT 1456923; CLONE 1006934; ANNOT 1532963; ANNOT 1532963; ANNOT 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1479711; ANNOT 1440649; ANNOT 1440649; ANNOT 1464547; ANNOT 1464547; ANNOT 1454104; ANNOT 1454104; CDNA 23530467; CDNA 23551244; ANNOT 1454030; ANNOT 1454030; ANNOT 1475651; ANNOT 1475651; ANNOT 3650947; ANNOT 1497025; ANNOT 1497025; CDNA 3651446; ANNOT 1475322; ANNOT 1475322; CDNA 3653571; ANNOT 1451133; ANNOT 1451133; ANNOT 1456774; ANNOT 1456774; | 1709; 1710; 1711; 1712; 1713; 1774; 1775; 1776; 1791; 1792; 1793; 1794; 1795; 1801; 1802; 1803; 1804; 1805; 1904; 1905; 1906; 1930; 1931; 1932; 2030; 2031; 2032; 2033; 2034; 2035; 2036; 2085; 2086; 2087; 2088; 2089; 2090; 2091; 2092; 2093; 2094; 2100; 2101; 2102; 2191; 2192; 2193; 2194; 2195; 2407; 2408; 2409; 2410; 2411; 2501; 2502; 2503; 2528; 2529; 2530; 2531; 2532; 2577; 2578; 2579; 2619; 2620; 2621; 2718; 2719; 2720; 2721; 2722; 2723; 2724; 2774; 2775; 2776; 2777; 2778; 3314; 3315; 3316; 3317; 3318; 3345; 3346; 3347; 3348; 3349; 3350; 3351; 3352; 3353; 3354; 3355; 3356; 3357; 3358; 3359; 3360; 3437; 3438; 3439; 3440; 3441; 3442; 3443; 3444; 3445; 3446; 3447; 3448; 3449; 3450; 3451; 3452; 3453; 3454; 3455; 3456; 3786; 3821; 3822; 3823; 3824; 3825; 3890; 3891; 3892; 3905; 3906; 3907; 3956; 3957; 3958; 3959; 3960; |
| FLOWER | Appearance | Large | The flowers are abnormally large. | Useful for making ornamental plants with modified flowers | CLONE 21563; ANNOT 1438905; ANNOT 1438905; ANNOT 1483143; ANNOT 1483143; ANNOT 1451783; ANNOT 1451783; CLONE 112955; | 842; 843; 844; 845; 846; 2247; 2248; 2249; 2330; |
| | | | | | ANNOT 1447634; ANNOT 1447634; | 2331; 2332; |
| ROSETTE LEAVES | Appearance | Leaf Fused to Inflorescence | The leaf is fused to an inflorescence | Useful for making ornamental plants with flowers and leaves fused | CLONE 11214; ANNOT 1501485; ANNOT 1501485; ANNOT 1490496; ANNOT 1490496; ANNOT 1448498; ANNOT 1448498; ANNOT 1474848; ANNOT 1474848; | 448; 449; 450; 451; 452; 453; 454; 455; 456; |

TABLE 1-continued

| Tissue | Phenotype Category | Phenotype | Phenotype Description | Applications | Ceres ID | SEQ ID NO |
|---|---|---|---|---|---|---|
| ROSETTE LEAVES | Appearance | Leaf Fused to Leaf | The leaf is fused to itself or another leaf. | Useful for making ornamental plants with fused leaves | CLONE 3000; ANNOT 1518918; ANNOT 1535677; ANNOT 1535677; ANNOT 1482181; ANNOT 1482181; | 111; 112; 113; 114; 115; 116; 117; |
| ROSETTE LEAVES | Appearance | Lobed Shaped | The leaves have very deep and rounded serrations, giving an appearance of many lobes forming the margins of the leaves. | Useful for making ornamental plants with altered leaf shape | CLONE 20945; ANNOT 1519797; ANNOT 1519797; CLONE 537272; ANNOT 1518918; ANNOT 1535677; ANNOT 1535677; | 818; 819; 820; 3163; 3164; 3165; 3166; 3167; |
| INFLORESCENCE | Appearance | Multi-Inflorescence Fusion | The inflorescence is fused to another inflorescence, creating a celery-like appearance. | Useful for making ornamental plants with modified flowers | CLONE 105554; ANNOT 1451783; ANNOT 1451783; | 2247; 2248; 2249; |
| ROSETTE LEAVES | Appearance | Other | The plants have a morphological phenotype in leaves. | Useful for making ornamental plants with modified leaves | CLONE 332; ANNOT 1474923; CLONE 907; ANNOT 1502138; ANNOT 1502138; ANNOT 1449135; ANNOT 1449135; CLONE 1241; ANNOT 1453081; ANNOT 1453081; ANNOT 1442349; ANNOT 1442349; CLONE 1355; ANNOT 1515808; ANNOT 1515808; ANNOT 1469219; ANNOT 1469219; ANNOT 1462513; ANNOT 1462513; CLONE 1496; ANNOT 1490668; ANNOT 1490668; ANNOT 1474027; ANNOT 1474027; ANNOT 1497865; ANNOT 1497865; ANNOT 1471512; ANNOT 1471512; ANNOT 1443061; ANNOT 1443061; ANNOT 1504203; ANNOT 1504203; ANNOT 1505468; ANNOT 1505468; ANNOT 1452369; ANNOT 1452369; CLONE 2561; ANNOT 1450958; ANNOT 1450958; ANNOT 1456475; ANNOT 1456475; ANNOT 1446945; ANNOT 1446945; CLONE 3000; ANNOT 1518918; ANNOT 1518918; ANNOT 1535677; ANNOT 1535677; ANNOT 1482181; ANNOT 1482181; CLONE 3006; ANNOT 1472173; ANNOT 1472173; CLONE 3036; ANNOT 1456840; ANNOT 1456840; CLONE 3997; ANNOT 1455209; ANNOT 1455209; ANNOT 1446198; ANNOT 1446198; ANNOT 1450889; ANNOT 1450889; ANNOT 1456395; ANNOT 1456395; ANNOT 1456400; ANNOT 1456400; ANNOT 1509111; ANNOT 1509111; ANNOT 1447193; ANNOT 1447193; CLONE 6287; ANNOT 1509111; ANNOT 1509111; ANNOT 1541620; ANNOT 1541620; CLONE 5198; ANNOT 1472153; ANNOT 1472153; CLONE 5968; ANNOT 1450891; ANNOT 1450891; ANNOT 1456400; CLONE 8254; ANNOT 1543042; ANNOT 1543042; ANNOT 1489655; ANNOT 1489655; CLONE 8265; ANNOT 1438919; ANNOT 1438919; ANNOT 1499398; ANNOT 1499398; ANNOT 1446419; ANNOT 1446419; CLONE 8877; ANNOT 1507340; ANNOT 1507340; ANNOT 1529361; ANNOT 1529361; CLONE 9221; ANNOT 1535229; ANNOT 1535229; CLONE 9897; ANNOT 1445849; ANNOT 1445849; ANNOT 1500561; ANNOT 1500561; ANNOT 1464458; ANNOT 1464458; CLONE 10879; ANNOT 1467184; ANNOT 1467184; CLONE 11214; ANNOT 1501485; ANNOT 1501485; ANNOT 1490496; ANNOT 1490496; ANNOT 1448498; ANNOT 1448498; ANNOT 1474848; ANNOT 1474848; CLONE 11929; ANNOT 1518415; ANNOT 1518415; | 12; 13; 14; 30; 31; 32; 33; 34; 38; 39; 40; 41; 42; 43; 44; 45; 46; 47; 48; 49; 50; 51; 52; 53; 54; 55; 56; 57; 58; 59; 60; 61; 62; 63; 64; 65; 66; 104; 105; 106; 107; 108; 109; 110; 111; 112; 113; 114; 115; 116; 117; 118; 119; 120; 121; 122; 123; 178; 179; 180; 181; 182; 183; 184; 185; 186; 230; 231; 232; 250; 251; 252; 253; 254; 255; 256; 257; 258; 259; 260; 285; 286; 287; 288; 289; 357; 358; 359; 360; 361; 362; 363; 364; 365; 366; 367; 368; 383; 384; 385; 386; 387; 394; 395; 396; 405; 406; 407; 408; 409; 410; 411; 437; 438; 439; 448; 449; 450; 451; 452; 453; 454; 455; 456; 480; 481; 482; 483; 484; 485; 486; 487; 488; 489; 490; 491; 492; 493; 494; 495; 496; 507; 508; 509; 515; 516; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1475405; ANNOT 1475405; ANNOT 1457917; ANNOT 1515353; ANNOT 1515353; ANNOT 1484925; ANNOT 1484924; ANNOT 1484924; ANNOT 1462053; ANNOT 1450576; ANNOT 1450576; CLONE 12071; ANNOT 1466704; CLONE 12272; ANNOT 1506387; ANNOT 1506387; ANNOT 1474522; CLONE 13186; ANNOT 1464566; ANNOT 1464566; ANNOT 1458408; ANNOT 1458408; CLONE 13263; ANNOT 1470919; CLONE 13625; ANNOT 1455211; ANNOT 1455211; CLONE 13757; ANNOT 1471425; ANNOT 1471425; CLONE 13800; ANNOT 1458335; ANNOT 1458335; ANNOT 1464663; ANNOT 1464663; CLONE 16461; ANNOT 1479013; ANNOT 1479013; CLONE 16865; ANNOT 1454311; ANNOT 1454311; ANNOT 1483290; ANNOT 1483290; ANNOT 1533930; ANNOT 1533930; ANNOT 1450556; ANNOT 1533218; ANNOT 1533218; ANNOT 1512378; ANNOT 1512378; CLONE 17356; ANNOT 1478584; ANNOT 1478584; ANNOT 1487130; CLONE 17761; ANNOT 1481206; ANNOT 1481206; ANNOT 1534689; ANNOT 1534689; CLONE 18246; ANNOT 1489791; ANNOT 1489791; ANNOT 1470953; ANNOT 1470953; CLONE 18612; ANNOT 1522299; ANNOT 1522299; ANNOT 1527718; ANNOT 1527718; CLONE 19481; ANNOT 1475146; ANNOT 1475146; ANNOT 1454933; ANNOT 1454933; CLONE 19486; ANNOT 1452204; ANNOT 1452204; ANNOT 1443204; ANNOT 1443204; CLONE 19510; ANNOT 1501412; ANNOT 1501412; ANNOT 1490383; ANNOT 1490383; ANNOT 1448419; CLONE 19586; ANNOT 1476446; ANNOT 1476446; ANNOT 1451126; ANNOT 1451126; CLONE 21068; ANNOT 1463333; ANNOT 1463333; ANNOT 1505772; ANNOT 1505772; ANNOT 1495675; ANNOT 1495676; ANNOT 1469576; ANNOT 1469576; ANNOT 1442758; ANNOT 1442758; CLONE 23518; ANNOT 1475658; ANNOT 1475658; ANNOT 1449267; ANNOT 1449267; ANNOT 1507191; ANNOT 1507191; CLONE 23523; ANNOT 1453919; ANNOT 1453919; CLONE 25380; ANNOT 1512618; ANNOT 1512618; ANNOT 1459357; ANNOT 1459357; ANNOT 1463526; ANNOT 1463526; ANNOT 1480776; ANNOT 1480776; CLONE 26560; ANNOT 1536088; ANNOT 1536088; ANNOT 1482610; ANNOT 1482610; CLONE 26907; ANNOT 1484074; ANNOT 1484074; ANNOT 1440016; ANNOT 1440016; ANNOT 1461728; ANNOT 1461728; ANNOT 1518242; ANNOT 1518242; CLONE 28602; ANNOT 1461728; ANNOT 1460480; ANNOT 1460480; ANNOT 1488330; ANNOT 1461614; ANNOT 1461614; ANNOT 1479711; ANNOT 1479711; ANNOT 1479712; ANNOT 1479712; ANNOT 1488329; ANNOT 1488329; ANNOT 1460481; ANNOT 1460481; ANNOT 1461613; ANNOT 1461613; ANNOT 1458198; ANNOT 1458198; ANNOT 1488327; ANNOT 1488327; CLONE 31044; ANNOT 1486207; ANNOT 1486207; ANNOT 1496976; ANNOT 1496976; CLONE 32361; ANNOT 1471776; ANNOT 1471776; ANNOT 1445033; ANNOT 1445033; CLONE 32548; ANNOT 1450324; ANNOT 1450324; ANNOT 1460836; ANNOT 1460836; CLONE 32615; ANNOT 1471372; ANNOT 1471372; CLONE 32737; ANNOT 1536373; ANNOT 1536373; ANNOT 1482905; ANNOT 1482905; CLONE 32791; ANNOT 1538733; ANNOT 1538733; ANNOT 1540248; ANNOT 1540248; CLONE 34167; ANNOT 1538733; ANNOT 1485323; ANNOT 1485323; ANNOT 1499810; ANNOT 1499810; ANNOT 1485323; CLONE 34783; ANNOT 1466952; ANNOT 1466952; ANNOT 1523551; ANNOT 1523551; ANNOT 1470164; ANNOT 1470164; CLONE 37288; ANNOT 1453650; ANNOT 1453650; CLONE 37298; ANNOT 1476538; ANNOT 1476538; ANNOT 1493576; ANNOT 1493576; CLONE 37493; ANNOT 1494370; ANNOT 1494370; ANNOT 1441478; ANNOT 1441478; ANNOT 1440727; ANNOT 1440727; CLONE 37663; ANNOT 1447659; ANNOT 1447659; ANNOT 1443878; | 517; 518; 519; 531; 532; 533; 534; 535; 536; 537; 538; 544; 545; 546; 564; 565; 566; 572; 573; 574; 575; 576; 647; 648; 649; 650; 651; 652; 653; 654; 655; 656; 657; 658; 659; 660; 661; 662; 673; 674; 675; 676; 677; 700; 701; 702; 703; 704; 715; 716; 717; 718; 719; 720; 721; 722; 723; 724; 762; 763; 764; 765; 766; 767; 768; 769; 770; 771; 772; 773; 774; 775; 776; 777; 778; 784; 785; 786; 787; 788; 821; 822; 823; 824; 825; 826; 827; 828; 829; 830; 831; 907; 908; 909; 910; 911; 912; 913; 914; 915; 916; 960; 961; 962; 963; 964; 965; 966; 967; 968; 969; 1015; 1016; 1017; 1018; 1019; 1043; 1044; 1045; 1046; 1047; 1048; 1049; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1190; 1191; 1192; 1193; 1194; 1226; 1227; 1228; 1229; 1230; 1231; 1232; 1233; 1234; 1235; 1239; 1240; 1241; 1242; 1243; 1244; 1245; 1246; 1255; 1256; 1257; 1343; 1344; 1345; 1346; 1347; 1348; 1349; 1423; 1424; 1425; 1426; 1427; 1428; 1429; 1622; 1623; 1624; 1625; 1626; 1627; 1628; 1629; 1637; 1638; 1639; 1640; 1641; 1651; 1652; 1653; 1657; 1658; 1659; 1660; 1661; 1697; 1698; 1699; 1700; 1701; 1702; 1703; 1747; 1748; 1749; 1750; 1751; 1752; 1753; 1769; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1438478; CLONE 38105; ANNOT 1473032; ANNOT 1467499; ANNOT 1467499; ANNOT 1526442; ANNOT 1526442; CLONE 38419; ANNOT 1542971; ANNOT 1542971; ANNOT 1521332; ANNOT 1521332; ANNOT 1467961; ANNOT 1467961; CLONE 38635; ANNOT 1489751; ANNOT 1489751; ANNOT 1446209; ANNOT 1446209; CLONE 38690; ANNOT 1525183; ANNOT 1525183; CLONE 38743; ANNOT 1448369; ANNOT 1448369; CLONE 38873; ANNOT 1451899; ANNOT 1451899; ANNOT 1496367; ANNOT 1496367; CLONE 39286; ANNOT 1447961; ANNOT 1447961; ANNOT 1490936; ANNOT 1490936; CLONE 39890; ANNOT 1511886; ANNOT 1511886; ANNOT 1517635; ANNOT 1517635; CLONE 40436; ANNOT 1441645; ANNOT 1441645; CLONE 40508; ANNOT 1453626; ANNOT 1453626; CLONE 40692; ANNOT 1455695; ANNOT 1455695; CLONE 40729; ANNOT 1481678; ANNOT 1481678; CLONE 40766; ANNOT 1450499; ANNOT 1450499; CLONE 40824; ANNOT 1509015; ANNOT 1509015; ANNOT 1535964; ANNOT 1535964; ANNOT 1535962; ANNOT 1455815; ANNOT 1455815; ANNOT 1455817; ANNOT 1455817; ANNOT 1482502; ANNOT 1482502; ANNOT 1509035; ANNOT 1509035; ANNOT 1482477; ANNOT 1482477; ANNOT 1509013; ANNOT 1509013; ANNOT 1535990; ANNOT 1535990; ANNOT 1455837; ANNOT 1455837; CLONE 4214l; ANNOT 1473839; ANNOT 1473839; CLONE 42925; ANNOT 1462354; ANNOT 1462354; CLONE 92670; ANNOT 1531919; ANNOT 1531919; ANNOT 95135; ANNOT 1527449; ANNOT 1527449; ANNOT 1537653; ANNOT 1537653; ANNOT 1473733; ANNOT 1473733; ANNOT 1468537; ANNOT 1468537; CLONE 97415; ANNOT 1481701; ANNOT 1481701; CLONE 97434; ANNOT 1488311; ANNOT 1488311; ANNOT 1518776; ANNOT 1518776; CLONE 98855; ANNOT 1460836; ANNOT 1460836; ANNOT 1450324; ANNOT 1450324; CLONE 105554; ANNOT 1451783; ANNOT 1451783; CLONE 107988; ANNOT 1459927; ANNOT 1459927; CLONE 109912; ANNOT 1451138; ANNOT 1451138; ANNOT 1456780; ANNOT 1456780; CLONE 111209; ANNOT 1494507; ANNOT 1494507; CLONE 116237; ANNOT 1455816; ANNOT 1455816; ANNOT 1482502; ANNOT 1482502; ANNOT 1482508; ANNOT 1482508; ANNOT 1535990; ANNOT 1535990; ANNOT 1509013; ANNOT 1509013; CLONE 117369; ANNOT 1499284; ANNOT 1499284; ANNOT 1481671; ANNOT 1481671; CLONE 123279; ANNOT 1508945; ANNOT 1508945; ANNOT 1531332; ANNOT 1531332; ANNOT 1551332; ANNOT 1482544; ANNOT 1482544; ANNOT 1487826; ANNOT 1487826; ANNOT 1478226; CLONE 124720; ANNOT 1441430; ANNOT 1441430; CLONE 147358; ANNOT 1493111; ANNOT 1493111; ANNOT 1461452; ANNOT 1461452; CLONE 148943; ANNOT 1472949; ANNOT 1472949; CLONE 150912; ANNOT 1533910; ANNOT 1533910; ANNOT 1480439; ANNOT 1480439; CLONE 151087; ANNOT 1504145; ANNOT 1504145; ANNOT 1451079; ANNOT 1451079; CLONE 154718; ANNOT 1457453; ANNOT 1457453; CLONE 156655; ANNOT 1441740; ANNOT 1441740; CLONE 157547; ANNOT 1473898; ANNOT 1473898; CLONE 158333; ANNOT 1466505; ANNOT 1466505; ANNOT 1449026; ANNOT 1449026; CLONE 158702; ANNOT 1501773; ANNOT 1501773; CLONE 227651; ANNOT 1474222; ANNOT 1474222; ANNOT 1468994; ANNOT 1468994; ANNOT 1497043; ANNOT 1497043; CLONE 241379; ANNOT 1526950; ANNOT 1526950; ANNOT 1508362; ANNOT 1508362; ANNOT 1477361; ANNOT 1477361; CLONE 254065; ANNOT 1485544; ANNOT 1485544; ANNOT 1447051; ANNOT 1447051; ANNOT 1517016; ANNOT 1517016; CLONE 262460; ANNOT 1530053; ANNOT 1530053; ANNOT 1493414; ANNOT 1493414; CLONE 292789; ANNOT 1442040; ANNOT 1442040; ANNOT 1482966; ANNOT 1482966; ANNOT 1454656; ANNOT 1454656; ANNOT 1458103; ANNOT 1458103; ANNOT 1464899; ANNOT 1464899; ANNOT 1474837; | 1770; 1771; 1772; 1773; 1774; 1775; 1776; 1788; 1789; 1790; 1818; 1819; 1820; 1821; 1822; 1838; 1839; 1840; 1841; 1842; 1882; 1883; 1884; 1885; 1886; 1904; 1905; 1906; 1912; 1913; 1914; 1918; 1919; 1920; 1930; 1931; 1932; 1933; 1934; 1935; 1939; 1940; 1941; 1942; 1943; 1944; 1945; 1946; 1947; 1948; 1949; 1950; 1951; 1952; 1953; 1954; 1955; 1956; 1957; 1958; 1959; 1960; 1961; 2015; 2016; 2017; 2045; 2046; 2047; 2061; 2062; 2063; 2076; 2077; 2078; 2079; 2080; 2081; 2082; 2083; 2084; 2100; 2101; 2102; 2103; 2104; 2105; 2106; 2107; 2118; 2119; 2120; 2121; 2122; 2247; 2248; 2249; 2278; 2279; 2280; 2303; 2304; 2305; 2306; 2307; 2314; 2315; 2316; 2383; 2384; 2385; 2386; 2387; 2388; 2389; 2390; 2391; 2392; 2393; 2407; 2408; 2409; 2410; 2411; 2492; 2493; 2494; 2495; 2496; 2497; 2498; 2499; 2500; 2501; 2502; 2503; 2528; 2529; 2530; 2531; 2532; 2543; 2544; 2545; 2555; 2556; 2557; 2558; 2559; 2560; 2561; 2562; 2563; 2564; 2577; 2578; 2579; 2580; 2581; 2582; 2593; 2594; 2595; 2611; 2612; 2613; 2614; 2615; 2616; 2617; 2618; 2683; 2684; 2685; 2686; 2687; 2688; 2689; 2718; 2719; 2720; 2721; 2722; 2723; 2724; 2731; 2732; 2733; 2734; 2735; 2736; 2737; 2774; 2775; 2776; 2777; 2778; 2852; 2853; 2854; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1474837; ANNOT 1520449; ANNOT 1538169; ANNOT 1538169; CLONE 463203; ANNOT 1511505; CLONE 563522; ANNOT 1460321; ANNOT 1460321; ANNOT 1508144; ANNOT 1541886; ANNOT 1541886; ANNOT 1475178; ANNOT 1508144; ANNOT 1508184; ANNOT 1508184; ANNOT 1528645; CLONE 660003; ANNOT 1001432; ANNOT 1475043; ANNOT 1454586; CLONE 1507756; ANNOT 1507756; ANNOT 1469708; CLONE 1002819; ANNOT 1474290; ANNOT 1522314; ANNOT 1522314; ANNOT 1497147; ANNOT 1497147; ANNOT 1471045; CLONE 1006934; ANNOT 1532963; CLONE 1007549; ANNOT 1458198; ANNOT 1458198; ANNOT 1439989; ANNOT 1464789; ANNOT 1464789; ANNOT 1461728; ANNOT 1479711; ANNOT 1440649; ANNOT 1440649; ANNOT 1464547; ANNOT 1464547; ANNOT 1454104; CDNA 23498145; ANNOT 1482362; ANNOT 1489077; ANNOT 1489077; ANNOT 1510416; ANNOT 1510416; ANNOT 1541253; CDNA 23545147; ANNOT 1443044; ANNOT 1443044; CDNA 36507011; ANNOT 1442604; ANNOT 1442612; ANNOT 1442612; ANNOT 1442608; ANNOT 1452827; ANNOT 1452827; CDNA 36507407; ANNOT 1457193; ANNOT 1487854; ANNOT 1487854; CDNA 36508177; CDNA 36512904; ANNOT 1471370; ANNOT 1471370; ANNOT 1444471; ANNOT 1491278; ANNOT 1491278; ANNOT 1447690; ANNOT 1447690; CDNA 36545500; ANNOT 1449045; ANNOT 1449045; ANNOT 1470714; ANNOT 1470714; CDNA 36571789; ANNOT 1444156; ANNOT 1444156; ANNOT 1497097; CDNA 36579424; ANNOT 1455663; ANNOT 1455663; ANNOT 1438024; ANNOT 1451434; ANNOT 1448068; ANNOT 1448068; CDNA 36695523; ANNOT 1461440; ANNOT 1461427; ANNOT 1461427; ANNOT 1461440; ANNOT 1461430; ANNOT 1440253; | 2855; 2856; 2857; 2858; 2859; 2860; 2861; 2862; 2863; 2864; 2865; 2866; 2867; 2868; 3003; 3004; 3005; 3227; 3228; 3229; 3230; 3231; 3232; 3233; 3234; 3235; 3314; 3315; 3316; 3317; 3318; 3319; 3420; 3421; 3422; 3423; 3424; 3425; 3426; 3427; 3428; 3429; 3430; 3431; 3432; 3433; 3434; 3435; 3436; 3437; 3438; 3439; 3440; 3441; 3442; 3443; 3444; 3445; 3446; 3447; 3448; 3449; 3450; 3451; 3452; 3453; 3454; 3455; 3456; 3641; 3642; 3643; 3644; 3645; 3704; 3705; 3706; 3707; 3708; 3813; 3814; 3815; 3875; 3876; 3877; 3878; 3879; 3880; 3881; 3882; 3883; 3884; 3885; 3886; 3887; 3888; 3889; 3896; 3897; 3898; 3899; 3900; 3901; 3902; 3903; 3904; 3979; 3980; 3981; 3982; 3983; 4043; 4044; 4045; 4046; 4047; 4063; 4064; 4065; 4066; 4067; 4068; 4069; 4070; 4071; 4072; 4073; 4074; 4075; 4076; 4077; 4078; 4079; 4080; 4081; |
| CAULINE LEAVES | Appearance | Other | The plant has a morphological phenotype in cauline leaves. | Useful for making ornamental plants with modified leaves | CLONE 13186; ANNOT 1464566; ANNOT 1458408; ANNOT 1458408; CLONE 13757; ANNOT 1471425; ANNOT 1471425; CLONE 26560; ANNOT 1536088; ANNOT 1536088; ANNOT 1482610; ANNOT 1482610; CLONE 37288; ANNOT 1531721; ANNOT 1453650; CLONE 37398; ANNOT 1531721; ANNOT 1531721; ANNOT 1478221; ANNOT 1478221; ANNOT 1482547; ANNOT 1482547; CLONE 156655; ANNOT 1441740; ANNOT 1441740; | 531; 532; 533; 534; 535; 564; 565; 566; 1015; 1016; 1017; 1018; 1019; 1622; 1623; 1624; 1630; 1631; 1632; 1633; 1634; 1635; 1636; 2580; 2581; 2582; |
| FLOWER | Appearance | Other | The plants have a morphological phenotype in flowers. | Useful for making ornamental plants with modified flowers | CLONE 2036; ANNOT 1526068; CLONE 3000; ANNOT 1518918; ANNOT 1518918; ANNOT 1535677; ANNOT 1482181; ANNOT 1482181; CLONE 6397; ANNOT 1486285; CLONE 9132; ANNOT 1458620; CLONE 13186; ANNOT 1464566; ANNOT 1458408; ANNOT 1458408; CLONE 13757; ANNOT 1471425; ANNOT 1471425; CLONE 14555; ANNOT 1511392; ANNOT 1469356; ANNOT 1469356; ANNOT 1517500; ANNOT 1458151; ANNOT 1458151; ANNOT 1522757; CLONE 14583; ANNOT 1530256; ANNOT 1530256; ANNOT 1476783; ANNOT 1503166; ANNOT | 84; 85; 86; 111; 112; 113; 114; 115; 116; 117; 290; 291; 292; 391; 392; 393; 531; 532; 533; 534; 535; 564; 565; 566; 608; 609; 610; 611; 612; 613; 614; 615; 616; 617; 618; 619; 620; 621; 622; 623; 624; 625; 784; 785; 786; |

TABLE 1-continued

| Tissue | Phenotype Category | Phenotype | Phenotype Description | Applications | Ceres ID | SEQ ID NO |
|---|---|---|---|---|---|---|
| | | | | | 1503166; CLONE 19586; ANNOT 1476446; ANNOT 1451126; ANNOT 1451126; CLONE 21563; ANNOT 1438905; ANNOT 1483143; ANNOT 1483143; CLONE 25538; ANNOT 1480776; ANNOT 1480776; CLONE 30759; ANNOT 1520359; ANNOT 1494753; ANNOT 1494753; ANNOT 1441875; ANNOT 1441875; ANNOT 1467006; ANNOT 1467006; ANNOT 1441867; ANNOT 1441867; ANNOT 1441871; ANNOT 1441871; ANNOT 1441864; ANNOT 1441864; ANNOT 1441868; ANNOT 1441868; ANNOT 1441859; ANNOT 1441859; ANNOT 1467009; CLONE 3791; ANNOT 3791; ANNOT 1540248; ANNOT 1540248; CLONE 37298; ANNOT 1476538; ANNOT 1476538; ANNOT 1493576; ANNOT 1493576; CLONE 37398; ANNOT 1531721; ANNOT 1531721; ANNOT 1478221; ANNOT 1478221; ANNOT 1482547; ANNOT 1482547; ANNOT 1494370; ANNOT 1494370; CLONE 37493; ANNOT 1494370; ANNOT 1441478; ANNOT 1441478; CLONE 38370; ANNOT 1471869; ANNOT 1471869; ANNOT 1448032; ANNOT 1448032; ANNOT 1448031; ANNOT 1448031; ANNOT 1438060; ANNOT 1438060; ANNOT 1438061; ANNOT 1438061; ANNOT 1438030; ANNOT 1438030; ANNOT 1437831; CLONE 38743; ANNOT 1448369; ANNOT 1448369; CLONE 39890; ANNOT 1511886; ANNOT 1511886; ANNOT 1517635; CLONE 40729; ANNOT 1481678; ANNOT 1481678; CLONE 41337; ANNOT 1516613; ANNOT 1516613; ANNOT 1513097; ANNOT 1513097; ANNOT 1463324; ANNOT 1463324; ANNOT 95453; ANNOT 1460836; ANNOT 1460836; ANNOT 1450324; ANNOT 1450324; ANNOT 1450324; CLONE 98855; ANNOT 1460836; ANNOT 1503141; ANNOT 1521524; CLONE 105554; ANNOT 1451783; ANNOT 1451783; CLONE 112955; ANNOT 1447634; ANNOT 1447634; | 787; 788; 842; 843; 844; 845; 846; 967; 968; 969; 1164; 1165; 1166; 1167; 1168; 1169; 1170; 1171; 1172; 1173; 1174; 1175; 1176; 1177; 1178; 1179; 1180; 1181; 1182; 1183; 1184; 1255; 1256; 1257; 1625; 1626; 1627; 1628; 1629; 1630; 1631; 1632; 1633; 1634; 1635; 1636; 1637; 1638; 1639; 1640; 1641; 1732; 1733; 1734; 1735; 1736; 1737; 1738; 1739; 1740; 1741; 1742; 1743; 1744; 1745; 1746; 1788; 1789; 1790; 1882; 1883; 1884; 1885; 1886; 1930; 1931; 1932; 1988; 1989; 1990; 1991; 1992; 1993; 1994; 2085; 2086; 2087; 2088; 2089; 2118; 2119; 2120; 2121; 2122; 2191; 2192; 2193; 2194; 2195; 2247; 2248; 2249; 2330; 2331; 2332; |
| INFLORESCENCE | Appearance | Other | The plants have a morphological phenotype in inflorescences. | Useful for making ornamental plants with modified flowers | CLONE 314; ANNOT 1543129; CLONE 1543129; ANNOT 1474923; ANNOT 1474923; CLONE 332; ANNOT 1474923; ANNOT 1474923; CLONE 3000; ANNOT 1518918; ANNOT 1518918; ANNOT 1535677; ANNOT 1535677; ANNOT 1482181; ANNOT 1482181; CLONE 3036; ANNOT 1456840; ANNOT 1456840; CLONE 4058; ANNOT 4058; ANNOT 1468992; ANNOT 1468992; ANNOT 1444098; ANNOT 1444098; ANNOT 1474224; ANNOT 1474224; ANNOT 1524351; ANNOT 1524351; CLONE 4067; ANNOT 4067; ANNOT 1514362; ANNOT 1514362; ANNOT 1494090; ANNOT 1494090; CLONE 6387; ANNOT 6387; ANNOT 1509111; ANNOT 1509111; ANNOT 1541620; CLONE 6397; ANNOT 6397; ANNOT 1486285; ANNOT 1486285; CLONE 8068; ANNOT 8068; ANNOT 1510462; ANNOT 1510462; ANNOT 1471422; ANNOT 1471422; ANNOT 1497509; ANNOT 1497509; CLONE 8265; ANNOT 8265; ANNOT 1438919; ANNOT 1438919; ANNOT 1499398; ANNOT 1499398; ANNOT 1446419; ANNOT 1446419; CLONE 8633; ANNOT 8633; ANNOT 1527560; ANNOT 1527560; ANNOT 1522449; ANNOT 1522449; CLONE 9132; ANNOT 9132; ANNOT 1458620; ANNOT 1458620; CLONE 11214; ANNOT 11214; ANNOT 1501485; ANNOT 1501485; ANNOT 1490496; ANNOT 1490496; CLONE 11214; ANNOT 1448498; ANNOT 1448498; ANNOT 1474848; ANNOT 1474848; ANNOT 1474848; CLONE 13186; ANNOT 1464566; ANNOT 1464566; ANNOT 1458408; ANNOT 1458408; CLONE 13391; ANNOT 13391; ANNOT 1445555; ANNOT 1445555; ANNOT 1462963; ANNOT 1462963; ANNOT 1502315; CLONE 13741; ANNOT 13741; ANNOT 1462963; ANNOT 1462963; ANNOT 1459563; CLONE 13757; ANNOT 13757; ANNOT 1471425; ANNOT 1471425; CLONE 19510; ANNOT 1501412; ANNOT 1501412; ANNOT 1490383; ANNOT 1490383; ANNOT 1438905; ANNOT 1438905; ANNOT 1444819; ANNOT 1444819; CLONE 21563; ANNOT 23322; ANNOT 1512337; ANNOT 1512337; ANNOT 1483143; ANNOT 1483143; ANNOT 1517094; ANNOT 1517094; CLONE 23518; ANNOT 1475658; ANNOT 1475658; ANNOT 1449267; ANNOT 1449267; | 9; 10; 11; 12; 13; 14; 111; 112; 113; 114; 115; 116; 117; 121; 122; 123; 187; 188; 189; 190; 191; 192; 193; 194; 195; 196; 197; 198; 199; 200; 285; 286; 287; 288; 289; 290; 291; 292; 345; 346; 347; 348; 349; 350; 351; 362; 363; 364; 365; 366; 367; 368; 375; 376; 377; 378; 379; 391; 392; 393; 448; 449; 450; 451; 452; 453; 454; 455; 456; 531; 532; 533; 534; 535; 539; 540; 541; 542; 543; 550; 551; 552; 553; 554; 564; 565; 566; 772; 773; 774; 775; 776; 777; 778; 842; 843; 844; 845; 846; 897; 898; 899; 900; 901; 907; 908; 909; 910; 911; 912; 913; 960; 961; 962; 963; 964; 965; 966; 967; 968; 969; |

TABLE 1-continued

| Tissue | Phenotype Category | Phenotype | Phenotype Description | Applications | Ceres ID | SEQ ID NO |
|---|---|---|---|---|---|---|
| | | | | | 1449267; ANNOT 1507191; CLONE 25380; ANNOT 1512618; ANNOT 1512618; ANNOT 1459357; ANNOT 1459357; ANNOT 1463526; ANNOT 1463526; CLONE 25538; ANNOT 1480776; CLONE 25758; ANNOT 1473748; CLONE 25886; ANNOT 1446650; ANNOT 1446650; ANNOT 1439514; ANNOT 1439514; ANNOT 1477202; ANNOT 1477202; ANNOT 1455325; ANNOT 1455325; CLONE 27460; ANNOT 1474847; ANNOT 1474847; ANNOT 1507835; CLONE 27835; CLONE 28643; ANNOT 1469464; ANNOT 1469464; ANNOT 1463508; ANNOT 1463508; ANNOT 1459366; ANNOT 1459366; ANNOT 1542246; ANNOT 1542246; CLONE 31507; ANNOT 1447204; ANNOT 1447204; CLONE 32082; ANNOT 1446894; ANNOT 1446894; ANNOT 1481146; ANNOT 1543513; ANNOT 1481150; CLONE 33559; ANNOT 1481146; ANNOT 1481138; ANNOT 1481138; ANNOT 1485824; ANNOT 1485824; ANNOT 1534622; ANNOT 1534622; CLONE 34412; ANNOT 1449739; ANNOT 1449739; ANNOT 1449738; ANNOT 1449738; ANNOT 1458830; CLONE 35493; ANNOT 1457751; ANNOT 1457751; ANNOT 1518757; ANNOT 1465420; ANNOT 1465420; CLONE 36891; ANNOT 1480518; ANNOT 1480518; ANNOT 1442194; ANNOT 1442194; ANNOT 1454127; ANNOT 1454127; ANNOT 1461716; ANNOT 1461716; ANNOT 1440277; ANNOT 1461414; ANNOT 1461415; ANNOT 1461414; ANNOT 1461414; ANNOT 1447424; ANNOT 1447424; ANNOT 1528127; ANNOT 1528127; ANNOT 1438717; ANNOT 1440276; ANNOT 1440276; ANNOT 1442556; ANNOT 1442556; ANNOT 1452873; ANNOT 1452873; ANNOT 1453483; ANNOT 1453483; ANNOT 1473384; ANNOT 1473384; ANNOT 1475808; ANNOT 1475808; ANNOT 1474708; ANNOT 1474708; ANNOT 1438698; ANNOT 1438698; CLONE 37019; ANNOT 1517849; ANNOT 1517849; ANNOT 1511684; ANNOT 1511684; ANNOT 1464532; ANNOT 1464532; ANNOT 1458439; ANNOT 1458439; ANNOT 1540674; ANNOT 1540674; CLONE 37288; ANNOT 1453650; ANNOT 1453650; ANNOT 1476538; ANNOT 1476538; ANNOT 1493576; CLONE 37298; CLONE 37398; ANNOT 1531721; ANNOT 1531721; ANNOT 1478221; ANNOT 1478221; ANNOT 1482547; ANNOT 1482547; CLONE 38214; ANNOT 1466779; ANNOT 1466779; ANNOT 1465769; ANNOT 1465769; ANNOT 1538318; ANNOT 1538318; CLONE 38743; ANNOT 1448369; ANNOT 1448369; CLONE 38973; ANNOT 1451899; ANNOT 1451899; ANNOT 1496367; ANNOT 1496367; CLONE 39890; ANNOT 1511886; ANNOT 1511886; ANNOT 1517635; ANNOT 1517635; CLONE 40153; ANNOT 1453549; ANNOT 1453549; ANNOT 1528184; ANNOT 1528184; ANNOT 1474758; ANNOT 1474758; CLONE 41337; ANNOT 1516613; ANNOT 1516613; ANNOT 1513097; ANNOT 1513097; ANNOT 1463324; ANNOT 1463324; CLONE 42925; ANNOT 1462354; ANNOT 1462354; CLONE 96020; ANNOT 1450365; ANNOT 1450365; ANNOT 1460794; ANNOT 1460794; CLONE 97434; ANNOT 1488311; ANNOT 1488311; ANNOT 1518776; ANNOT 1518776; CLONE 100319; ANNOT 1503141; ANNOT 1503141; ANNOT 1521524; ANNOT 1521524; CLONE 101686; ANNOT 1479756; ANNOT 1479756; ANNOT 1540137; ANNOT 1540137; ANNOT 1486722; ANNOT 1486722; CLONE 106301; CLONE 112955; ANNOT 1447634; ANNOT 1447634; CLONE 117369; ANNOT 1499284; ANNOT 1499284; ANNOT 1481671; ANNOT 1481671; CLONE 126592; ANNOT 1474017; ANNOT 1474017; ANNOT 1468796; ANNOT 1468796; CLONE 147593; ANNOT 1475653; ANNOT 1475653; ANNOT 1458131; ANNOT 1458131; ANNOT 1461780; ANNOT 1461780; CLONE 156655; ANNOT 1441740; CLONE 157547; ANNOT 1473898; ANNOT 1473898; CLONE 157730; ANNOT 1532681; ANNOT 1469739; ANNOT | 973; 974; 975; 986; 987; 988; 989; 990; 991; 992; 993; 994; 1055; 1056; 1057; 1058; 1059; 1122; 1123; 1124; 1125; 1126; 1127; 1128; 1129; 1130; 1195; 1196; 1197; 1201; 1202; 1203; 1204; 1205; 1310; 1311; 1312; 1313; 1314; 1315; 1316; 1317; 1318; 1319; 1320; 1376; 1377; 1378; 1379; 1380; 1381; 1382; 1460; 1461; 1462; 1463; 1464; 1465; 1466; 1548; 1549; 1550; 1551; 1552; 1553; 1554; 1555; 1556; 1557; 1558; 1559; 1560; 1561; 1562; 1563; 1564; 1565; 1566; 1567; 1568; 1569; 1570; 1571; 1572; 1573; 1574; 1575; 1576; 1577; 1578; 1579; 1580; 1581; 1582; 1583; 1584; 1599; 1600; 1601; 1602; 1603; 1604; 1605; 1606; 1607; 1608; 1609; 1622; 1623; 1624; 1625; 1626; 1627; 1628; 1629; 1630; 1631; 1632; 1633; 1634; 1635; 1636; 1707; 1708; 1709; 1710; 1711; 1712; 1713; 1788; 1789; 1790; 1818; 1819; 1820; 1821; 1822; 1882; 1883; 1884; 1885; 1886; 1897; 1898; 1899; 1900; 1901; 1902; 1903; 1988; 1989; 1990; 1991; 1992; 1993; 1994; 2045; 2046; 2047; 2095; 2096; 2097; 2098; 2099; 2103; 2104; 2105; 2106; 2107; 2191; 2192; 2193; 2194; 2195; 2212; 2213; 2214; 2215; 2216; 2217; 2218; 2262; 2330; 2331; 2332; 2407; 2408; 2409; 2410; 2411; 2512; 2513; 2514; 2515; 2516; 2533; 2534; 2535; 2536; 2537; 2538; 2539; |

TABLE 1-continued

| Tissue | Phenotype Category | Phenotype | Phenotype Description | Applications | Ceres ID | SEQ ID NO |
|---|---|---|---|---|---|---|
| | | | | | 1469739; CLONE 158734; ANNOT 1477956; CLONE 225601; ANNOT 1457617; ANNOT 1465289; ANNOT 1438014; ANNOT 1478647; ANNOT 1478647; ANNOT 1453865; ANNOT 1438014; ANNOT 1438014; CLONE 226818; ANNOT 1503617; ANNOT 1450560; ANNOT 1450560; ANNOT 1460622; CLONE 241379; ANNOT 1526950; ANNOT 1508362; ANNOT 1508362; ANNOT 1477361; ANNOT 1477361; ANNOT 1473933; ANNOT 1473933; ANNOT 1468704; CLONE 267564; ANNOT 1442040; ANNOT 1442040; ANNOT 1482966; ANNOT 1454656; ANNOT 1454656; ANNOT 1458103; ANNOT 1458103; ANNOT 1464899; ANNOT 1464899; ANNOT 1474837; ANNOT 1474837; ANNOT 1520449; ANNOT 1538169; ANNOT 1538169; CLONE 536726; ANNOT 1499826; ANNOT 1499826; ANNOT 1445243; ANNOT 1525386; ANNOT 1448522; ANNOT 1448522; ANNOT 1465506; ANNOT 1497017; ANNOT 1497017; ANNOT 1447240; ANNOT 1447240; ANNOT 1539566; ANNOT 1539566; ANNOT 1458198; ANNOT 1444070; ANNOT 1439989; ANNOT 1464789; ANNOT 1500987; ANNOT 1500987; ANNOT 1490915; CLONE 1002819; ANNOT 1474290; ANNOT 1474290; ANNOT 1522314; ANNOT 1497147; ANNOT 1497147; ANNOT 1471045; CLONE 1007549; ANNOT 1458198; ANNOT 1458198; ANNOT 1461728; ANNOT 1479711; ANNOT 1479711; ANNOT 1464789; ANNOT 1440649; ANNOT 1464547; ANNOT 1464547; ANNOT 1454104; ANNOT 1454104; CDNA 23498145; ANNOT 1482362; ANNOT 1482362; ANNOT 1489077; ANNOT 1489077; CDNA 2505103; CDNA 36512904; ANNOT 1471370; ANNOT 1471370; ANNOT 1444471; ANNOT 1491278; ANNOT 1491278; ANNOT 1447690; CDNA 36521407; ANNOT 1514988; ANNOT 1514988; CDNA 36532976; ANNOT 1445379; ANNOT 1445379; ANNOT 1449468; CDNA 36545500; ANNOT 1449045; ANNOT 1449045; ANNOT 1470714; ANNOT 1447690; ANNOT 1447690; ANNOT 1491278; ANNOT 1491278; ANNOT 1500987; ANNOT 1490915; ANNOT 1490915; | 2580; 2581; 2582; 2593; 2594; 2595; 2601; 2602; 2603; 2604; 2605; 2619; 2620; 2621; 2665; 2666; 2667; 2668; 2669; 2670; 2671; 2672; 2673; 2674; 2675; 2676; 2677; 2678; 2679; 2680; 2681; 2682; 2718; 2719; 2720; 2721; 2722; 2723; 2724; 2789; 2790; 2791; 2792; 2793; 2852; 2853; 2854; 2855; 2856; 2857; 2858; 2859; 2860; 2861; 2862; 2863; 2864; 2865; 2866; 2867; 2868; 3135; 3136; 3137; 3138; 3139; 3140; 3141; 3142; 3143; 3144; 3145; 3146; 3147; 3148; 3149; 3150; 3151; 3152; 3153; 3299; 3300; 3301; 3302; 3303; 3428; 3429; 3430; 3431; 3432; 3433; 3434; 3435; 3436; 3440; 3441; 3442; 3443; 3444; 3445; 3446; 3447; 3448; 3449; 3450; 3451; 3452; 3453; 3454; 3455; 3456; 3641; 3642; 3643; 3644; 3645; 3687; 3896; 3897; 3898; 3899; 3900; 3901; 3902; 3903; 3904; 3908; 3909; 3910; 3928; 3929; 3930; 3931; 3932; 3979; 3980; 3981; 3982; 3983; 3688; 3689; 3690; 3691; 3692; 3693; 3694; 3695; |
| WHOLE PLANT | Appearance | Other | The plants have a morphological phenotype. | Useful for making ornamental plants | CLONE 314; ANNOT 1543129; CLONE 332; ANNOT 1474923; ANNOT 1474923; CLONE 1355; ANNOT 1515808; ANNOT 1515808; ANNOT 1469219; ANNOT 1469219; ANNOT 1462513; CLONE 3000; ANNOT 1518918; ANNOT 1518918; ANNOT 1535677; ANNOT 1482181; ANNOT 1482181; CLONE 5167; ANNOT 1465422; ANNOT 1465422; ANNOT 1457750; ANNOT 1457750; ANNOT 1513544; ANNOT 1513544; CLONE 5605; ANNOT 1437939; ANNOT 1437939; CLONE 6220; ANNOT 1488463; ANNOT 1488463; ANNOT 1541879; ANNOT 1541879; CLONE 9132; ANNOT 1458620; ANNOT 1458620; CLONE 9683; ANNOT 1471514; ANNOT 1471514; CLONE 10857; ANNOT 1464446; ANNOT 1464446; CLONE 13186; ANNOT 1464566; ANNOT 1464566; ANNOT 1458408; ANNOT 1458408; CLONE 13757; ANNOT 1471425; ANNOT 1471425; CLONE 14909; ANNOT 1499838; ANNOT 1497838; ANNOT 1522523; ANNOT 1522523; ANNOT 1471525; ANNOT 1471525; ANNOT | 9; 10; 11; 12; 13; 14; 43; 44; 45; 46; 47; 48; 49; 111; 112; 113; 114; 115; 116; 117; 223; 224; 225; 226; 227; 228; 229; 238; 239; 240; 275; 276; 277; 278; 279; 391; 392; 393; 402; 403; 404; 434; 435; 436; 531; 532; 533; 534; 535; 564; 565; 566; 626; 627; 628; 629; 630; 631; 632; 633; 634; 635; 636; 637; 638; 639; 640; 678; |

TABLE 1-continued

| Tissue | Phenotype Category | Phenotype | Phenotype Description | Applications | Ceres ID | SEQ ID NO |
|---|---|---|---|---|---|---|
| | | | | | 1511908; ANNOT 1511908; ANNOT 1451416; ANNOT 1464305; ANNOT 1451416; ANNOT 1451416; ANNOT 1461050; ANNOT 1461050; CLONE 17409; ANNOT 1457617; ANNOT 1457617; ANNOT 1465289; ANNOT 1478647; ANNOT 1478647; ANNOT 1478647; ANNOT 1453865; ANNOT 1453865; CLONE 19188; ANNOT 1445089; ANNOT 1445089; CLONE 19481; ANNOT 1475146; ANNOT 1475146; ANNOT 1454933; ANNOT 1454933; CLONE 19486; ANNOT 1452204; ANNOT 1452204; ANNOT 1452204; ANNOT 1443204; CLONE 23523; ANNOT 1453919; ANNOT 1453919; CLONE 24266; ANNOT 1463475; ANNOT 1463475; ANNOT 1540920; ANNOT 1540920; ANNOT 1487528; ANNOT 1487528; CLONE 25607; ANNOT 1450220; ANNOT 1450220; CLONE 26542; ANNOT 1475323; ANNOT 1475323; ANNOT 1538272; ANNOT 1538272; CLONE 26907; ANNOT 1484074; ANNOT 1484074; ANNOT 1440016; ANNOT 1440016; ANNOT 1451842; ANNOT 1518242; CLONE 27464; ANNOT 1453044; ANNOT 1453044; ANNOT 1451171; ANNOT 1451171; CLONE 32753; ANNOT 1480607; ANNOT 1480607; ANNOT 1472242; ANNOT 1472242; CLONE 35051; ANNOT 1443033; ANNOT 1443033; ANNOT 1452408; ANNOT 1452408; ANNOT 1505508; ANNOT 1505508; CLONE 36518; ANNOT 1471507; ANNOT 1471507; ANNOT 1444893; ANNOT 1444893; ANNOT 1458642; ANNOT 1458642; ANNOT 1522497; ANNOT 1522497; ANNOT 1469105; ANNOT 1469105; ANNOT 1484993; ANNOT 1484993; CLONE 36701; ANNOT 1487885; ANNOT 1487885; ANNOT 1457156; ANNOT 1457156; ANNOT 1449371; ANNOT 1449371; ANNOT 1445504; ANNOT 1445504; CLONE 37298; ANNOT 1476538; ANNOT 1476538; ANNOT 1493576; CLONE 38697; ANNOT 1470862; ANNOT 1470862; ANNOT 1443740; ANNOT 1443740; ANNOT 1461162; ANNOT 1461162; ANNOT 1526959; ANNOT 1526959; ANNOT 1468331; ANNOT 1468331; CLONE 39890; ANNOT 1511886; ANNOT 1511886; ANNOT 1517635; ANNOT 1517635; CLONE 41439; CLONE 95135; ANNOT 1527449; ANNOT 1527449; ANNOT 1537653; ANNOT 1537653; ANNOT 1473733; ANNOT 1473733; ANNOT 1468537; ANNOT 1468537; CLONE 96020; ANNOT 1450365; ANNOT 1450365; ANNOT 1460794; ANNOT 1460794; CLONE 97434; ANNOT 1488311; ANNOT 1488311; ANNOT 1518776; CLONE 113719; ANNOT 1513206; ANNOT 1513206; ANNOT 1516003; ANNOT 1462703; ANNOT 1462703; CLONE 123279; ANNOT 1508945; ANNOT 1508945; ANNOT 1531332; ANNOT 1531332; ANNOT 1482544; ANNOT 1478226; ANNOT 1478226; CLONE 141830; ANNOT 1488335; ANNOT 1488335; CLONE 147593; ANNOT 1475653; ANNOT 1475653; ANNOT 1458131; ANNOT 1458131; ANNOT 1461780; ANNOT 1461780; CLONE 152076; ANNOT 1493664; ANNOT 1493664; CLONE 225601; ANNOT 1457617; ANNOT 1457617; ANNOT 1465289; ANNOT 1465289; ANNOT 1478647; ANNOT 1478647; ANNOT 1453865; ANNOT 1453865; ANNOT 1438014; CLONE 262460; ANNOT 1530053; ANNOT 1530053; ANNOT 1493414; ANNOT 1493414; CLONE 536796; ANNOT 1484779; ANNOT 1484779; ANNOT 1538185; ANNOT 1538185; ANNOT 1455109; ANNOT 1455109; ANNOT 1477384; ANNOT 1477384; CLONE 557009; ANNOT 1474923; ANNOT 1474923; CLONE 660003; ANNOT 1508184; ANNOT 1508184; ANNOT 1528645; ANNOT 1528645; CDNA 3655438l; ANNOT 1523115; ANNOT 1523115; ANNOT 1479243; ANNOT 1479243; CDNA 3657579; ANNOT 1486224; ANNOT 1486224; ANNOT 1444021; ANNOT 1444021; | 679; 680; 681; 682; 683; 684; 685; 686; 747; 748; 749; 762; 763; 764; 765; 766; 767; 768; 769; 770; 771; 914; 915; 916; 937; 938; 939; 940; 941; 942; 943; 970; 971; 972; 1010; 1011; 1012; 1013; 1014; 1043; 1044; 1045; 1046; 1047; 1048; 1049; 1060; 1061; 1062; 1063; 1064; 1250; 1251; 1252; 1253; 1254; 1441; 1442; 1443; 1444; 1445; 1446; 1447; 1505; 1506; 1507; 1508; 1509; 1510; 1511; 1512; 1513; 1514; 1515; 1516; 1517; 1536; 1537; 1538; 1539; 1540; 1541; 1542; 1543; 1544; 1625; 1626; 1627; 1628; 1629; 1777; 1778; 1779; 1780; 1781; 1782; 1783; 1784; 1785; 1786; 1787; 1882; 1883; 1884; 1885; 1886; 1998; 2076; 2077; 2078; 2079; 2080; 2081; 2082; 2083; 2084; 2095; 2096; 2097; 2098; 2099; 2103; 2104; 2105; 2106; 2107; 2333; 2334; 2335; 2336; 2337; 2338; 2339; 2492; 2493; 2494; 2495; 2496; 2497; 2498; 2499; 2500; 2520; 2521; 2522; 2533; 2534; 2535; 2536; 2537; 2538; 2539; 2565; 2566; 2567; 2665; 2666; 2667; 2668; 2669; 2670; 2671; 2672; 2673; 2674; 2675; 2774; 2775; 2776; 2777; 2778; 3154; 3155; 3156; 3157; 3158; 3159; 3160; 3161; 3162; 3221; 3222; 3223; 3314; 3315; 3316; 3317; 3318; 4000; 4001; 4002; 4003; 4004; 4053; 4054; 4055; 4056; 4057; |
| ROSETTE LEAVES | Appearance | Oval Shaped | The leaves are much rounder | Useful for making | CLONE 907; ANNOT 1502138; ANNOT 1502138; ANNOT 1449135; ANNOT 1449135; CLONE 1241; ANNOT 1453081; ANNOT 1453081; ANNOT 1442349; | 30; 31; 32; 33; 34; 38; 39; 40; 41; 42; 67; 68; |

TABLE 1-continued

| Tissue | Phenotype Category | Phenotype | Phenotype Description | Applications | Ceres ID | SEQ ID NO |
|---|---|---|---|---|---|---|
| | | | than wild-type. | ornamental plants with altered leaf shape | ANNOT 1442349; CLONE 1610; ANNOT 1454586; ANNOT 1454586; ANNOT 1475043; ANNOT 1475043; ANNOT 1507756; ANNOT 1507756; ANNOT 1469708; ANNOT 1469708; CLONE 3036; ANNOT 1456840; ANNOT 1456840; CLONE 3363; ANNOT 1445515; ANNOT 1445515; ANNOT 1446198; ANNOT 1446198; ANNOT 1446198; ANNOT 1518517; ANNOT 1449363; ANNOT 1449363; ANNOT 1466198; ANNOT 1466198; ANNOT 1461861; ANNOT 1518517; CLONE 3542; ANNOT 1471301; ANNOT 1471301; CLONE 3858; ANNOT 1459068; ANNOT 1459068; CLONE 6082; ANNOT 1443416; ANNOT 1443416; ANNOT 1505047; ANNOT 1505047; ANNOT 1496339; ANNOT 1496339; CLONE 8254; ANNOT 1543042; ANNOT 1543042; ANNOT 1489655; ANNOT 1489655; CLONE 8265; ANNOT 1438919; ANNOT 1438919; ANNOT 1499398; ANNOT 1499398; ANNOT 1446419; ANNOT 1446419; CLONE 9221; ANNOT 1535229; ANNOT 1535229; CLONE 9683; ANNOT 1471514; ANNOT 1471514; ANNOT 1445849; ANNOT 1445849; ANNOT 1500561; ANNOT 1500561; ANNOT 1464458; ANNOT 1464458; CLONE 10879; ANNOT 1467184; ANNOT 1467184; CLONE 12272; ANNOT 1506387; ANNOT 1506387; ANNOT 1474522; ANNOT 1474522; CLONE 12993; ANNOT 1479464; ANNOT 1479464; CLONE 13741; ANNOT 1462963; ANNOT 1462963; ANNOT 1459563; ANNOT 1459563; CLONE 17434; ANNOT 1455741; ANNOT 1455741; ANNOT 1477832; ANNOT 1477832; CLONE 17632; ANNOT 1474847; ANNOT 1474847; ANNOT 1507835; ANNOT 1507835; CLONE 17912; ANNOT 1514378; ANNOT 1514378; ANNOT 1494118; ANNOT 1494118; CLONE 19116; ANNOT 1467522; ANNOT 1467522; ANNOT 1526421; ANNOT 1526421; CLONE 19486; ANNOT 1452204; ANNOT 1452204; ANNOT 1443204; ANNOT 1443204; ANNOT 1490383; ANNOT 1490383; ANNOT 19510; ANNOT 1501412; ANNOT 1501412; ANNOT 1490383; ANNOT 1490383; ANNOT 1448419; ANNOT 1448419; CLONE 19586; ANNOT 1476446; ANNOT 1476446; ANNOT 1451126; ANNOT 1451126; CLONE 23523; ANNOT 1453919; ANNOT 1453919; CLONE 28602; ANNOT 1461728; ANNOT 1461728; ANNOT 1488330; ANNOT 1488330; ANNOT 1460480; ANNOT 1460480; ANNOT 1461614; ANNOT 1461614; ANNOT 1479711; ANNOT 1479711; ANNOT 1479712; ANNOT 1479712; ANNOT 1460481; ANNOT 1460481; ANNOT 1461613; ANNOT 1461613; ANNOT 1488329; ANNOT 1488329; ANNOT 1458198; ANNOT 1458198; ANNOT 1488327; ANNOT 1488327; ANNOT 1488327; CLONE 31507; ANNOT 1447204; ANNOT 1447204; CLONE 32348; ANNOT 1470719; ANNOT 1470719; ANNOT 1543728; ANNOT 1543728; ANNOT 1451171; ANNOT 1451171; ANNOT 1482066; ANNOT 1482066; CLONE 32751; ANNOT 1540248; ANNOT 1540248; CLONE 34385; ANNOT 1445331; ANNOT 1445331; ANNOT 1498316; ANNOT 1498316; CLONE 34783; ANNOT 1466952; ANNOT 1466952; ANNOT 1523551; ANNOT 1523551; ANNOT 1455815; ANNOT 1455817; ANNOT 1470164; ANNOT 1470164; CLONE 34976; ANNOT 1507231; ANNOT 1507231; CLONE 35051; ANNOT 1443033; ANNOT 1443033; ANNOT 1452408; ANNOT 1452408; ANNOT 1452408; ANNOT 1505508; ANNOT 1505508; CLONE 36334; ANNOT 1464715; ANNOT 1464715; ANNOT 1511511; ANNOT 1511511; CLONE 36904; ANNOT 1526083; ANNOT 1526083; ANNOT 1498856; ANNOT 1498856; ANNOT 1445872; ANNOT 1445872; ANNOT 1472663; ANNOT 1472663; CLONE 37658; ANNOT 1497485; ANNOT 1497485; ANNOT 1525183; ANNOT 1525183; CLONE 38690; ANNOT 1481678; CLONE 40824; ANNOT 40729; ANNOT 1481678; ANNOT 1535964; ANNOT 1535964; ANNOT 1509015; ANNOT 1509015; ANNOT 1535962; ANNOT 1535962; ANNOT 1455815; ANNOT 1455815; ANNOT 1455817; ANNOT 1455817; ANNOT 1535817; ANNOT 1482502; ANNOT 1482502; ANNOT 1509035; ANNOT 1509035; 1455817; ANNOT 1482477; ANNOT 1482477; ANNOT 1509013; ANNOT 1509013; ANNOT 1455837; CLONE 41439; ANNOT 1535990; ANNOT 1535990; ANNOT 1455837; ANNOT 1455837; | 69; 70; 71; 72; 73; 74; 75; 121; 122; 123; 129; 130; 131; 132; 133; 134; 135; 136; 137; 138; 139; 145; 146; 147; 175; 176; 177; 268; 269; 270; 271; 272; 273; 274; 357; 358; 359; 360; 361; 362; 363; 364; 365; 366; 367; 368; 394; 395; 396; 402; 403; 404; 405; 406; 407; 408; 409; 410; 411; 437; 438; 439; 515; 516; 517; 518; 519; 520; 521; 522; 550; 551; 552; 553; 554; 687; 688; 689; 690; 691; 695; 696; 697; 698; 699; 705; 706; 707; 708; 709; 735; 736; 737; 738; 739; 767; 768; 769; 770; 771; 772; 773; 774; 775; 776; 777; 778; 784; 785; 786; 787; 788; 914; 915; 916; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1195; 1196; 1197; 1219; 1220; 1221; 1222; 1223; 1224; 1225; 1247; 1248; 1249; 1255; 1256; 1257; 1364; 1365; 1366; 1367; 1368; 1423; 1424; 1425; 1426; 1427; 1428; 1429; 1435; 1436; 1437; 1441; 1442; 1443; 1444; 1445; 1446; 1447; 1500; 1501; 1502; 1503; 1504; 1585; 1586; 1587; 1588; 1589; 1590; 1591; 1592; 1593; 1654; 1655; 1656; 1774; 1775; 1776; 1930; 1931; 1932; 1939; 1940; 1941; 1942; 1943; 1944; 1945; 1946; 1947; 1948; 1949; 1950; 1951; 1952; 1953; 1954; 1955; 1956; 1957; 1958; 1959; 1960; 1961; 1998; |

TABLE 1-continued

| Tissue | Phenotype Category | Phenotype | Phenotype Description | Applications | Ceres ID | SEQ ID NO |
|---|---|---|---|---|---|---|
| | | | | | CLONE 42141; ANNOT 1473839; CLONE 42925; ANNOT 1462354; ANNOT 1462354; CLONE 95135; ANNOT 1527449; ANNOT 1527449; ANNOT 1537653; ANNOT 1537653; ANNOT 1473733; ANNOT 1473733; ANNOT 1468537; ANNOT 1468537; CLONE 96020; ANNOT 1450365; ANNOT 1450365; ANNOT 1460794; ANNOT 1460794; CLONE 98855; ANNOT 160836; ANNOT 160836; ANNOT 1450324; ANNOT 1450324; CLONE 100047; ANNOT 1532164; ANNOT 1532164; ANNOT 1479341; ANNOT 1479341; ANNOT 1479350; ANNOT 1479350; ANNOT 1442450; CLONE 102248; ANNOT 1456981; ANNOT 1456981; CLONE 103581; ANNOT 1486398; ANNOT 1486398; ANNOT 1496840; CLONE 109912; ANNOT 1451138; ANNOT 1451138; ANNOT 1456780; ANNOT 1456780; CLONE 110454; CLONE 113719; ANNOT 1513206; ANNOT 1513206; ANNOT 1516003; ANNOT 1462703; ANNOT 1462703; CLONE 114602; ANNOT 1450785; ANNOT 1450785; ANNOT 1456283; ANNOT 1456283; ANNOT 1460638; ANNOT 1513900; ANNOT 1513900; ANNOT 1540271; ANNOT 1540271; CLONE 115946; ANNOT 1458342; ANNOT 1458342; CLONE 116257; ANNOT 1520806; ANNOT 1520806; ANNOT 1473089; ANNOT 1473089; ANNOT 1500150; CLONE 117895; ANNOT 1448592; ANNOT 1448592; ANNOT 1448594; ANNOT 1448594; CLONE 118337; ANNOT 1454773; ANNOT 1454773; ANNOT 1511811; ANNOT 1511811; ANNOT 1478364; ANNOT 1464394; ANNOT 1464394; CLONE 122353; ANNOT 1472265; ANNOT 1472265; CLONE 147358; ANNOT 1493111; ANNOT 1493111; ANNOT 1461452; CLONE 157547; ANNOT 1473898; ANNOT 1473898; CLONE 157709; ANNOT 1515067; ANNOT 1515067; ANNOT 1492780; ANNOT 1492780; CLONE 158333; ANNOT 1466505; ANNOT 1466505; ANNOT 1449026; ANNOT 1449026; CLONE 235706; ANNOT 1462351; ANNOT 1462351; ANNOT 1469462; ANNOT 1469462; ANNOT 1488821; ANNOT 1488821; CLONE 46203; ANNOT 1511505; ANNOT 1511505; CLONE 536796; ANNOT 1484779; ANNOT 1484779; ANNOT 1538185; ANNOT 1538185; ANNOT 1455109; ANNOT 1455109; ANNOT 1477384; ANNOT 1477384; CLONE 541719; ANNOT 1518918; ANNOT 1518918; ANNOT 1535677; ANNOT 1535677; CLONE 641355; ANNOT 1463334; ANNOT 1463334; ANNOT 1463335; ANNOT 1463335; ANNOT 1463334; ANNOT 1452665; ANNOT 1452665; CLONE 708342; ANNOT 1538185; ANNOT 1538185; CLONE 1001432; ANNOT 1475043; ANNOT 1475043; ANNOT 1454586; ANNOT 1454586; ANNOT 1507756; ANNOT 1507756; ANNOT 1469708; ANNOT 1469708; CLONE 1006934; ANNOT 1532963; ANNOT 1532963; CLONE 1029167; ANNOT 1453409; ANNOT 1453409; ANNOT 1474630; ANNOT 1474630; ANNOT 1450948; ANNOT 1450948; CDNA 2351870S; ANNOT 1463957; ANNOT 1463957; ANNOT 1458961; ANNOT 1458961; CDNA 23545147; ANNOT 1443044; ANNOT 1443044; CDNA 36507011; ANNOT 1442604; ANNOT 1442604; ANNOT 1442612; ANNOT 1442612; ANNOT 1442608; ANNOT 1442608; ANNOT 1452827; ANNOT 1452827; CDNA 36507407; ANNOT 1457193; ANNOT 1457193; ANNOT 1457794; ANNOT 1487854; ANNOT 1487854; CDNA 36508177; CDNA 36512904; ANNOT 1471370; ANNOT 1471370; ANNOT 1444471; ANNOT 1444471; ANNOT 1491278; ANNOT 1491278; ANNOT 1447690; ANNOT 1447690; CDNA 36534269; CDNA 36535618; ANNOT 1457794; ANNOT 1457794; ANNOT 1524172; CDNA 36536865; ANNOT 1459998; ANNOT 1459998; ANNOT 1513263; ANNOT 1513263; CDNA 36536865; ANNOT 1505326; ANNOT 1505326; ANNOT 1496106; ANNOT 1496106; CDNA 36539960; ANNOT 1448952; ANNOT 1448952; CDNA 36542397; ANNOT 1497958; ANNOT 149795S; ANNOT 1471743; ANNOT 1471743; ANNOT 1458313; ANNOT 1458313; CDNA 36560856; ANNOT 1517998; ANNOT 1517998; ANNOT 1458313; ANNOT 1458313; CDNA 36566773; | 2015; 2016; 2017; 2045; 2046; 2047; 2076; 2077; 2078; 2079; 2080; 2081; 2082; 2083; 2084; 2095; 2096; 2097; 2098; 2099; 2118; 2119; 2120; 2121; 2122; 2173; 2174; 2175; 2176; 2177; 2178; 2179; 2180; 2181; 2229; 2230; 2231; 2232; 2233; 2234; 2235; 2236; 2303; 2304; 2305; 2306; 2307; 2313; 2333; 2334; 2335; 2336; 2337; 2338; 2339; 2350; 2351; 2352; 2353; 2354; 2355; 2356; 2357; 2358; 2359; 2360; 2370; 2371; 2372; 2394; 2395; 2396; 2397; 2398; 2399; 2400; 2412; 2413; 2414; 2415; 2416; 2417; 2418; 2419; 2420; 2421; 2422; 2423; 2424; 2425; 2481; 2482; 2483; 2528; 2529; 2530; 2531; 2532; 2593; 2594; 2595; 2596; 2597; 2598; 2599; 2600; 2611; 2612; 2613; 2614; 2615; 2705; 2706; 2707; 2708; 2709; 2710; 2711; 3003; 3004; 3005; 3154; 3155; 3156; 3157; 3158; 3159; 3160; 3161; 3162; 3173; 3174; 3175; 3176; 3177; 3304; 3305; 3306; 3307; 3308; 3309; 3310; 3361; 3362; 3363; 3419; 3420; 3421; 3422; 3423; 3424; 3425; 3426; 3427; 3437; 3438; 3439; 3474; 3475; 3476; 3477; 3478; 3479; 3480; 3748; 3749; 3750; 3751; 3752; 3813; 3814; 3815; 3875; 3876; 3877; 3878; 3879; 3880; 3881; 3882; 3883; 3884; 3885; 3886; 3887; 3888; 3889; 3896; 3897; 3898; 3899; 3900; 3901; 3902; 3903; 3904; 3938; 3939; 3940; 3941; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1464046; ANNOT 1464046; ANNOT 1458861; ANNOT 1463445; ANNOT 1463445; ANNOT 1512677; CDNA 3656910S; ANNOT 1459412; ANNOT 1459412; CDNA 3672659; ANNOT 1512677; ANNOT 1455805; ANNOT 1455211; ANNOT 1529744; CDNA 3697835; ANNOT 1455805; ANNOT 1461440; ANNOT 1461440; ANNOT 1461427; ANNOT 1461427; ANNOT 1461430; ANNOT 1461430; ANNOT 1440253; ANNOT 1440253; | 3942; 3951; 3952; 3953; 3954; 3955; 3961; 3962; 3963; 3964; 3965; 3966; 3967; 3968; 3969; 3970; 3971; 3972; 3973; 4008; 4009; 4010; 4011; 4012; 4018; 4019; 4020; 4021; 4022; 4036; 4037; 4038; 4039; 4040; 4041; 4042; 4048; 4049; 4050; 4051; 4052; 4073; 4074; 4075; 4076; 4077; 4078; 4079; 4080; 4081; |
| ROSETTE LEAVES | Appearance | Ovate Shaped | The leaves are wider at base than at apex, otherwise similar to wild-type | Useful for making ornamental plants with altered leaf shape | CLONE 9897; ANNOT 1445849; ANNOT 1500561; ANNOT 1445849; ANNOT 1445849; ANNOT 1500561; ANNOT 1455211; ANNOT 1464458; CLONE 13625; ANNOT 1455211; ANNOT 1455211; ANNOT 18612; ANNOT 1522299; ANNOT 1527718; ANNOT 1527718; CLONE 24885; ANNOT 1485102; CLONE 32361; ANNOT 1471776; ANNOT 1445033; ANNOT 1445033; CLONE 34385; ANNOT 1445331; ANNOT 1498316; ANNOT 1498316; CLONE 42925; ANNOT 1462354; ANNOT 1462354; | 405; 406; 407; 408; 409; 410; 411; 544; 545; 546; 720; 721; 722; 723; 724; 949; 950; 951; 1226; 1227; 1228; 1229; 1230; 1364; 1365; 1366; 1367; 1368; 2045; 2046; 2047; |
| ROSETTE LEAVES | Appearance | Serrate Margins | The leaf margins are serrated. | Useful for making ornamental plants with altered leaf shape | CLONE 907; ANNOT 1502138; ANNOT 1449135; ANNOT 1449135; ANNOT 1502138; ANNOT 1449135; CLONE 1496; ANNOT 1490668; ANNOT 1474027; ANNOT 1474027; ANNOT 1497865; ANNOT 1471512; ANNOT 1471512; ANNOT 1443061; ANNOT 1504203; ANNOT 1505468; ANNOT 1505468; ANNOT 1452369; CLONE 3036; ANNOT 1456840; CLONE 5167; ANNOT 1465422; ANNOT 1465422; ANNOT 1457750; ANNOT 1513544; ANNOT 1513544; CLONE 5198; ANNOT 1472153; CLONE 6220; ANNOT 1488463; ANNOT 1488463; ANNOT 1472153; ANNOT 1541879; ANNOT 1499398; ANNOT 1446419; ANNOT 1438919; ANNOT 1438919; CLONE 8877; ANNOT 1507340; ANNOT 1507340; ANNOT 1446419; CLONE 8265; ANNOT 1529361; ANNOT 1529361; CLONE 9221; ANNOT 1535229; ANNOT 1535229; CLONE 9683; ANNOT 1471514; ANNOT 1471514; CLONE 9897; ANNOT 1445849; ANNOT 1445849; ANNOT 1500561; ANNOT 1464458; ANNOT 1464458; CLONE 10879; ANNOT 1467184; CLONE 12272; ANNOT 1506387; ANNOT 1506387; ANNOT 1474522; ANNOT 1474522; CLONE 13625; ANNOT 1455211; ANNOT 1455211; ANNOT 13757; ANNOT 1471425; ANNOT 1471425; CLONE 17761; ANNOT 1481206; ANNOT 1481206; ANNOT 1534689; ANNOT 1534689; CLONE 19481; ANNOT 1475146; ANNOT 1475146; ANNOT 1454933; ANNOT 1454933; CLONE 19486; ANNOT 1452204; ANNOT 1452204; ANNOT 1443204; ANNOT 1443204; CLONE 23518; ANNOT 1475658; ANNOT 1475658; ANNOT 1449267; ANNOT 1449267; ANNOT 1457346; ANNOT 1457346; ANNOT 1541170; ANNOT 1507191; CLONE 25172; ANNOT 1457346; ANNOT 1450220; ANNOT 1450220; CLONE 25796; ANNOT 1541170; CLONE 25607; ANNOT 1522583; ANNOT 1475323; ANNOT 1475323; CLONE 26542; ANNOT 1475323; ANNOT 1475323; CLONE 26825; ANNOT 1538272; ANNOT 1538272; CLONE 26907; ANNOT 1513438; ANNOT 1460167; ANNOT 1460167; CLONE 26907; ANNOT 1518242; ANNOT 1484074; ANNOT 1484074; ANNOT 1440016; ANNOT 1518242; ANNOT 1484207; ANNOT 1484207; ANNOT 1527449; ANNOT 1527449; ANNOT 1484207; ANNOT 1484207; ANNOT 1488207; CLONE 32348; ANNOT 1470719; ANNOT 1470719; ANNOT 1488207; | 30; 31; 32; 33; 34; 50; 51; 52; 53; 54; 55; 56; 57; 58; 59; 60; 61; 62; 63; 64; 65; 66; 121; 122; 123; 223; 224; 225; 226; 227; 228; 229; 230; 231; 232; 275; 276; 277; 278; 279; 362; 363; 364; 365; 366; 367; 368; 383; 384; 385; 386; 387; 394; 395; 396; 402; 403; 404; 405; 406; 407; 408; 409; 410; 411; 437; 438; 439; 515; 516; 517; 518; 519; 544; 545; 546; 564; 565; 566; 700; 701; 702; 703; 704; 762; 763; 764; 765; 766; 767; 768; 769; 770; 771; 907; 908; 909; 910; 911; 912; 913; 952; 953; 954; 955; 956; 970; 971; 972; 983; 984; 985; 1010; 1011; 1012; 1013; 1014; 1030; 1031; 1032; 1033; 1034; 1043; 1044; 1045; 1046; 1047; 1048; 1049; 1185; 1186; 1187; 1188; 1189; 1219; 1220; 1221; 1222; 1223; 1224; 1225; 1231; 1232; 1233; 1234; |

TABLE 1-continued

| Tissue | Phenotype Category | Phenotype | Phenotype Description | Applications | Ceres ID | SEQ ID NO |
|---|---|---|---|---|---|---|
| | | | | | 1470719; ANNOT 1543728; ANNOT 1482066; ANNOT 1482066; CLONE 32548; ANNOT 1450324; ANNOT 1460836; ANNOT 1460836; CLONE 32737; CLONE 33232; ANNOT 1536373; ANNOT 1482905; ANNOT 1482905; CLONE 33232; CLONE 34385; ANNOT 1504045; ANNOT 1450983; ANNOT 1450983; CLONE 34385; ANNOT 1445331; ANNOT 1445331; ANNOT 1498316; ANNOT 1498316; CLONE 34552; ANNOT 1516449; ANNOT 1516449; ANNOT 1512976; CLONE 34612; ANNOT 1479009; ANNOT 1479009; ANNOT 1469640; CLONE 3478; ANNOT 1466952; ANNOT 1466952; ANNOT 1523551; ANNOT 1523551; ANNOT 1470164; ANNOT 1470164; CLONE 35493; ANNOT 1457751; ANNOT 1457751; ANNOT 1518757; ANNOT 1518757; ANNOT 1465420; ANNOT 1465420; CLONE 36518; ANNOT 1471507; ANNOT 1471507; ANNOT 1444893; ANNOT 1444893; ANNOT 1458642; ANNOT 1458642; ANNOT 1522497; ANNOT 1522497; ANNOT 1469105; ANNOT 1469105; ANNOT 1484993; ANNOT 1484993; CLONE 36904; ANNOT 1526083; ANNOT 1526083; ANNOT 1498856; ANNOT 1498856; ANNOT 1445872; ANNOT 1445872; ANNOT 1479009; ANNOT 1472663; ANNOT 1472663; CLONE 37288; ANNOT 1453650; ANNOT 1453650; CLONE 37493; ANNOT 1494370; ANNOT 1494370; ANNOT 1441478; ANNOT 1441478; CLONE 37543; ANNOT 1539972; ANNOT 1539972; ANNOT 1486562; ANNOT 1486562; ANNOT 1496735; ANNOT 1496735; ANNOT 1443794; ANNOT 1443794; ANNOT 1443794; ANNOT 1440727; ANNOT 1440727; CLONE 38419; ANNOT 1542971; ANNOT 1542971; ANNOT 1521332; ANNOT 1521332; ANNOT 1467961; ANNOT 1467961; CLONE 38690; ANNOT 1525183; ANNOT 1525183; CLONE 38843; ANNOT 1447896; ANNOT 1447896; ANNOT 1438197; ANNOT 1438197; ANNOT 1439286; ANNOT 1447961; ANNOT 1447961; ANNOT 1490936; ANNOT 1490936; CLONE 39740; ANNOT 1483180; ANNOT 1483180; ANNOT 1483180; ANNOT 1480950; ANNOT 1480950; CLONE 40729; ANNOT 1481678; ANNOT 1481678; CLONE 40766; ANNOT 1450499; ANNOT 1450499; CLONE 42925; ANNOT 1462354; ANNOT 1462354; CLONE 42955; ANNOT 1505155; ANNOT 1505155; CLONE 92670; ANNOT 1531919; ANNOT 1531919; CLONE 95677; ANNOT 1459723; ANNOT 1459723; ANNOT 1516455; ANNOT 1516455; CLONE 96020; ANNOT 1450365; ANNOT 1450365; ANNOT 1460794; ANNOT 1460794; CLONE 97434; CLONE 97415; ANNOT 1481701; ANNOT 1481701; CLONE 97434; ANNOT 1488311; ANNOT 1488311; ANNOT 1518776; CLONE 98855; ANNOT 1460836; ANNOT 1460836; ANNOT 1450324; ANNOT 1450324; CLONE 104929; ANNOT 1449020; CLONE 117369; ANNOT 1499284; ANNOT 1499284; ANNOT 1481671; ANNOT 1481671; CLONE 119256; ANNOT 1469636; ANNOT 1469636; ANNOT 1479002; ANNOT 1479002; CLONE 141830; ANNOT 1488335; ANNOT 1488335; CLONE 147358; ANNOT 1493111; ANNOT 1493111; ANNOT 1461452; CLONE 147593; ANNOT 1475653; ANNOT 1475653; ANNOT 1458131; ANNOT 1458131; ANNOT 1461780; CLONE 148943; ANNOT 1472949; ANNOT 1472949; CLONE 151087; ANNOT 1504145; ANNOT 1504145; ANNOT 1451079; ANNOT 1451079; CLONE 157547; ANNOT 1473898; ANNOT 1473898; ANNOT 1466505; ANNOT 1466505; ANNOT 1449026; CLONE 158333; ANNOT 225200; ANNOT 1471976; ANNOT 1471976; ANNOT 1465507; ANNOT 1465507; CLONE 267626; ANNOT 1484074; ANNOT 1484074; ANNOT 1518242; ANNOT 1518242; ANNOT 1464923; ANNOT 1464923; ANNOT 1456223; CLONE 382267; ANNOT 1456223; ANNOT 1453458; ANNOT 1453458; ANNOT 1467304; CLONE 534397; ANNOT 1489056; ANNOT 1489056; ANNOT 1442794; ANNOT 1442794; ANNOT 1442797; ANNOT 1495713; ANNOT 1495713; ANNOT 1442797; ANNOT | 1235; 1242; 1243; 1244; 1245; 1246; 1263; 1264; 1265; 1266; 1267; 1364; 1365; 1366; 1367; 1368; 1406; 1407; 1408; 1409; 1410; 1411; 1412; 1413; 1414; 1415; 1423; 1424; 1425; 1426; 1427; 1428; 1429; 1460; 1461; 1462; 1463; 1464; 1465; 1466; 1505; 1506; 1507; 1508; 1509; 1510; 1511; 1512; 1513; 1514; 1515; 1516; 1517; 1585; 1586; 1587; 1588; 1589; 1590; 1591; 1592; 1593; 1622; 1623; 1624; 1637; 1638; 1639; 1640; 1641; 1642; 1643; 1644; 1645; 1646; 1647; 1648; 1649; 1650; 1651; 1652; 1653; 1747; 1748; 1749; 1750; 1751; 1752; 1753; 1774; 1775; 1776; 1801; 1802; 1803; 1804; 1805; 1838; 1839; 1840; 1841; 1842; 1877; 1878; 1879; 1880; 1881; 1930; 1931; 1932; 1933; 1934; 1935; 2045; 2046; 2047; 2048; 2049; 2050; 2061; 2062; 2063; 2090; 2091; 2092; 2093; 2094; 2095; 2096; 2097; 2098; 2099; 2100; 2101; 2102; 2103; 2104; 2105; 2106; 2107; 2118; 2119; 2120; 2121; 2122; 2237; 2238; 2239; 2407; 2408; 2409; 2410; 2411; 2451; 2452; 2453; 2454; 2455; 2520; 2521; 2522; 2528; 2529; 2530; 2531; 2532; 2533; 2534; 2535; 2536; 2537; 2538; 2539; 2543; 2544; 2545; 2560; 2561; 2562; 2563; 2564; 2593; 2594; 2595; 2611; 2612; 2613; 2614; 2615; 2655; 2656; 2657; 2658; 2659; 2794; 2795; 2796; 2797; 2798; 2799; |

TABLE 1-continued

| Tissue | Phenotype Category | Phenotype | Phenotype Description | Applications | Ceres ID | SEQ ID NO |
|---|---|---|---|---|---|---|
| | | | | | 1442797; ANNOT 1468612; ANNOT 1460503; ANNOT 1460503; ANNOT 1488307; ANNOT 1440343; ANNOT 1493212; ANNOT 1493212; CLONE 536726; ANNOT 1498226; ANNOT 1445243; ANNOT 1445243; ANNOT 1525386; ANNOT 1448522; ANNOT 1448522; ANNOT 1465506; ANNOT 1497017; ANNOT 1497017; ANNOT 1447240; ANNOT 1539566; ANNOT 1539566; ANNOT 1444070; CLONE 536796; ANNOT 1484779; ANNOT 1484779; ANNOT 1538185; ANNOT 1455109; ANNOT 1455109; ANNOT 1477384; CLONE 563522; ANNOT 1460321; ANNOT 1460321; ANNOT 1508144; ANNOT 1541886; ANNOT 1541886; ANNOT 1475178; CLONE 664365; ANNOT 1463333; ANNOT 1463333; ANNOT 1505772; ANNOT 1478872; ANNOT 1478872; ANNOT 1442758; ANNOT 1495675; ANNOT 1469576; ANNOT 1452666; ANNOT 1452668; ANNOT 1442757; CLONE 1002819; ANNOT 1461728; ANNOT 1522314; ANNOT 1474290; ANNOT 1474290; ANNOT 1471045; ANNOT 1497147; ANNOT 1497147; CLONE 1006934; ANNOT 1532963; CLONE 1007549; ANNOT 1458198; ANNOT 1458198; ANNOT 1439989; ANNOT 1464789; ANNOT 1461728; ANNOT 1461728; ANNOT 1479711; ANNOT 1440649; ANNOT 1464547; ANNOT 1454104; ANNOT 1454104; ANNOT 1460973; CDNA 23494371; ANNOT 1485236; ANNOT 1485236; ANNOT 1446740; CDNA 23495481; ANNOT 1485271; ANNOT 1485271; ANNOT 1447245; ANNOT 1447245; CDNA 23498145; ANNOT 1482362; ANNOT 1489077; ANNOT 1489077; CDNA 36534269; ANNOT 1457794; ANNOT 1524172; ANNOT 1524172; ANNOT 1465208; ANNOT 1465208; CDNA 36566404; ANNOT 1465208; ANNOT 1465207; ANNOT 1465207; CDNA 36575796; ANNOT 1486224; ANNOT 1486224; ANNOT 1444021; ANNOT 1444021; | 2800; 2986; 2987; 2988; 2989; 2990; 3109; 3110; 3111; 3112; 3113; 3114; 3115; 3116; 3117; 3118; 3119; 3120; 3121; 3122; 3123; 3124; 3125; 3126; 3127; 3128; 3129; 3135; 3136; 3137; 3138; 3139; 3140; 3141; 3142; 3143; 3144; 3145; 3146; 3147; 3148; 3149; 3150; 3151; 3152; 3153; 3154; 3155; 3156; 3157; 3158; 3159; 3160; 3161; 3162; 3227; 3228; 3229; 3230; 3231; 3232; 3233; 3234; 3235; 3319; 3320; 3321; 3322; 3323; 3324; 3325; 3326; 3327; 3328; 3329; 3330; 3331; 3332; 3333; 3334; 3335; 3336; 3337; 3428; 3429; 3430; 3431; 3432; 3433; 3434; 3435; 3436; 3437; 3438; 3439; 3440; 3441; 3442; 3443; 3444; 3445; 3446; 3447; 3448; 3449; 3450; 3451; 3452; 3453; 3454; 3455; 3456; 3613; 3614; 3615; 3616; 3617; 3618; 3619; 3620; 3622; 3623; 3624; 3625; 3626; 3641; 3642; 3643; 3644; 3645; 3938; 3939; 3940; 3941; 3942; 4013; 4014; 4015; 4016; 4017; 4053; 4054; 4055; 4056; 4057; |
| FLOWER | Appearance | Short Sepals | The sepals are abnormally short. | Useful for making ornamental plants with modified flowers | CLONE 32791; ANNOT 1540248; ANNOT 1540248; | 1255; 1256; 1257; |
| FLOWER | Appearance | Small | The flowers are abnormally small. | Useful for making ornamental plants with modified flowers | CLONE 3000; ANNOT 1518918; ANNOT 1535677; ANNOT 1535677; ANNOT 1482181; ANNOT 1482181; CLONE 13757; ANNOT 1471425; ANNOT 1471425; CLONE 32791; ANNOT 1540248; ANNOT 1540248; | 111; 112; 113; 114; 115; 116; 117; 564; 565; 566; 1255; 1256; 1257; |
| ROSETTE | Appearance | Trident Shaped | The leaves have | Useful for | CLONE 3000; ANNOT 1518918; ANNOT 1535677; ANNOT | 111; 112; 113; 114; 115; |

TABLE 1-continued

| Tissue | Phenotype Category | Phenotype | Phenotype Description | Applications | Ceres ID | SEQ ID NO |
|---|---|---|---|---|---|---|
| LEAVES | | | a sharp point at the apex, and a sharp point on each side. | making ornamental plants with altered leaf shape | 1535677; ANNOT 1482181; ANNOT 1471514; CLONE 9683; ANNOT 1471514; ANNOT 1471514; CLONE 42925; ANNOT 1462354; ANNOT 1462354; CLONE 147358; ANNOT 1493111; ANNOT 1493111; ANNOT 1461452; ANNOT 1461452; CDNA 2349548l; ANNOT 1485271; ANNOT 1485271; ANNOT 1447245; ANNOT 1447245; | 116; 117; 402; 403; 404; 2045; 2046; 2047; 2528; 2529; 2530; 2531; 2532; 3622; 3623; 3624; 3625; 3626; |
| INFLORESCENCE | Appearance | Undulate Appearance | The inflorescence is wavy in appearance compared to control. | Useful for making ornamental plants with modified flowers | CLONE 38690; ANNOT 1525183; ANNOT 1525183; | 1774; 1775; 1776; |
| ROSETTE LEAVES | Appearance | Undulate Shaped | The leaves are wavy in appearance compared to wild-type plants. | Useful for making ornamental plants with altered leaf shape | CLONE 3000; ANNOT 1518918; ANNOT 1535677; ANNOT 1535677; ANNOT 1482181; ANNOT 1518918; ANNOT 1482181; CLONE 36904; ANNOT 1526083; ANNOT 1526083; ANNOT 1498856; ANNOT 1445872; ANNOT 1445872; ANNOT 1472663; ANNOT 1472663; CLONE 38690; ANNOT 1525183; ANNOT 1525183; ANNOT 158333; CLONE 1466505; ANNOT 1449026; ANNOT 1449026; CLONE 541719; ANNOT 1518918; ANNOT 1535677; ANNOT 1535677; CDNA 2349371; ANNOT 1485236; ANNOT 1485236; ANNOT 1446740; ANNOT 1446740; ANNOT 1446740; CDNA 3657011; ANNOT 1442604; ANNOT 1442604; ANNOT 1442604; ANNOT 1442612; ANNOT 1442608; ANNOT 1442608; ANNOT 1452827; ANNOT 1452827; CDNA 3639960; ANNOT 1448952; ANNOT 1448952; CDNA 36566404; ANNOT 1465208; ANNOT 1465208; ANNOT 1465207; ANNOT 1465207; | 111; 112; 113; 114; 115; 116; 117; 1585; 1586; 1587; 1588; 1589; 1590; 1591; 1592; 1593; 1774; 1775; 1776; 2611; 2612; 2613; 2614; 2615; 3173; 3174; 3175; 3176; 3177; 3616; 3617; 3618; 3619; 3620; 3875; 3876; 3877; 3878; 3879; 3880; 3881; 3882; 3883; 3966; 3967; 3968; 4013; 4014; 4015; 4016; 4017; |
| WHOLE PLANT | Biomass | Bushy Rosette Shaped | The petioles have very varied liminal angles, giving the plant a very bushy appearance. The rosette leaves often do not appear in the normal fashion, i.e., their phyllotaxy may be abnormal or too many leaves may be emerging in comparison to the control. | Useful for making plants with increased biomass and foliage | CLONE 13757; ANNOT 1471425; CLONE 13800; ANNOT 1458335; ANNOT 1458335; ANNOT 1464663; CLONE 40766; ANNOT 1450499; ANNOT 1450499; | 564; 565; 566; 572; 573; 574; 575; 576; 1933; 1934; 1935; |
| ROSETTE LEAVES | Biomass | Disorganized Rosette | The rosette leaves do not appear in the normal fashion, i.e., their phyllotaxy may be abnormal or too many leaves | Useful for making plants with increased biomass | CLONE 332; ANNOT 1474923; CLONE 1496; ANNOT 1474923; CLONE 1496; ANNOT 1490668; ANNOT 1490668; ANNOT 1474027; ANNOT 1474027; ANNOT 1497865; ANNOT 1497865; ANNOT 1471512; ANNOT 1443061; ANNOT 1443061; ANNOT 1504203; ANNOT 1504203; ANNOT 1505468; ANNOT 1505468; ANNOT 1452369; CLONE 3000; ANNOT 1518918; ANNOT 1518918; ANNOT 1452369; ANNOT 1535677; ANNOT 1482181; ANNOT 1482181; CLONE 3858; ANNOT 1459068; CLONE 11214; ANNOT 1501485; ANNOT 1501485; ANNOT 1490496; ANNOT 1490496; ANNOT 1448498; ANNOT | 12; 13; 14; 50; 51; 52; 53; 54; 55; 56; 57; 58; 59; 60; 61; 62; 63; 64; 65; 66; 111; 112; 113; 114; 115; 116; 117; 175; 176; 177; 448; 449; 450; 451; 452; 453; 454; 455; 456; 515; 516; 517; 518; |

TABLE 1-continued

| Tissue | Phenotype Category | Phenotype | Phenotype Description | Applications | Ceres ID | SEQ ID NO |
|---|---|---|---|---|---|---|
| | | | may be emerging in comparison to the control. | | 1448498; ANNOT 1474848; ANNOT 1474848; CLONE 12272; ANNOT 1506387; ANNOT 1506387; ANNOT 1474522; ANNOT 1474522; CLONE 13186; ANNOT 1464566; ANNOT 1464566; ANNOT 1458408; CLONE 13757; ANNOT 1471425; ANNOT 1471425; CLONE 13800; ANNOT 1458335; ANNOT 1458335; ANNOT 1464663; ANNOT 1464663; CLONE 14555; ANNOT 1511392; ANNOT 1511392; ANNOT 1469356; ANNOT 1469356; ANNOT 1517500; ANNOT 1517500; ANNOT 1458151; ANNOT 1458151; ANNOT 1522757; ANNOT 1522757; CLONE 20760; ANNOT 1462351; ANNOT 1462351; ANNOT 1488821; ANNOT 1488821; ANNOT 1469462; ANNOT 1469462; CLONE 23771; ANNOT 1444030; ANNOT 1444030; ANNOT 1486813; ANNOT 1486813; ANNOT 1485303; ANNOT 1485303; ANNOT 1446796; ANNOT 1446796; CLONE 25538; ANNOT 1480776; ANNOT 1480776; ANNOT 1471372; ANNOT 1471372; CLONE 34552; ANNOT 1516449; ANNOT 1516449; ANNOT 1512976; ANNOT 1512976; CLONE 37019; ANNOT 1517849; ANNOT 1517849; ANNOT 1511684; ANNOT 1511684; ANNOT 1464532; ANNOT 1464532; ANNOT 1458439; ANNOT 1458439; ANNOT 1540674; ANNOT 1540674; ANNOT 37298; ANNOT 1476538; ANNOT 1476538; ANNOT 1493576; ANNOT 1493576; CLONE 37658; ANNOT 1497485; ANNOT 1497485; CLONE 37663; ANNOT 1447659; ANNOT 1447659; ANNOT 1438478; ANNOT 1438478; CLONE 38101; ANNOT 1454656; ANNOT 1454656; ANNOT 1528263; ANNOT 1528263; ANNOT 1458103; ANNOT 1458103; ANNOT 1464899; ANNOT 1464899; ANNOT 1482966; ANNOT 1482966; ANNOT 1441039; ANNOT 1441039; ANNOT 1520449; ANNOT 1520449; CLONE 38419; ANNOT 1542971; ANNOT 1542971; ANNOT 1521332; ANNOT 1521332; ANNOT 1467961; ANNOT 1467961; ANNOT 1447896; ANNOT 1447896; ANNOT 1438197; ANNOT 1438197; CLONE 39890; ANNOT 1511886; ANNOT 1511886; ANNOT 1517635; ANNOT 1517635; ANNOT 1441645; ANNOT 1441645; CLONE 40436; ANNOT 1441645; CLONE 40508; ANNOT 1453626; ANNOT 1453626; CLONE 40692; ANNOT 1455695; ANNOT 1455695; CLONE 42925; ANNOT 1462354; ANNOT 1462354; CLONE 95135; ANNOT 1527449; ANNOT 1527449; ANNOT 1537653; ANNOT 1537663; ANNOT 1473733; ANNOT 1473733; ANNOT 1468537; ANNOT 1468537; CLONE 115975; ANNOT 1507138; ANNOT 1507138; CLONE 117369; ANNOT 1499284; ANNOT 1499284; ANNOT 1481671; ANNOT 1481671; CLONE 124720; ANNOT 1441430; ANNOT 1441430; CLONE 157058; ANNOT 1528285; ANNOT 1528285; ANNOT 1454671; ANNOT 1454671; CLONE 157547; ANNOT 1473898; ANNOT 1473898; CLONE 158333; ANNOT 1466505; ANNOT 1466505; ANNOT 1449026; ANNOT 1449026; CLONE 227651; ANNOT 1474222; ANNOT 1474222; ANNOT 1468994; ANNOT 1468994; ANNOT 1497043; ANNOT 1497043; CLONE 241379; ANNOT 1526950; ANNOT 1526950; ANNOT 1508362; ANNOT 1508362; ANNOT 1477361; ANNOT 1477361; CLONE 262460; ANNOT 1530053; ANNOT 1530053; ANNOT 1493414; ANNOT 1493414; CLONE 283597; ANNOT 1482074; ANNOT 1482074; ANNOT 1453923; ANNOT 1453923; CLONE 292789; ANNOT 1442040; ANNOT 1442040; ANNOT 1482966; ANNOT 1482966; ANNOT 1464899; ANNOT 1454656; ANNOT 1454656; ANNOT 1458103; ANNOT 1458103; ANNOT 1464899; ANNOT 1520449; ANNOT 1520449; ANNOT 1474837; ANNOT 1474837; ANNOT 1520449; ANNOT 1463335; ANNOT 1538169; ANNOT 1538169; ANNOT 641355; ANNOT 1463335; ANNOT 1463335; ANNOT 1463334; ANNOT 1463334; ANNOT 1452665; ANNOT 1452665; CLONE 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1440649; ANNOT 1440649; ANNOT 1464547; ANNOT 1464547; ANNOT 1454104; CLONE | 519; 531; 532; 533; 534; 535; 564; 565; 566; 572; 573; 574; 575; 576; 608; 609; 610; 611; 612; 613; 614; 615; 616; 617; 618; 808; 809; 810; 811; 812; 813; 814; 928; 929; 930; 931; 932; 933; 934; 935; 936; 967; 968; 969; 1239; 1240; 1241; 1406; 1407; 1408; 1409; 1410; 1599; 1600; 1601; 1602; 1603; 1604; 1605; 1606; 1607; 1608; 1609; 1625; 1626; 1627; 1628; 1629; 1654; 1655; 1656; 1657; 1658; 1659; 1660; 1661; 1682; 1683; 1684; 1685; 1686; 1687; 1688; 1689; 1690; 1691; 1692; 1693; 1694; 1695; 1696; 1747; 1748; 1749; 1750; 1751; 1752; 1753; 1801; 1802; 1803; 1804; 1881; 1882; 1883; 1884; 1885; 1886; 1904; 1905; 1906; 1912; 1913; 1914; 1918; 1919; 1920; 2045; 2046; 2047; 2076; 2077; 2078; 2079; 2080; 2081; 2082; 2083; 2084; 2373; 2374; 2375; 2407; 2408; 2409; 2410; 2411; 2501; 2502; 2503; 2588; 2589; 2590; 2591; 2592; 2593; 2594; 2595; 2611; 2612; 2613; 2614; 2615; 2683; 2684; 2685; 2686; 2687; 2688; 2689; 2718; 2719; 2720; 2721; 2722; 2723; 2724; 2774; 2775; 2776; 2777; 2778; 2833; 2834; 2835; 2836; 2837; 2852; 2853; 2854; 2855; 2856; 2857; 2858; 2859; 2860; 2861; 2862; 2863; 2864; 2865; 2866; 2867; 2868; 3304; 3305; 3306; 3307; 3308; 3309; 3310; 3440; 3441; 3442; 3443; 3444; 3445; 3446; |

TABLE 1-continued

| Tissue | Phenotype Category | Phenotype | Phenotype Description | Applications | Ceres ID | SEQ ID NO |
|---|---|---|---|---|---|---|
| | | | | | 1043081; ANNOT 1478584; ANNOT 1455564; ANNOT 1455564; ANNOT 1508764; ANNOT 1477651; ANNOT 1487130; ANNOT 1487193; CDNA 3657l789; ANNOT 1444156; ANNOT 1497097; ANNOT 1497097; | 3447; 3448; 3449; 3450; 3451; 3452; 3453; 3454; 3455; 3456; 3481; 3482; 3483; 3484; 3485; 3486; 3487; 3488; 3489; 3490; 3491; 4043; 4044; 4045; 4046; 4047; |
| CAULINE LEAVES | Biomass | Lanceolate Shaped | The leaves are narrow and come to a dull point at the apex. | Useful for making plants with increased biomass and foliage | CLONE 5968; ANNOT 1450891; ANNOT 1450891; ANNOT 1456400; ANNOT 1456400; ANNOT 1450889; ANNOT 1456395; ANNOT 1447193; CLONE 13186; ANNOT 1464566; ANNOT 1464566; ANNOT 1458408; CLONE 13757; ANNOT 1471425; ANNOT 1471425; | 250; 251; 252; 253; 254; 255; 256; 257; 258; 259; 260; 531; 532; 533; 534; 535; 564; 565; 566; |
| WHOLE PLANT | Biomass | Large | The plant is abnormally large. | Useful for making bigger plants | CLONE 332; ANNOT 1474923; CLONE 949; ANNOT 1449721; ANNOT 1449721; CLONE 2036; ANNOT 1526068; CLONE 5597; ANNOT 1507708; ANNOT 1507708; ANNOT 1475094; ANNOT 1475094; CLONE 8265; ANNOT 1438919; ANNOT 1438919; ANNOT 1499398; ANNOT 1446419; ANNOT 1446419; CLONE 9683; ANNOT 1471514; ANNOT 1471514; CLONE 12272; ANNOT 1506387; ANNOT 1506387; ANNOT 1474522; ANNOT 1474522; CLONE 16461; ANNOT 1479013; ANNOT 1479013; CLONE 17356; ANNOT 1478584; ANNOT 1478584; ANNOT 1487130; ANNOT 1487130; CLONE 23518; ANNOT 1475658; ANNOT 1475658; ANNOT 1449267; ANNOT 1449267; ANNOT 1507191; CLONE 37288; ANNOT 1453650; ANNOT 1453650; CLONE 98855; ANNOT 1460836; ANNOT 1460836; ANNOT 1450324; CLONE 105554; ANNOT 1451783; ANNOT 1451783; CLONE 118648; ANNOT 1510664; ANNOT 1457458; ANNOT 1457458; ANNOT 1443693; ANNOT 1496628; ANNOT 1496628; ANNOT 1451509; ANNOT 1451509; ANNOT 1540402; ANNOT 1540402; ANNOT 1487005; ANNOT 1487005; CLONE 119925; ANNOT 1473490; ANNOT 1473490; ANNOT 1526901; ANNOT 1526901; CLONE 148680; ANNOT 1487130; ANNOT 1522509; ANNOT 1522509; CLONE 151087; ANNOT 1504145; ANNOT 1504145; ANNOT 1451079; ANNOT 1451079; CLONE 156655; ANNOT 1441740; ANNOT 1441740; CLONE 157730; ANNOT 1532681; ANNOT 1532681; ANNOT 1469739; ANNOT 1469739; CLONE 158333; ANNOT 1466505; ANNOT 1466505; ANNOT 1449026; ANNOT 1449026; CLONE 227651; ANNOT 1474222; ANNOT 1474222; ANNOT 1468994; ANNOT 1468994; ANNOT 1497043; ANNOT 1497043; CLONE 536457; ANNOT 1490030; ANNOT 1490030; ANNOT 1493787; ANNOT 1493787; ANNOT 1508184; ANNOT 1508184; ANNOT 1528645; CDNA 23507479; ANNOT 1510416; ANNOT 1510416; ANNOT 1541253; ANNOT 1541253; CDNA 3657002; ANNOT 1483397; ANNOT 1483397; CDNA 36529808; ANNOT 1440346; ANNOT 1440346; ANNOT 1463445; ANNOT 1463445; ANNOT 1512677; ANNOT 1512677; ANNOT 1459412; ANNOT 1459412; | 12; 13; 14; 35; 36; 37; 84; 85; 86; 233; 234; 235; 236; 237; 362; 363; 364; 365; 366; 367; 368; 402; 403; 404; 515; 516; 517; 518; 519; 647; 648; 649; 673; 674; 675; 676; 677; 907; 908; 909; 910; 911; 912; 913; 1622; 1623; 1624; 2118; 2119; 2120; 2121; 2122; 2247; 2248; 2249; 2429; 2430; 2431; 2432; 2433; 2434; 2435; 2436; 2437; 2438; 2439; 2440; 2441; 2442; 2443; 2461; 2462; 2463; 2464; 2465; 2540; 2541; 2542; 2560; 2561; 2562; 2563; 2564; 2580; 2581; 2582; 2601; 2602; 2603; 2604; 2605; 2611; 2612; 2613; 2614; 2615; 2683; 2684; 2685; 2686; 2687; 2688; 2689; 3130; 3131; 3132; 3133; 3134; 3314; 3315; 3316; 3317; 3318; 3704; 3705; 3706; 3707; 3708; 3916; 3917; 3918; 3920; 3921; 3922; 4036; 4037; 4038; 4039; 4040; 4041; 4042; |
| CAULINE LEAVES | Biomass | Large | The cauline leaves are abnormally large. | Useful for making plants with increased biomass and foliage | CLONE 1496; ANNOT 1490668; ANNOT 1490668; ANNOT 1474027; ANNOT 1474027; ANNOT 1497865; ANNOT 1471512; ANNOT 1471512; ANNOT 1443061; ANNOT 1443061; ANNOT 1504203; ANNOT 1504203; ANNOT 1505468; ANNOT 1505468; ANNOT 1452369; CLONE 21563; CLONE 32361; ANNOT 1438905; ANNOT 1438905; ANNOT 1483143; ANNOT 1483143; CLONE 32361; ANNOT 1471776; ANNOT 1471776; ANNOT 1445033; ANNOT 1445033; ANNOT CLONE 105554; ANNOT 1451783; ANNOT 1451783; CLONE 1007549; ANNOT | 50; 51; 52; 53; 54; 55; 56; 57; 58; 59; 60; 61; 62; 63; 64; 65; 66; 842; 843; 844; 845; 846; 1226; 1227; 1228; 1229; 1230; 2247; 2248; 2249; 3440; 3441; 3442; 3443; |

TABLE 1-continued

| Tissue | Phenotype Category | Phenotype | Phenotype Description | Applications | Ceres ID | SEQ ID NO |
|---|---|---|---|---|---|---|
| | | | | | 1458198; ANNOT 1458198; ANNOT 1439989; ANNOT 1464789; ANNOT 1464789; ANNOT 1461728; ANNOT 1461728; ANNOT 1479711; ANNOT 1479711; ANNOT 1440649; ANNOT 1464547; ANNOT 1464547; ANNOT 1454104; ANNOT 1454104; | 3444; 3445; 3446; 3447; 3448; 3449; 3450; 3451; 3452; 3453; 3454; 3455; 3456; |
| HYPOCOTYL | Biomass | Long | The hypocotyl is longer than in wild-type. | Useful for making taller plants | CLONE 24644; ANNOT 1463301; ANNOT 1459811; CLONE 28602; ANNOT 1488330; ANNOT 1488330; ANNOT 1461728; ANNOT 1460480; ANNOT 1460480; ANNOT 1461614; ANNOT 1461614; ANNOT 1479711; ANNOT 1479711; ANNOT 1479712; ANNOT 1488329; ANNOT 1488329; ANNOT 1460481; ANNOT 1460481; ANNOT 1461613; ANNOT 1461613; ANNOT 1458198; ANNOT 1488327; ANNOT 1488327; | 944; 945; 946; 947; 948; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; |
| INFLORESCENCE | Biomass | Long Internode | The internode is abnormally long. | Useful for making taller plants and plants with longer flowers | CDNA 2350103; ANNOT 1447690; ANNOT 1447690; ANNOT 1491278; ANNOT 1491278; ANNOT 1500987; ANNOT 1490915; ANNOT 1490915; | 3687; 3688; 3689; 3690; 3691; 3692; 3693; 3694; 3695; |
| WHOLE PLANT | Biomass | Misc. Dwarf | The plants are small. | Useful for modulating plant size | CLONE 463; ANNOT 1542632; CLONE 3000; ANNOT 1518918; ANNOT 1518918; ANNOT 1535677; ANNOT 1482181; ANNOT 1482181; CLONE 6082; ANNOT 1443416; ANNOT 1505047; ANNOT 1505047; ANNOT 1496339; CLONE 8916; ANNOT 1462804; ANNOT 1462804; CLONE 9683; ANNOT 1471514; ANNOT 1471514; ANNOT 1451126; CLONE 19586; ANNOT 1476446; ANNOT 1451126; ANNOT 23771; ANNOT 1444030; ANNOT 1444030; ANNOT 1486813; ANNOT 1486813; ANNOT 1485303; ANNOT 1446796; ANNOT 1481806; ANNOT 1446796; CLONE 27477; ANNOT 1535293; ANNOT 1481806; CLONE 28003; ANNOT 1527756; ANNOT 1481806; ANNOT 1468882; CLONE 32753; ANNOT 1480607; ANNOT 1480607; ANNOT 1472242; ANNOT 37663; ANNOT 1437663; ANNOT 1447659; ANNOT 1438478; CLONE 38101; ANNOT 1454656; ANNOT 1454656; ANNOT 1528263; ANNOT 1458103; ANNOT 1458103; ANNOT 1464899; ANNOT 1482966; ANNOT 1482966; ANNOT 1441039; ANNOT 1490459; ANNOT 1520449; CLONE 39678; ANNOT 1490459; ANNOT 1437663; ANNOT 1437663; ANNOT 1437666; ANNOT 1437689; ANNOT 1437689; CLONE 40153; ANNOT 1453549; ANNOT 1453549; ANNOT 1528184; ANNOT 1528184; ANNOT 1474758; CLONE 40729; ANNOT 1481678; ANNOT 1474758; ANNOT 1481678; ANNOT 1476817; ANNOT 1503063; ANNOT 1503063; ANNOT 1450022; ANNOT 1450022; ANNOT 1447022; CLONE 206224; ANNOT 1485509; ANNOT 1485509; ANNOT 1447022; ANNOT 1443744; CDNA 3655053; ANNOT 1496682; ANNOT 1496682; ANNOT 1464088; ANNOT 1458774; ANNOT 1458774; CDNA 36360856; ANNOT 1517998; ANNOT 1458313; ANNOT 1458313; | 15; 16; 17; 111; 112; 113; 114; 115; 116; 117; 268; 269; 270; 271; 272; 273; 274; 388; 389; 390; 402; 403; 404; 784; 785; 786; 787; 788; 928; 929; 930; 931; 932; 933; 934; 935; 936; 1065; 1066; 1067; 1068; 1069; 1080; 1081; 1082; 1083; 1084; 1250; 1251; 1252; 1253; 1254; 1657; 1658; 1659; 1660; 1661; 1682; 1683; 1684; 1685; 1686; 1687; 1688; 1689; 1690; 1691; 1692; 1693; 1694; 1695; 1696; 1868; 1869; 1870; 1871; 1872; 1873; 1874; 1875; 1876; 1897; 1898; 1899; 1900; 1901; 1902; 1903; 1931; 1932; 2240; 2241; 2242; 2243; 2244; 2245; 2246; 2630; 2631; 2632; 2633; 2634; 2806; 2807; 2808; 2809; 2810; 3990; 3991; 3992; 3993; 3994; 4008; 4009; 4010; 4011; 4012; |
| CAULINE LEAVES | Biomass | Oval Shaped | The leaves are much rounder than wild-type. | Useful for making plants with increased biomass and foliage | CLONE 32361; ANNOT 1471776; ANNOT 1445033; ANNOT 1445033; CLONE 102248; ANNOT 1456981; CLONE 157709; ANNOT 1515067; ANNOT 1515067; ANNOT 1492780; ANNOT 1492780; CDNA 36359960; ANNOT 1448952; ANNOT 1448952; | 1226; 1227; 1228; 1229; 1230; 2229; 2230; 2231; 2596; 2597; 2598; 2599; 2600; 3966; 3967; 3968; |
| CAULINE | Biomass | Ovate Shaped | The leaves are | Useful for | CLONE 304574; ANNOT 1481465; ANNOT 1481465; ANNOT 1482095; ANNOT | 2884; 2885; 2886; 2887; |

TABLE 1-continued

| Tissue | Phenotype Category | Phenotype | Phenotype Description | Applications | Ceres ID | SEQ ID NO |
|---|---|---|---|---|---|---|
| LEAVES | | | wider at base than at the apex, otherwise similar to wild-type | making plants with increased biomass and foliage | 1482095; ANNOT 1482093; ANNOT 1440823; ANNOT 1440823; | 2888; 2889; 2890; 2891; 2892; |
| WHOLE PLANT | Biomass | Plant Size | The plants have increased size compared to wild type. | Useful for making plants with increased size and biomass | CLONE 37288; ANNOT 1453650; ANNOT 1453650; | 1622; 1623; 1624; |
| INFLORESCENCE | Biomass | Reduced Apical Dominance | The dominance of the primary inflorescence is diminished. The secondary inflorescences are as dominant or nearly as dominant as the primary inflorescence. | Useful for modifying plant structure, i.e. increased branching | CLONE 463; ANNOT 1542632; CLONE 3036; ANNOT 1456840; ANNOT 1456840; CLONE 9132; ANNOT 1458620; CLONE 13757; ANNOT 1471425; ANNOT 1471425; CLONE 19586; ANNOT 1476446; ANNOT 1476446; ANNOT 1451126; CLONE 31507; ANNOT 1447204; ANNOT 1447204; CLONE 37298; ANNOT 1476538; ANNOT 1476538; ANNOT 1493576; ANNOT 1493576; CLONE 39890; ANNOT 1511886; ANNOT 1511886; ANNOT 1517635; ANNOT 1517635; CLONE 40708; ANNOT 1457313; ANNOT 1457313; ANNOT 1487784; ANNOT 1505885; ANNOT 1505885; ANNOT 1495571; CLONE 40729; ANNOT 1481678; ANNOT 1481678; ANNOT 1495571; ANNOT 1462354; ANNOT 1462354; CLONE 96020; ANNOT 1450365; ANNOT 1450365; ANNOT 1460794; ANNOT 1460794; CLONE 101686; ANNOT 1479756; ANNOT 1540137; ANNOT 1540137; ANNOT 1486722; ANNOT 1486722; CLONE 115946; ANNOT 1458342; ANNOT 1458342; ANNOT 480332; ANNOT 1511016; ANNOT 1511016; ANNOT 1518556; ANNOT 1518556; ANNOT 1457793; ANNOT 1457793; ANNOT 1465233; ANNOT 1465233; CLONE 536726; ANNOT 1498226; ANNOT 1498226; ANNOT 1445243; ANNOT 1445243; ANNOT 1525386; ANNOT 1448522; ANNOT 1448522; ANNOT 1447017; ANNOT 1465506; ANNOT 1465506; ANNOT 1497017; ANNOT 1447240; ANNOT 1447240; ANNOT 1539566; ANNOT 1539566; ANNOT 1444070; ANNOT 1444070; CLONE 572121; ANNOT 1477450; ANNOT 1477450; CDNA 3652976; ANNOT 1445379; ANNOT 1449468; ANNOT 1449468; | 15; 16; 17; 121; 122; 123; 391; 392; 393; 564; 565; 566; 784; 785; 786; 787; 788; 1195; 1196; 1197; 1625; 1626; 1627; 1628; 1629; 1882; 1883; 1884; 1885; 1886; 1921; 1922; 1923; 1924; 1925; 1926; 1927; 1928; 1929; 1930; 1931; 1932; 2045; 2046; 2047; 2095; 2096; 2097; 2098; 2099; 2212; 2213; 2214; 2215; 2216; 2217; 2218; 2370; 2371; 2372; 3034; 3035; 3036; 3037; 3038; 3039; 3040; 3041; 3042; 3135; 3136; 3137; 3138; 3139; 3140; 3141; 3142; 3143; 3144; 3145; 3146; 3147; 3148; 3149; 3150; 3151; 3152; 3153; 3252; 3253; 3254; 3928; 3929; 3930; 3931; 3932; |
| CAULINE LEAVES | Biomass | Serrate Margins | The leaf margins are serrated. | Useful for making plants with increased biomass and foliage | CLONE 1496; ANNOT 1474027; ANNOT 1490668; ANNOT 1490668; ANNOT 1497865; ANNOT 1471512; ANNOT 1471512; ANNOT 1443061; ANNOT 1443061; ANNOT 1504203; ANNOT 1505468; ANNOT 1505468; ANNOT 1452369; ANNOT 1452369; CLONE 25172; ANNOT 1457346; ANNOT 1457346; ANNOT 1504045; ANNOT 1541170; CLONE 33232; ANNOT 1504045; ANNOT 1450045; ANNOT 1450983; ANNOT 1450983; CLONE 34552; ANNOT 1516449; ANNOT 1516449; ANNOT 1512976; CLONE 304574; ANNOT 1481465; ANNOT 1482095; ANNOT 1482095; ANNOT 1482093; ANNOT 1440823; ANNOT 1440823; ANNOT 1475043; ANNOT 1475043; ANNOT 1454586; ANNOT 1454586; ANNOT 1507756; ANNOT 1507756; ANNOT 1469708; ANNOT 1469708; | 50; 51; 52; 53; 54; 55; 56; 57; 58; 59; 60; 61; 62; 63; 64; 65; 66; 952; 953; 954; 955; 956; 1263; 1264; 1265; 1266; 1267; 1406; 1407; 1408; 1409; 1410; 2884; 2885; 2886; 2887; 2888; 2889; 2890; 2891; 2892; 3419; 3420; 3421; 3422; 3423; 3424; 3425; 3426; 3427; |
| INFLORESCENCE | Biomass | Short | The inflorescences of the plants are abnormally | Useful for modulating plant height | CLONE 332; ANNOT 1474923; CLONE 1496; ANNOT 1490668; ANNOT 1490668; ANNOT 1474027; ANNOT 1474027; ANNOT 1497865; ANNOT 1497865; ANNOT 1471512; ANNOT 1471512; ANNOT 1443061; ANNOT 1443061; ANNOT 1504203; ANNOT 1504203; ANNOT 1505468; ANNOT 1505468; | 12; 13; 14; 50; 51; 52; 53; 54; 55; 56; 57; 58; 59; 60; 61; 62; 63; 64; 65; 66; 67; 68; 69; 70; |

TABLE 1-continued

| Tissue | Phenotype Category | Phenotype | Phenotype Description | Ceres ID | SEQ ID NO |
|---|---|---|---|---|---|
| | | | short. | 1452369; ANNOT 1452369; CLONE 1610; ANNOT 1454586; ANNOT 1454586; ANNOT 1475043; ANNOT 1475043; ANNOT 1507756; ANNOT 1507756; ANNOT 1469708; ANNOT 1469708; CLONE 2561; ANNOT 1450958; ANNOT 1450958; ANNOT 1456475; ANNOT 1456475; ANNOT 1446945; ANNOT 1446945; CLONE 3062; ANNOT 1504677; ANNOT 1504677; ANNOT 1451593; ANNOT 1451593; CLONE 3997; ANNOT 1455209; ANNOT 1455209; ANNOT 1446198; ANNOT 1446198; ANNOT 1490273; ANNOT 1490273; ANNOT 1530603; ANNOT 1530603; CLONE 5198; ANNOT 1472153; ANNOT 1472153; CLONE 6387; ANNOT 1509111; ANNOT 1509111; ANNOT 1541620; ANNOT 1541620; CLONE 8254; ANNOT 1543042; ANNOT 1543042; ANNOT 1489655; ANNOT 1489655; CLONE 8265; ANNOT 1438919; ANNOT 1438919; ANNOT 1499398; ANNOT 1499398; ANNOT 1446419; ANNOT 1446419; CLONE 8633; ANNOT 1500561; ANNOT 1500561; ANNOT 1527560; ANNOT 1527560; ANNOT 1522449; ANNOT 1522449; CLONE 8877; ANNOT 1507340; ANNOT 1507340; ANNOT 1529361; ANNOT 1529361; CLONE 9132; ANNOT 1458620; ANNOT 1458620; CLONE 9221; ANNOT 1535229; ANNOT 1535229; CLONE 9897; ANNOT 1445849; ANNOT 1445849; ANNOT 1150561; ANNOT 1150561; ANNOT 1464446; ANNOT 1464446; ANNOT 1464458; ANNOT 1464458; CLONE 10857; ANNOT 1464446; ANNOT 1464446; CLONE 10879; ANNOT 1467184; ANNOT 1467184; CLONE 11214; ANNOT 1501485; ANNOT 1501485; ANNOT 1490496; ANNOT 1490496; ANNOT 1448498; ANNOT 1448498; ANNOT 1474848; ANNOT 1474848; CLONE 11854; ANNOT 1506763; ANNOT 1506763; ANNOT 1453614; ANNOT 1453614; CLONE 12071; ANNOT 1466704; ANNOT 1466704; CLONE 12272; ANNOT 1506387; ANNOT 1506387; ANNOT 1474522; ANNOT 1474522; CLONE 12993; ANNOT 1479464; ANNOT 1479464; ANNOT 1464566; ANNOT 1464566; ANNOT 1458408; ANNOT 1458408; CLONE 13186; ANNOT 1470919; ANNOT 1470919; CLONE 13625; ANNOT 1455211; ANNOT 1455211; CLONE 13757; ANNOT 1471425; ANNOT 1471425; CLONE 13767; ANNOT 1542158; ANNOT 1542158; ANNOT 1488730; ANNOT 1488730; CLONE 14583; ANNOT 1530256; ANNOT 1530256; ANNOT 1476783; ANNOT 1476783; ANNOT 1503166; ANNOT 1503166; CLONE 14909; ANNOT 1497838; ANNOT 1497838; ANNOT 1522523; ANNOT 1522523; ANNOT 1471525; ANNOT 1471525; ANNOT 1511908; ANNOT 1511908; ANNOT 1464305; ANNOT 1464305; ANNOT 1451416; ANNOT 1451416; ANNOT 1461050; ANNOT 1461050; CLONE 17434; ANNOT 1455741; ANNOT 1455741; ANNOT 1477832; ANNOT 1477832; CLONE 17761; ANNOT 1481206; ANNOT 1481206; ANNOT 1534689; ANNOT 1534689; CLONE 18612; ANNOT 1522299; ANNOT 1522299; ANNOT 1527718; ANNOT 1527718; CLONE 19116; ANNOT 1467522; ANNOT 1467522; ANNOT 1526421; ANNOT 1526421; CLONE 19586; ANNOT 1476446; ANNOT 1476446; ANNOT 1451126; ANNOT 1451126; CLONE 22007; ANNOT 1464350; ANNOT 1464350; ANNOT 1458591; ANNOT 1458591; ANNOT 1517094; ANNOT 1517094; ANNOT 1512337; ANNOT 1512337; CLONE 23771; CLONE 23322; ANNOT 1444030; ANNOT 1444030; ANNOT 1486813; ANNOT 1486813; CLONE 25172; ANNOT 1485303; ANNOT 1485303; ANNOT 1457346; ANNOT 1457346; ANNOT 1446796; ANNOT 1446796; ANNOT 1541170; CLONE 25538; ANNOT 1480776; ANNOT 1480776; CLONE 25758; ANNOT 1473748; ANNOT 1473748; CLONE 26907; ANNOT 1484074; ANNOT 1484074; ANNOT 1440016; ANNOT 1440016; ANNOT 1518242; ANNOT 1518242; CLONE 27810; ANNOT 1503622; ANNOT 1503622; ANNOT 1450565; ANNOT 1450565; CLONE 28326; ANNOT 1468461; ANNOT 1468461; CLONE 29363; ANNOT 1471301; ANNOT 1471301; ANNOT 1494753; ANNOT 1494753; ANNOT 1441875; ANNOT 1441875; CLONE 30759; ANNOT 1520359; ANNOT 1520359; ANNOT | 71; 72; 73; 74; 75; 104; 105; 106; 107; 108; 109; 110; 124; 125; 126; 127; 128; 178; 179; 180; 181; 182; 183; 184; 185; 186; 230; 231; 232; 285; 286; 287; 288; 289; 357; 358; 359; 360; 361; 362; 363; 364; 365; 366; 367; 368; 375; 376; 377; 378; 379; 383; 384; 385; 386; 387; 391; 392; 393; 394; 395; 396; 405; 406; 407; 408; 409; 410; 411; 434; 435; 436; 437; 438; 439; 448; 449; 450; 451; 452; 453; 454; 455; 456; 475; 476; 477; 478; 479; 507; 508; 509; 515; 516; 517; 518; 519; 520; 521; 522; 531; 532; 533; 534; 535; 536; 537; 538; 544; 545; 546; 564; 565; 566; 567; 568; 569; 570; 571; 619; 620; 621; 622; 623; 624; 625; 626; 627; 628; 629; 630; 631; 632; 633; 634; 635; 636; 637; 638; 639; 640; 687; 688; 689; 690; 691; 700; 701; 702; 703; 704; 720; 721; 722; 723; 724; 735; 736; 737; 738; 739; 784; 785; 786; 787; 788; 876; 877; 878; 879; 880; 897; 898; 899; 900; 901; 928; 929; 930; 931; 932; 933; 934; 935; 936; 952; 953; 954; 955; 956; 967; 968; 969; 973; 974; 975; 1043; 1044; 1045; 1046; 1047; 1048; 1049; 1075; 1076; 1077; 1078; 1079; 1088; 1089; 1090; 1143; 1144; 1145; 1164; 1165; 1166; 1167; 1168; 1169; 1170; 1171; 1172; 1173; 1174; 1175; 1176; 1177; 1178; 1179; 1180; 1181; 1182; 1183; 1184; 1195; 1196; 1197; 1219; 1220; |

TABLE 1-continued

| Tissue | Phenotype Category | Phenotype | Phenotype Description | Applications | Ceres ID | SEQ ID NO |
|---|---|---|---|---|---|---|
| | | | | | 1441875; ANNOT 1467006; ANNOT 1441867; ANNOT 1441871; ANNOT 1441864; ANNOT 1441868; ANNOT 1441859; ANNOT 1467009; ANNOT 1467009; CLONE 31507; ANNOT 1447204; ANNOT 32248; ANNOT 1470719; ANNOT 1543728; CLONE 1471776; ANNOT 1482066; CLONE 32361; ANNOT 1450324; ANNOT 1450324; ANNOT 1445033; CLONE 32548; ANNOT 1460836; ANNOT 1471372; CLONE 32791; ANNOT 1540248; ANNOT 1498316; CLONE 34385; ANNOT 1445531; ANNOT 1498316; ANNOT 1449358; CLONE 34480; ANNOT 1502362; ANNOT 1449358; ANNOT 1452408; CLONE 35051; ANNOT 1443033; ANNOT 1457751; ANNOT 1452408; ANNOT 1505508; CLONE 35493; ANNOT 1465420; CLONE 35733; ANNOT 1518757; ANNOT 1453650; ANNOT 1443988; CLONE 37288; ANNOT 1486258; ANNOT 1493576; CLONE 37298; ANNOT 1476538; ANNOT 1465769; ANNOT 1465769; CLONE 38214; ANNOT 1466779; ANNOT 1467961; ANNOT 1542971; ANNOT 1521332; CLONE 38318; ANNOT 1514466; CLONE 38785; ANNOT 1461193; ANNOT 1448369; ANNOT 1480950; CLONE 39740; ANNOT 1483180; ANNOT 1514466; ANNOT 1528184; ANNOT 1495571; ANNOT 1474758; ANNOT 1453549; ANNOT 1457313; ANNOT 1453626; CLONE 40708; ANNOT 1457313; ANNOT 1481678; ANNOT 1487784; ANNOT 1505885; ANNOT 1455815; ANNOT 1495571; ANNOT 1482477; ANNOT 1481678; ANNOT 1535964; CLONE 40824; ANNOT 1509015; ANNOT 1535964; ANNOT 1535815; ANNOT 1455817; ANNOT 1482502; ANNOT 1509035; ANNOT 1509035; ANNOT 1482477; ANNOT 1482502; ANNOT 1509013; ANNOT 1535990; ANNOT 1455837; ANNOT 1455837; CLONE 41337; ANNOT 1516613; ANNOT 1513097; ANNOT 1513097; ANNOT 1463324; CLONE 92670; ANNOT 1531919; ANNOT 1531919; CLONE 95677; ANNOT 1459723; ANNOT 1459723; ANNOT 1516455; CLONE 96020; ANNOT 1450365; ANNOT 1450365; ANNOT 1460794; CLONE 97434; ANNOT 1488311; ANNOT 1488311; ANNOT 1518776; CLONE 100047; ANNOT 1532164; ANNOT 1532164; ANNOT 1479341; ANNOT 1479350; ANNOT 1442450; CLONE 100245; ANNOT 1535451; ANNOT 1535451; ANNOT 1532285; ANNOT 1480241; ANNOT 1480241; ANNOT 1446025; CLONE 100319; ANNOT 1503141; ANNOT 1503141; ANNOT 1521524; ANNOT 1453127; 102248; ANNOT 1456981; CLONE 115924; ANNOT 1453127; ANNOT 1453127; ANNOT 1506261; ANNOT 1480332; ANNOT 1480332; ANNOT 1454197; CLONE 116117; ANNOT 1456955; ANNOT 1456955; ANNOT 1451365; ANNOT 1451365; ANNOT 1504433; ANNOT 1504433; CLONE 116237; ANNOT 1455816; ANNOT 1482502; ANNOT 1482502; ANNOT 1482508; ANNOT 1535990; ANNOT | 1221; 1222; 1223; 1224; 1225; 1226; 1227; 1228; 1229; 1230; 1231; 1232; 1233; 1234; 1235; 1239; 1240; 1241; 1255; 1256; 1257; 1364; 1365; 1366; 1367; 1368; 1398; 1399; 1400; 1401; 1402; 1441; 1442; 1443; 1444; 1445; 1446; 1447; 1460; 1461; 1462; 1463; 1464; 1465; 1466; 1476; 1477; 1478; 1479; 1480; 1622; 1623; 1624; 1625; 1626; 1627; 1628; 1629; 1707; 1708; 1709; 1710; 1711; 1712; 1713; 1747; 1748; 1749; 1750; 1751; 1752; 1753; 1788; 1789; 1790; 1796; 1797; 1798; 1799; 1800; 1877; 1878; 1879; 1880; 1881; 1897; 1898; 1899; 1900; 1901; 1902; 1903; 1912; 1913; 1914; 1921; 1922; 1923; 1924; 1925; 1926; 1927; 1928; 1929; 1930; 1931; 1932; 1939; 1940; 1941; 1946; 1947; 1944; 1945; 1946; 1947; 1948; 1949; 1950; 1951; 1952; 1953; 1954; 1955; 1956; 1957; 1958; 1959; 1960; 1961; 1988; 1989; 1990; 1991; 1992; 1993; 1994; 2061; 2062; 2063; 2090; 2091; 2092; 2093; 2094; 2095; 2096; 2097; 2098; 2099; 2103; 2104; 2105; 2106; 2107; 2173; 2174; 2175; 2176; 2177; 2178; 2179; 2180; 2181; 2182; 2183; 2184; 2185; 2186; 2187; 2188; 2189; 2190; 2191; 2192; 2193; 2194; 2195; 2229; 2230; 2231; 2361; 2362; 2363; 2364; 2365; 2366; 2367; 2368; 2369; 2376; 2377; 2378; 2379; 2380; 2381; 2382; 2383; 2384; 2385; |

TABLE 1-continued

| Tissue | Phenotype Category | Phenotype | Phenotype Description | Applications | Ceres ID | SEQ ID NO |
|---|---|---|---|---|---|---|
| | | | | | 1535990; ANNOT 1509013; CLONE 118337; ANNOT 1454773; | 2386; 2387; 2388; 2389; |
| | | | | | ANNOT 1454773; ANNOT 1511811; ANNOT 1478364; ANNOT | 2390; 2391; 2392; 2393; |
| | | | | | 1478364; ANNOT 1464394; CLONE 123279; ANNOT 1508945; | 2417; 2418; 2419; 2420; |
| | | | | | ANNOT 1508945; ANNOT 1531332; ANNOT 1482544; ANNOT | 2421; 2422; 2423; 2424; |
| | | | | | 1482544; ANNOT 1478226; ANNOT 1478226; CLONE 141830; ANNOT 1488335; | 2425; 2492; 2493; 2494; |
| | | | | | ANNOT 1488335; CLONE 147358; ANNOT 1493111; ANNOT | 2495; 2496; 2497; 2498; |
| | | | | | 1461452; ANNOT 1461452; CLONE 147593; ANNOT 1475653; | 2499; 2500; 2520; 2521; |
| | | | | | ANNOT 1458131; ANNOT 1458131; ANNOT 1461780; ANNOT 1461780; CLONE | 2522; 2528; 2529; 2530; |
| | | | | | 148680; ANNOT 1522509; CLONE 149380; ANNOT 1461440; | 2531; 2532; 2533; 2534; |
| | | | | | ANNOT 1461440; ANNOT 1461430; ANNOT 1461427; ANNOT | 2535; 2536; 2537; 2538; |
| | | | | | 1461427; ANNOT 1440253; CLONE 150912; ANNOT 1533910; | 2539; 2540; 2541; 2542; |
| | | | | | ANNOT 1533910; ANNOT 1480439; ANNOT 1480439; CLONE 157547; ANNOT | 2546; 2547; 2548; 2549; |
| | | | | | 1473898; ANNOT 1473898; CLONE 206224; ANNOT 1485509; ANNOT 1485509; | 2550; 2551; 2552; 2553; |
| | | | | | ANNOT 1447022; ANNOT 1447022; CLONE 226818; ANNOT 1503617; ANNOT | 2554; 2555; 2556; 2557; |
| | | | | | 1503617; ANNOT 1450560; ANNOT 1450560; ANNOT 1460622; ANNOT 1460622; ANNOT | 2558; 2559; 2593; 2594; |
| | | | | | CLONE 241379; ANNOT 1526950; ANNOT 1526950; ANNOT 1508362; ANNOT | 2595; 2630; 2631; 2632; |
| | | | | | 1508362; ANNOT 1477361; ANNOT 1477361; CLONE 254065; ANNOT 1485544; | 2633; 2634; 2676; 2677; |
| | | | | | ANNOT 1485544; ANNOT 1447051; ANNOT 1517016; ANNOT | 2678; 2679; 2680; 2681; |
| | | | | | 1517016; CLONE 262460; ANNOT 1530053; ANNOT 1493414; | 2682; 2718; 2719; 2720; |
| | | | | | ANNOT 1493414; CLONE 267657; ANNOT 1471473; ANNOT | 2721; 2722; 2723; 2724; |
| | | | | | 1471473; ANNOT 1444931; CLONE 304574; ANNOT 1481465; | 2731; 2732; 2733; 2734; |
| | | | | | ANNOT 1481465; ANNOT 1482095; ANNOT 1482093; ANNOT | 2735; 2736; 2737; 2774; |
| | | | | | 1482093; ANNOT 1440823; CLONE 480332; ANNOT 1511016; | 2775; 2776; 2777; 2778; |
| | | | | | ANNOT 1511016; ANNOT 1518556; ANNOT 1457793; ANNOT 1457793; ANNOT | 2801; 2802; 2803; 2804; |
| | | | | | 1465233; ANNOT 1465233; CLONE 536726; ANNOT 1498226; ANNOT 1498226; | 2805; 2884; 2885; 2886; |
| | | | | | ANNOT 1445243; ANNOT 1445243; ANNOT 1525386; ANNOT 1525386; ANNOT | 2887; 2888; 2889; 2890; |
| | | | | | 1448522; ANNOT 1448522; ANNOT 1465506; ANNOT 1497017; | 2891; 2892; 3034; 3035; |
| | | | | | ANNOT 1497017; ANNOT 1447240; ANNOT 1447240; ANNOT 1539566; ANNOT | 3036; 3037; 3038; 3039; |
| | | | | | 1539566; ANNOT 1444070; ANNOT 1444070; ANNOT 1466193; ANNOT | 3040; 3041; 3042; 3135; |
| | | | | | ANNOT 1466193; ANNOT 1494416; ANNOT 1494416; CLONE 566317; ANNOT | 3136; 3137; 3138; 3139; |
| | | | | | 1489585; ANNOT 1489585; ANNOT 1467905; ANNOT 1517371; | 3140; 3141; 3142; 3143; |
| | | | | | ANNOT 1517371; ANNOT 1512104; ANNOT 1512104; ANNOT 1458837; | 3144; 3145; 3146; 3147; |
| | | | | | 1458837; CLONE 1001432; ANNOT 1475043; ANNOT 1454586; | 3148; 3149; 3150; 3151; |
| | | | | | ANNOT 1454586; ANNOT 1507756; ANNOT 1507756; ANNOT 1469708; ANNOT | 3152; 3153; 3168; 3169; |
| | | | | | 1469708; CLONE 1002819; ANNOT 1474290; ANNOT 1522314; | 3170; 3171; 3172; 3241; |
| | | | | | ANNOT 1522314; ANNOT 1497147; ANNOT 1497147; ANNOT 1471045; ANNOT | 3242; 3243; 3244; 3245; |
| | | | | | 1471045; ANNOT 1006934; ANNOT 1532963; CLONE 1007549; | 3246; 3247; 3248; 3249; |
| | | | | | ANNOT 1458198; ANNOT 1458198; ANNOT 1439989; ANNOT 1439989; ANNOT | 3250; 3251; 3419; 3420; |
| | | | | | 1464789; ANNOT 1464789; ANNOT 1461728; ANNOT 1479711; | 3421; 3422; 3423; 3424; |
| | | | | | ANNOT 1479711; ANNOT 1440649; ANNOT 1440649; ANNOT 1464547; ANNOT | 3425; 3426; 3427; 3428; |
| | | | | | 1464547; ANNOT 1454104; CLONE 1011386; ANNOT 1531134; | 3429; 3430; 3431; 3432; |
| | | | | | ANNOT 1531134; ANNOT 1508758; ANNOT 1508758; CLONE 1011537; ANNOT | 3433; 3434; 3435; 3436; |
| | | | | | 1473879; ANNOT 1473879; ANNOT 1468666; ANNOT 1438163; | 3437; 3438; 3439; 3440; |
| | | | | | ANNOT 1438163; CDNA 23493481; ANNOT 1460973; CDNA | 3441; 3442; 3443; 3444; |
| | | | | | 23498145; ANNOT 1482362; ANNOT 1489077; ANNOT 1489077; | 3445; 3446; 3447; 3448; |
| | | | | | CDNA 23305182; ANNOT 1525474; ANNOT 1525474; CDNA 23545147; ANNOT | 3449; 3450; 3451; 3452; |
| | | | | | 1443044; ANNOT 1443044; CDNA 36512904; ANNOT 1471370; ANNOT | 3453; 3454; 3455; 3456; |
| | | | | | ANNOT 1444471; ANNOT 1444471; ANNOT 1491278; ANNOT 1491278; ANNOT | 3462; 3463; 3464; 3465; |
| | | | | | 1447690; ANNOT 1447690; CDNA 36521407; ANNOT 1514988; | 3466; 3467; 3468; 3469; |
| | | | | | CDNA 36535419; ANNOT 1524972; ANNOT 1524972; CDNA 36542853; ANNOT | 3470; 3471; 3472; 3473; |

TABLE 1-continued

| Tissue | Phenotype Category | Phenotype | Phenotype Description | Applications | Ceres ID | SEQ ID NO |
|---|---|---|---|---|---|---|
| | | | | | 1524883; ANNOT 1524883; ANNOT 149918; ANNOT 1497918; CDNA 36545500; ANNOT 1449045; ANNOT 1444156; ANNOT 1470714; ANNOT 1470714; CDNA 36571789; ANNOT 1444156; ANNOT 1497097; ANNOT 1497097; CDNA 3695523; ANNOT 1451434; ANNOT 1451434; CDNA 36697835; ANNOT 1461440; ANNOT 1461440; ANNOT 1461427; ANNOT 1461430; ANNOT 1461430; ANNOT 1440253; ANNOT 1440253; | 3613; 3614; 3615; 3641; 3642; 3643; 3644; 3645; 3696; 3697; 3698; 3813; 3814; 3815; 3896; 3897; 3898; 3899; 3900; 3901; 3902; 3903; 3904; 3908; 3909; 3910; 3948; 3949; 3950; 3974; 3975; 3976; 3977; 3978; 3979; 3980; 3981; 3982; 3983; 4043; 4044; 4045; 4046; 4047; 4070; 4071; 4072; 4073; 4074; 4075; 4076; 4077; 4078; 4079; 4080; 4081; |
| ROSETTE LEAVES | Biomass | Short Petioles | The leaf petioles are abnormally short. | Useful for modulating plant size | CLONE 332; ANNOT 1474923; ANNOT 1474923; CLONE 2403; ANNOT 1509972; ANNOT 1509972; ANNOT 1504203; ANNOT 1504203; ANNOT 1443061; ANNOT 1443061; ANNOT 1452369; ANNOT 1452369; CLONE 3000; ANNOT 1518918; ANNOT 1518918; ANNOT 1535677; ANNOT 1535677; ANNOT 1482181; ANNOT 1482181; CLONE 3036; ANNOT 1456840; ANNOT 1456840; CLONE 3858; ANNOT 1459068; ANNOT 1459068; CLONE 6387; ANNOT 1509111; ANNOT 1509111; ANNOT 1541620; ANNOT 1541620; CLONE 12272; ANNOT 1506387; ANNOT 1506387; ANNOT 1474522; ANNOT 1474522; CLONE 13741; ANNOT 1462963; ANNOT 1462963; ANNOT 1459563; ANNOT 1459563; CLONE 14583; ANNOT 1530256; ANNOT 1530256; ANNOT 1476783; ANNOT 1476783; ANNOT 1503166; ANNOT 1503166; CLONE 14909; ANNOT 1497838; ANNOT 1497838; ANNOT 1522523; ANNOT 1522523; ANNOT 1471525; ANNOT 1471525; ANNOT 1511908; ANNOT 1511908; ANNOT 1464305; ANNOT 1464305; ANNOT 1451416; ANNOT 1451416; ANNOT 1461050; ANNOT 1461050; CLONE 19586; ANNOT 1476446; ANNOT 1476446; ANNOT 1451126; ANNOT 1451126; CLONE 21563; ANNOT 1438905; ANNOT 1438905; ANNOT 1483143; ANNOT 1483143; CLONE 23523; ANNOT 1453919; ANNOT 1453919; CLONE 25172; ANNOT 1457346; ANNOT 1457346; ANNOT 1541170; ANNOT 1541170; CLONE 25538; ANNOT 1480776; ANNOT 1480776; CLONE 31507; ANNOT 1447204; ANNOT 1447204; CLONE 32751; ANNOT 1451171; ANNOT 1451171; CLONE 36334; ANNOT 1464715; ANNOT 1464715; ANNOT 1511511; ANNOT 1511511; CLONE 36518; ANNOT 1471507; ANNOT 1471507; ANNOT 1444893; ANNOT 1444893; ANNOT 1458642; ANNOT 1458642; ANNOT 1522497; ANNOT 1522497; ANNOT 1469105; ANNOT 1469105; ANNOT 1484993; ANNOT 1484993; CLONE 37288; ANNOT 1453650; ANNOT 1453650; ANNOT 1454656; ANNOT 1454656; ANNOT 1528263; ANNOT 1528263; ANNOT 1458103; ANNOT 1458103; ANNOT 1464899; ANNOT 1464899; ANNOT 1482966; ANNOT 1482966; ANNOT 1441039; ANNOT 1441039; ANNOT 1520449; ANNOT 1520449; CLONE 40508; ANNOT 1453626; ANNOT 1453626; CLONE 40824; ANNOT 1509015; ANNOT 1509015; ANNOT 1535964; ANNOT 1535964; ANNOT 1535962; ANNOT 1535962; ANNOT 1455815; ANNOT 1455815; ANNOT 1455817; ANNOT 1455817; ANNOT 1482502; ANNOT 1482502; ANNOT 1509035; ANNOT 1509035; ANNOT 1482477; ANNOT 1482477; ANNOT 1509013; ANNOT 1509013; ANNOT 1535990; ANNOT 1535990; ANNOT 1455837; ANNOT 1455837; CLONE 38101; CLONE 41439; ANNOT 100047; ANNOT 1532164; ANNOT 1532164; ANNOT 1442450; ANNOT 1442450; CLONE 102248; ANNOT 1445981; ANNOT 1479350; ANNOT 1479350; ANNOT 1479341; ANNOT 1479341; | 12; 13; 14; 95; 96; 97; 98; 99; 100; 101; 102; 103; 111; 112; 113; 114; 115; 116; 117; 121; 122; 123; 175; 176; 177; 285; 286; 287; 288; 289; 515; 516; 517; 518; 519; 550; 551; 552; 553; 554; 619; 620; 621; 622; 623; 624; 625; 626; 627; 628; 629; 630; 631; 632; 633; 634; 635; 636; 637; 638; 639; 640; 784; 785; 786; 787; 788; 842; 843; 844; 845; 846; 914; 915; 916; 952; 953; 954; 955; 956; 967; 968; 969; 1195; 1196; 1197; 1247; 1248; 1249; 1500; 1501; 1502; 1503; 1504; 1505; 1506; 1507; 1508; 1509; 1510; 1511; 1512; 1513; 1514; 1515; 1516; 1517; 1622; 1623; 1624; 1682; 1683; 1684; 1685; 1686; 1687; 1688; 1689; 1690; 1691; 1692; 1693; 1694; 1695; 1696; 1912; 1913; 1914; 1939; 1940; 1941; 1942; 1943; 1944; 1945; 1946; 1947; 1948; 1949; 1950; 1951; 1952; 1953; 1954; 1955; 1956; 1957; 1958; 1959; 1960; 1961; 1998; 2173; 2174; 2175; 2176; 2177; 2178; 2179; 2180; 2181; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1456981; CLONE 114602; ANNOT 1450785; ANNOT 1456283; ANNOT 1456283; ANNOT 1460638; ANNOT 1513900; ANNOT 1513900; ANNOT 1455816; ANNOT 1540271; ANNOT 116237; ANNOT 1455816; ANNOT 1482508; ANNOT 1482502; ANNOT 1482508; ANNOT 1482508; ANNOT 1535990; ANNOT 1509013; ANNOT 1509013; CLONE 122353; ANNOT 1472265; CLONE 123279; ANNOT 1508945; ANNOT 1508945; ANNOT 1531332; ANNOT 1531332; ANNOT 1482544; ANNOT 1482544; ANNOT 1478226; CLONE 206224; ANNOT 1485509; ANNOT 1485509; ANNOT 1447022; ANNOT 1447022; CLONE 235706; ANNOT 1462351; ANNOT 1462351; ANNOT 1469462; ANNOT 1469462; ANNOT 1488821; ANNOT 1488821; ANNOT 1485750; ANNOT 1485750; ANNOT 1485750; ANNOT 1440730; ANNOT 1440730; CLONE 482122; ANNOT 1438776; ANNOT 1438776; CLONE 536726; ANNOT 1498226; ANNOT 1498226; ANNOT 1445243; ANNOT 1445243; ANNOT 1525386; ANNOT 1448522; ANNOT 1448522; ANNOT 1465506; ANNOT 1465506; ANNOT 1497017; ANNOT 1497017; ANNOT 1497017; ANNOT 1447240; ANNOT 1539566; ANNOT 1539566; ANNOT 1444070; ANNOT 1444070; CLONE 536796; ANNOT 1484779; ANNOT 1484779; ANNOT 1538185; ANNOT 1538185; ANNOT 1455109; ANNOT 1455109; ANNOT 1477384; ANNOT 1477384; CLONE 537272; ANNOT 1518918; ANNOT 1518918; ANNOT 1535677; ANNOT 1535677; CLONE 541719; ANNOT 1518918; ANNOT 1518918; ANNOT 1535677; ANNOT 1535677; ANNOT 708342; ANNOT 1538185; ANNOT 1538185; CLONE 965175; ANNOT 1479013; ANNOT 1479013; CDNA 23498145; ANNOT 1482362; ANNOT 1482362; ANNOT 1489077; ANNOT 1489077; CDNA 23507479; ANNOT 1510416; ANNOT 1510416; ANNOT 1541253; ANNOT 1541253; CDNA 23518705; ANNOT 1463957; ANNOT 1463957; ANNOT 1458961; ANNOT 1458961; CDNA 36507407; ANNOT 1457193; ANNOT 1457193; ANNOT 1487854; ANNOT 1487854; CDNA 36508177; CDNA 36536865; ANNOT 1505326; ANNOT 1505326; ANNOT 1496106; ANNOT 1496106; CDNA 36560639; ANNOT 1437702; ANNOT 1437702; CDNA 36572659; ANNOT 1455805; ANNOT 1455805; ANNOT 1529744; ANNOT 1529744; | 2229; 2230; 2231; 2350; 2351; 2352; 2353; 2354; 2355; 2356; 2357; 2358; 2359; 2360; 2383; 2384; 2385; 2386; 2387; 2388; 2389; 2390; 2391; 2392; 2393; 2481; 2482; 2483; 2492; 2493; 2494; 2495; 2496; 2497; 2498; 2499; 2500; 2630; 2631; 2632; 2633; 2634; 2705; 2706; 2707; 2708; 2709; 2710; 2711; 2779; 2780; 2781; 2782; 2783; 3049; 3050; 3051; 3135; 3136; 3137; 3138; 3139; 3140; 3141; 3142; 3143; 3144; 3145; 3146; 3147; 3148; 3149; 3150; 3151; 3152; 3153; 3154; 3155; 3156; 3157; 3158; 3159; 3160; 3161; 3162; 3163; 3164; 3165; 3166; 3167; 3173; 3174; 3175; 3176; 3177; 3361; 3362; 3363; 3388; 3389; 3390; 3641; 3642; 3643; 3644; 3645; 3704; 3705; 3706; 3707; 3708; 3748; 3749; 3750; 3751; 3752; 3884; 3885; 3886; 3887; 3888; 3889; 3961; 3962; 3963; 3964; 3965; 4005; 4006; 4007; 4048; 4049; 4050; 4051; 4052; |
| WHOLE PLANT | Biomass | Small | The plant is abnormally small. | Useful for modulating plant size | CLONE 332; ANNOT 1474923; CLONE 907; ANNOT 1502138; ANNOT 1502138; ANNOT 1449135; ANNOT 1449135; CLONE 1241; ANNOT 1453081; ANNOT 1515808; ANNOT 1442349; CLONE 1355; ANNOT 1515808; ANNOT 1469219; ANNOT 1469219; ANNOT 1462513; ANNOT 1462513; CLONE 1610; ANNOT 1454586; ANNOT 1454586; ANNOT 1475043; ANNOT 1475043; ANNOT 1507756; ANNOT 1507756; ANNOT 1469708; CLONE 2561; ANNOT 1450958; ANNOT 1450958; ANNOT 1456475; ANNOT 1456475; ANNOT 1446945; ANNOT 1446945; CLONE 3000; ANNOT 1518918; ANNOT 1518918; ANNOT 1535677; ANNOT 1535677; ANNOT 1482181; ANNOT 1482181; CLONE 3006; ANNOT 1472173; ANNOT 1472173; CLONE 3036; ANNOT 1456840; ANNOT 1456840; CLONE 3363; ANNOT 1445515; ANNOT 1445515; ANNOT 1461861; ANNOT 1461861; ANNOT 1449363; ANNOT 1449363; ANNOT 1465198; ANNOT 1465198; ANNOT 1518517; ANNOT 1518517; CLONE 3542; ANNOT 1471301; ANNOT 1471301; CLONE 3819; ANNOT 1441039; ANNOT 1441039; ANNOT 1482966; ANNOT 1482966; ANNOT 1454656; ANNOT 1454656; ANNOT 1528263; ANNOT 1528263; ANNOT 1464899; ANNOT | 12; 13; 14; 30; 31; 32; 33; 34; 38; 39; 40; 41; 42; 43; 44; 45; 46; 47; 48; 49; 67; 68; 69; 70; 71; 72; 73; 74; 75; 104; 105; 106; 107; 108; 109; 110; 111; 112; 113; 114; 115; 116; 117; 118; 119; 120; 121; 122; 123; 129; 130; 131; 132; 133; 134; 135; 136; 137; 138; 139; 145; 146; 147; 153; 154; 155; 156; 157; 158; 159; 160; 161; 162; 163; 164; 165; 166; 167; 168; 169; 175; 176; 177; 178; 179; |

TABLE 1-continued

| Tissue | Phenotype Category | Phenotype | Phenotype Description | Applications | Ceres ID | SEQ ID NO |
|---|---|---|---|---|---|---|
| | | | | | 1464899; ANNOT 1458103; ANNOT 1458103; ANNOT 1442040; ANNOT 1442040; ANNOT 1520449; ANNOT 1520449; CLONE 3858; ANNOT 1459068; ANNOT 1459068; CLONE 3997; ANNOT 1455209; ANNOT 1455209; ANNOT 1446198; ANNOT 1446198; CLONE 3997; ANNOT 1490273; ANNOT 1490273; ANNOT 1530603; ANNOT 1530603; CLONE 4058; ANNOT 1468992; ANNOT 1468992; ANNOT 1444098; ANNOT 1444098; CLONE 4058; ANNOT 1474224; ANNOT 1474224; ANNOT 1524351; ANNOT 1524351; CLONE 5055; ANNOT 1438157; ANNOT 1438157; ANNOT 1500936; ANNOT 1500936; CLONE 5167; ANNOT 1465422; ANNOT 1465422; ANNOT 1457750; ANNOT 1457750; ANNOT 1513544; CLONE 5198; ANNOT 1472153; ANNOT 1472153; CLONE 5605; ANNOT 1437939; ANNOT 1437939; CLONE 5710; ANNOT 1464658; ANNOT 1464658; ANNOT 1458337; ANNOT 1458337; ANNOT 1454234; ANNOT 1454234; ANNOT 1475996; ANNOT 1475996; CLONE 6082; ANNOT 1443416; ANNOT 1443416; ANNOT 1505047; ANNOT 1505047; ANNOT 1496339; ANNOT 1496339; CLONE 6411; ANNOT 1505322; ANNOT 1505322; ANNOT 1496110; ANNOT 1496110; ANNOT 1496111; ANNOT 1496111; CLONE 6630; ANNOT 1529141; ANNOT 1529141; ANNOT 1475689; ANNOT 1475689; ANNOT 1476577; ANNOT 1476577; CLONE 7191; ANNOT 1493787; ANNOT 1493787; CLONE 8254; ANNOT 1543042; ANNOT 1543042; ANNOT 1489655; ANNOT 1489655; CLONE 8265; ANNOT 1438919; ANNOT 1438919; ANNOT 1499398; ANNOT 1499398; ANNOT 1446419; ANNOT 1446419; CLONE 9221; ANNOT 1535229; ANNOT 1535229; CLONE 9683; ANNOT 1471514; ANNOT 1471514; CLONE 9897; ANNOT 1445849; ANNOT 1445849; ANNOT 1500561; ANNOT 1500561; ANNOT 1464458; ANNOT 1464458; CLONE 10159; ANNOT 1439969; ANNOT 1439969; CLONE 10879; ANNOT 1467184; ANNOT 1467184; ANNOT 1467184; CLONE 11214; ANNOT 1501485; ANNOT 1501485; ANNOT 1490496; ANNOT 1490496; ANNOT 1448498; ANNOT 1448498; ANNOT 1474848; ANNOT 1474848; CLONE 11843; ANNOT 1443460; ANNOT 1443460; ANNOT 1504967; ANNOT 1504967; CLONE 11854; ANNOT 1506763; ANNOT 1506763; ANNOT 1452827; ANNOT 1452827; CLONE 13757; ANNOT 1471425; ANNOT 1471425; ANNOT 1453614; ANNOT 1453614; CLONE 11975; ANNOT 1460142; ANNOT 1460142; ANNOT 1460142; ANNOT 1483807; ANNOT 1483807; CLONE 12071; ANNOT 1466704; ANNOT 1466704; CLONE 12272; ANNOT 1506387; ANNOT 1506387; ANNOT 1474522; ANNOT 1474522; CLONE 12993; ANNOT 1479464; ANNOT 1479464; CLONE 13092; ANNOT 1471785; ANNOT 1471785; CLONE 13186; ANNOT 1464566; ANNOT 1464566; ANNOT 1458408; ANNOT 1458408; CLONE 13625; ANNOT 1455211; ANNOT 1455211; CLONE 13745; ANNOT 1442604; ANNOT 1442604; ANNOT 1442612; ANNOT 1442612; ANNOT 1442608; ANNOT 1442608; ANNOT 1452827; ANNOT 1452827; CLONE 13757; ANNOT 1471425; ANNOT 1471425; CLONE 13767; ANNOT 1542158; ANNOT 1542158; ANNOT 1488730; ANNOT 1488730; CLONE 13800; ANNOT 1458335; ANNOT 1458335; ANNOT 1464663; ANNOT 1464663; CLONE 14033; ANNOT 1480322; ANNOT 1480322; ANNOT 1493735; ANNOT 1493735; CLONE 14555; ANNOT 1511392; ANNOT 1511392; ANNOT 1511392; ANNOT 1469356; ANNOT 1469356; ANNOT 1517500; ANNOT 1517500; CLONE 14909; ANNOT 1497838; ANNOT 1497838; ANNOT 1522523; ANNOT 1522523; ANNOT 1471525; ANNOT 1471525; ANNOT 1511908; ANNOT 1511908; ANNOT 1464305; ANNOT 1464305; ANNOT 1451416; ANNOT 1451416; ANNOT 1461050; ANNOT 1461050; CLONE 16461; ANNOT 1479013; ANNOT 1479013; CLONE 17409; ANNOT 1457617; ANNOT 1457617; ANNOT 1465289; ANNOT 1465289; ANNOT 1478647; ANNOT 1478647; ANNOT 1453865; ANNOT 1453865; CLONE 17434; ANNOT 1455741; ANNOT 1455741; ANNOT 1477832; ANNOT 1477832; | 180; 181; 182; 183; 184; 185; 186; 187; 188; 189; 190; 191; 192; 193; 194; 195; 215; 216; 217; 218; 219; 223; 224; 225; 226; 227; 228; 229; 230; 231; 232; 238; 239; 240; 241; 242; 243; 244; 245; 246; 247; 248; 249; 268; 269; 270; 271; 272; 273; 274; 293; 294; 295; 296; 297; 298; 299; 305; 306; 307; 308; 309; 310; 311; 317; 318; 319; 357; 358; 359; 360; 361; 362; 363; 364; 365; 366; 367; 368; 394; 395; 396; 402; 403; 404; 405; 406; 407; 408; 409; 410; 411; 428; 429; 430; 437; 438; 439; 448; 449; 450; 451; 452; 453; 454; 455; 456; 470; 471; 472; 473; 474; 475; 476; 477; 478; 479; 502; 503; 504; 505; 506; 507; 508; 509; 515; 516; 517; 518; 519; 520; 521; 522; 528; 529; 530; 531; 532; 533; 534; 535; 544; 545; 546; 555; 556; 557; 558; 559; 560; 561; 562; 563; 564; 565; 566; 567; 568; 569; 570; 571; 572; 573; 574; 575; 576; 582; 583; 584; 585; 586; 608; 609; 610; 611; 612; 613; 614; 615; 616; 617; 618; 626; 627; 628; 629; 630; 631; 632; 633; 634; 635; 636; 637; 638; 639; 640; 647; 648; 649; 678; 679; 680; 681; 682; 683; 684; 685; 686; 687; 688; 689; 690; 691; 695; 696; 697; 698; 699; 700; 701; 702; 703; 704; 705; 706; 707; 708; 709; 720; 721; 722; 723; 724; 735; 736; 737; 738; 739; 740; 741; 742; 743; 744; 745; 746; 747; 748; 749; 767; |

TABLE 1-continued

| Tissue | Phenotype Category | Phenotype | Phenotype Description | Applications | Ceres ID | SEQ ID NO |
|---|---|---|---|---|---|---|
| | | | | | CLONE 17632; ANNOT 1474847; ANNOT 1474847; ANNOT 1507835; ANNOT 1507835; CLONE 17761; ANNOT 1481206; ANNOT 1481206; ANNOT 1534689; ANNOT 1534689; CLONE 17912; ANNOT 1514378; ANNOT 1514378; ANNOT 1494118; ANNOT 1494118; CLONE 18612; ANNOT 1522299; ANNOT 1522299; ANNOT 1527718; ANNOT 1527718; CLONE 19116; ANNOT 1467522; ANNOT 1467522; ANNOT 1467522; ANNOT 1526421; CLONE 19143; ANNOT 1442860; ANNOT 1442860; ANNOT 1442860; ANNOT 1459442; ANNOT 1452580; ANNOT 1452580; CLONE 19188; ANNOT 1445089; ANNOT 1445089; CLONE 19486; ANNOT 1452204; ANNOT 1452204; ANNOT 1443204; CLONE 19510; ANNOT 1501412; ANNOT 1501412; ANNOT 1490383; ANNOT 1490383; ANNOT 1448419; ANNOT 1448419; CLONE 20945; ANNOT 1519797; ANNOT 1519797; CLONE 21068; ANNOT 1463333; ANNOT 1463333; ANNOT 1505772; ANNOT 1505772; ANNOT 1495675; ANNOT 1495675; ANNOT 1469576; ANNOT 1469576; ANNOT 1442758; ANNOT 1442758; CLONE 21563; ANNOT 1438905; ANNOT 1438905; ANNOT 1483143; ANNOT 1483143; CLONE 23322; ANNOT 1512337; ANNOT 1517094; ANNOT 1517094; CLONE 23518; ANNOT 1475658; ANNOT 1475658; ANNOT 1449267; ANNOT 1449267; ANNOT 1507191; ANNOT 1507191; CLONE 23523; ANNOT 1453919; ANNOT 1453919; CLONE 23771; ANNOT 1444030; ANNOT 1444030; ANNOT 1486813; ANNOT 1486813; ANNOT 1485303; ANNOT 1485303; ANNOT 1446796; ANNOT 1446796; CLONE 24644; ANNOT 1463301; ANNOT 1463301; ANNOT 1459811; ANNOT 1459811; CLONE 24885; ANNOT 1485102; ANNOT 1485102; CLONE 25380; ANNOT 1512618; ANNOT 1512618; ANNOT 1459357; ANNOT 1459357; ANNOT 1463526; ANNOT 1463526; CLONE 25538; ANNOT 1480776; ANNOT 1480776; CLONE 25796; ANNOT 1522583; ANNOT 1522583; CLONE 25886; ANNOT 1446650; ANNOT 1446650; ANNOT 1439514; ANNOT 1439514; ANNOT 1477202; ANNOT 1477202; ANNOT 1455325; ANNOT 1455325; CLONE 26542; ANNOT 1475323; ANNOT 1475323; ANNOT 1538272; ANNOT 1538272; CLONE 26560; ANNOT 1536088; ANNOT 1536088; ANNOT 1482610; ANNOT 1482610; CLONE 26637; ANNOT 1451045; ANNOT 1451045; CLONE 26907; ANNOT 1484074; ANNOT 1484074; ANNOT 1440016; ANNOT 1440016; ANNOT 1477202; ANNOT 1518242; ANNOT 1518242; ANNOT 1448819; ANNOT 1448819; ANNOT 1465787; ANNOT 1465787; ANNOT 1465787; ANNOT 1474460; ANNOT 1474847; ANNOT 1474847; ANNOT 1507835; CLONE 27460; CLONE 27464; ANNOT 1453044; ANNOT 1453044; ANNOT 1507835; ANNOT 1507835; ANNOT 1451171; ANNOT 1451171; CLONE 28033; ANNOT 1459086; ANNOT 1459086; CLONE 28528; ANNOT 1477416; ANNOT 1477416; CLONE 28602; ANNOT 1461728; ANNOT 1461728; ANNOT 1488330; ANNOT 1488330; ANNOT 1479711; ANNOT 1460480; ANNOT 1460480; ANNOT 1461614; ANNOT 1461614; ANNOT 1479711; ANNOT 1479711; ANNOT 1479712; ANNOT 1479712; ANNOT 1488329; ANNOT 1488329; ANNOT 1488329; ANNOT 1460481; ANNOT 1460481; ANNOT 1461613; ANNOT 1461613; ANNOT 1458198; ANNOT 1458198; ANNOT 1488327; ANNOT 1488327; CLONE 31014; ANNOT 1527449; ANNOT 1527449; ANNOT 1484207; ANNOT 1484207; CLONE 31044; ANNOT 1486207; ANNOT 1486207; ANNOT 1446894; ANNOT 1446894; ANNOT 1496976; ANNOT 1496976; CLONE 32082; ANNOT 1446894; ANNOT 1446894; ANNOT 1543513; ANNOT 1543513; CLONE 32348; ANNOT 1470719; ANNOT 1470719; ANNOT 1543728; ANNOT 1543728; ANNOT 1482066; ANNOT 1482066; CLONE 32548; ANNOT 1450324; ANNOT 1450324; ANNOT 1460836; ANNOT 1460836; CLONE 32612; ANNOT 1484890; ANNOT 1484890; CLONE 32737; ANNOT 1536373; ANNOT 1536373; ANNOT 1451171; ANNOT 1482905; ANNOT 1482905; CLONE 32751; ANNOT 1480607; ANNOT 1480607; ANNOT 1451171; CLONE 32753; ANNOT 1480607; ANNOT 1480607; | 768; 769; 770; 771; 772; 773; 774; 775; 776; 777; 778; 818; 819; 820; 821; 822; 823; 824; 825; 826; 827; 828; 829; 830; 831; 842; 843; 844; 845; 846; 897; 898; 899; 900; 901; 907; 908; 909; 910; 911; 912; 913; 914; 915; 916; 928; 929; 930; 931; 932; 933; 934; 935; 936; 944; 945; 946; 947; 948; 949; 950; 951; 960; 961; 962; 963; 964; 965; 966; 967; 968; 969; 983; 984; 985; 986; 987; 988; 989; 990; 991; 992; 993; 994; 1010; 1011; 1012; 1013; 1014; 1015; 1016; 1017; 1018; 1019; 1020; 1021; 1022; 1043; 1044; 1045; 1046; 1047; 1048; 1049; 1050; 1051; 1052; 1053; 1054; 1055; 1056; 1057; 1058; 1059; 1060; 1061; 1062; 1063; 1064; 1085; 1086; 1087; 1096; 1097; 1098; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1185; 1186; 1187; 1188; 1189; 1190; 1191; 1192; 1193; 1194; 1201; 1202; 1203; 1204; 1205; 1219; 1220; 1221; 1222; 1223; 1224; 1225; 1231; 1232; 1233; 1234; 1235; 1236; 1237; 1238; 1242; 1243; 1244; 1245; 1246; 1247; 1248; 1249; 1250; 1251; 1252; 1253; 1254; 1255; 1256; 1257; 1263; 1264; 1265; 1266; 1267; 1287; 1288; 1289; 1290; 1291; 1292; 1293; 1294; 1295; 1296; 1297; 1298; 1299; 1300; 1301; 1302; 1303; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1472242; ANNOT 1472242; CLONE 3791; ANNOT 1540248; ANNOT 1540248; CLONE 33232; ANNOT 1504045; ANNOT 1504045; ANNOT 1450983; ANNOT 1450983; CLONE 33554; ANNOT 1445599; ANNOT 1445599; ANNOT 1471882; ANNOT 1471882; ANNOT 1452398; ANNOT 1452398; ANNOT 1443041; ANNOT 1443041; ANNOT 1452397; ANNOT 1452397; ANNOT 1505498; ANNOT 1505498; ANNOT 1505497; ANNOT 1505497; ANNOT 1443040; ANNOT 1443040; ANNOT 1495964; ANNOT 1495964; ANNOT 1498580; ANNOT 1498580; ANNOT 1495637; ANNOT 1495637; ANNOT 1466060; CLONE 33802; ANNOT 1452709; ANNOT 1452709; ANNOT 1442724; ANNOT 1442724; CLONE 34167; ANNOT 1538733; ANNOT 1538733; ANNOT 1499810; ANNOT 1499810; ANNOT 1485323; ANNOT 1485323; CLONE 34385; ANNOT 1445331; ANNOT 1445331; ANNOT 1498316; ANNOT 1498316; CLONE 34412; ANNOT 1449739; ANNOT 1449739; ANNOT 1449738; ANNOT 1449738; ANNOT 1458830; ANNOT 1458830; CLONE 34480; ANNOT 1502362; ANNOT 1502362; ANNOT 1449358; ANNOT 1449358; CLONE 34549; ANNOT 1442496; ANNOT 1442496; CLONE 34552; ANNOT 1516449; ANNOT 1516449; ANNOT 1512976; ANNOT 1512976; ANNOT 34612; CLONE 34612; ANNOT 1479009; ANNOT 1479009; ANNOT 1469640; ANNOT 1469640; CLONE 34635; ANNOT 1487773; ANNOT 1487773; ANNOT 1457333; ANNOT 1457333; ANNOT 1442634; ANNOT 1442634; CLONE 34783; ANNOT 1466952; ANNOT 1466952; ANNOT 1523551; ANNOT 1523551; ANNOT 1470164; ANNOT 1470164; CLONE 34976; ANNOT 1507231; ANNOT 1507231; CLONE 35015; ANNOT 1443033; ANNOT 1443033; ANNOT 1438730; CLONE 1438730; ANNOT 1452408; ANNOT 1452408; ANNOT 1505508; ANNOT 1505508; CLONE 35733; ANNOT 1486258; ANNOT 1486258; ANNOT 1443988; ANNOT 1443988; CLONE 35742; ANNOT 1478035; ANNOT 1478035; CLONE 35999; ANNOT 1515818; ANNOT 1515818; CLONE 36094; ANNOT 1440660; ANNOT 1440660; CLONE 36518; ANNOT 1471507; ANNOT 1471507; ANNOT 1444893; ANNOT 1444893; ANNOT 1458642; ANNOT 1458642; ANNOT 1522497; ANNOT 1522497; ANNOT 1469105; ANNOT 1469105; ANNOT 1484993; ANNOT 1484993; CLONE 36709; ANNOT 1495936; ANNOT 1495936; CLONE 36891; ANNOT 1480518; ANNOT 1480518; ANNOT 1442194; ANNOT 1442194; ANNOT 1454127; ANNOT 1454127; ANNOT 1461716; ANNOT 1461716; ANNOT 1440277; ANNOT 1440277; ANNOT 1461415; ANNOT 1461415; ANNOT 1461414; ANNOT 1461414; ANNOT 1447424; ANNOT 1447424; ANNOT 1528127; ANNOT 1528127; ANNOT 1438717; ANNOT 1438717; ANNOT 1440276; ANNOT 1440276; ANNOT 1442556; ANNOT 1442556; ANNOT 1452873; ANNOT 1452873; ANNOT 1453483; ANNOT 1453483; ANNOT 1473384; ANNOT 1473384; ANNOT 1475808; ANNOT 1475808; ANNOT 1474708; ANNOT 1474708; ANNOT 1438698; ANNOT 1438698; CLONE 36904; ANNOT 1526083; ANNOT 1526083; ANNOT 1498856; ANNOT 1498856; ANNOT 1445872; ANNOT 1445872; ANNOT 1472663; ANNOT 1472663; CLONE 37019; ANNOT 1517849; ANNOT 1517849; ANNOT 1511684; ANNOT 1511684; ANNOT 1464532; ANNOT 1464532; ANNOT 1458439; ANNOT 1458439; ANNOT 1540674; ANNOT 1540674; CLONE 37229; ANNOT 1485157; ANNOT 1485157; ANNOT 1476218; ANNOT 1476218; CLONE 37298; ANNOT 1476538; ANNOT 1476538; ANNOT 1493576; ANNOT 1493576; CLONE 37493; ANNOT 1494370; ANNOT 1494370; ANNOT 1441478; ANNOT 1441478; ANNOT 1486562; ANNOT 1486562; CLONE 37543; ANNOT 1539972; ANNOT 1539972; ANNOT 1443794; ANNOT 1443794; CLONE 37589; ANNOT 1496735; ANNOT 1496735; ANNOT 1443794; ANNOT 1443794; CLONE 37658; ANNOT 1440727; ANNOT 1440727; ANNOT 1497485; ANNOT 1497485; ANNOT 1497485; ANNOT 1454656; ANNOT 1454656; ANNOT 1528263; CLONE 38101; | 1304; 1305; 1306; 1307; 1308; 1309; 1321; 1322; 1323; 1324; 1325; 1326; 1327; 1343; 1344; 1345; 1346; 1347; 1348; 1349; 1364; 1365; 1366; 1367; 1368; 1376; 1377; 1378; 1379; 1380; 1381; 1382; 1398; 1399; 1400; 1401; 1402; 1403; 1404; 1405; 1406; 1407; 1408; 1409; 1410; 1411; 1412; 1413; 1414; 1415; 1416; 1417; 1418; 1419; 1420; 1421; 1422; 1423; 1424; 1425; 1426; 1427; 1428; 1429; 1435; 1436; 1437; 1438; 1439; 1440; 1441; 1442; 1443; 1444; 1445; 1446; 1447; 1476; 1477; 1478; 1479; 1480; 1481; 1482; 1483; 1487; 1488; 1489; 1490; 1491; 1492; 1505; 1506; 1507; 1508; 1509; 1510; 1511; 1512; 1513; 1514; 1515; 1516; 1517; 1545; 1546; 1547; 1548; 1549; 1550; 1551; 1552; 1553; 1554; 1555; 1556; 1557; 1558; 1559; 1560; 1561; 1562; 1563; 1564; 1565; 1566; 1567; 1568; 1569; 1570; 1571; 1572; 1573; 1574; 1575; 1576; 1577; 1578; 1579; 1580; 1581; 1582; 1583; 1584; 1585; 1586; 1587; 1588; 1589; 1590; 1591; 1592; 1593; 1599; 1600; 1601; 1602; 1603; 1604; 1605; 1606; 1607; 1608; 1609; 1617; 1618; 1619; 1620; 1621; 1625; 1626; 1627; 1628; 1629; 1637; 1638; 1639; 1640; 1641; 1642; 1643; 1644; 1645; 1646; 1647; 1648; 1649; 1650; 1651; 1652; 1653; 1654; 1655; 1656; 1682; 1683; 1684; 1685; 1686; 1687; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1528263; ANNOT 1458103; ANNOT 1458103; ANNOT 1464899; ANNOT 1464899; ANNOT 1482966; ANNOT 1482966; ANNOT 1441039; ANNOT 1441039; ANNOT 1520449; ANNOT 1520449; CLONE 38105; ANNOT 1473032; ANNOT 1473032; ANNOT 1467499; ANNOT 1467499; ANNOT 1526442; ANNOT 1526442; CLONE 38277; ANNOT 1512884; ANNOT 1512884; CLONE 38370; ANNOT 1471869; ANNOT 1471869; ANNOT 1448032; ANNOT 1448032; ANNOT 1448031; ANNOT 1448031; ANNOT 1438060; ANNOT 1438060; ANNOT 1438061; ANNOT 1438061; ANNOT 1448030; ANNOT 1448030; ANNOT 1437831; ANNOT 1437831; ANNOT 38419; ANNOT 1542971; ANNOT 1542971; ANNOT 1521332; ANNOT 1521332; ANNOT 1528846; ANNOT 1528846; ANNOT 1467961; ANNOT 1467961; CLONE 38757; ANNOT 1528846; ANNOT 1528846; ANNOT 1538329; ANNOT 1538329; CLONE 38843; ANNOT 1447896; ANNOT 1447896; ANNOT 1438197; ANNOT 1438197; CLONE 39286; ANNOT 1447961; ANNOT 1447961; ANNOT 1490936; ANNOT 1490936; CLONE 39319; ANNOT 1456036; ANNOT 1456036; ANNOT 1470131; ANNOT 1470131; ANNOT 1466936; ANNOT 1466936; ANNOT 1541455; ANNOT 1541455; ANNOT 1456037; CLONE 39740; ANNOT 1483180; ANNOT 1483180; ANNOT 1480950; ANNOT 1480950; CLONE 39890; ANNOT 1511886; ANNOT 1511886; ANNOT 1517635; ANNOT 1517635; CLONE 40508; ANNOT 1453626; ANNOT 1453626; CLONE 40538; ANNOT 1452757; ANNOT 1452757; CLONE 40692; ANNOT 1455695; ANNOT 1455695; CLONE 40729; ANNOT 1481678; ANNOT 1481678; CLONE 40824; ANNOT 1509015; ANNOT 1509015; ANNOT 1535964; ANNOT 1535962; ANNOT 1535962; ANNOT 1458815; ANNOT 1455815; ANNOT 1455817; ANNOT 1455817; ANNOT 1482502; ANNOT 1482502; ANNOT 1482502; ANNOT 1527449; ANNOT 1509035; ANNOT 1509035; ANNOT 1482477; ANNOT 1482477; ANNOT 1509013; ANNOT 1509013; ANNOT 1535990; ANNOT 1535990; ANNOT 1455837; ANNOT 1455837; CLONE 41306; ANNOT 1475806; ANNOT 1475806; ANNOT 1454125; ANNOT 1454125; CLONE 41320; ANNOT 1541929; ANNOT 1541929; ANNOT 1460282; ANNOT 1460282; ANNOT 1488507; ANNOT 1488507; CLONE 41439; CLONE 42141; ANNOT 1473839; ANNOT 1473839; CLONE 42925; ANNOT 1462354; ANNOT 1462354; CLONE 92670; ANNOT 1531919; ANNOT 1531919; CLONE 93867; ANNOT 1474944; ANNOT 1474944; ANNOT 1506849; ANNOT 1506849; ANNOT 1492957; ANNOT 1492957; CLONE 95135; ANNOT 1527449; ANNOT 1537653; ANNOT 1537653; ANNOT 1473733; ANNOT 1473733; ANNOT 1468537; ANNOT 1468537; CLONE 95453; ANNOT 1460836; ANNOT 1460836; ANNOT 1450324; ANNOT 1450324; CLONE 95677; ANNOT 1459723; ANNOT 1459723; ANNOT 1516455; ANNOT 1516455; CLONE 96020; ANNOT 1450365; ANNOT 1450365; ANNOT 1460794; ANNOT 1460794; CLONE 97434; ANNOT 1488311; ANNOT 1488311; ANNOT 1518776; ANNOT 1518776; CLONE 99784; ANNOT 1521032; ANNOT 1521032; ANNOT 1472909; ANNOT 1472909; ANNOT 1467665; ANNOT 1467665; ANNOT 100047; ANNOT 1532164; ANNOT 1532164; ANNOT 1479341; ANNOT 1479341; ANNOT 1479350; ANNOT 1479350; ANNOT 1442450; CLONE 100245; ANNOT 1535451; ANNOT 1535451; ANNOT 1532285; ANNOT 1532285; ANNOT 1480241; ANNOT 1480241; ANNOT 1446025; CLONE 100319; ANNOT 1503141; ANNOT 1503141; ANNOT 1521524; ANNOT 1521524; CLONE 100465; ANNOT 1466439; ANNOT 1466439; ANNOT 1448977; ANNOT 1448977; ANNOT 1519767; ANNOT 1519767; ANNOT 1501982; ANNOT 1501982; CLONE 101798; ANNOT 1449432; ANNOT 1449432; ANNOT 1449431; ANNOT 1449431; ANNOT 1502439; CLONE 102017; ANNOT 1448974; ANNOT 1448974; ANNOT 1496840; ANNOT | 1688; 1689; 1690; 1691; 1692; 1693; 1694; 1695; 1696; 1697; 1698; 1699; 1700; 1701; 1702; 1703; 1714; 1715; 1716; 1732; 1733; 1734; 1735; 1736; 1737; 1738; 1739; 1740; 1741; 1742; 1743; 1744; 1745; 1746; 1747; 1748; 1749; 1750; 1751; 1752; 1753; 1791; 1792; 1793; 1794; 1795; 1801; 1802; 1803; 1804; 1805; 1838; 1839; 1840; 1841; 1842; 1843; 1844; 1845; 1846; 1847; 1848; 1849; 1850; 1851; 1852; 1853; 1877; 1878; 1879; 1880; 1881; 1882; 1883; 1884; 1885; 1886; 1912; 1913; 1914; 1915; 1916; 1917; 1918; 1919; 1920; 1930; 1931; 1932; 1939; 1940; 1941; 1942; 1943; 1944; 1945; 1946; 1947; 1948; 1949; 1950; 1951; 1952; 1953; 1954; 1955; 1956; 1957; 1958; 1959; 1960; 1961; 1976; 1977; 1978; 1979; 1980; 1981; 1982; 1983; 1984; 1985; 1986; 1987; 1998; 2015; 2016; 2017; 2045; 2046; 2047; 2061; 2062; 2063; 2064; 2065; 2066; 2067; 2068; 2069; 2070; 2076; 2077; 2078; 2079; 2080; 2081; 2082; 2083; 2084; 2085; 2086; 2087; 2088; 2089; 2090; 2091; 2092; 2093; 2094; 2095; 2096; 2097; 2098; 2099; 2103; 2104; 2105; 2106; 2107; 2161; 2162; 2163; 2164; 2165; 2166; 2167; 2173; 2174; 2175; 2176; 2177; 2178; 2179; 2180; 2181; 2182; 2183; 2184; 2185; 2186; 2187; 2188; 2189; 2190; 2191; 2192; 2193; 2194; 2195; |

TABLE 1-continued

| Tissue | Phenotype Category | Phenotype | Phenotype Description | Applications | Ceres ID | SEQ ID NO |
|---|---|---|---|---|---|---|
| | | | | | 1496840; CLONE 104929; ANNOT 1449020; CLONE 108056; ANNOT 1464935; ANNOT 1464935; ANNOT 1458064; ANNOT 1458064; ANNOT 1511298; ANNOT 1511298; ANNOT 1458065; ANNOT 1458065; ANNOT 1511299; ANNOT 1511299; CLONE 110454; CLONE 111209; ANNOT 1494507; ANNOT 1494507; CLONE 113719; ANNOT 1513206; ANNOT 1513206; ANNOT 1516003; ANNOT 1516003; ANNOT 1462703; CLONE 113990; ANNOT 1438327; ANNOT 1438327; ANNOT 1447769; ANNOT 1447769; CLONE 114602; ANNOT 1450785; ANNOT 1450785; ANNOT 1456283; ANNOT 1456283; ANNOT 1460638; ANNOT 1460638; ANNOT 1513900; ANNOT 1513900; ANNOT 1540271; ANNOT 1540271; CLONE 115975; ANNOT 1507138; ANNOT 1507138; CLONE 116117; ANNOT 1456955; ANNOT 1456955; ANNOT 1451365; ANNOT 1451365; ANNOT 1504433; ANNOT 1504433; CLONE 116237; ANNOT 1455816; ANNOT 1455816; ANNOT 1482502; ANNOT 1482502; ANNOT 1482508; ANNOT 1482508; CLONE 1535990; ANNOT 1535990; ANNOT 1509013; ANNOT 1509013; CLONE 119256; ANNOT 1469636; ANNOT 1469636; ANNOT 1479002; ANNOT 1479002; CLONE 123279; ANNOT 1508945; ANNOT 1508945; ANNOT 1531332; ANNOT 1531332; ANNOT 1482544; ANNOT 1482544; ANNOT 1478226; ANNOT 1478226; CLONE 124720; ANNOT 1441430; ANNOT 1441430; CLONE 141890; ANNOT 1494533; ANNOT 1494533; ANNOT 1466313; ANNOT 1466313; CLONE 147358; ANNOT 1493111; ANNOT 1493111; ANNOT 1461452; ANNOT 1461452; CLONE 147593; ANNOT 1475653; ANNOT 1475653; ANNOT 1458131; ANNOT 1458131; ANNOT 1461780; ANNOT 1461780; CLONE 148943; ANNOT 1472949; ANNOT 1472949; CLONE 149380; ANNOT 1461440; ANNOT 1461440; ANNOT 1461430; ANNOT 1461430; ANNOT 1461427; ANNOT 1461427; ANNOT 1440253; ANNOT 1440253; ANNOT 1440253; CLONE 150912; ANNOT 1533910; ANNOT 1533910; ANNOT 1480439; ANNOT 1480439; CLONE 152076; ANNOT 1493664; ANNOT 1493664; CLONE 152141; ANNOT 1439403; ANNOT 1439403; CLONE 154718; ANNOT 1457453; ANNOT 1457453; CLONE 157547; ANNOT 1473898; ANNOT 1473898; CLONE 158333; ANNOT 1466505; ANNOT 1466505; ANNOT 1449026; ANNOT 1449026; CLONE 158734; ANNOT 1477956; ANNOT 1477956; CLONE 159318; ANNOT 1485362; ANNOT 1485362; CLONE 205648; ANNOT 1456842; ANNOT 1456842; ANNOT 1504224; ANNOT 1504224; CLONE 225200; ANNOT 1471976; ANNOT 1471976; ANNOT 1465507; ANNOT 1465507; CLONE 225601; ANNOT 1457617; ANNOT 1457617; ANNOT 1465289; ANNOT 1465289; ANNOT 1478647; ANNOT 1478647; ANNOT 1453865; ANNOT 1453865; ANNOT 1438014; ANNOT 1438014; CLONE 235706; ANNOT 1462351; ANNOT 1462351; ANNOT 1469462; ANNOT 1469462; ANNOT 1488821; ANNOT 1488821; CLONE 241379; ANNOT 1526950; ANNOT 1526950; ANNOT 1477361; ANNOT 1508362; ANNOT 1508362; ANNOT 1477361; CLONE 254065; ANNOT 1485544; ANNOT 1485544; ANNOT 1447051; ANNOT 1447051; ANNOT 1517016; ANNOT 1517016; CLONE 262460; ANNOT 1530053; ANNOT 1530053; ANNOT 1493414; ANNOT 1493414; CLONE 264705; ANNOT 1485750; ANNOT 1485750; ANNOT 1440730; ANNOT 1440730; CLONE 266142; ANNOT 1449110; ANNOT 1449110; ANNOT 1448105; ANNOT 1448105; CLONE 267564; ANNOT 1473933; ANNOT 1473933; ANNOT 1468704; ANNOT 1468704; CLONE 267626; ANNOT 1484074; ANNOT 1484074; ANNOT 1518242; ANNOT 1518242; ANNOT 1464923; ANNOT 1464923; CLONE 268505; ANNOT 1496682; ANNOT 1496682; ANNOT 1443744; ANNOT 1443744; CLONE 283597; ANNOT 1482074; ANNOT 1482074; ANNOT 1453923; ANNOT 1453923; CLONE 292789; ANNOT 1442040; ANNOT 1442040; ANNOT 1482966; ANNOT 1482966; ANNOT 1454656; ANNOT 1454656; ANNOT 1458103; ANNOT 1458103; ANNOT | 2196; 2197; 2198; 2199; 2200; 2201; 2202; 2203; 2204; 2219; 2220; 2221; 2222; 2223; 2224; 2225; 2226; 2227; 2228; 2232; 2233; 2234; 2235; 2236; 2237; 2238; 2239; 2281; 2282; 2283; 2284; 2285; 2286; 2287; 2288; 2289; 2290; 2291; 2313; 2314; 2315; 2316; 2333; 2334; 2335; 2336; 2337; 2338; 2339; 2340; 2341; 2342; 2343; 2344; 2350; 2351; 2352; 2353; 2354; 2355; 2356; 2357; 2358; 2359; 2360; 2373; 2374; 2375; 2376; 2377; 2378; 2379; 2380; 2381; 2382; 2383; 2384; 2385; 2386; 2387; 2388; 2389; 2390; 2391; 2392; 2393; 2451; 2452; 2453; 2454; 2455; 2492; 2493; 2494; 2495; 2496; 2497; 2498; 2499; 2500; 2501; 2502; 2503; 2523; 2524; 2525; 2526; 2527; 2528; 2529; 2530; 2531; 2532; 2533; 2534; 2535; 2536; 2537; 2538; 2539; 2543; 2544; 2545; 2546; 2547; 2548; 2549; 2550; 2551; 2552; 2553; 2554; 2555; 2556; 2557; 2558; 2559; 2565; 2566; 2567; 2568; 2569; 2570; 2577; 2578; 2579; 2593; 2594; 2595; 2611; 2612; 2613; 2614; 2615; 2619; 2620; 2621; 2622; 2623; 2624; 2625; 2626; 2627; 2628; 2629; 2655; 2656; 2657; 2658; 2659; 2665; 2666; 2667; 2668; 2669; 2670; 2671; 2672; 2673; 2674; 2675; 2705; 2706; 2707; 2708; 2709; 2710; 2711; 2718; 2719; 2720; 2721; 2722; 2723; 2724; 2731; 2732; 2733; 2734; 2735; |

TABLE 1-continued

| Tissue | Phenotype Category | Phenotype | Phenotype Description | Applications | Ceres ID | SEQ ID NO |
|---|---|---|---|---|---|---|
| | | | | | 1464899; ANNOT 1464899; ANNOT 1474837; ANNOT 1520449; ANNOT 1520449; ANNOT 1538169; ANNOT 1538169; ANNOT 1511505; ANNOT 1511505; CLONE 464504; ANNOT 1438401; ANNOT 1438401; CLONE 536457; ANNOT 1490030; ANNOT 1493787; ANNOT 1493787; CLONE 536726; ANNOT 1498226; ANNOT 1498226; ANNOT 1445243; ANNOT 1445243; ANNOT 1525386; ANNOT 1448522; ANNOT 1448522; ANNOT 1465506; ANNOT 1497017; ANNOT 1497017; ANNOT 1447240; ANNOT 1447240; ANNOT 1539566; ANNOT 1539566; ANNOT 1444070; ANNOT 1444070; CLONE 536796; ANNOT 1484779; ANNOT 1484779; ANNOT 1538185; ANNOT 1538185; ANNOT 1455109; ANNOT 1455109; ANNOT 1477384; ANNOT 1477384; CLONE 537272; ANNOT 1518918; ANNOT 1518918; ANNOT 1535677; ANNOT 1535677; CLONE 538933; ANNOT 1466193; ANNOT 1466193; ANNOT 1494416; ANNOT 1494416; CLONE 557009; ANNOT 1474923; ANNOT 1474923; CLONE 590462; ANNOT 1490788; ANNOT 1490788; ANNOT 1502230; ANNOT 1502230; CLONE 608818; ANNOT 1528780; ANNOT 1528780; ANNOT 1518351; ANNOT 1518351; ANNOT 1525569; ANNOT 1525569; ANNOT 1453192; ANNOT 1453192; ANNOT 1441586; ANNOT 1441586; ANNOT 1509714; ANNOT 1509714; CLONE 609573; ANNOT 1473808; ANNOT 1473808; ANNOT 1476668; ANNOT 1476668; ANNOT 1474436; ANNOT 1474436; ANNOT 1513750; ANNOT 1513750; ANNOT 1510994; ANNOT 1510994; ANNOT 1457771; ANNOT 1457771; CLONE 627596; ANNOT 1500987; ANNOT 1500987; ANNOT 1490915; ANNOT 1490915; CLONE 641355; ANNOT 1463335; ANNOT 1463335; ANNOT 1463334; ANNOT 1463334; ANNOT 1452665; ANNOT 1452665; CLONE 660003; ANNOT 1508184; ANNOT 1508184; ANNOT 1528645; ANNOT 1528645; CLONE 681088; ANNOT 1471330; ANNOT 1471330; ANNOT 1444437; ANNOT 1444437; ANNOT 1444439; ANNOT 1444439; ANNOT 1486891; ANNOT 1486891; ANNOT 1479637; ANNOT 1479637; ANNOT 1446530; ANNOT 1446530; CLONE 708342; ANNOT 1538185; ANNOT 1538185; CLONE 965175; ANNOT 1479013; ANNOT 1479013; CLONE 1002819; ANNOT 1474290; ANNOT 1474290; ANNOT 1522314; ANNOT 1522314; ANNOT 1497147; ANNOT 1497147; ANNOT 1471045; ANNOT 1471045; CLONE 1006934; ANNOT 1532963; ANNOT 1532963; CLONE 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1479711; ANNOT 1440649; ANNOT 1440649; ANNOT 1464547; ANNOT 1464547; ANNOT 1454104; ANNOT 1454104; CLONE 1011386; ANNOT 1531134; ANNOT 1531134; ANNOT 1508758; ANNOT 1508758; CLONE 1011537; ANNOT 1473879; ANNOT 1473879; ANNOT 1468666; ANNOT 1468666; ANNOT 1438163; ANNOT 1438163; CLONE 1029167; ANNOT 1453409; ANNOT 1453409; ANNOT 1474630; ANNOT 1474630; ANNOT 1450948; ANNOT 1450948; CDNA 12672729; ANNOT 1500350; ANNOT 1500350; CDNA 23493481; ANNOT 1460973; ANNOT 1460973; CDNA 23494371; ANNOT 1485236; ANNOT 1485236; ANNOT 1446740; ANNOT 1446740; CDNA 23494432; CDNA 23495481; ANNOT 1485271; ANNOT 1485271; ANNOT 1447245; ANNOT 1447245; CDNA 23498145; ANNOT 1482362; ANNOT 1482362; ANNOT 1489077; ANNOT 1489077; CDNA 23505103; CDNA 23507479; ANNOT 1510416; ANNOT 1510416; ANNOT 1541253; ANNOT 1541253; CDNA 23345147; ANNOT 1443044; ANNOT 1443044; CDNA 36507011; ANNOT 1442604; ANNOT 1442604; ANNOT 1442612; ANNOT 1442612; ANNOT 1442608; ANNOT 1442608; ANNOT 1452827; ANNOT 1452827; CDNA 36514446; ANNOT 1460973; CDNA 23494371; ANNOT 1475322; ANNOT 1475322; CDNA 36534269; ANNOT 1457794; ANNOT 1457794; ANNOT 1524172; ANNOT 1524172; CDNA 36535618; ANNOT 1459998; ANNOT | 2736; 2737; 2774; 2775; 2776; 2777; 2778; 2779; 2780; 2781; 2782; 2783; 2784; 2785; 2786; 2787; 2788; 2789; 2790; 2791; 2792; 2793; 2794; 2795; 2796; 2797; 2798; 2799; 2800; 2806; 2807; 2808; 2809; 2810; 2833; 2834; 2835; 2836; 2837; 2852; 2853; 2854; 2855; 2856; 2857; 2858; 2859; 2860; 2861; 2862; 2863; 2864; 2865; 2866; 2867; 2868; 3003; 3004; 3005; 3006; 3007; 3008; 3130; 3131; 3132; 3133; 3134; 3135; 3136; 3137; 3138; 3139; 3140; 3141; 3142; 3143; 3144; 3145; 3146; 3147; 3148; 3149; 3150; 3151; 3152; 3153; 3154; 3155; 3156; 3157; 3158; 3159; 3160; 3161; 3162; 3163; 3164; 3165; 3166; 3167; 3168; 3169; 3170; 3171; 3172; 3221; 3222; 3223; 3255; 3256; 3257; 3258; 3259; 3273; 3274; 3275; 3276; 3277; 3278; 3279; 3280; 3281; 3282; 3283; 3284; 3285; 3286; 3287; 3288; 3289; 3290; 3291; 3292; 3293; 3294; 3295; 3296; 3297; 3298; 3299; 3300; 3301; 3302; 3303; 3304; 3305; 3306; 3307; 3308; 3309; 3310; 3314; 3315; 3316; 3317; 3318; 3345; 3346; 3347; 3348; 3349; 3350; 3351; 3352; 3353; 3354; 3355; 3356; 3357; 3361; 3362; 3363; 3388; 3389; 3390; 3428; 3429; 3430; 3431; 3432; 3433; 3434; 3435; 3436; 3437; 3438; 3439; 3440; 3441; 3442; 3443; 3444; 3445; 3446; 3447; 3448; 3449; 3450; 3451; 3452; |

TABLE 1-continued

| Tissue | Phenotype Category | Phenotype | Phenotype Description | Applications | Ceres ID | SEQ ID NO |
|---|---|---|---|---|---|---|
| | | | | | 1459998; ANNOT 1513263; CDNA 36566773; ANNOT 1464046; ANNOT 1464046; ANNOT 1458861; ANNOT 1458861; CDNA 36571789; ANNOT 1444156; ANNOT 1444156; ANNOT 1497097; CDNA 36575796; ANNOT 1486224; ANNOT 1486224; ANNOT 1444021; ANNOT 1444021; CDNA 36579424; ANNOT 1455663; ANNOT 1455663; ANNOT 1438024; ANNOT 1448068; ANNOT 1448068; CDNA 36697835; ANNOT 1451434; ANNOT 1451434; CDNA 36697835; ANNOT 1461440; ANNOT 1461427; ANNOT 1461427; ANNOT 1461430; ANNOT 1461440; ANNOT 1461253; ANNOT 1440253; ANNOT 1447690; ANNOT 1491278; ANNOT 1491278; ANNOT 1500987; ANNOT 1500987; ANNOT 1490915; ANNOT 1490915; | 3453; 3454; 3455; 3456; 3462; 3463; 3464; 3465; 3466; 3467; 3468; 3469; 3470; 3471; 3472; 3473; 3474; 3475; 3476; 3477; 3478; 3479; 3480; 3517; 3518; 3519; 3613; 3614; 3615; 3616; 3617; 3618; 3619; 3620; 3621; 3622; 3623; 3624; 3625; 3626; 3641; 3642; 3643; 3644; 3645; 3687; 3704; 3705; 3706; 3707; 3708; 3813; 3814; 3815; 3875; 3876; 3877; 3878; 3879; 3880; 3881; 3882; 3883; 3905; 3906; 3907; 3938; 3939; 3940; 3941; 3942; 3951; 3952; 3953; 3954; 3955; 4018; 4019; 4020; 4021; 4022; 4043; 4044; 4045; 4046; 4047; 4053; 4054; 4055; 4056; 4057; 4063; 4064; 4065; 4066; 4067; 4068; 4069; 4070; 4071; 4072; 4073; 4074; 4075; 4076; 4077; 4078; 4079; 4080; 4081; 3688; 3689; 3690; 3691; 3692; 3693; 3694; 3695; |
| CAULINE LEAVES | Biomass | Small | The cauline leaves are abnormally small. | Useful for making plants with increased biomass and foliage | CLONE 13757; ANNOT 1471425; ANNOT 1503551; ANNOT 1471425; CLONE 39351; ANNOT 1503551; ANNOT 1513952; ANNOT 1460689; ANNOT 1513952; ANNOT 1513952; ANNOT 1450495; ANNOT 1450495; CLONE 40508; ANNOT 1453626; ANNOT 1453626; CLONE 267657; ANNOT 1471473; ANNOT 1471473; ANNOT 1444931; ANNOT 1444931; | 564; 565; 566; 1854; 1855; 1856; 1857; 1858; 1859; 1860; 1861; 1862; 1912; 1913; 1914; 2801; 2802; 2803; 2804; 2805; |
| WHOLE PLANT | Biomass, Architecture | Standing Rosette Shaped | The petioles have a very large liminal angle, i.e., it appears as though the leaves are standing up instead of having their usual small vertical angle from the soil. | Useful for making plants with improved architecture and with increased biomass and foliage | CLONE 13757; ANNOT 1471425; CLONE 28602; ANNOT 1461728; ANNOT 1471425; CLONE 28602; ANNOT 1460480; ANNOT 1488330; ANNOT 1460480; ANNOT 1460480; ANNOT 1461614; ANNOT 1479711; ANNOT 1479711; ANNOT 1479712; ANNOT 1488329; ANNOT 1488329; ANNOT 1460481; ANNOT 1460481; ANNOT 1461613; ANNOT 1461613; ANNOT 1458198; ANNOT 1458198; ANNOT 1488327; CLONE 38690; ANNOT 1525183; ANNOT 1525183; CLONE 158333; ANNOT 1466505; ANNOT 1466505; ANNOT 1449026; ANNOT 1449026; | 564; 565; 566; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1774; 1775; 1776; 2611; 2612; 2613; 2614; 2615; |
| INFLORESCENCE | Biomass | Tall | The inflorescences | Useful for making taller | CLONE 332; ANNOT 1474923; ANNOT 1474923; CLONE 4067; ANNOT 1514362; ANNOT 1514362; ANNOT 1494090; ANNOT 1494090; CLONE 5597; ANNOT | 12; 13; 14; 196; 197; 198; 199; 200; 233; 234; |

TABLE 1-continued

| Tissue | Phenotype Category | Phenotype | Phenotype Description | Applications | Ceres ID | SEQ ID NO |
|---|---|---|---|---|---|---|
| | | | of the plants are abnormally long. | plants and plants with longer inflorescences | 1507708; ANNOT 1507708; ANNOT 1475094; CLONE 23322; ANNOT 1512337; ANNOT 1512337; ANNOT 1517094; CLONE 28643; ANNOT 1469464; ANNOT 1469464; ANNOT 1463508; ANNOT 1459366; ANNOT 1459366; ANNOT 1542246; ANNOT 1463508; CLONE 32152; ANNOT 1450535; ANNOT 1450535; ANNOT 1513913; ANNOT 1460651; ANNOT 1460651; ANNOT 1442535; ANNOT 1513913; ANNOT 1452888; ANNOT 1452888; ANNOT 148705; CLONE 33559; ANNOT 1481146; ANNOT 1481146; ANNOT 1481150; ANNOT 148705; ANNOT 1481138; ANNOT 1481138; ANNOT 1485824; ANNOT 1534622; ANNOT 1534622; CLONE 98855; ANNOT 1460836; ANNOT 1460836; ANNOT 1450324; ANNOT 1450324; CLONE 99657; ANNOT 1461858; ANNOT 1461858; ANNOT 1461858; ANNOT 1461858; ANNOT 1440018; ANNOT 1440018; ANNOT 1440018; ANNOT 1440019; ANNOT 1511305; ANNOT 1511305; ANNOT 1511305; ANNOT 1440019; ANNOT 1511305; ANNOT 1464927; ANNOT 1464927; ANNOT 1464927; CLONE 99784; ANNOT 1521032; ANNOT 1521032; ANNOT 1472909; ANNOT 1472909; ANNOT 1467665; ANNOT 1467665; CLONE 100319; ANNOT 1503141; ANNOT 1503141; ANNOT 1521524; ANNOT 1521524; CLONE 105554; ANNOT 1451783; ANNOT 1451783; CLONE 106011; ANNOT 1533498; ANNOT 1533498; ANNOT 1524067; ANNOT 1524067; CLONE 110247; ANNOT 1528846; ANNOT 1528846; ANNOT 1538329; CLONE 112955; ANNOT 1447634; ANNOT 1447634; CLONE 156655; ANNOT 1538329; ANNOT 1441740; ANNOT 1441740; CLONE 157730; ANNOT 1532681; ANNOT 1532681; ANNOT 1469739; ANNOT 1469739; CLONE 270875; ANNOT 1457048; ANNOT 1457048; ANNOT 1510252; ANNOT 1510252; CLONE 1002819; ANNOT 1474290; ANNOT 1474290; ANNOT 1522314; ANNOT 1522314; ANNOT 1497147; ANNOT 1497147; ANNOT 1471045; ANNOT 1471045; CLONE 1011386; ANNOT 1531134; ANNOT 1531134; ANNOT 1508758; ANNOT 1508758; CDNA 2305103; CDNA 3651290; ANNOT 1471370; ANNOT 1471370; ANNOT 1447690; ANNOT 1444471; ANNOT 1491278; ANNOT 1491278; ANNOT 1447690; ANNOT 1447690; CDNA 3656910S; ANNOT 1463445; ANNOT 1463445; ANNOT 1512677; ANNOT 1512677; ANNOT 1459412; ANNOT 1459412; ANNOT 1447690; ANNOT 1491278; ANNOT 1491278; ANNOT 1491278; ANNOT 1500987; ANNOT 1500987; ANNOT 1490915; ANNOT 1490915; | 235; 236; 237; 897; 898; 899; 900; 901; 1122; 1123; 1124; 1125; 1126; 1127; 1128; 1129; 1130; 1206; 1207; 1208; 1209; 1210; 1211; 1212; 1213; 1214; 1215; 1216; 1217; 1218; 1310; 1311; 1312; 1313; 1314; 1315; 1316; 1317; 1318; 1319; 1320; 2118; 2119; 2120; 2121; 2122; 2142; 2143; 2144; 2145; 2146; 2147; 2148; 2149; 2150; 2151; 2152; 2153; 2154; 2155; 2156; 2157; 2158; 2159; 2160; 2161; 2162; 2163; 2164; 2165; 2166; 2167; 2191; 2192; 2193; 2194; 2195; 2247; 2248; 2249; 2250; 2251; 2252; 2253; 2254; 2308; 2309; 2310; 2311; 2312; 2330; 2331; 2332; 2580; 2581; 2582; 2601; 2602; 2603; 2604; 2605; 2811; 2812; 2813; 2814; 2815; 3428; 3429; 3430; 3431; 3432; 3433; 3434; 3435; 3436; 3462; 3463; 3464; 3465; 3466; 3687; 3896; 3897; 3898; 3899; 3900; 3901; 3902; 3903; 3904; 4036; 4037; 4038; 4039; 4040; 4041; 4042; 3688; 3689; 3690; 3691; 3692; 3693; 3694; 3695; |
| CAULINE LEAVES | Biomass | Undulate Shaped | The leaves are wavy in appearance compared to wild-type plants. | Useful for making plants with increased biomass and foliage | CLONE 4067; ANNOT 1514362; ANNOT 1494090; ANNOT 1494090; CLONE 36904; ANNOT 1526083; ANNOT 1498856; ANNOT 1498856; ANNOT 1445872; ANNOT 1472663; ANNOT 1472663; | 196; 197; 198; 199; 200; 1585; 1586; 1587; 1588; 1589; 1590; 1591; 1592; 1593; |
| INFLORESCENCE | Biomass, Architecture | No Branching | There is no branching. | Useful for modifying plant architecture, i.e. amount of branching | CLONE 3000; ANNOT 1518918; ANNOT 1535677; ANNOT 1535677; ANNOT 1482181; ANNOT 1482181; CLONE 13391; ANNOT 1445555; ANNOT 1445555; ANNOT 1445555; ANNOT 1502315; ANNOT 1502315; CLONE 13757; ANNOT 1471425; ANNOT 1471425; CLONE 14555; ANNOT 1511392; ANNOT 1511392; ANNOT 1469356; ANNOT 1469356; ANNOT 1517500; ANNOT 1517500; ANNOT 1458151; ANNOT 1458151; ANNOT 1522757; CLONE 20760; ANNOT 1462351; ANNOT 1462351; ANNOT 1488821; ANNOT 1488821; ANNOT 1469462; ANNOT 1469462; CLONE 34412; ANNOT 1449739; ANNOT 1449739; ANNOT 1449738; ANNOT 1449738; ANNOT 1458830; ANNOT 1458830; CLONE | 111; 112; 113; 114; 115; 116; 117; 539; 540; 541; 542; 543; 564; 565; 566; 608; 609; 610; 611; 612; 613; 614; 615; 616; 617; 618; 808; 809; 810; 811; 812; 813; 814; 1376; 1377; 1378; 1379; 1380; 1381; 1382; 1545; 1546; |

TABLE 1-continued

| Tissue | Phenotype Category | Phenotype | Phenotype Description | Applications | Ceres ID | SEQ ID NO |
|---|---|---|---|---|---|---|
| INFLORESCENCE | Biomass, Architecture | Short Internode | The internode is abnormally short. | Useful for making modulating plant height and plants with modified flowers | 36709; ANNOT 1499936; ANNOT 1499936; CLONE 157547; ANNOT 1473898; ANNOT 1473898; CLONE 241379; ANNOT 1526950; ANNOT 1526950; ANNOT 1508362; ANNOT 1508362; ANNOT 1477361; ANNOT 1477361; CLONE 641355; ANNOT 1463335; ANNOT 1463335; ANNOT 1463334; ANNOT 1463334; ANNOT 1452665; ANNOT 1452665; CLONE 332; ANNOT 1474923; ANNOT 1474923; CLONE 3062; ANNOT 1504677; ANNOT 1504677; ANNOT 1451593; ANNOT 1451593; CLONE 9132; ANNOT 1458620; ANNOT 1458620; CLONE 12993; ANNOT 1479464; ANNOT 1479464; CLONE 13186; ANNOT 1464566; ANNOT 1464566; ANNOT 1458408; ANNOT 1458408; CLONE 13757; ANNOT 1471425; ANNOT 1471425; CLONE 14555; ANNOT 1511392; ANNOT 1511392; ANNOT 1469356; ANNOT 1469356; ANNOT 1517500; ANNOT 1517500; ANNOT 1458151; ANNOT 1458151; ANNOT 1522757; ANNOT 1522757; CLONE 14583; ANNOT 1530256; ANNOT 1530256; ANNOT 1476783; ANNOT 1476783; ANNOT 1503166; ANNOT 1503166; CLONE 19116; ANNOT 1467522; ANNOT 1467522; ANNOT 1526421; ANNOT 1526421; CLONE 24266; ANNOT 1463475; ANNOT 1463475; ANNOT 1443033; ANNOT 1540920; ANNOT 1540920; ANNOT 1487528; ANNOT 1487528; CLONE 25758; ANNOT 1473748; ANNOT 1473748; CLONE 28326; ANNOT 1468461; ANNOT 1468461; CLONE 34385; ANNOT 1445331; ANNOT 1445331; ANNOT 1498316; ANNOT 1498316; CLONE 35051; ANNOT 1443033; ANNOT 1443033; ANNOT 1452408; ANNOT 1452408; ANNOT 1505508; ANNOT 1505508; CLONE 40508; ANNOT 1453626; ANNOT 1453626; CLONE 40538; ANNOT 1452757; ANNOT 1452757; CLONE 40729; ANNOT 1481678; ANNOT 1481678; CLONE 40824; ANNOT 1509015; ANNOT 1509015; ANNOT 1535964; ANNOT 1535964; ANNOT 1535962; ANNOT 1455815; ANNOT 1455815; ANNOT 1455817; ANNOT 1455817; ANNOT 1482502; ANNOT 1482502; ANNOT 1509035; ANNOT 1509035; ANNOT 1482477; ANNOT 1482477; ANNOT 1509013; ANNOT 1509013; ANNOT 1535990; ANNOT 1535990; ANNOT 1455837; ANNOT 1455837; CLONE 100047; ANNOT 1532164; ANNOT 1532164; ANNOT 1479341; ANNOT 1479341; ANNOT 1479350; ANNOT 1479350; ANNOT 1442450; ANNOT 1442450; CLONE 102248; ANNOT 1456981; ANNOT 1456981; CLONE 115946; ANNOT 1456342; ANNOT 1456342; CLONE 118337; ANNOT 1454773; ANNOT 1454773; ANNOT 1511811; ANNOT 1511811; ANNOT 1478364; ANNOT 1478364; ANNOT 1464394; ANNOT 1464394; CLONE 147593; ANNOT 1475653; ANNOT 1475653; ANNOT 1458131; ANNOT 1458131; ANNOT 1461780; ANNOT 1461780; CLONE 222601; ANNOT 1457617; ANNOT 1457617; ANNOT 1465289; ANNOT 1465289; ANNOT 1478647; ANNOT 1478647; ANNOT 1453865; ANNOT 1453865; ANNOT 1438014; ANNOT 1438014; CLONE 464504; ANNOT 1438401; ANNOT 1438401; CLONE 482122; ANNOT 1438776; ANNOT 1438776; CLONE 536726; ANNOT 1498226; ANNOT 1498226; ANNOT 1445243; ANNOT 1445243; ANNOT 1525386; ANNOT 1525386; ANNOT 1448522; ANNOT 1448522; ANNOT 1465506; ANNOT 1465506; ANNOT 1497017; ANNOT 1497017; ANNOT 1447240; ANNOT 1447240; ANNOT 1539566; ANNOT 1539566; ANNOT 1444070; ANNOT 1444070; | 1547; 2593; 2594; 2595; 2718; 2719; 2720; 2721; 2722; 2723; 2724; 3304; 3305; 3306; 3307; 3308; 3309; 3310; 12; 13; 14; 124; 125; 126; 127; 128; 391; 392; 393; 520; 521; 522; 531; 532; 533; 534; 535; 564; 565; 566; 608; 609; 610; 611; 612; 613; 614; 615; 616; 617; 618; 619; 620; 621; 622; 623; 624; 625; 735; 736; 737; 738; 739; 937; 938; 939; 940; 941; 942; 943; 973; 974; 975; 1088; 1089; 1090; 1364; 1365; 1366; 1367; 1368; 1441; 1442; 1443; 1444; 1445; 1446; 1447; 1912; 1913; 1914; 1915; 1916; 1917; 1930; 1931; 1932; 1939; 1940; 1941; 1942; 1943; 1944; 1945; 1946; 1947; 1948; 1949; 1950; 1951; 1952; 1953; 1954; 1955; 1956; 1957; 1958; 1959; 1960; 1961; 2173; 2174; 2175; 2176; 2177; 2178; 2179; 2180; 2181; 2229; 2230; 2231; 2370; 2371; 2372; 2417; 2418; 2419; 2420; 2421; 2422; 2423; 2424; 2425; 2533; 2534; 2535; 2536; 2537; 2538; 2539; 2665; 2666; 2667; 2668; 2669; 2670; 2671; 2672; 2673; 2674; 2675; 3006; 3007; 3008; 3049; 3050; 3051; 3135; 3136; 3137; 3138; 3139; 3140; 3141; 3142; 3143; 3144; 3145; 3146; 3147; 3148; 3149; 3150; 3151; 3152; 3153; |
| INFLORESCENCE | Biomass, Architecture | Two Leaf Branching | Two cauline leaves subtend branches instead of one. | Useful for modifying plant architecture, i.e. increasing | CLONE 38973; ANNOT 1451899; ANNOT 1451899; ANNOT 1496367; ANNOT 1496367; | 1818; 1819; 1820; 1821; 1822; |

TABLE 1-continued

| Tissue | Phenotype Category | Phenotype | Phenotype Description | Applications | Ceres ID | SEQ ID NO |
|---|---|---|---|---|---|---|
| WHOLE PLANT | Composition | Activates expression of the gene endogenous to the AtATCPS1 (SEQ ID NO 4091) regulatory region | Overexpression of the regulatory protein is able to promote the expression of the gene operably linked to the AtATCPS1 (SEQ ID NO 4091) regulatory region | foliage Useful for modulating Terpenoid Biosynthesis | CLONE ID no. 475689; ANNOT 1472897; ANNOT 1472897; ANNOT 1467673; ANNOT 1467673; ANNOT 1445014; ANNOT 1445014; ANNOT 1471808; ANNOT 1471808; ANNOT 1454998; ANNOT 1454998; ANNOT 1475212; ANNOT 1475212; | 3021; 3022; 3023; 3024; 3025; 3026; 3027; 3028; 3029; 3030; 3031; 3032; 3033; |
| WHOLE PLANT | Composition | Activates expression of the gene endogenous to the AtATTPS3 (SEQ ID NO 4108) regulatory region | Overexpression of the regulatory protein is able to promote the expression of the gene operably linked to the AtATTPS3 (SEQ ID NO 4108) regulatory region | Useful for modulating Terpenoid Biosynthesis | CLONE ID no. 45; ANNOT 1447323; ANNOT 1447323; ANNOT 1491680; ANNOT 1491680; CLONE ID no. 3997; ANNOT 1455209; ANNOT 1455209; ANNOT 1446198; ANNOT 1446198; ANNOT 1490273; ANNOT 1490273; ANNOT 1530603; ANNOT 1530603; CLONE ID no. 11130; ANNOT 1466979; ANNOT 1466979; CLONE ID no. 14246; ANNOT 1454534; ANNOT 1454534; ANNOT 1507701; ANNOT 1507701; CLONE ID no. 21075; ANNOT 1520467; ANNOT 1520467; ANNOT 1494915; ANNOT 1494915; CLONE ID no. 25795; ANNOT 1471291; ANNOT 1471291; ANNOT 1444391; ANNOT 1444391; ANNOT 1488042; ANNOT 1488042; CLONE ID no. 29310; ANNOT 1455209; ANNOT 1455209; ANNOT 1446198; ANNOT 1446198; ANNOT 1490273; ANNOT 1490273; ANNOT 1530603; ANNOT 1530603; CLONE ID no. 36927; ANNOT 1447997; ANNOT 1447997; ANNOT 1438091; ANNOT 1438091; ANNOT 143891; CLONE ID no. 98140; ANNOT 1518036; ANNOT 1518036; ANNOT 1518036; ANNOT 1511508; ANNOT 1511508; ANNOT 1464717; ANNOT 1464717; CLONE ID no. 103581; ANNOT 1486398; ANNOT 1486398; ANNOT 1496840; ANNOT 1496840; CLONE ID no. 119104; ANNOT 1465284; ANNOT 1465284; ANNOT 1518608; ANNOT 1518608; ANNOT 1443642; ANNOT 1443642; CLONE ID no. 286402; ANNOT 1539856; ANNOT 1539856; ANNOT 1486441; ANNOT 1486441; ANNOT 1443875; ANNOT 1443875; CLONE ID no. 306497; ANNOT 1529923; ANNOT 1529923; ANNOT 1440964; ANNOT 1440964; ANNOT 1493847; ANNOT 1493847; ANNOT 1533800; CLONE ID no. 333416; ANNOT 1469082; ANNOT 1469082; ANNOT 1522474; ANNOT 1522474; ANNOT 1486441; ANNOT 1486441; ANNOT 1511636; ANNOT 1511636; ANNOT 1517906; ANNOT 1517906; CLONE ID no. 335011; ANNOT 481915; ANNOT 481915; ANNOT 1466775; ANNOT 1466775; ANNOT 1517906; CLONE ID no. 660003; ANNOT 1508184; ANNOT 1508184; ANNOT 1528645; ANNOT 1528645; CLONE ID no. 955048; ANNOT 1466002; ANNOT 1466002; ANNOT 1450256; ANNOT 1450256; | 1; 2; 3; 4; 5; 178; 179; 180; 181; 182; 183; 184; 185; 186; 445; 446; 447; 603; 604; 605; 606; 607; 832; 833; 834; 835; 836; 976; 977; 978; 979; 980; 981; 982; 1134; 1135; 1136; 1137; 1138; 1139; 1140; 1141; 1142; 1594; 1595; 1596; 1597; 1598; 2111; 2112; 2113; 2114; 2115; 2116; 2117; 2232; 2233; 2234; 2235; 2236; 2444; 2445; 2446; 2447; 2448; 2449; 2450; 2838; 2839; 2840; 2841; 2842; 2843; 2844; 2893; 2894; 2895; 2896; 2897; 2898; 2899; 2900; 2901; 2919; 2920; 2921; 2922; 2923; 2929; 2930; 2931; 2932; 2933; 3046; 3047; 3048; 3314; 3315; 3316; 3317; 3318; 3372; 3373; 3374; 3375; 3376; |
| WHOLE PLANT | Composition | Activates expression of the gene endogenous to the AtBBE2 (SEQ ID NO 4094) regulatory region | Overexpression of the regulatory protein is able to promote the expression of the gene operably linked to the AtBBE2 (SEQ ID NO 4094) regulatory region | Useful for modulating Alkaloid Biosynthesis | CLONE ID no. 355209; ANNOT 1498695; CLONE ID no. 475001; ANNOT 1467833; ANNOT 1467833; ANNOT 1526695; ANNOT 1526695; ANNOT 1521201; ANNOT 1521201; CLONE ID no. 534282; ANNOT 1515278; ANNOT 1515278; ANNOT 1439721; ANNOT 1439721; ANNOT 1474632; ANNOT 1474632; CLONE ID no. 563878; ANNOT 1474489; ANNOT 1474489; ANNOT 1453294; ANNOT 1453294; | 2975; 2976; 2977; 3014; 3015; 3016; 3017; 3018; 3019; 3020; 3086; 3087; 3088; 3089; 3090; 3091; 3092; 3236; 3237; 3238; 3239; 3240; |

TABLE 1-continued

| Tissue | Phenotype Category | Phenotype | Phenotype Description | Applications | Ceres ID | SEQ ID NO |
|---|---|---|---|---|---|---|
| WHOLE PLANT | Composition | Activates expression of the gene endogenous to the AtCR2 (SEQ ID NO 4096) regulatory region and/or the AtROX6 (SEQ ID NO 4097) regulatory region. | Overexpression of the regulatory protein is able to promote the expression of the gene operably linked to the AtCR2 (SEQ ID NO 4096) regulatory region and/or the AtROX6(SEQ ID NO 4097) regulatory region. | Useful for modulating Alkaloid Biosynthesis | CLONE ID no. 8788; ANNOT 1474018; ANNOT 1474018; CLONE ID no. 11130; ANNOT 1466979; ANNOT 1466979; CLONE ID no. 21634; ANNOT 1458524; ANNOT 1458524; ANNOT 1464441; ANNOT 1464441; CLONE ID no. 34385; ANNOT 1445331; ANNOT 1445331; ANNOT 1498316; ANNOT 1498316; CLONE ID no. 34414; ANNOT 1471525; ANNOT 1471525; ANNOT 1497838; ANNOT 1497838; ANNOT 1511908; ANNOT 1511908; ANNOT 1464305; ANNOT 1464305; ANNOT 1451416; ANNOT 1451416; ANNOT 1514324; ANNOT 1514324; ANNOT 1461050; ANNOT 1461050; CLONE ID no. 34944; ANNOT 1485544; ANNOT 1485544; ANNOT 1447051; ANNOT 1447051; CLONE ID no. 35228; ANNOT 1445433; ANNOT 1445433; ANNOT 1498413; ANNOT 1498413; CLONE ID no. 35594; ANNOT 1514436; ANNOT 1514436; ANNOT 1461164; ANNOT 1461164; ANNOT 1494183; ANNOT 1494183; ANNOT 1441280; ANNOT 1441280; CLONE ID no. 39231; ANNOT 1511404; ANNOT 1511404; ANNOT 1464821; ANNOT 1464821; CLONE ID no. 39893; ANNOT 1530660; ANNOT 1530660; ANNOT 1455308; ANNOT 1455308; CLONE ID no. 41104; ANNOT 1489751; ANNOT 1489751; ANNOT 1446209; ANNOT 1446209; CLONE ID no. 41105; ANNOT 1500974; ANNOT 1500974; ANNOT 1490929; ANNOT 1490929; ANNOT 1438118; ANNOT 1438118; ANNOT 1482024; ANNOT 1482024; CLONE ID no. 208429; ANNOT 1457538; ANNOT 1457538; ANNOT 1510743; ANNOT 1510743; CLONE ID no. 229604; ANNOT 1480703; ANNOT 1480703; ANNOT 1454366; ANNOT 1454366; CLONE ID no. 471089; ANNOT 1531777; ANNOT 1531777; ANNOT 1508033; ANNOT 1508033; CLONE ID no. 480900; ANNOT 1461433; ANNOT 1461433; ANNOT 1487252; ANNOT 1487252; CLONE ID no. 597609; ANNOT 1538274; ANNOT 1538274; ANNOT 1528771; ANNOT 1528771; ANNOT 1484866; ANNOT 1484866; CLONE ID no. 957981; ANNOT 1515625; ANNOT 1515625; ANNOT 1489205; ANNOT 1489205; CLONE ID no. 960560; ANNOT 1446751; ANNOT 1446751; CLONE ID no. 965028; ANNOT 1438401; ANNOT 1438401; CDNA ID no. 12676498; ANNOT 1522070; ANNOT 1525070; ANNOT 1525070; ANNOT 1471655; ANNOT 1471655; ANNOT 1525069; ANNOT 1525069; ANNOT 1471654; ANNOT 1471654; CDNA ID no. 13579142; ANNOT 1522260; ANNOT 1522260; ANNOT 1527806; ANNOT 1527806; CDNA ID no. 13610509; ANNOT 1531291; ANNOT 1531291; CDNA ID no. 13653045; ANNOT 1463563; ANNOT 1463563; CDNA ID no. 23447462; ANNOT 1440467; ANNOT 1440467; ANNOT 1476600; ANNOT 1476600; ANNOT 1493336; ANNOT 1493336; CDNA ID no. 23458190; ANNOT 1522260; ANNOT 1522260; ANNOT 1527806; ANNOT 1527806; CDNA ID no. 23477523; ANNOT 1443651; ANNOT 1443651; ANNOT 1451622; ANNOT 1451622; ANNOT 1455533; ANNOT 1455533; CDNA ID no. 23503364; CDNA ID no. 23544026; ANNOT 1508925; ANNOT 1508925; ANNOT 1531291; ANNOT 1531291; CDNA ID no. 23640482; ANNOT 1446359; ANNOT 1446359; ANNOT 1464743; ANNOT 1464743; ANNOT 1438865; ANNOT 1438865; CDNA ID no. 24374230; ANNOT 1464743; ANNOT 1464743; | 380; 381; 382; 445; 446; 447; 854; 855; 856; 857; 858; 1364; 1365; 1366; 1367; 1368; 1383; 1384; 1385; 1386; 1387; 1388; 1389; 1390; 1391; 1392; 1393; 1394; 1395; 1396; 1397; 1430; 1431; 1432; 1433; 1434; 1455; 1456; 1457; 1458; 1459; 1467; 1468; 1469; 1470; 1471; 1472; 1473; 1474; 1475; 1826; 1827; 1828; 1829; 1830; 1887; 1888; 1889; 1890; 1891; 1962; 1963; 1964; 1965; 1966; 1967; 1968; 1969; 1970; 1971; 1972; 1973; 1974; 1975; 2644; 2645; 2646; 2647; 2648; 2697; 2698; 2699; 2700; 2701; 3009; 3010; 3011; 3012; 3013; 3043; 3044; 3045; 3197; 3198; 3199; 3260; 3261; 3262; 3263; 3264; 3265; 3266; 3377; 3378; 3379; 3380; 3381; 3382; 3383; 3384; 3385; 3386; 3387; 3520; 3521; 3522; 3523; 3524; 3525; 3526; 3527; 3528; 3546; 3547; 3548; 3549; 3550; 3551; 3552; 3553; 3554; 3563; 3564; 3565; 3566; 3567; 3568; 3569; 3570; 3571; 3572; 3573; 3574; 3594; 3595; 3596; 3597; 3598; 3681; 3797; 3798; 3799; 3816; 3817; 3818; 3819; 3820; 3835; 3836; 3837; 3838; 3839; 3869; 3870; 3871; |
| WHOLE PLANT | Composition | Activates expression of the gene endogenous to the AtDXPR (SEQ ID NO 4086) regulatory region | Overexpression of the regulatory protein is able to promote the expression of the gene operably linked to the AtDXPR (SEQ ID NO | Useful for modulating Terpenoid Biosynthesis | CLONE ID no. 6066; ANNOT 1458359; ANNOT 1458359; ANNOT 1517940; ANNOT 1517940; CLONE ID no. 8788; ANNOT 1474018; ANNOT 1474018; ANNOT 1464628; ANNOT 1464628; CLONE ID no. 12997; ANNOT 1483367; ANNOT 1483367; ANNOT 1483367; ANNOT 1483367; ANNOT 1474088; ANNOT 1474088; CLONE ID no. 27793; ANNOT 1517449; ANNOT 1517449; ANNOT 1512061; ANNOT 1512061; CLONE ID no. 34060; ANNOT 1507094; ANNOT 1507094; ANNOT 1535523; ANNOT 1535523; ANNOT 1490409; ANNOT 1490409; ANNOT 1535523; CLONE ID no. 34406; ANNOT 1437614; ANNOT 1437614; CLONE ID no. 36272; ANNOT 1501426; ANNOT 1501426; ANNOT 1513277; ANNOT 1513277; ANNOT 1469342; ANNOT 1469342; | 261; 262; 263; 264; 265; 266; 267; 380; 381; 382; 523; 524; 525; 526; 527; 1070; 1071; 1072; 1073; 1074; 1333; 1334; 1335; 1336; 1337; 1369; 1370; 1371; 1372; 1373; 1374; 1375; 1493; 1494; 1495; 1496; 1497; 1498; 1499; |

TABLE 1-continued

| Tissue | Phenotype Category | Phenotype | Phenotype Description | Applications | Ceres ID | SEQ ID NO |
|---|---|---|---|---|---|---|
| | | | 4086) regulatory region | | ANNOT 1470275; ANNOT 1470275; CLONE ID no. 37792; ANNOT 1467441; ANNOT 1467441; ANNOT 1473092; ANNOT 1473092; ANNOT 1476838; ANNOT 1476838; CLONE ID no. 38950; ANNOT 1528409; ANNOT 1528409; ANNOT 1526895; ANNOT 1526895; ANNOT 1453647; ANNOT 1453647; CLONE ID no. 42713; ANNOT 1477897; ANNOT 1477897; ANNOT 1480898; ANNOT 1480898; CLONE ID no. 99519; ANNOT 1520166; ANNOT 1520166; ANNOT 1519131; ANNOT 1519131; ANNOT 1501805; ANNOT 1501805; CLONE ID no. 106078; ANNOT 1469354; ANNOT 1469354; ANNOT 1522753; ANNOT 1522753; ANNOT 1488939; ANNOT 1488939; CLONE ID no. 108509; ANNOT 1469082; ANNOT 1469082; ANNOT 1522474; ANNOT 1522474; CLONE ID no. 115924; ANNOT 1453127; ANNOT 1453127; ANNOT 1506261; ANNOT 1506261; ANNOT 1480332; ANNOT 1480332; ANNOT 1454197; ANNOT 1454197; CLONE ID no. 117089; ANNOT 1471301; ANNOT 1471301; CLONE ID no. 154718; ANNOT 1457453; ANNOT 1457453; CLONE ID no. 207419; ANNOT 1517208; ANNOT 1517208; CLONE ID no. 208303; ANNOT 1477838; ANNOT 1477838; CLONE ID no. 225321; ANNOT 1504670; ANNOT 1504670; ANNOT 1451585; ANNOT 1451585; CLONE ID no. 237356; ANNOT 1480939; ANNOT 1480939; CLONE ID no. 272716; ANNOT 1497642; ANNOT 1497642; ANNOT 1471648; ANNOT 1471648; CLONE ID no. 283597; ANNOT 1482074; ANNOT 1482074; ANNOT 1453923; ANNOT 1453923; CLONE ID no. 304523; ANNOT 1445647; ANNOT 1445647; ANNOT 1448043; ANNOT 1448043; ANNOT 1438053; ANNOT 1438053; CLONE ID no. 306497; ANNOT 1529923; ANNOT 1529923; ANNOT 1440964; ANNOT 1440964; ANNOT 1493847; ANNOT 1493847; ANNOT 1533800; ANNOT 1533800; CLONE ID no. 389585; ANNOT 1500154; ANNOT 1500154; ANNOT 534311; ANNOT 1440272; ANNOT 1440272; ANNOT 1474707; ANNOT 1474707; CDNA ID no. 1653045; ANNOT 1463563; ANNOT 1463563; CDNA ID no. 23486285; ANNOT 1452123; ANNOT 1452123; CDNA ID no. 23515088; ANNOT 1462217; ANNOT 1462217; ANNOT 1535433; ANNOT 1535433; ANNOT 1475615; ANNOT 1475615; CDNA ID no. 23522373; ANNOT 1538994; ANNOT 1538994; ANNOT 1447080; ANNOT 1447080; CDNA ID no. 23529806; ANNOT 1443631; ANNOT 1443631; CDNA ID no. 23544992; ANNOT 1454621; ANNOT 1454621; CDNA ID no. 23651543; ANNOT 1447411; ANNOT 1447411; CDNA ID no. 24374230; ANNOT 1464743; ANNOT 1464743; | 1662; 1663; 1664; 1665; 1666; 1667; 1668; 1811; 1812; 1813; 1814; 1815; 1816; 1817; 2040; 2041; 2042; 2043; 2044; 2135; 2136; 2137; 2138; 2139; 2140; 2141; 2255; 2256; 2257; 2258; 2259; 2260; 2261; 2293; 2294; 2295; 2296; 2297; 2361; 2362; 2363; 2364; 2365; 2366; 2367; 2368; 2369; 2404; 2405; 2406; 2577; 2578; 2579; 2635; 2636; 2637; 2641; 2642; 2643; 2660; 2661; 2662; 2663; 2664; 2715; 2716; 2717; 2821; 2822; 2823; 2824; 2825; 2833; 2834; 2835; 2836; 2837; 2877; 2878; 2879; 2880; 2881; 2882; 2883; 2893; 2894; 2895; 2896; 2897; 2898; 2899; 2900; 2901; 2991; 2992; 2993; 3093; 3094; 3095; 3096; 3097; 3552; 3553; 3554; 3604; 3605; 3606; 3717; 3718; 3719; 3720; 3721; 3722; 3723; 3761; 3762; 3763; 3764; 3765; 3778; 3779; 3780; 3810; 3811; 3812; 3840; 3841; 3842; 3869; 3870; 3871; |
| WHOLE PLANT | Composition | Activates expression of the gene endogenous to the AtFPPS (SEQ ID NO 4088) regulatory region and/or the AtHMGR(SEQ ID NO 4107) regulatory region. | Overexpression of the regulatory protein is able to promote the expression of the gene operably linked to the AtFPPS (SEQ ID NO 4088) regulatory region and/or the AtHMGR(SEQ ID NO 4107) regulatory region. | Useful for modulating Terpenoid Biosynthesis | CLONE ID no. 42960; ANNOT 1481711; ANNOT 1481711; ANNOT 1446703; CLONE ID no. 36323; ANNOT 1491629; ANNOT 1491629; ANNOT 1531927; ANNOT 1531927; ANNOT 1507861; ANNOT 1507861; CLONE ID no. 374674; ANNOT 1522299; ANNOT 1522299; ANNOT 1527718; ANNOT 1527718; CLONE ID no. 471089; ANNOT 1531777; ANNOT 1531777; ANNOT 1508033; ANNOT 1508033; CLONE ID no. 533314; ANNOT 1528846; ANNOT 1528846; ANNOT 1538329; ANNOT 1538329; CLONE ID no. 556734; ANNOT 1495750; ANNOT 1495750; ANNOT 1522920; ANNOT 1522920; ANNOT 1469532; ANNOT 1469532; ANNOT 1488767; ANNOT 1488767; ANNOT 1542198; ANNOT 1542198; ANNOT 1452612; ANNOT 1452612; ANNOT 1459467; ANNOT 1459467; ANNOT 1442831; ANNOT 1442831; ANNOT 1516688; ANNOT 1516688; ANNOT 1463396; CDNA ID no. 23492765; ANNOT 1521278; ANNOT 1521278; ANNOT 1467911; ANNOT 1467911; | 2051; 2052; 2053; 2054; 2055; 2947; 2948; 2949; 2950; 2951; 2952; 2953; 2981; 2982; 2983; 2984; 2985; 3009; 3010; 3011; 3012; 3013; 3076; 3077; 3078; 3079; 3080; 3200; 3201; 3202; 3203; 3204; 3205; 3206; 3207; 3208; 3209; 3210; 3211; 3212; 3213; 3214; 3215; 3216; 3217; 3218; 3219; 3220; 3607; 3608; 3609; 3610; 3611; |
| WHOLE PLANT | Composition | Activates | Overexpression | Useful for | CLONE ID no. 7805; ANNOT 1518351; ANNOT 1518351; ANNOT 1475331; | 333; 334; 335; 336; 337; |

| Tissue | Phenotype Category | Phenotype | Phenotype Description | Applications | Ceres ID | SEQ ID NO |
|---|---|---|---|---|---|---|
| | | | expression of the gene endogenous to the AtHMGS (SEQ ID NO 4087) regulatory region | modulating Terpenoid Biosynthesis | ANNOT 1475331; CLONE ID no. 13930; ANNOT 1475265; ANNOT 1455046; ANNOT 1455046; CLONE ID no. 14234; ANNOT 1502448; ANNOT 1502448; ANNOT 1498406; ANNOT 1498406; ANNOT 1441275; ANNOT 1441275; ANNOT 1445426; ANNOT 1445426; CLONE ID no. 17632; ANNOT 1474847; ANNOT 1474847; ANNOT 1507835; ANNOT 1507835; CLONE ID no. 19340; ANNOT 1524357; ANNOT 1524357; ANNOT 1497053; ANNOT 1497053; ANNOT 1500296; ANNOT 1500296; CLONE ID no. 26867; ANNOT 1486918; ANNOT 1486918; CLONE ID no. 29637; ANNOT 1458617; ANNOT 1458617; ANNOT 1464333; ANNOT 1464333; CLONE ID no. 31894; ANNOT 1478160; ANNOT 1478160; CLONE ID no. 35786; ANNOT 1447278; ANNOT 1447278; CLONE ID no. 38950; ANNOT 1528409; ANNOT 1528409; ANNOT 1526895; ANNOT 1526895; ANNOT 1453647; ANNOT 1453647; CLONE ID no. 39279; ANNOT 1525349; ANNOT 1525349; ANNOT 1445751; ANNOT 1445751; ANNOT 1498733; ANNOT 1498733; CLONE ID no. 98140; ANNOT 1518036; ANNOT 1518036; ANNOT 1511508; ANNOT 1511508; ANNOT 1464717; ANNOT 1464717; CLONE ID no. 99075; ANNOT 1490832; ANNOT 1490832; ANNOT 1501068; ANNOT 1501068; ANNOT 1438021; ANNOT 1438021; CLONE ID no. 158155; ANNOT 1446954; ANNOT 1446954; ANNOT 1514228; ANNOT 1514228; CLONE ID no. 333753; ANNOT 1442401; ANNOT 1442401; ANNOT 1506142; ANNOT 1506142; CLONE ID no. 335471; ANNOT 1514745; ANNOT 1514745; ANNOT 1493080; ANNOT 1493080; ANNOT 1461474; ANNOT 1461474; ANNOT 1440205; ANNOT 1440205; ANNOT 1501185; ANNOT 1501185; ANNOT 1437922; ANNOT 1437922; CLONE ID no. 362309; ANNOT 1539865; ANNOT 1539865; CLONE ID no. 674157; ANNOT 1469521; ANNOT 1469521; ANNOT 1488782; ANNOT 1488782; ANNOT 1542209; ANNOT 1542209; ANNOT 1492433; ANNOT 1492433; ANNOT 1439568; ANNOT 1439568; CDNA ID no. 2999012; ANNOT 2345742; ANNOT 1449879; ANNOT 1449879; CDNA ID no. 23500996; ANNOT 1459998; ANNOT 1459998; ANNOT 1513263; ANNOT 1513263; CDNA ID no. 23509939; ANNOT 1527683; ANNOT 1527683; CDNA ID no. 2354461; ANNOT 1541623; ANNOT 1541623; ANNOT 1509108; ANNOT 1509108; CDNA ID no. 23557940; ANNOT 1446018; ANNOT 1446018; | 577; 578; 579; 580; 581; 594; 595; 596; 597; 598; 599; 600; 601; 602; 695; 696; 697; 698; 699; 755; 756; 757; 758; 759; 760; 761; 1040; 1041; 1042; 1146; 1147; 1148; 1149; 1150; 1198; 1199; 1200; 1484; 1485; 1486; 1811; 1812; 1813; 1814; 1815; 1816; 1817; 1831; 1832; 1833; 1834; 1835; 1836; 1837; 2111; 2112; 2113; 2114; 2115; 2116; 2117; 2123; 2124; 2125; 2126; 2127; 2128; 2129; 2606; 2607; 2608; 2609; 2610; 2924; 2925; 2926; 2927; 2928; 2934; 2935; 2936; 2937; 2938; 2939; 2940; 2941; 2942; 2943; 2944; 2945; 2946; 2978; 2979; 2980; 3338; 3339; 3340; 3341; 3342; 3343; 3344; 3506; 3507; 3508; 3509; 3510; 3627; 3628; 3629; 3661; 3662; 3663; 3664; 3665; 3709; 3710; 3711; 3800; 3801; 3802; 3803; 3804; 3832; 3833; 3834; |
| WHOLE PLANT | Composition | Activates expression of the gene endogenous to the AtPES (SEQ ID NO 4085) regulatory region | Overexpression of the regulatory protein is able to promote the expression of the gene operably linked to the AtPES (SEQ ID NO 4085) regulatory region | Useful for modulating Terpenoid Biosynthesis | CLONE ID no. 7201; ANNOT 1531932; ANNOT 1531932; ANNOT 1454684; CLONE ID no. 10375; ANNOT 1449163; ANNOT 1449163; CLONE ID no. 92102; ANNOT 1484557; ANNOT 1484557; ANNOT 1438401; ANNOT 1438401; CLONE ID no. 125922; ANNOT 1450377; ANNOT 1450377; ANNOT 1438401; ANNOT 1514052; ANNOT 1514052; CLONE ID no. 208303; ANNOT 1477838; ANNOT 1477838; CLONE ID no. 316658; ANNOT 1470444; ANNOT 1470444; CLONE ID no. 331626; ANNOT 1479649; ANNOT 1479649; CLONE ID no. 336888; ANNOT 1449337; ANNOT 1449337; ANNOT 1498512; ANNOT 1498512; ANNOT 1517165; ANNOT 1517165; ANNOT 1539315; ANNOT 1539315; ANNOT 1463865; ANNOT 1463865; ANNOT 1502340; ANNOT 1502340; ANNOT 1512274; ANNOT 1512274; ANNOT 1459009; ANNOT 1459009; ANNOT 1445529; ANNOT 1445529; ANNOT 1485901; ANNOT 1485901; CLONE ID no. 968026; ANNOT 1473516; ANNOT 1473516; ANNOT 1526929; ANNOT 1526929; ANNOT 1513366; ANNOT 1513366; ANNOT 1460097; ANNOT 1460097; ANNOT 1459838; ANNOT 1459838; ANNOT 1463865; ANNOT 1474764; ANNOT 1474764; ANNOT 1453555; ANNOT 1453555; ANNOT 1512274; ANNOT 1448253; ANNOT 1448253; ANNOT 1437849; ANNOT 1437849; ANNOT 1443270; ANNOT 1443270; ANNOT 1496190; ANNOT 1496190; CDNA ID no. 23480178; ANNOT 1529639; ANNOT 1529639; ANNOT 1507454; ANNOT 1507454; CDNA ID no. 23497949; ANNOT 1452863; ANNOT 1452863; ANNOT 1442568; ANNOT 1442568; | 320; 321; 322; 323; 324; 431; 432; 433; 2056; 2057; 2058; 2059; 2060; 2507; 2508; 2509; 2510; 2511; 2641; 2642; 2643; 2902; 2903; 2904; 2916; 2917; 2918; 2954; 2955; 2956; 2957; 2958; 2959; 2960; 2961; 2962; 2963; 2964; 2965; 2966; 2967; 2968; 2969; 2970; 2971; 2972; 2973; 2974; 3391; 3392; 3393; 3394; 3395; 3396; 3397; 3398; 3399; 3400; 3401; 3402; 3403; 3404; 3405; 3406; 3407; 3408; 3409; 3410; 3411; 3412; 3413; 3599; 3600; 3601; 3602; 3603; 3630; |

| Tissue | Phenotype Category | Phenotype | Phenotype Description | Applications | Ceres ID | SEQ ID NO |
|---|---|---|---|---|---|---|
| | | | | | 1442568; ANNOT 1486734; ANNOT 1468322; ANNOT 1468322; ANNOT 1473531; ANNOT 1473531; CDNA ID no. 2303138; ANNOT 1507158; ANNOT 1507158; ANNOT 1454014; ANNOT 1454014; CDNA ID no. 23521525; ANNOT 1491996; ANNOT 1491996; ANNOT 1439136; ANNOT 1439136; CDNA ID no. 23544687; ANNOT 1517998; ANNOT 1517998; ANNOT 1458313; ANNOT 1458313; CDNA ID no. 23653450; ANNOT 1441536; ANNOT 1441536; | 3631; 3632; 3633; 3634; 3635; 3636; 3637; 3638; 3639; 3640; 3673; 3674; 3675; 3676; 3677; 3756; 3757; 3758; 3759; 3760; 3805; 3806; 3807; 3808; 3809; 3843; 3844; 3845; |
| WHOLE PLANT | Composition | Activates expression of the gene endogenous to the AtROX7 (SEQ ID NO 4098) regulatory region | Overexpression of the regulatory protein is able to promote the expression of the gene operably linked to the AtROX7 (SEQ ID NO 4098) regulatory region | Useful for modulating Alkaloid Biosynthesis | CDNA ID no. 24373996; ANNOT 1534046; ANNOT 1534046; ANNOT 1480559; ANNOT 1480559; | 3864; 3865; 3866; 3867; 3868; |
| WHOLE PLANT | Composition | Activates expression of the gene endogenous to the AtSQS1 (SEQ ID NO 4093) regulatory region | Overexpression of the regulatory protein is able to promote the expression of the gene operably linked to the AtSQS1 (SEQ ID NO 4093) regulatory region | Useful for modulating Terpenoid Biosynthesis | CLONE ID no. 20769; ANNOT 1443644; ANNOT 1443644; | 815; 816; 817; |
| WHOLE PLANT | Composition | Activates expression of the gene endogenous to the AtSS1 (SEQ ID NO 4101) regulatory region | Overexpression of the regulatory protein is able to promote the expression of the gene operably linked to the AtSS1 (SEQ ID NO 4101) regulatory region | Useful for modulating Alkaloid Biosynthesis | CLONE ID no. 11938; ANNOT 1442401; ANNOT 1442401; ANNOT 1506142; ANNOT 1506142; CDNA ID no. 12676498; ANNOT 1525070; ANNOT 1525070; ANNOT 1471655; ANNOT 1471655; ANNOT 1525069; ANNOT 1471654; ANNOT 1471654; CDNA ID no. 23539673; ANNOT 1472261; ANNOT 1472261; ANNOT 1445638; ANNOT 1445638; ANNOT 1483570; ANNOT 1483570; CDNA ID no. 24365511; ANNOT 1466223; ANNOT 1466223; ANNOT 1494350; ANNOT 1494350; | 497; 498; 499; 500; 501; 3520; 3521; 3522; 3523; 3524; 3525; 3526; 3527; 3528; 3790; 3791; 3792; 3793; 3794; 3795; 3796; 3859; 3860; 3861; 3862; 3863; |
| WHOLE PLANT | Composition | Activates expression of the gene endogenous to the AtSS3 (SEQ ID NO 4102) regulatory region and/or the AtROX7(SEQ | Overexpression of the regulatory protein is able to promote the expression of the gene operably linked to the AtSS3 (SEQ ID NO 4102) regulatory region | Useful for modulating Alkaloid Biosynthesis | CLONE ID no. 109490; ANNOT 1443194; ANNOT 1505312; ANNOT 1505312; CLONE ID no. 115946; ANNOT 1458342; ANNOT 1458342; CLONE ID no. 223419; ANNOT 1485423; ANNOT 1485423; CLONE ID no. 230582; ANNOT 1502431; ANNOT 1502431; CLONE ID no. 306497; ANNOT 1529923; ANNOT 1529923; ANNOT 1440964; ANNOT 1440964; ANNOT 1493847; ANNOT 1493847; ANNOT 1533800; ANNOT 1533800; CLONE ID no. 325800; ANNOT 1517851; ANNOT 1517851; ANNOT 1464534; ANNOT 1464534; ANNOT 1511678; ANNOT 1511678; ANNOT 1458433; ANNOT 1458433; ANNOT 1529923; ANNOT 1449885; CLONE ID no. 599633; ANNOT 1449885; CLONE ID no. 942964; ANNOT 1440785; ANNOT 1440785; CLONE ID no. 982869; ANNOT | 2298; 2299; 2300; 2301; 2302; 2370; 2371; 2372; 2649; 2650; 2651; 2702; 2703; 2704; 2893; 2894; 2895; 2896; 2897; 2898; 2899; 2900; 2901; 2905; 2906; 2907; 2908; 2909; 2910; 2911; 2912; 2913; 2914; 2915; 3270; 3271; 3272; 3364; 3365; 3366; |

TABLE 1-continued

| Tissue | Phenotype Category | Phenotype | Phenotype Description | Applications | Ceres ID | SEQ ID NO |
|---|---|---|---|---|---|---|
| | | ID NO 4098) regulatory region. | region and/or the AtROX7(SEQ ID NO 4098) regulatory region. | | 1458219; ANNOT 1458219; ANNOT 1464757; CDNA ID no. 23461192; ANNOT 1504431; ANNOT 1504431; ANNOT 1510151; ANNOT 1510151; ANNOT 1451363; ANNOT 1451363; ANNOT 1456957; ANNOT 1456957; ANNOT 1481026; ANNOT 1481026; CDNA ID no. 23467433; ANNOT 1488031; ANNOT 1488031; CDNA ID no. 23467847; ANNOT 1469679; ANNOT 1469679; ANNOT 1479180; ANNOT 1479180; CDNA ID no. 23493156; CDNA ID no. 23498294; ANNOT 1465158; ANNOT 1465158; ANNOT 23498685; ANNOT 1460742; ANNOT 1460742; CDNA ID no. 23502516; ANNOT 1449874; ANNOT 1449874; ANNOT 1492655; ANNOT 1492655; ANNOT 1439788; ANNOT 1439788; CDNA ID no. 2350138; ANNOT 1507158; ANNOT 1507158; ANNOT 1454014; ANNOT 1454014; CDNA ID no. 23503210; ANNOT 1455082; ANNOT 1455082; CDNA ID no. 23503364; CDNA ID no. 23503971; ANNOT 1452812; ANNOT 1452812; ANNOT 1442627; ANNOT 1442627; CDNA ID no. 23515088; ANNOT 1462217; ANNOT 1462217; ANNOT 1535433; ANNOT 1535433; ANNOT 1475615; ANNOT 1475615; CDNA ID no. 23515246; ANNOT 1539565; ANNOT 1539565; ANNOT 1486151; ANNOT 1486151; ANNOT 1497018; ANNOT 1497018; ANNOT 1444071; ANNOT 1444071; ANNOT 1497013; ANNOT 1497013; ANNOT 1444066; ANNOT 1444066; CDNA ID no. 23516818; ANNOT 1444427; ANNOT 1444427; CDNA ID no. 23522373; ANNOT 1538994; ANNOT 1538994; ANNOT 1447080; ANNOT 1447080; CDNA ID no. 23245514; ANNOT 1459467; ANNOT 1459467; ANNOT 1516688; ANNOT 1516688; ANNOT 1488767; ANNOT 1488767; ANNOT 1495750; ANNOT 1495750; ANNOT 1452612; ANNOT 1452612; CDNA ID no. 23529931; ANNOT 1520459; ANNOT 1520459; ANNOT 1494925; ANNOT 1494925; CDNA ID no. 23544992; ANNOT 1454621; ANNOT 1454621; CDNA ID no. 23553534; ANNOT 1469045; ANNOT 1469045; CDNA ID no. 23653450; ANNOT 1441536; ANNOT 1441536; CDNA ID no. 23655935; ANNOT 1459700; ANNOT 1459700; CDNA ID no. 23660631; ANNOT 1457646; ANNOT 1457646; ANNOT 1518640; ANNOT 1518640; CDNA ID no. 23660778; ANNOT 1510945; ANNOT 1510945; ANNOT 1465368; ANNOT 1465368; ANNOT 1459467; ANNOT 1466223; ANNOT 1466223; ANNOT 1466223; ANNOT 1494350; ANNOT 1494350; CDNA ID no. 24365511; ANNOT 24380616; ANNOT 1445708; ANNOT 1445708; | 3414; 3415; 3416; 3417; 3418; 3575; 3576; 3577; 3578; 3579; 3580; 3581; 3582; 3583; 3584; 3585; 3586; 3587; 3588; 3589; 3590; 3591; 3592; 3593; 3612; 3646; 3647; 3648; 3649; 3650; 3651; 3666; 3667; 3668; 3669; 3670; 3671; 3672; 3673; 3674; 3675; 3676; 3677; 3678; 3679; 3680; 3681; 3682; 3683; 3684; 3685; 3686; 3717; 3718; 3719; 3720; 3721; 3722; 3723; 3724; 3725; 3726; 3727; 3728; 3729; 3730; 3731; 3732; 3733; 3734; 3735; 3736; 3745; 3746; 3747; 3761; 3762; 3763; 3764; 3765; 3767; 3768; 3769; 3770; 3771; 3772; 3773; 3774; 3775; 3776; 3777; 3781; 3782; 3783; 3784; 3785; 3810; 3811; 3812; 3826; 3827; 3828; 3843; 3844; 3845; 3846; 3847; 3848; 3849; 3850; 3851; 3852; 3853; 3854; 3855; 3856; 3857; 3858; 3859; 3860; 3861; 3862; 3863; 3872; 3873; 3874; |
| WHOLE PLANT | Composition | Activates expression of the gene endogenous to the EcBBE (SEQ ID NO 4099) regulatory region and/or the EcNMCH3(SEQ ID NO 4100) regulatory region. | Overexpression of the regulatory protein is able to promote the expression of the gene operably linked to the EcBBE (SEQ ID NO 4099) regulatory region and/or the EcNMCH3(SEQ ID NO 4100) regulatory region. | Useful for modulating Alkaloid Biosynthesis | CLONE ID no. 4228; ANNOT 1504263; ANNOT 1504263; CLONE ID no. 6493; ANNOT 1446643; ANNOT 1446643; ANNOT 1492373; ANNOT 1492373; CLONE ID no. 7559; ANNOT 1469241; ANNOT 1469241; CLONE ID no. 7805; ANNOT 1518351; ANNOT 1518351; ANNOT 1475331; ANNOT 1475331; CLONE ID no. 8788; ANNOT 1474018; ANNOT 1474018; CLONE ID no. 18903; ANNOT 1490030; ANNOT 1490030; CLONE ID no. 21075; ANNOT 1520467; ANNOT 1520467; ANNOT 1494915; ANNOT 1494915; CLONE ID no. 21604; ANNOT 1473854; ANNOT 1473854; ANNOT 1521997; ANNOT 1521997; ANNOT 1468633; ANNOT 1468633; CLONE ID no. 28451; ANNOT 1486525; ANNOT 1486525; ANNOT 1443820; ANNOT 1443820; CLONE ID no. 32791; ANNOT 1540248; ANNOT 1540248; CLONE ID no. 33498; ANNOT 1511064; ANNOT 1511064; ANNOT 1518490; ANNOT 1518490; CLONE ID no. 34167; ANNOT 1538733; ANNOT 1538733; ANNOT 1499810; ANNOT 1499810; ANNOT 1485323; ANNOT 1485323; CLONE ID no. 38529; ANNOT 1511049; ANNOT 1511049; ANNOT 1457826; ANNOT 1457826; ANNOT 1530660; ANNOT 1530660; ANNOT 1518508; ANNOT 1518508; CLONE ID no. 39893; ANNOT 1455308; ANNOT 1455308; CLONE ID no. 39922; ANNOT 1485544; ANNOT 1485544; ANNOT 1447051; ANNOT 1447051; ANNOT 1482074; ANNOT 1482074; CLONE ID no. 40501; ANNOT 40501; ANNOT | 201; 202; 203; 300; 301; 302; 303; 304; 325; 326; 327; 333; 334; 335; 336; 337; 380; 381; 382; 732; 733; 734; 832; 833; 834; 835; 836; 847; 848; 849; 850; 851; 852; 853; 1091; 1092; 1093; 1094; 1095; 1255; 1256; 1257; 1282; 1283; 1284; 1285; 1286; 1343; 1344; 1345; 1346; 1347; 1348; 1349; 1754; 1755; 1756; 1757; 1758; 1759; 1760; 1887; 1888; 1889; 1890; 1891; 1892; 1893; 1894; 1895; 1896; 1907; 1908; 1909; 1910; 1911; 1930; 1931; |

TABLE 1-continued

| Tissue | Phenotype Category | Phenotype | Phenotype Description | Applications | Ceres ID | SEQ ID NO |
|---|---|---|---|---|---|---|
| | | Activates expression of the gene endogenous to the PsBBE (SEQ ID NO 4103) regulatory region | Overexpression of the regulatory protein is able to promote the expression of the gene operably linked to the PsBBE (SEQ ID NO 4103) regulatory region | Useful for modulating Alkaloid Biosynthesis | 1453923; CLONE ID no. 40729; ANNOT 1481678; ANNOT 1481678; CLONE ID no. 42530; ANNOT 1490273; ANNOT 1490273; ANNOT 1446198; ANNOT 1446198; ANNOT 1455209; ANNOT 1530603; ANNOT 1530603; CLONE ID no. 42654; ANNOT 1454375; ANNOT 1454375; CLONE ID no. 95453; ANNOT 1460836; ANNOT 1460836; ANNOT 1450324; CLONE ID no. 100319; ANNOT 1503141; ANNOT 1450324; ANNOT 1521524; ANNOT 1521524; CLONE ID no. 108109; CLONE ID no. 120302; ANNOT 1450548; ANNOT 1450548; ANNOT 1460633; ANNOT 1460633; CLONE ID no. 1480232; ANNOT 1480232; ANNOT 1478804; ANNOT 1478804; CLONE ID no. 123105; ANNOT 1498819; ANNOT 1498819; CLONE ID no. 152633; ANNOT 1469954; ANNOT 1469954; CLONE ID no. 158734; ANNOT 1477956; ANNOT 1477956; CLONE ID no. 236747; ANNOT 1519379; CLONE ID no. 244916; ANNOT 1510619; CLONE ID no. 297374; ANNOT 1510619; ANNOT 1510619; ANNOT 1496506; CLONE ID no. 325800; ANNOT 1517851; ANNOT 1517851; ANNOT 1464534; ANNOT 1464534; ANNOT 1511678; ANNOT 1511678; ANNOT 1458433; ANNOT 1458433; ANNOT 1529923; ANNOT 1529923; CLONE ID no. 531768; ANNOT 1456366; ANNOT 1456366; ANNOT 1450869; ANNOT 1450869; ANNOT 1447944; ANNOT 1447944; CLONE ID no. 533314; ANNOT 1528846; ANNOT 1528846; ANNOT 1538329; ANNOT 1538329; CLONE ID no. 534311; ANNOT 1440272; ANNOT 1440272; ANNOT 1474707; ANNOT 1474707; CLONE ID no. 534367; ANNOT 1479391; ANNOT 1479391; ANNOT 1469954; ANNOT 1469954; ANNOT 1447025; ANNOT 1447025; ANNOT 1558933; ANNOT 1558933; ANNOT 1485513; ANNOT 1485513; CLONE ID no. 942964; ANNOT 1440785; ANNOT 1440785; CLONE ID no. 982869; ANNOT 1458219; ANNOT 1458219; ANNOT 1464757; ANNOT 1464757; CDNA ID no. 23368554; ANNOT 1444863; ANNOT 1444863; CDNA ID no. 23486285; ANNOT 1452123; ANNOT 1452123; CDNA ID no. 23492765; ANNOT 1521278; ANNOT 1521278; ANNOT 1467911; ANNOT 1467911; CDNA ID no. 2499742; ANNOT 1449879; ANNOT 1449879; CDNA ID no. 23499964; ANNOT 1441358; ANNOT 1441358; ANNOT 1457434; ANNOT 1457434; ANNOT 1514509; ANNOT 1514509; ANNOT 1461236; ANNOT 1461236; CDNA ID no. 23503364; CDNA ID no. 23505323; ANNOT 1473621; ANNOT 1473621; ANNOT 1521779; ANNOT 1521779; CDNA ID no. 23516633; ANNOT 1524883; ANNOT 1524883; ANNOT 1499918; ANNOT 1499918; ANNOT 1471472; ANNOT 1471472; CDNA ID no. 23523867; CDNA ID no. 23544992; ANNOT 1454621; ANNOT 1454621; | 1932; 2021; 2022; 2023; 2024; 2025; 2026; 2027; 2028; 2029; 2037; 2038; 2039; 2085; 2086; 2087; 2088; 2089; 2191; 2192; 2193; 2194; 2195; 2292; 2466; 2467; 2468; 2469; 2470; 2471; 2472; 2473; 2474; 2484; 2485; 2486; 2571; 2572; 2573; 2619; 2620; 2621; 2712; 2713; 2714; 2725; 2726; 2727; 2869; 2870; 2871; 2872; 2873; 2905; 2906; 2907; 2908; 2909; 2910; 2911; 2912; 2913; 2914; 2915; 3069; 3070; 3071; 3072; 3073; 3074; 3075; 3076; 3077; 3078; 3079; 3080; 3093; 3094; 3095; 3096; 3097; 3098; 3099; 3100; 3101; 3102; 3103; 3104; 3105; 3106; 3107; 3108; 3364; 3365; 3366; 3414; 3415; 3416; 3417; 3418; 3560; 3561; 3562; 3604; 3605; 3606; 3607; 3608; 3609; 3610; 3611; 3627; 3628; 3629; 3652; 3653; 3654; 3655; 3656; 3657; 3658; 3659; 3660; 3681; 3699; 3700; 3701; 3702; 3703; 3738; 3739; 3740; 3741; 3742; 3743; 3744; 3766; 3810; 3811; 3812; |
| WHOLE PLANT | Composition | | | | CLONE ID no. 6397; ANNOT 1486285; ANNOT 1486285; CLONE ID no. 7559; ANNOT 1469241; ANNOT 1469241; CLONE ID no. 7805; ANNOT 1518351; ANNOT 1518351; ANNOT 1475331; ANNOT 1475331; CLONE ID no. 21604; ANNOT 1473854; ANNOT 1473854; ANNOT 1521997; ANNOT 1521997; ANNOT 1468633; ANNOT 1468633; CLONE ID no. 21863; ANNOT 1464854; ANNOT 1464854; ANNOT 1511378; ANNOT 1511378; ANNOT 1454043; ANNOT 1454043; CLONE ID no. 32791; ANNOT 1540248; ANNOT 1540248; CLONE ID no. 35228; ANNOT 1445433; ANNOT 1445433; ANNOT 1498413; ANNOT 1498413; CLONE ID no. 94688; ANNOT 1498587; ANNOT 1498587; ANNOT 1525287; ANNOT 1525287; ANNOT 1525287; CLONE ID no. 208429; ANNOT 1457538; ANNOT 1457538; ANNOT 1510743; ANNOT 1510743; CLONE ID no. 297374; ANNOT 1510619; ANNOT 1510619; ANNOT 1496506; CLONE ID no. 355209; ANNOT 1498695; ANNOT 1498695; CLONE ID no. 480900; ANNOT 1461433; ANNOT 1461433; ANNOT 1438399; ANNOT 1438399; CLONE ID no. 952275; ANNOT 1515625; ANNOT 1484559; ANNOT 1484559; ANNOT 957981; ANNOT 1515625; ANNOT | 290; 291; 292; 325; 326; 327; 333; 334; 335; 336; 337; 847; 848; 849; 850; 851; 852; 853; 866; 867; 868; 869; 870; 871; 872; 1255; 1256; 1257; 1455; 1456; 1457; 1458; 1459; 2071; 2072; 2073; 2074; 2075; 2644; 2645; 2646; 2647; 2648; 2869; 2870; 2871; 2872; 2873; 2975; 2976; 2977; 3043; 3044; 3045; 3367; 3368; 3369; 3370; 3371; 3377; 3378; 3379; 3380; 3381; 3385; |

TABLE 1-continued

| Tissue | Phenotype Category | Phenotype | Phenotype Description | Applications | Ceres ID | SEQ ID NO |
|---|---|---|---|---|---|---|
| | | | | | 1515625; ANNOT 1489205; CLONE ID no. 965028; ANNOT 1438401; ANNOT 1438401; CDNA ID no. 13579142; ANNOT 1522260; ANNOT 1522260; ANNOT 1527806; ANNOT 1527806; CDNA ID no. 2348190; ANNOT 1522260; ANNOT 1522260; ANNOT 1527806; ANNOT 1527806; CDNA ID no. 2350216; ANNOT 1449874; ANNOT 1449874; ANNOT 1492655; ANNOT 1492655; ANNOT 1439788; ANNOT 1439788; | 3386; 3387; 3546; 3547; 3548; 3549; 3550; 3570; 3571; 3572; 3573; 3574; 3666; 3667; 3668; 3669; 3670; 3671; 3672; |
| WHOLE PLANT | Composition | Activates expression of the gene endogenous to the PsHMCOMT2 (SEQ ID NO 4105) regulatory region | Overexpression of the regulatory protein is able to promote the expression of the gene operably linked to the PsHMCOMT2 (SEQ ID NO 4105) regulatory region | Useful for modulating Alkaloid Biosynthesis | CLONE ID no. 11130; ANNOT 1466979; CLONE ID no. 21868; ANNOT 1446703; ANNOT 1446703; CLONE ID no. 35228; ANNOT 1445433; ANNOT 1445433; ANNOT 1498413; ANNOT 1498413; CLONE ID no. 39922; ANNOT 1485544; ANNOT 1485544; ANNOT 1447051; ANNOT 1447051; CLONE ID no. 40729; ANNOT 1481678; ANNOT 1481678; CLONE ID no. 41104; ANNOT 1489751; ANNOT 1489751; ANNOT 1446209; ANNOT 1446209; CLONE ID no. 325800; ANNOT 1517851; ANNOT 1517851; ANNOT 1464534; ANNOT 1464534; ANNOT 1511678; ANNOT 1511678; ANNOT 1458433; ANNOT 1458433; ANNOT 1529923; ANNOT 1529923; CLONE ID no. 471089; ANNOT 1531777; ANNOT 1531777; ANNOT 1508033; CLONE ID no. 480900; ANNOT 1461433; ANNOT 1461433; CLONE ID no. 965028; ANNOT 1460742; ANNOT 1460742; CDNA ID no. 1438401; CDNA ID no. 23498685; ANNOT 1459700; ANNOT 1459700; CDNA ID no. 23523867; CDNA ID no. 23655935; ANNOT 1457646; ANNOT 1457646; ANNOT 1518640; ANNOT 1518640; | 445; 446; 447; 873; 874; 875; 1455; 1456; 1457; 1458; 1459; 1892; 1893; 1894; 1895; 1896; 1930; 1931; 1932; 1962; 1963; 1964; 1965; 1966; 2905; 2906; 2907; 2908; 2909; 2910; 2911; 2912; 2913; 2914; 2915; 3009; 3010; 3011; 3012; 3013; 3043; 3044; 3045; 3385; 3386; 3387; 3649; 3650; 3651; 3766; 3846; 3847; 3848; 3849; 3850; 3851; 3852; 3853; |
| WHOLE PLANT | Composition | Activates expression of the gene endogenous to the PsROMT (SEQ ID NO 4104) regulatory region | Overexpression of the regulatory protein is able to promote the expression of the gene operably linked to the PsROMT (SEQ ID NO 4104) regulatory region | Useful for modulating Alkaloid Biosynthesis | CLONE ID no. 7805; ANNOT 1518351; ANNOT 1518351; ANNOT 1475331; ANNOT 1475331; CLONE ID no. 8788; ANNOT 1474018; ANNOT 1474018; CLONE ID no. 11130; ANNOT 1466979; CLONE ID no. 21863; ANNOT 1443194; ANNOT 1443194; ANNOT 1464854; ANNOT 1464854; ANNOT 1511378; ANNOT 1511378; ANNOT 1454043; ANNOT 1454043; ANNOT 1454043; CLONE ID no. 21868; ANNOT 1446703; ANNOT 1446703; CLONE ID no. 22350; ANNOT 1471704; ANNOT 1471704; CLONE ID no. 33333; ANNOT 1501772; ANNOT 1501772; ANNOT 1519164; ANNOT 1519164; ANNOT 1480076; ANNOT 1480076; ANNOT 1524008; ANNOT 1524008; ANNOT 1480159; ANNOT 1480159; CLONE ID no. 34944; ANNOT 1485544; ANNOT 1485544; ANNOT 1447051; ANNOT 1447051; CLONE ID no. 39893; ANNOT 1530660; ANNOT 1530660; ANNOT 1455308; ANNOT 1455308; CLONE ID no. 42654; ANNOT 1454375; ANNOT 1454375; ANNOT 1443194; ANNOT 1443194; ANNOT 1505312; ANNOT 1505312; CLONE ID no. 297374; ANNOT 1510619; ANNOT 1510619; ANNOT 1496506; ANNOT 1496506; CLONE ID no. 534311; ANNOT 1440272; ANNOT 1440272; ANNOT 1474707; ANNOT 1474707; CLONE ID no. 597609; ANNOT 1538274; ANNOT 1538274; ANNOT 1528771; ANNOT 1528771; ANNOT 1484866; ANNOT 1484866; CLONE ID no. 597624; ANNOT 1464039; ANNOT 1464039; CDNA ID no. 13610509; CDNA ID no. 23640482; ANNOT 1446359; ANNOT 1446359; ANNOT 1438865; ANNOT 1438865; CDNA ID no. 23653450; ANNOT 1441536; ANNOT 1441536; CDNA ID no. 23660631; ANNOT 1457646; ANNOT 1457646; ANNOT 1518640; ANNOT 1518640; | 333; 334; 335; 336; 337; 380; 381; 382; 445; 446; 447; 866; 867; 868; 869; 870; 871; 872; 873; 874; 875; 881; 882; 883; 1268; 1269; 1270; 1271; 1272; 1273; 1274; 1275; 1276; 1277; 1278; 1430; 1431; 1432; 1433; 1434; 1887; 1888; 1889; 1890; 1891; 2037; 2038; 2039; 2298; 2299; 2300; 2301; 2302; 2869; 2870; 2871; 2872; 2873; 3093; 3094; 3095; 3096; 3097; 3260; 3261; 3262; 3263; 3264; 3265; 3266; 3267; 3268; 3269; 3551; 3835; 3836; 3837; 3838; 3839; 3843; 3844; 3845; 3849; 3850; 3851; 3852; 3853; |
| WHOLE PLANT | Stress tolerance | Cold Growth | The plant grows faster at cold temperatures compared to control. | Useful for making plants with increased tolerance to cold stress | CLONE 2083; ANNOT 1441581; ANNOT 1441581; CLONE 4928; ANNOT 1442935; ANNOT 1442935; CLONE 4524; ANNOT 1442935; ANNOT 1466929; CLONE 7822; ANNOT 1446929; ANNOT 1466929; ANNOT 1447816; ANNOT 1447816; ANNOT 1500283; ANNOT 1500283; ANNOT 1511303; ANNOT 1511303; CLONE 19234; ANNOT 1469459; ANNOT 1469459; ANNOT 1542250; ANNOT 1542250; CLONE 33559; ANNOT 1481146; ANNOT 1481146; ANNOT 1481150; ANNOT 1481150; ANNOT 1481138; ANNOT 1485824; ANNOT 1485824; ANNOT 1534622; ANNOT 1534622; CLONE | 87; 88; 89; 204; 205; 206; 212; 213; 214; 338; 339; 340; 341; 342; 343; 344; 750; 751; 752; 753; 754; 1310; 1311; 1312; 1313; 1314; 1315; 1316; 1317; 1318; 1319; 1320; |

TABLE 1-continued

| Tissue | Phenotype Category | Phenotype | Phenotype Description | Applications | Ceres ID | SEQ ID NO |
|---|---|---|---|---|---|---|
| COTYLEDONS | Composition | Cup-shaped | The cotyledons are curled up at the cotyledon margins such that they form a cup or bowl-like shape | Useful for modifying seed structure and composition | 38277; ANNOT 1512884; ANNOT 1512884; CDNA 3653419; ANNOT 1459723; ANNOT 1459723; ANNOT 1516455; ANNOT 1516455; CLONE 13186; ANNOT 1464566; ANNOT 1464566; ANNOT 1458408; ANNOT 1458408; | 1714; 1715; 1716; 3995; 3996; 3997; 3998; 3999; 531; 532; 533; 534; 535; |
| ROSETTE LEAVES | Composition | Glabrous | The trichomes are totally absent. | Useful for making plants with altered chemical composition | CLONE 332; ANNOT-1474923; ANNOT 1474923; | 12; 13; 14; |
| WHOLE PLANT | Composition | High Anthocyanin | The plant is purple in color | Useful for modulating anthocyanin content | CLONE 1610; ANNOT 1454586; ANNOT 1454586; ANNOT 1475043; ANNOT 1475043; ANNOT 1507756; ANNOT 1507756; ANNOT 1469708; ANNOT 1469708; CLONE 6082; ANNOT 1443416; ANNOT 1443416; ANNOT 1505047; ANNOT 1505047; ANNOT 1496339; ANNOT 1496339; CLONE 8633; ANNOT 1527560; ANNOT 1527560; ANNOT 1522449; ANNOT 1522449; CLONE 13263; ANNOT 1470919; ANNOT 1470919; CLONE 13757; ANNOT 1471425; ANNOT 1471425; CLONE 32348; ANNOT 1470719; ANNOT 1470719; ANNOT 1543728; ANNOT 1543728; ANNOT 1482066; ANNOT 1482066; CLONE 32811; ANNOT 1475744; ANNOT 1475744; ANNOT 1454107; ANNOT 1454107; CLONE 36891; ANNOT 1480518; ANNOT 1480518; ANNOT 1442194; ANNOT 1442194; ANNOT 1454127; ANNOT 1454127; ANNOT 1461716; ANNOT 1461716; ANNOT 1440277; ANNOT 1440277; ANNOT 1461415; ANNOT 1461415; ANNOT 1461414; ANNOT 1461414; ANNOT 1447424; ANNOT 1447424; ANNOT 1528127; ANNOT 1528127; ANNOT 1438717; ANNOT 1438717; ANNOT 1440276; ANNOT 1440276; ANNOT 1471425; ANNOT 1442556; ANNOT 1442556; ANNOT 1452873; ANNOT 1452873; ANNOT 1453483; ANNOT 1453483; ANNOT 1473384; ANNOT 1473384; ANNOT 1475808; ANNOT 1475808; CLONE 42925; ANNOT 1462354; ANNOT 1462354; ANNOT 1474708; ANNOT 1474708; ANNOT 1438698; ANNOT 1438698; CLONE 92670; ANNOT 153191; ANNOT 153191; CLONE 101686; ANNOT 1479756; ANNOT 1479756; ANNOT 1540137; ANNOT 1540137; ANNOT 1486722; ANNOT 1486722; CLONE 107311; ANNOT 1480518; ANNOT 1442194; ANNOT 1442194; ANNOT 1454127; ANNOT 1454127; ANNOT 1461414; ANNOT 1461414; ANNOT 1447424; ANNOT 1447424; ANNOT 1447424; ANNOT 1452556; ANNOT 1452873; ANNOT 1452873; ANNOT 1474708; ANNOT 1474708; ANNOT 1474708; CLONE 110454; CLONE 224062; ANNOT 1541034; ANNOT 1541034; CLONE 254065; ANNOT 1485544; ANNOT 1485544; ANNOT 1447051; ANNOT 1447051; ANNOT 1517016; ANNOT 1517016; CLONE 1001432; ANNOT 1475043; ANNOT 1475043; ANNOT 1454586; ANNOT 1454586; ANNOT 1507756; ANNOT 1507756; ANNOT 1469708; | 67; 68; 69; 70; 71; 72; 73; 74; 75; 268; 269; 270; 271; 272; 273; 274; 375; 376; 377; 378; 379; 536; 537; 538; 564; 565; 566; 1219; 1220; 1221; 1222; 1223; 1224; 1225; 1258; 1259; 1260; 1261; 1262; 1548; 1549; 1550; 1551; 1552; 1553; 1554; 1555; 1556; 1557; 1558; 1559; 1560; 1561; 1562; 1563; 1564; 1565; 1566; 1567; 1568; 1569; 1570; 1571; 1572; 1573; 1574; 1575; 1576; 1577; 1578; 1579; 1580; 1581; 1582; 1583; 1584; 2045; 2046; 2047; 2061; 2062; 2063; 2212; 2213; 2214; 2215; 2216; 2217; 2218; 2263; 2264; 2265; 2266; 2267; 2268; 2269; 2270; 2271; 2272; 2273; 2274; 2275; 2276; 2277; 2313; 2652; 2653; 2654; 2731; 2732; 2733; 2734; 2735; 2736; 2737; 3419; 3420; 3421; 3422; 3423; 3424; 3425; 3426; 3427; |
| SEED | Composition | Light Color | The seed is abnormally light in color. | Useful for modifying fiber content in seed | CLONE 38370; ANNOT 1471869; ANNOT 1471869; ANNOT 1448032; ANNOT 1448032; ANNOT 1448031; ANNOT 1448031; ANNOT 1438060; ANNOT 1438060; ANNOT 1438061; ANNOT 1438061; ANNOT 1448030; ANNOT 1448030; ANNOT 1437831; ANNOT 1437831; | 1732; 1733; 1734; 1735; 1736; 1737; 1738; 1739; 1740; 1741; 1742; 1743; 1744; 1745; 1746; |
| WHOLE PLANT | Composition | Metabolic | The plants have | Useful for | CLONE 2121; ANNOT 1500813; ANNOT 1500813; ANNOT 1491102; ANNOT | 90; 91; 92; 93; 94; 902; |

TABLE 1-continued

| Tissue | Phenotype Category | Phenotype | Phenotype Description | Applications | Ceres ID | SEQ ID NO |
|---|---|---|---|---|---|---|
| | | Profiling | altered metabolic profiles. | making plants with enhanced metabolite accumulation | 1491102; CLONE 23439; ANNOT 1461748; ANNOT 1492747; ANNOT 1492747; CLONE 39378; ANNOT 1527229; ANNOT 1473809; ANNOT 1473809; | 903; 904; 905; 906; 1863; 1864; 1865; 1866; 1867; |
| COTYLEDONS | Composition | Other | The plants have a morphological phenotype in cotyledons. | Useful for modifying seed structure and composition | CLONE 13800; ANNOT 1458335; ANNOT 1464663; ANNOT 1464663; | 572; 573; 574; 575; 576; |
| SEED | Composition | Other | The plants have a morphological phenotype in seeds. | Useful for modifying seed content | CLONE 4058; ANNOT 1468992; ANNOT 1468992; ANNOT 1444098; ANNOT 1444098; ANNOT 1474224; ANNOT 1524351; ANNOT 1524351; | 187; 188; 189; 190; 191; 192; 193; 194; 195; |
| SILIQUES | Composition, Yield | Bent | The silique has a sharp bend to it part of the way down the length of the silique; this bend can be as much as approaching 90 degrees | Useful for modifying fruit shape, composition and seed yield | CLONE 35493; ANNOT 1457751; ANNOT 1518757; ANNOT 1518757; ANNOT 1465420; CLONE 100245; ANNOT 1535451; ANNOT 1535451; ANNOT 1532285; ANNOT 1532285; ANNOT 1480241; ANNOT 1480241; ANNOT 1446025; ANNOT 1446025; CLONE 158333; ANNOT 1466505; ANNOT 1466505; ANNOT 1449026; ANNOT 1449026; | 1460; 1461; 1462; 1463; 1464; 1465; 1466; 2182; 2183; 2184; 2185; 2186; 2187; 2188; 2189; 2190; 2611; 2612; 2613; 2614; 2615; |
| SILIQUES | Composition, Yield | Clubbed | The silique is somewhat bulbous at its terminal end. | Useful for modifying fruit shape, composition and seed yield | CLONE 38743; ANNOT 1448369; CLONE 38743; ANNOT 1448369; ANNOT 1535451; ANNOT 1532285; ANNOT 1480241; ANNOT 1480241; ANNOT 1446025; ANNOT 1446025; ANNOT 1447690; ANNOT 1491278; ANNOT 1500987; ANNOT 1500987; ANNOT 1490915; ANNOT 1490915; | 1788; 1789; 1790; 2182; 2183; 2184; 2185; 2186; 2187; 2188; 2189; 2190; 3687; 3688; 3689; 3690; 3691; 3692; 3693; 3694; 3695; |
| SILIQUES | Composition, Yield | Long | Then silique is abnormally long. | Useful for increasing seed/fruit yield or modifying fruit content | CLONE 23322; ANNOT 1512337; ANNOT 1512337; ANNOT 1517094; ANNOT 1517094; | 897; 898; 899; 900; 901; |
| SILIQUES | Composition, Yield | Other | The plants have a morphological phenotype in siliques. | Useful for increasing seed/fruit yield or modifying fruit content | CLONE 13092; ANNOT 1471785; ANNOT 1471785; CLONE 13186; ANNOT 1464566; ANNOT 1464566; ANNOT 1458408; CLONE 13263; ANNOT 1470919; CLONE 20760; ANNOT 1462351; ANNOT 1462351; ANNOT 1488821; ANNOT 1488821; ANNOT 1469462; ANNOT 1469462; CLONE 32791; ANNOT 1540248; ANNOT 1540248; CLONE 35493; ANNOT 1457751; ANNOT 1457751; ANNOT 1518757; ANNOT 1518757; ANNOT 1465420; ANNOT 1465420; CLONE 40729; ANNOT 1481678; ANNOT 1481678; CLONE 9741S; ANNOT 1481701; ANNOT 1481701; CLONE 101250; CLONE 1506849; ANNOT 1506849; CLONE 13833; ANNOT 1474944; ANNOT 1474944; ANNOT 1492957; ANNOT 1492957; CLONE 158333; ANNOT 1466505; ANNOT 1466505; ANNOT 1449026; ANNOT 1449026; CLONE 283597; ANNOT 1482074; ANNOT 1482074; ANNOT 1482074; CLONE 292789; ANNOT 1442040; ANNOT 1442040; ANNOT 1453923; ANNOT 1453923; CLONE 292789; ANNOT 1482966; ANNOT 1454656; ANNOT 1454656; ANNOT 1458103; ANNOT 1458103; ANNOT 1482966; ANNOT 1464899; ANNOT 1464899; ANNOT 1474837; ANNOT 1474837; ANNOT 1520449; ANNOT 1538169; ANNOT | 528; 529; 530; 531; 532; 533; 534; 535; 536; 537; 538; 808; 809; 810; 811; 812; 813; 814; 1255; 1256; 1257; 1460; 1461; 1462; 1463; 1464; 1465; 1466; 1930; 1931; 1932; 2100; 2101; 2102; 2205; 2206; 2207; 2208; 2209; 2210; 2211; 2611; 2612; 2613; 2614; 2615; 2833; 2834; 2835; 2836; 2837; 2852; 2853; 2854; 2855; 2856; 2857; 2858; 2859; 2860; 2861; 2862; 2863; |

TABLE 1-continued

| Tissue | Phenotype Category | Phenotype | Phenotype Description | Applications | Ceres ID | SEQ ID NO |
|---|---|---|---|---|---|---|
| | | | | | 1538169; CDNA 2349814S; ANNOT 1482362; ANNOT 1489077; ANNOT 1489077; | 2864; 2865; 2866; 2867; 2868; 3641; 3642; 3643; 3644; 3645; |
| SILIQUES | Composition, Yield | Short | The siliques are abnormally short. | Useful for increasing seed/fruit yield or modifying fruit content | CLONE 4581; ANNOT 1489321; ANNOT 1462498; ANNOT 1462498; CLONE 6411; ANNOT 1505322; ANNOT 1496110; ANNOT 1496110; ANNOT 1496111; ANNOT 1496111; CLONE 9897; ANNOT 1445849; ANNOT 1445849; CLONE 13263; ANNOT 1500561; ANNOT 1464458; ANNOT 1464458; CLONE 13263; ANNOT 1470919; ANNOT 1470919; CLONE 13757; ANNOT 1471425; ANNOT 1471425; CLONE 14583; ANNOT 1530256; ANNOT 1530256; CLONE 23322; ANNOT 1476783; ANNOT 1476783; ANNOT 1503166; ANNOT 1503166; CLONE 23322; ANNOT 1512337; ANNOT 1512337; ANNOT 1517094; ANNOT 1517094; CLONE 32791; ANNOT 1540248; ANNOT 1540248; CLONE 34385; ANNOT 1445331; ANNOT 1445331; ANNOT 1498316; ANNOT 1498316; CLONE 34414; ANNOT 1471525; ANNOT 1471525; ANNOT 1497838; ANNOT 1497838; ANNOT 1511908; ANNOT 1511908; ANNOT 1464305; ANNOT 1464305; ANNOT 1451416; ANNOT 1451416; ANNOT 1521524; ANNOT 1514324; ANNOT 1514324; ANNOT 1461050; ANNOT 1461050; CLONE 40729; ANNOT 1481678; ANNOT 1481678; CLONE 99784; ANNOT 1521032; ANNOT 1521032; ANNOT 1472909; ANNOT 1472909; ANNOT 1467665; CLONE 100319; ANNOT 1503141; ANNOT 1503141; ANNOT 1521524; ANNOT 1103581; ANNOT 1486398; ANNOT 1486398; ANNOT 1496840; ANNOT 1496840; CLONE 105554; ANNOT 1451783; ANNOT 1451783; CLONE 10630I; CLONE 110247; ANNOT 1528846; ANNOT 1528846; ANNOT 1538329; CLONE 112955; ANNOT 1447634; ANNOT 1447634; CLONE 117369; ANNOT 1499284; ANNOT 1499284; ANNOT 1481671; ANNOT 1481671; CLONE 124720; ANNOT 1441430; ANNOT 1441430; CLONE 288251; ANNOT 1493218; ANNOT 1493218; ANNOT 1514617; ANNOT 1514617; ANNOT 1461345; ANNOT 1461345; CLONE 572121; ANNOT 1477450; ANNOT 1477450; CDNA 36531424; ANNOT 1474253; ANNOT 1474253; ANNOT 1473720; ANNOT 1473720; | 207; 208; 209; 210; 211; 293; 294; 295; 296; 297; 298; 299; 405; 406; 407; 408; 409; 410; 411; 536; 537; 538; 564; 565; 566; 619; 620; 621; 622; 623; 624; 625; 897; 898; 899; 900; 901; 1255; 1256; 1257; 1364; 1365; 1366; 1367; 1368; 1383; 1384; 1385; 1386; 1387; 1388; 1389; 1390; 1391; 1392; 1393; 1394; 1395; 1396; 1397; 1930; 1931; 1932; 2161; 2162; 2163; 2164; 2165; 2166; 2167; 2191; 2192; 2193; 2194; 2195; 2232; 2233; 2234; 2235; 2236; 2247; 2248; 2249; 2262; 2308; 2309; 2310; 2311; 2312; 2330; 2331; 2332; 2407; 2408; 2409; 2410; 2411; 2501; 2502; 2503; 2845; 2846; 2847; 2848; 2849; 2850; 2851; 3252; 3253; 3254; 3923; 3924; 3925; 3926; 3927; |
| SILIQUES | Composition, Yield | Sickle | The silique is curved. | Useful for modifying fruit shape, composition and seed yield | CLONE 28528; ANNOT 1477416; ANNOT 1477416; CDNA 36560856; ANNOT 1517998; ANNOT 1517998; ANNOT 1458313; ANNOT 1458313; | 1096; 1097; 1098; 4008; 4009; 4010; 4011; 4012; |
| FLOWER | Confinement | Aborted fertility | The ovule is unfertilized and appears as a brown or white speck in the | Useful for sterility, genetic confinement systems | CLONE 38973; ANNOT 1451899; ANNOT 1451899; ANNOT 1496367; ANNOT 1496367; CLONE 39890; ANNOT 1511886; ANNOT 1511886; ANNOT 1517635; ANNOT 1517635; CLONE 101250; ANNOT 1506849; ANNOT 1506849; ANNOT 1474944; ANNOT 1474944; ANNOT 1492957; ANNOT 1492957; | 1818; 1819; 1820; 1821; 1822; 1882; 1883; 1884; 1885; 1886; 2205; 2206; 2207; 2208; 2209; 2210; 2211; |
| FLOWER | Confinement | Male-sterile | mature silique There is a problem with the pollen such that no fertilization is occurring. | Useful for sterility, genetic confinement systems | CLONE 32791; ANNOT 1540248; ANNOT 1540248; | 1255; 1256; 1257; |

TABLE 1-continued

| Tissue | Phenotype Category | Phenotype | Phenotype Description | Applications | Ceres ID | SEQ ID NO |
|---|---|---|---|---|---|---|
| WHOLE SEEDLING | Confinement | Meristem Mutant | The plants have something significantly wrong with how the meristem is producing its leaves. | Useful for making lethal plants for genetic confinement systems | CLONE 907; ANNOT 1502138; ANNOT 1502138; ANNOT 1449135; ANNOT 1449135; | 30; 31; 32; 33; 34; |
| FLOWER | Confinement | Reduced fertility | The plant produces a reduced number of seeds. | Useful for sterility, genetic confinement systems | CLONE 75; ANNOT 1503293; CLONE 314; ANNOT 1503293; CLONE 332; ANNOT 1474923; ANNOT 1474923; CLONE 641; ANNOT 1543129; CLONE 332; ANNOT 1474923; ANNOT 1474923; CLONE 641; ANNOT 1488536; ANNOT 1488536; ANNOT 1460253; ANNOT 1460253; CLONE 907; ANNOT 1502138; ANNOT 1502138; ANNOT 1449135; ANNOT 1449135; CLONE 1496; ANNOT 1490668; ANNOT 1490668; ANNOT 1474027; ANNOT 1474027; ANNOT 1497865; ANNOT 1497865; ANNOT 1471512; ANNOT 1471512; ANNOT 1443061; ANNOT 1443061; ANNOT 1452369; ANNOT 1504203; ANNOT 1504203; ANNOT 1505468; ANNOT 1505468; ANNOT 1452369; CLONE 2036; ANNOT 1526068; CLONE 2561; CLONE 2561; ANNOT 1450958; ANNOT 1450958; ANNOT 1456475; ANNOT 1456475; ANNOT 1446945; ANNOT 1446945; CLONE 3000; ANNOT 1518918; ANNOT 1518918; ANNOT 1535677; ANNOT 1535677; ANNOT 1456840; ANNOT 1456840; CLONE 3363; CLONE 3036; ANNOT 1456840; ANNOT 1456840; CLONE 3363; ANNOT 1445515; ANNOT 1445515; ANNOT 1461861; ANNOT 1461861; ANNOT 1449363; ANNOT 1449363; ANNOT 1465198; ANNOT 1465198; ANNOT 1465198; ANNOT 1518517; ANNOT 1518517; CLONE 3819; ANNOT 1441039; ANNOT 1441039; ANNOT 1482966; ANNOT 1482966; ANNOT 1454656; ANNOT 1454656; ANNOT 1528263; CLONE 10857; ANNOT 1464899; ANNOT 1464899; ANNOT 1458103; ANNOT 1458103; ANNOT 1442040; ANNOT 1442040; ANNOT 1464899; ANNOT 1458103; CLONE 3853; ANNOT 1488920; ANNOT 1488920; ANNOT 1520449; CLONE 3853; ANNOT 1488920; ANNOT 1488920; ANNOT 1469361; ANNOT 1469361; CLONE 4067; ANNOT 1514362; ANNOT 1514362; ANNOT 1494090; ANNOT 1494090; CLONE 5167; ANNOT 1465422; ANNOT 1465422; ANNOT 1457750; ANNOT 1457750; ANNOT 1513544; ANNOT 1513544; CLONE 5597; ANNOT 1507708; ANNOT 1507708; ANNOT 1475094; ANNOT 1475094; CLONE 6387; ANNOT 1509111; ANNOT 1509111; ANNOT 1541620; ANNOT 1541620; CLONE 6397; ANNOT 1486285; ANNOT 1486285; CLONE 6630; CLONE 12914; ANNOT 1529141; ANNOT 1475689; ANNOT 1475689; ANNOT 1476577; ANNOT 1476577; CLONE 8265; ANNOT 1438919; ANNOT 1438919; ANNOT 1499398; ANNOT 1499398; ANNOT 1446419; ANNOT 1446419; CLONE 8916; ANNOT 1462804; ANNOT 1462804; CLONE 9132; ANNOT 1458620; ANNOT 1458620; CLONE 10857; ANNOT 1464446; ANNOT 1464446; CLONE 12250; ANNOT 1497150; ANNOT 1497150; ANNOT 1524446; ANNOT 1524446; CLONE 13092; ANNOT 1471785; ANNOT 1471785; CLONE 13263; ANNOT 1470919; ANNOT 1470919; CLONE 13391; ANNOT 1445555; ANNOT 1445555; CLONE 13745; ANNOT 1502315; ANNOT 1502315; ANNOT 1442612; ANNOT 1442612; ANNOT 1442608; ANNOT 1442604; ANNOT 1442604; ANNOT 1442608; ANNOT 1452827; ANNOT 1452827; CLONE 13757; ANNOT 1442158; ANNOT 1471425; ANNOT 1471425; CLONE 13767; ANNOT 1542158; ANNOT 1542158; ANNOT 1488730; ANNOT 1488730; CLONE 14583; ANNOT 1530256; ANNOT 1530256; ANNOT 1476783; ANNOT 1476783; ANNOT 1503166; ANNOT 1503166; CLONE 15343; ANNOT 1440753; ANNOT 1440753; CLONE 16865; ANNOT 1454311; ANNOT 1454311; ANNOT 1483290; ANNOT 1483290; ANNOT 1533930; ANNOT 1533930; ANNOT 1450556; ANNOT 1450556; ANNOT 1533218; ANNOT 1533218; ANNOT 1512378; ANNOT 1512378; CLONE 18246; ANNOT 1489791; | 6; 7; 8; 9; 10; 11; 12; 13; 14; 25; 26; 27; 28; 29; 30; 31; 32; 33; 34; 50; 51; 52; 53; 54; 55; 56; 57; 58; 59; 60; 61; 62; 63; 64; 65; 66; 84; 85; 86; 104; 105; 106; 107; 108; 109; 110; 111; 112; 113; 114; 115; 116; 117; 121; 122; 123; 129; 130; 131; 132; 133; 134; 135; 136; 137; 138; 139; 153; 154; 155; 156; 157; 158; 159; 160; 161; 162; 163; 164; 165; 166; 167; 168; 169; 170; 171; 172; 173; 174; 196; 197; 198; 199; 200; 223; 224; 225; 226; 227; 228; 229; 233; 234; 235; 236; 237; 285; 286; 287; 288; 289; 290; 291; 292; 305; 306; 307; 308; 309; 310; 311; 362; 363; 364; 365; 366; 367; 368; 388; 389; 390; 391; 392; 393; 434; 435; 436; 510; 511; 512; 513; 514; 528; 529; 530; 536; 537; 538; 539; 540; 541; 542; 543; 555; 556; 557; 558; 559; 560; 561; 562; 563; 564; 565; 566; 567; 568; 569; 570; 571; 619; 620; 621; 622; 623; 624; 625; 641; 642; 643; 650; 651; 652; 653; 654; 655; 656; 657; 658; 659; 660; 661; 662; 715; 716; 717; 718; 719; 762; 763; 764; 765; 766; 808; 809; 810; 811; 812; 813; 814; 876; 877; 878; 879; 880; 928; 929; 930; 931; 932; 933; 934; 935; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1489791; ANNOT 1470953; CLONE 19481; ANNOT 1475146; ANNOT 1475146; ANNOT 1454933; ANNOT 1470953; CLONE 20760; ANNOT 1462351; ANNOT 1462351; ANNOT 1488821; ANNOT 1488821; ANNOT 1469462; ANNOT 1469462; CLONE 22007; ANNOT 1464350; ANNOT 1464350; ANNOT 1458591; ANNOT 1458591; CLONE 23771; ANNOT 144030; ANNOT 1444030; ANNOT 1486813; ANNOT 1485303; ANNOT 1485303; ANNOT 1446796; ANNOT 1446796; CLONE 24266; ANNOT 1463475; ANNOT 1463475; ANNOT 1540920; ANNOT 1540920; ANNOT 1487528; ANNOT 1487528; CLONE 24644; ANNOT 1463301; ANNOT 1463301; ANNOT 1459811; ANNOT 1459811; CLONE 25172; ANNOT 1457346; ANNOT 1457346; ANNOT 1541170; ANNOT 1541170; CLONE 25607; ANNOT 1450220; ANNOT 1450220; CLONE 25886; ANNOT 1446650; ANNOT 1446650; ANNOT 1439514; ANNOT 1439514; ANNOT 1477202; ANNOT 1477202; ANNOT 1455325; ANNOT 1455325; CLONE 26560; ANNOT 1536088; ANNOT 1536088; ANNOT 1482610; ANNOT 1482610; ANNOT 26825; ANNOT 1513438; ANNOT 1513438; ANNOT 1460167; ANNOT 1460167; ANNOT 1460167; CLONE 27197; ANNOT 1448819; ANNOT 1448819; ANNOT 1465787; ANNOT 1465787; CLONE 28326; ANNOT 1468461; ANNOT 1468461; CLONE 28643; ANNOT 1469464; ANNOT 1469464; ANNOT 1463508; ANNOT 1463508; ANNOT 1459366; ANNOT 1459366; ANNOT 1542246; ANNOT 1542246; CLONE 32548; ANNOT 1450324; ANNOT 1450324; ANNOT 1460836; ANNOT 1460836; CLONE 32753; ANNOT 1480607; ANNOT 1480607; ANNOT 1472242; ANNOT 1472242; CLONE 32791; ANNOT 1540248; ANNOT 1540248; CLONE 33232; 33559; ANNOT 1504045; ANNOT 1504045; ANNOT 1450983; ANNOT 1450983; CLONE 1481138; ANNOT 1481146; ANNOT 1481146; ANNOT 1481150; ANNOT 1481150; ANNOT 1534622; ANNOT 1481138; ANNOT 1485824; ANNOT 1485824; ANNOT 1452709; ANNOT 1534622; CLONE 33802; ANNOT 1495637; ANNOT 1495637; ANNOT 34151; ANNOT 1452709; ANNOT 1442724; ANNOT 1442724; CLONE 34210; ANNOT 1473827; ANNOT 1473827; ANNOT 1468614; ANNOT 1468614; CLONE 1495936; CLONE 34385; ANNOT 1445331; ANNOT 1445331; ANNOT 1498316; ANNOT 1495936; CLONE 36891; ANNOT 1503622; ANNOT 1503622; ANNOT 1450565; ANNOT 1450565; ANNOT 1498316; CLONE 34414; ANNOT 1471525; ANNOT 1471525; ANNOT 1497838; ANNOT 1497838; ANNOT 1511908; ANNOT 1511908; ANNOT 1464305; ANNOT 1464305; ANNOT 1451416; ANNOT 1451416; ANNOT 1514324; ANNOT 1514324; ANNOT 1461050; ANNOT 1461050; CLONE 36701; ANNOT 1487885; ANNOT 1487885; ANNOT 1457156; ANNOT 1457156; ANNOT 1449371; ANNOT 1449371; ANNOT 1445504; ANNOT 1445504; CLONE 36709; ANNOT 1495936; ANNOT 1495936; ANNOT 1480518; ANNOT 1480518; ANNOT 1442194; ANNOT 1442194; ANNOT 1454127; ANNOT 1454127; ANNOT 1461716; ANNOT 1461716; ANNOT 1440277; ANNOT 1440277; ANNOT 1461415; ANNOT 1461415; ANNOT 1461414; ANNOT 1461414; ANNOT 1447424; ANNOT 1447424; ANNOT 1528127; ANNOT 1528127; ANNOT 1438717; ANNOT 1438717; ANNOT 1452873; ANNOT 1440276; ANNOT 1440276; ANNOT 1442556; ANNOT 1442556; ANNOT 1452873; ANNOT 1473384; ANNOT 1452873; ANNOT 1453483; ANNOT 1453483; ANNOT 1473384; ANNOT 1473384; ANNOT 1475808; ANNOT 1475808; ANNOT 1474708; ANNOT 1474708; ANNOT 1438698; ANNOT 1438698; CLONE 37288; ANNOT 1453650; ANNOT 1453650; CLONE 37398; ANNOT 1531721; ANNOT 1531721; ANNOT 1478221; ANNOT 1478221; ANNOT 1482547; ANNOT 1482547; CLONE 37493; ANNOT 1494370; ANNOT 1494370; ANNOT 1441478; ANNOT 1441478; CLONE 38370; ANNOT 1471869; ANNOT 1471869; ANNOT 1448032; ANNOT 1448032; ANNOT 1448031; ANNOT 1448031; ANNOT 1438060; ANNOT 1438060; ANNOT 1438061; | 936; 937; 938; 939; 940; 941; 942; 943; 944; 945; 946; 947; 948; 952; 953; 954; 955; 956; 970; 971; 972; 986; 987; 988; 989; 990; 991; 992; 993; 994; 1015; 1016; 1017; 1018; 1019; 1030; 1031; 1032; 1033; 1034; 1050; 1051; 1052; 1053; 1054; 1088; 1089; 1090; 1122; 1123; 1124; 1125; 1126; 1127; 1128; 1129; 1130; 1231; 1232; 1233; 1234; 1235; 1250; 1251; 1252; 1253; 1254; 1255; 1256; 1257; 1263; 1264; 1265; 1266; 1267; 1310; 1311; 1312; 1313; 1314; 1315; 1316; 1317; 1318; 1319; 1320; 1321; 1322; 1323; 1324; 1325; 1326; 1327; 1338; 1339; 1340; 1341; 1342; 1350; 1351; 1352; 1353; 1354; 1364; 1365; 1366; 1367; 1368; 1383; 1384; 1385; 1386; 1387; 1388; 1389; 1390; 1391; 1392; 1393; 1394; 1395; 1396; 1397; 1536; 1537; 1538; 1539; 1540; 1541; 1542; 1543; 1544; 1545; 1546; 1547; 1548; 1549; 1550; 1551; 1552; 1553; 1554; 1555; 1556; 1557; 1558; 1559; 1560; 1561; 1562; 1563; 1564; 1565; 1566; 1567; 1568; 1569; 1570; 1571; 1572; 1573; 1574; 1575; 1576; 1577; 1578; 1579; 1580; 1581; 1582; 1583; 1584; 1622; 1623; 1624; 1630; 1631; 1632; 1633; 1634; 1635; 1636; 1637; 1638; 1639; 1640; 1641; 1732; 1733; 1734; 1735; 1736; 1737; 1738; 1739; 1740; 1741; 1742; 1743; 1744; 1745; 1746; 1791; 1792; 1793; 1794; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1438061; ANNOT 1448030; ANNOT 1437831; ANNOT 1437831; CLONE 38757; ANNOT 1528846; ANNOT 1538329; ANNOT 1538329; CLONE 38785; ANNOT 1461193; ANNOT 1514466; ANNOT 1514466; CLONE 38843; ANNOT 1447896; ANNOT 1438197; ANNOT 1438197; CLONE 39127; ANNOT 1463852; ANNOT 1463852; CLONE 39286; ANNOT 1447961; ANNOT 1490936; ANNOT 1490936; CLONE 39351; ANNOT 1503551; ANNOT 1460689; ANNOT 1460689; ANNOT 1513952; ANNOT 1450495; ANNOT 1450495; CLONE 39740; ANNOT 1483180; ANNOT 1480950; ANNOT 1480950; CLONE 39890; ANNOT 1511886; ANNOT 1517635; ANNOT 1517635; CLONE 40153; ANNOT 1453549; ANNOT 1453549; ANNOT 1528184; ANNOT 1474758; CLONE 40729; ANNOT 1481678; CLONE 41320; ANNOT 1541929; ANNOT 1460282; ANNOT 1488507; ANNOT 1488507; CLONE 93867; ANNOT 1474944; ANNOT 1506849; ANNOT 1492957; CLONE 95453; ANNOT 1460836; ANNOT 1460836; ANNOT 1450324; ANNOT 1450324; CLONE 96020; ANNOT 1450365; ANNOT 1460794; ANNOT 1460794; CLONE 97415; ANNOT 1481701; CLONE 98855; ANNOT 1460836; ANNOT 1460836; ANNOT 1450324; CLONE 99784; ANNOT 1521032; ANNOT 1521032; ANNOT 1472909; ANNOT 1467665; ANNOT 1467665; CLONE 100245; ANNOT 1535451; ANNOT 1532285; ANNOT 1532285; ANNOT 1480241; ANNOT 1480241; ANNOT 1446025; ANNOT 1446025; CLONE 100319; ANNOT 1503141; ANNOT 1521524; ANNOT 1521524; CLONE 101798; ANNOT 1449432; ANNOT 1449432; ANNOT 1449431; ANNOT 1502439; ANNOT 1502439; CLONE 103581; ANNOT 1486398; ANNOT 1486398; ANNOT 1496840; ANNOT 1496840; CLONE 107988; ANNOT 1459927; ANNOT 1459927; CLONE 110247; ANNOT 1528846; ANNOT 1528846; ANNOT 1538329; ANNOT 1538329; CLONE 112955; ANNOT 1447634; ANNOT 1447634; CLONE 115975; ANNOT 1507138; ANNOT 1507138; CLONE 116257; ANNOT 1520806; ANNOT 1520806; ANNOT 1473089; ANNOT 1473089; ANNOT 1500150; CLONE 117369; ANNOT 1499284; ANNOT 1499284; ANNOT 1480439; ANNOT 1481671; CLONE 119256; ANNOT 1469636; ANNOT 1469636; ANNOT 1479002; ANNOT 1479002; CLONE 122353; ANNOT 1472265; ANNOT 1472265; CLONE 123279; ANNOT 1508945; ANNOT 1508945; ANNOT 1531332; ANNOT 1482544; ANNOT 1482544; ANNOT 1478226; CLONE 124720; ANNOT 1441430; ANNOT 1441430; CLONE 141830; ANNOT 1488335; ANNOT 1475653; ANNOT 1475653; ANNOT 1458131; ANNOT 1458131; ANNOT 1461780; ANNOT 1461780; CLONE 150912; ANNOT 1533910; ANNOT 1533910; ANNOT 1480439; ANNOT 1480439; CLONE 154718; ANNOT 1457453; ANNOT 1457453; CLONE 156655; ANNOT 1441740; ANNOT 1441740; CLONE 157730; ANNOT 1532681; ANNOT 1532681; ANNOT 1469739; ANNOT 1469739; CLONE 158333; ANNOT 1466505; ANNOT 1466505; ANNOT 1449026; ANNOT 1449026; ANNOT 1501773; ANNOT 1501773; CLONE 158702; ANNOT 158734; ANNOT 1477956; ANNOT 1477956; CLONE 226818; ANNOT 1503617; ANNOT 1503617; ANNOT 1450560; ANNOT 1450560; ANNOT 1460622; ANNOT 1460622; CLONE 267564; ANNOT 1473933; ANNOT 1473933; ANNOT 1468704; ANNOT 1468704; CLONE 267657; ANNOT 1471473; ANNOT 1471473; ANNOT 1457048; 1444931; ANNOT 1444931; CLONE 270875; ANNOT 1457048; | 1795; 1796; 1797; 1798; 1799; 1800; 1801; 1802; 1803; 1804; 1805; 1823; 1824; 1825; 1838; 1839; 1840; 1841; 1842; 1854; 1855; 1856; 1857; 1858; 1859; 1860; 1861; 1862; 1877; 1878; 1879; 1880; 1881; 1882; 1883; 1884; 1885; 1886; 1897; 1898; 1899; 1900; 1901; 1902; 1903; 1930; 1931; 1932; 1981; 1982; 1983; 1984; 1985; 1986; 1987; 2064; 2065; 2066; 2067; 2068; 2069; 2070; 2085; 2086; 2087; 2088; 2089; 2095; 2096; 2097; 2098; 2099; 2100; 2101; 2102; 2118; 2119; 2120; 2121; 2122; 2161; 2162; 2163; 2164; 2165; 2166; 2167; 2182; 2183; 2184; 2185; 2186; 2187; 2188; 2189; 2190; 2191; 2192; 2193; 2194; 2195; 2219; 2220; 2221; 2222; 2223; 2224; 2225; 2232; 2233; 2234; 2235; 2236; 2278; 2279; 2280; 2308; 2309; 2310; 2311; 2312; 2330; 2331; 2332; 2373; 2374; 2375; 2394; 2395; 2396; 2397; 2398; 2399; 2400; 2407; 2408; 2409; 2410; 2411; 2451; 2452; 2453; 2454; 2455; 2481; 2482; 2483; 2492; 2493; 2494; 2495; 2496; 2497; 2498; 2499; 2500; 2501; 2502; 2503; 2520; 2521; 2522; 2533; 2534; 2535; 2536; 2537; 2538; 2539; 2555; 2556; 2557; 2558; 2559; 2577; 2578; 2579; 2580; 2581; 2582; 2601; 2602; 2603; 2604; 2605; 2611; 2612; 2613; 2614; 2615; 2616; 2617; 2618; 2619; 2620; 2621; 2676; 2677; 2678; 2679; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1510252; ANNOT 1510252; CLONE 292789; ANNOT 1442040; ANNOT 1442040; ANNOT 1482966; ANNOT 1454656; ANNOT 1454656; ANNOT 1458103; ANNOT 1458103; ANNOT 1464899; ANNOT 1464899; ANNOT 1474837; ANNOT 1474837; ANNOT 1520449; ANNOT 1520449; ANNOT 1538169; ANNOT 1538169; CLONE 482122; ANNOT 1438776; ANNOT 1438776; CLONE 536726; ANNOT 1498226; ANNOT 1498226; ANNOT 1445243; ANNOT 1445243; ANNOT 1525386; ANNOT 1525386; ANNOT 1448522; ANNOT 1448522; ANNOT 1465506; ANNOT 1465506; ANNOT 1497017; ANNOT 1497017; ANNOT 1447240; ANNOT 1447240; ANNOT 1539566; ANNOT 1539566; ANNOT 1444070; ANNOT 1444070; CLONE 545208; ANNOT 1459998; ANNOT 1513263; ANNOT 1513263; ANNOT 1467410; ANNOT 1467410; CLONE 563522; ANNOT 1460321; ANNOT 1508144; ANNOT 1541886; ANNOT 1541886; ANNOT 1475178; ANNOT 1475178; CLONE 566317; ANNOT 1489585; ANNOT 1489585; ANNOT 1467905; ANNOT 1467905; ANNOT 1517371; ANNOT 1517371; ANNOT 1517371; ANNOT 1512104; ANNOT 1512104; ANNOT 1458837; ANNOT 1458837; CLONE 572121; ANNOT 1477450; CLONE 627596; ANNOT 1500987; ANNOT 1500987; ANNOT 1490915; ANNOT 1490915; CLONE 708342; ANNOT 1538185; ANNOT 1538185; CLONE 1002819; ANNOT 1474290; ANNOT 1474290; ANNOT 1522314; ANNOT 1522314; ANNOT 1497147; ANNOT 1497147; ANNOT 1471045; ANNOT 1471045; CLONE 1011386; ANNOT 1531134; ANNOT 1531134; ANNOT 1508758; ANNOT 1508758; CDNA 2349348l; ANNOT 1460973; ANNOT 1460973; CDNA 2349814S; ANNOT 1482362; ANNOT 1482362; ANNOT 1489077; ANNOT 1489077; CDNA 23501O3; CDNA 2350182; ANNOT 1525474; ANNOT 1525474; CDNA 2351657B; CDNA 3651294O; ANNOT 1471370; ANNOT 1471370; ANNOT 1444471; ANNOT 1444471; ANNOT 1491278; ANNOT 1491278; ANNOT 1447690; ANNOT 1447690; CDNA 3635149l; ANNOT 1524972; ANNOT 1524972; CDNA 3654285S; ANNOT 1524883; ANNOT 1524883; ANNOT 1497918; ANNOT 1497918; CDNA 3645500O; ANNOT 1449045; ANNOT 1449045; ANNOT 1470714; ANNOT 1470714; CDNA 3654796A; ANNOT 1491278; ANNOT 1503630; ANNOT 1503630; CDNA 3656085G; ANNOT 1517998; ANNOT 1517998; ANNOT 1458313; ANNOT 1458313; CDNA 3657269S; ANNOT 1455805; ANNOT 1455805; ANNOT 1455663; ANNOT 1455663; ANNOT 1529744; ANNOT 1529744; CDNA 3657942A; ANNOT 1448068; ANNOT 1448068; ANNOT 1438024; ANNOT 1438024; CDNA 3654796A; ANNOT 1491278; ANNOT 1491278; ANNOT 1447690; ANNOT 1447690; ANNOT 1500987; ANNOT 1500987; ANNOT 1490915; ANNOT 1490915; | 2680; 2681; 2682; 2789; 2790; 2791; 2792; 2793; 2801; 2802; 2803; 2804; 2805; 2811; 2812; 2813; 2814; 2815; 2852; 2853; 2854; 2855; 2856; 2857; 2858; 2859; 2860; 2861; 2862; 2863; 2864; 2865; 2866; 2867; 2868; 3049; 3050; 3051; 3135; 3136; 3137; 3138; 3139; 3140; 3141; 3142; 3143; 3144; 3145; 3146; 3147; 3148; 3149; 3150; 3151; 3152; 3153; 3189; 3190; 3191; 3192; 3193; 3194; 3195; 3227; 3228; 3229; 3230; 3231; 3232; 3233; 3234; 3235; 3241; 3242; 3243; 3244; 3245; 3246; 3247; 3248; 3249; 3250; 3251; 3252; 3253; 3254; 3299; 3300; 3301; 3302; 3303; 3361; 3362; 3363; 3428; 3429; 3430; 3431; 3432; 3433; 3434; 3435; 3436; 3462; 3463; 3464; 3465; 3466; 3613; 3614; 3615; 3641; 3642; 3643; 3644; 3645; 3687; 3696; 3697; 3698; 3737; 3896; 3897; 3898; 3899; 3900; 3901; 3902; 3903; 3904; 3948; 3949; 3950; 3974; 3975; 3976; 3977; 3978; 3979; 3980; 3981; 3982; 3983; 3987; 3988; 3989; 4008; 4009; 4010; 4011; 4012; 4048; 4049; 4050; 4051; 4052; 4063; 4064; 4065; 4066; 4067; 4068; 4069; 3688; 3689; 3690; 3691; 3692; 3693; 3694; 3695; |
| FLOWER | Confinement | Sterile | No seed is being produced by the plant | Useful for sterility, genetic confinement systems | CLONE 1496; ANNOT 1490668; ANNOT 1474027; ANNOT 1474027; ANNOT 1490668; ANNOT 1490668; ANNOT 1471512; ANNOT 1497865; ANNOT 1497865; ANNOT 1443061; ANNOT 1443061; ANNOT 1504203; ANNOT 1505468; ANNOT 1505468; ANNOT 1452369; ANNOT 1452369; CLONE 3000; ANNOT 1518918; ANNOT 1518918; ANNOT 1535677; ANNOT 1535677; ANNOT 1482181; ANNOT 1482181; CLONE 3363; ANNOT 1445515; ANNOT 1445515; ANNOT 1461861; ANNOT 1461861; ANNOT 1449363; ANNOT 1449363; ANNOT | 50; 51; 52; 53; 54; 55; 56; 57; 58; 59; 60; 61; 62; 63; 64; 65; 66; 111; 112; 113; 114; 115; 116; 117; 129; 130; 131; 132; 133; 134; 135; 136; 137; 138; 139; 153; 154; 155; |

TABLE 1-continued

| Tissue | Phenotype Category | Phenotype | Phenotype Description | Applications | Ceres ID | SEQ ID NO |
|---|---|---|---|---|---|---|
| | | | | | 1465198; ANNOT 1465198; ANNOT 1518517; CLONE 3819; ANNOT 1441039; ANNOT 1441039; ANNOT 1482966; ANNOT 1454656; ANNOT 1454656; ANNOT 1528263; ANNOT 1464899; ANNOT 1464899; ANNOT 1458103; ANNOT 1458103; ANNOT 1442040; ANNOT 1442040; ANNOT 1520449; ANNOT 1520449; CLONE 5597; ANNOT 1507708; ANNOT 1507708; ANNOT 1475094; ANNOT 1475094; CLONE 9132; ANNOT 1458620; ANNOT 1458620; CLONE 9683; ANNOT 1471514; ANNOT 1471514; CLONE 9897; ANNOT 1445849; ANNOT 1445849; ANNOT 150561; ANNOT 1500561; ANNOT 1464458; CLONE 13263; ANNOT 1470919; ANNOT 1470919; CLONE 13767; ANNOT 1542158; ANNOT 1542158; ANNOT 1488730; ANNOT 1488730; CLONE 15343; ANNOT 1440753; ANNOT 1440753; CLONE 18612; ANNOT 1522299; ANNOT 1527718; ANNOT 1527718; CLONE 23771; ANNOT 1444030; ANNOT 1444030; ANNOT 1486813; ANNOT 1486813; ANNOT 1485303; ANNOT 1446796; ANNOT 1446796; CLONE 28003; ANNOT 1527756; ANNOT 1527756; ANNOT 1468882; ANNOT 1468882; CLONE 32548; ANNOT 1450324; ANNOT 1450324; ANNOT 1460836; ANNOT 1460836; CLONE 32615; ANNOT 1471372; ANNOT 1471372; CLONE 32791; ANNOT 1540248; ANNOT 1540248; CLONE 33559; ANNOT 1481146; ANNOT 1481146; ANNOT 1481150; ANNOT 1481138; ANNOT 1481138; ANNOT 1485824; ANNOT 1485824; ANNOT 1534622; ANNOT 1534622; CLONE 33802; ANNOT 1495637; ANNOT 1495637; ANNOT 1452709; ANNOT 1452709; ANNOT 1442724; ANNOT 1442724; CLONE 36709; ANNOT 1495936; ANNOT 1495936; CLONE 37398; ANNOT 1531721; ANNOT 1531721; ANNOT 1478221; ANNOT 1478221; ANNOT 1482547; ANNOT 1482547; CLONE 38214; ANNOT 1466779; ANNOT 1466779; ANNOT 1465769; ANNOT 1465769; ANNOT 1538318; ANNOT 1538318; CLONE 99784; ANNOT 1521032; ANNOT 1521032; ANNOT 1472909; ANNOT 1472909; ANNOT 1467665; ANNOT 1467665; CLONE 100245; ANNOT 1533451; ANNOT 1533451; ANNOT 1532285; ANNOT 1532285; ANNOT 1448241; ANNOT 1448241; ANNOT 1446025; ANNOT 1446025; CLONE 100319; ANNOT 1503141; ANNOT 1503141; ANNOT 1521524; ANNOT 1521524; CLONE 101798; ANNOT 1449432; ANNOT 1449432; ANNOT 1449431; ANNOT 1449431; ANNOT 1502439; ANNOT 1502439; CLONE 106011; ANNOT 1533498; ANNOT 1533498; ANNOT 1524067; ANNOT 1524067; CLONE 149380; ANNOT 1461440; ANNOT 1461440; ANNOT 1461430; ANNOT 1461430; ANNOT 1461427; ANNOT 1461427; ANNOT 1440253; ANNOT 1440253; CLONE 150912; ANNOT 1533910; ANNOT 1533910; ANNOT 1480439; ANNOT 1480439; CLONE 157547; ANNOT 1473898; ANNOT 1473898; CLONE 627596; ANNOT 1500987; ANNOT 1500987; ANNOT 1490915; ANNOT 1490915; CLONE 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1479711; ANNOT 1440649; ANNOT 1440649; ANNOT 1464547; ANNOT 1464547; ANNOT 1454104; ANNOT 1454104; CLONE 1011537; ANNOT 1473879; ANNOT 1473879; ANNOT 1468666; ANNOT 1468666; ANNOT 1438163; ANNOT 1438163 | 156; 157; 158; 159; 160; 161; 162; 163; 164; 165; 166; 167; 168; 169; 233; 234; 235; 236; 237; 391; 392; 393; 402; 403; 404; 405; 406; 407; 408; 409; 410; 411; 536; 537; 538; 567; 568; 569; 570; 571; 641; 642; 643; 720; 721; 722; 723; 724; 928; 929; 930; 931; 932; 933; 934; 935; 936; 1080; 1081; 1082; 1083; 1084; 1231; 1232; 1233; 1234; 1235; 1239; 1240; 1241; 1255; 1256; 1257; 1310; 1311; 1312; 1313; 1314; 1315; 1316; 1317; 1318; 1319; 1320; 1321; 1322; 1323; 1324; 1325; 1326; 1327; 1545; 1546; 1547; 1630; 1631; 1632; 1633; 1634; 1635; 1636; 1707; 1708; 1709; 1710; 1711; 1712; 1713; 2161; 2162; 2163; 2164; 2165; 2166; 2167; 2182; 2183; 2184; 2185; 2186; 2187; 2188; 2189; 2190; 2191; 2192; 2193; 2194; 2195; 2219; 2220; 2221; 2222; 2223; 2224; 2225; 2250; 2251; 2252; 2253; 2254; 2546; 2547; 2548; 2549; 2550; 2551; 2552; 2553; 2554; 2555; 2556; 2557; 2558; 2559; 2593; 2594; 2595; 3299; 3300; 3301; 3302; 3303; 3440; 3441; 3442; 3443; 3444; 3445; 3446; 3447; 3448; 3449; 3450; 3451; 3452; 3453; 3454; 3455; 3456; 3467; 3468; 3469; 3470; 3471; 3472; 3473; |
| WHOLE PLANT | | Yellow-Green Viable 1 | The leaves and cotyledons are yellow-green in color. | | CLONE 907; ANNOT 1502138; ANNOT 1502138; ANNOT 1449135; ANNOT 1449135; CLONE 1610; ANNOT 1454586; ANNOT 1454586; ANNOT 1475043; ANNOT 1475043; ANNOT 1475043; ANNOT 1507756; ANNOT 1507756; ANNOT 1469708; ANNOT 1469708; CLONE 3699; ANNOT 1527319; ANNOT 1527319; ANNOT 1473907; ANNOT 1473907; ANNOT 1473907; CLONE 5198; ANNOT 1472153; ANNOT 1472153; CLONE 6630; ANNOT 1529141; ANNOT 1529141; ANNOT 1475689; ANNOT 1475689; ANNOT | 30; 31; 32; 33; 34; 67; 68; 69; 70; 71; 72; 73; 74; 75; 148; 149; 150; 151; 152; 230; 231; 232; 305; 306; 307; 308; 309; 310; 311; 567; 568; 569; |
| | Confinement | | | Useful for making lethal plants for genetic confinement systems | | |

TABLE 1-continued

| Tissue | Phenotype Category | Phenotype | Phenotype Description | Applications | Ceres ID | SEQ ID NO |
|---|---|---|---|---|---|---|
| | | | | | 1476577; ANNOT 1476577; CLONE 13767; ANNOT 1542158; ANNOT 1542158; ANNOT 1488730; ANNOT 1488730; CLONE 17482; ANNOT 1501311; ANNOT 1501311; CLONE 25538; ANNOT 1480776; ANNOT 1480776; CLONE 29150; ANNOT 1485362; ANNOT 1485362; CLONE 34167; ANNOT 1538733; ANNOT 1538733; ANNOT 1499810; ANNOT 1499810; ANNOT 1485323; ANNOT 1485323; CLONE 34480; CLONE 34783; ANNOT 1502362; ANNOT 1502362; ANNOT 1449358; ANNOT 1449358; CLONE 38625; ANNOT 1466952; ANNOT 1466952; ANNOT 1523551; ANNOT 1523551; ANNOT 1470164; ANNOT 1470164; CLONE 39351; ANNOT 1503551; ANNOT 1503551; ANNOT 1461141; ANNOT 1461141; CLONE 39351; ANNOT 1460689; ANNOT 1460689; ANNOT 1513952; ANNOT 1513952; ANNOT 1450495; ANNOT 1450495; CLONE 92670; ANNOT 1531919; ANNOT 1531919; CLONE 95677; ANNOT 1459723; ANNOT 1459723; ANNOT 1516455; ANNOT 1516455; CLONE 113719; ANNOT 1513206; ANNOT 1513206; ANNOT 1516003; ANNOT 1516003; CLONE 120988; CLONE 147358; ANNOT 1493111; ANNOT 1493111; ANNOT 1462703; ANNOT 1462703; ANNOT 1461452; ANNOT 1461452; CLONE 152141; ANNOT 1439403; ANNOT 1439403; ANNOT 1485362; ANNOT 1485362; CLONE 159318; ANNOT 1485362; ANNOT 1485362; CLONE 241379; ANNOT 1526950; ANNOT 1526950; ANNOT 1508362; ANNOT 1508362; ANNOT 1477361; ANNOT 1477361; CLONE 1011386; ANNOT 1531134; ANNOT 1531134; ANNOT 1508758; ANNOT 1508758; ANNOT 2307479; ANNOT 1510416; ANNOT 1510416; ANNOT 1541253; ANNOT 1541253; | 570; 571; 692; 693; 694; 967; 968; 969; 1131; 1132; 1133; 1343; 1344; 1345; 1346; 1347; 1348; 1349; 1398; 1399; 1400; 1401; 1402; 1423; 1424; 1425; 1426; 1427; 1428; 1429; 1766; 1767; 1768; 1854; 1855; 1856; 1857; 1858; 1859; 1860; 1861; 1862; 2061; 2062; 2063; 2090; 2091; 2092; 2093; 2094; 2333; 2334; 2335; 2336; 2337; 2338; 2339; 2480; 2528; 2529; 2530; 2531; 2532; 2568; 2569; 2570; 2574; 2575; 2576; 2622; 2623; 2624; 2718; 2719; 2720; 2721; 2722; 2723; 2724; 3462; 3463; 3464; 3465; 3466; 3704; 3705; 3706; 3707; 3708; |
| WHOLE PLANT | Confinement | Yellow-Green Viable 2 | The leaves are yellow-green in color but the cotyledons are a wild-type green in color. | Useful for making lethal plants for genetic confinement systems | CLONE 6220; ANNOT 1488463; ANNOT 1488463; ANNOT 1541879; ANNOT 1541879; ANNOT 19143; ANNOT 1442860; ANNOT 1442860; ANNOT 1459442; ANNOT 1459442; ANNOT 1452580; ANNOT 1452580; CLONE 42925; ANNOT 1462354; ANNOT 1462354; CLONE 267626; ANNOT 1484074; ANNOT 1484074; ANNOT 1518242; ANNOT 1518242; ANNOT 1464923; ANNOT 1464923; | 275; 276; 277; 278; 279; 740; 741; 742; 743; 744; 745; 746; 2045; 2046; 2047; 2794; 2795; 2796; 2797; 2798; 2799; 2800; |
| WHOLE PLANT | Confinement | Yellow-Green Viable 3 | The leaves start out wild-type green and gradually turn yellow-green in color, while the cotyledons stay wild-type green. | Useful for making lethal plants for genetic confinement systems | CLONE 25380; ANNOT 1512618; ANNOT 1512618; ANNOT 1459357; ANNOT 1459357; ANNOT 1463526; ANNOT 1463526; CLONE 33232; ANNOT 1504045; ANNOT 1504045; ANNOT 1450983; ANNOT 1450983; CLONE 267626; ANNOT 1484074; ANNOT 1484074; ANNOT 1518242; ANNOT 1464923; ANNOT 1464923; CDNA 23522373; ANNOT 1538994; ANNOT 1538994; ANNOT 1447080; ANNOT 1447080; CDNA 36521975; ANNOT 1455981; ANNOT 1455981; ANNOT 1541512; ANNOT 1541512; | 960; 961; 962; 963; 964; 965; 966; 1263; 1264; 1265; 1266; 1267; 2794; 2795; 2796; 2797; 2798; 2799; 2800; 3761; 3762; 3763; 3764; 3765; 3911; 3912; 3913; 3914; 3915; |
| INFLORESCENCE | Development | Early Flowering | The plant flowers significantly earlier than wild-type. | Useful for modulating flowering time | CLONE 32791; ANNOT 1540248; ANNOT 1540248; CLONE 39319; ANNOT 1456036; ANNOT 1456036; ANNOT 1470131; ANNOT 1470131; ANNOT 1466936; ANNOT 1466936; ANNOT 1541455; ANNOT 1541455; ANNOT 1456037; ANNOT 1456037; CLONE 41337; ANNOT 1516613; ANNOT 1516613; ANNOT 1513097; ANNOT 1513097; ANNOT 1463324; ANNOT 1463324; CLONE 536726; ANNOT 1498226; ANNOT 1498226; ANNOT 1445243; ANNOT 1445243; ANNOT 1525386; ANNOT 1525386; ANNOT 1448522; ANNOT 1448522; ANNOT 1465506; ANNOT 1465506; ANNOT 1497017; ANNOT 1497017; ANNOT 1447240; ANNOT 1447240; ANNOT 1539566; ANNOT 1539566; ANNOT 1444070; ANNOT 1444070; | 1255; 1256; 1257; 1843; 1844; 1845; 1846; 1847; 1848; 1849; 1850; 1851; 1852; 1853; 1988; 1989; 1990; 1991; 1992; 1993; 1994; 3135; 3136; 3137; 3138; 3139; 3140; 3141; 3142; 3143; 3144; 3145; 3146; 3147; 3148; 3149; 3150; 3151; 3152; 3153; |
| WHOLE PLANT | Development | Early Senescence | The plant senesces | Useful for modulating | CLONE 75; ANNOT 1503293; ANNOT 1503293; CLONE 34412; ANNOT 1449739; ANNOT 1449739; ANNOT 1449738; ANNOT 1449738; ANNOT 1458830; ANNOT | 6; 7; 8; 1376; 1377; 1378; 1379; 1380; 1381; |

TABLE 1-continued

| Tissue | Phenotype Category | Phenotype | Phenotype Description | Applications | Ceres ID | SEQ ID NO |
|---|---|---|---|---|---|---|
| | | | significantly earlier than wild-type. | crop development and harvest | 1458830; CDNA 23493481; ANNOT 1460973; ANNOT 1460973; CDNA 23505182; ANNOT 1525474; ANNOT 1525474; | 1382; 3613; 3614; 3615; 3696; 3697; 3698; |
| INFLORESCENCE | Development | Late Flowering | The plant flowers significantly late compared to wild-type. | Useful for modulating flowering time | CLONE 314; ANNOT 1543129; ANNOT 1543129; CLONE 332; ANNOT 1474923; ANNOT 1474923; CLONE 907; ANNOT 1502138; ANNOT 1502138; ANNOT 1449135; ANNOT 1449135; CLONE 1241; ANNOT 1453081; ANNOT 1453081; ANNOT 1442349; ANNOT 1442349; CLONE 1610; ANNOT 1454586; ANNOT 1454586; ANNOT 1475043; ANNOT 1475043; ANNOT 1507756; ANNOT 1507756; ANNOT 1469708; ANNOT 1469708; CLONE 2403; ANNOT 1509972; ANNOT 1509972; ANNOT 1504203; ANNOT 1504203; ANNOT 1443061; ANNOT 1443061; ANNOT 1452369; ANNOT 1452369; CLONE 3000; ANNOT 1518918; ANNOT 1518918; ANNOT 1535677; ANNOT 1535677; ANNOT 1482181; ANNOT 1482181; CLONE 3036; ANNOT 1456840; ANNOT 1456840; CLONE 3363; ANNOT 1445515; ANNOT 1445515; ANNOT 1461861; ANNOT 1461861; ANNOT 1449363; ANNOT 1449363; ANNOT 1465198; ANNOT 1465198; ANNOT 1518517; ANNOT 1518517; CLONE 3457; ANNOT 1458875; ANNOT 1458875; ANNOT 1449635; ANNOT 1449635; CLONE 3542; ANNOT 1471301; ANNOT 1471301; CLONE 3699; ANNOT 1527319; ANNOT 1527319; ANNOT 1473907; ANNOT 1473907; CLONE 3858; ANNOT 1459068; ANNOT 1459068; CLONE 3997; ANNOT 1455209; ANNOT 1455209; ANNOT 1446198; ANNOT 1446198; ANNOT 1490273; ANNOT 1490273; ANNOT 1530603; ANNOT 1530603; CLONE 5597; ANNOT 1507708; ANNOT 1507708; ANNOT 1475094; ANNOT 1475094; CLONE 5605; ANNOT 1437939; ANNOT 1437939; CLONE 6387; ANNOT 1509111; ANNOT 1509111; ANNOT 1541620; ANNOT 1541620; CLONE 8265; ANNOT 1438919; ANNOT 1438919; ANNOT 1499398; ANNOT 1499398; ANNOT 1446419; ANNOT 1446419; CLONE 9132; ANNOT 1458620; ANNOT 1458620; CLONE 9683; ANNOT 1471514; ANNOT 1471514; CLONE 9897; ANNOT 1445849; ANNOT 1445849; ANNOT 1500561; ANNOT 1500561; ANNOT 1464458; ANNOT 1464458; CLONE 11494; ANNOT 1438708; ANNOT 1438708; CLONE 11854; ANNOT 1506763; ANNOT 1506763; ANNOT 1453614; ANNOT 1453614; CLONE 12272; ANNOT 1506387; ANNOT 1506387; ANNOT 1474522; ANNOT 1474522; CLONE 13092; ANNOT 1471785; ANNOT 1471785; ANNOT 1470919; ANNOT 1470919; CLONE 13741; ANNOT 1462963; ANNOT 1462963; ANNOT 1459563; ANNOT 1459563; CLONE 13757; ANNOT 1471425; ANNOT 1471425; CLONE 13800; ANNOT 1458335; ANNOT 1458335; ANNOT 1464663; ANNOT 1464663; CLONE 14583; ANNOT 1530256; ANNOT 1530256; ANNOT 1476783; ANNOT 1476783; CLONE 14663; ANNOT 1503166; ANNOT 1503166; CLONE 14909; ANNOT 1497838; ANNOT 1497838; ANNOT 1522523; ANNOT 1522523; ANNOT 1471525; ANNOT 1471525; ANNOT 1511908; ANNOT 1511908; ANNOT 1464305; ANNOT 1464305; ANNOT 1451416; ANNOT 1451416; ANNOT 1461050; ANNOT 1461050; CLONE 16461; ANNOT 1479013; ANNOT 1479013; CLONE 17409; ANNOT 1457617; ANNOT 1457617; ANNOT 1478647; ANNOT 1478647; ANNOT 1453865; ANNOT 1453865; CLONE 17482; ANNOT 1501311; ANNOT 1501311; CLONE 17632; ANNOT 1474847; ANNOT 1474847; ANNOT 1507835; ANNOT 1507835; CLONE 17761; ANNOT 1481206; ANNOT 1481206; ANNOT 1534689; ANNOT 1534689; CLONE 17912; ANNOT 1514378; ANNOT 1514378; ANNOT 1494118; ANNOT 1494118; CLONE 18612; ANNOT 1522299; ANNOT 1522299; ANNOT 1527718; CLONE 19188; ANNOT 1445089; ANNOT 1445089; CLONE 20257; ANNOT 1442444; ANNOT 1442444; ANNOT 1452966; ANNOT 1452966; CLONE 20945; ANNOT 1519797; ANNOT 1519797; CLONE | 9; 10; 11; 12; 13; 14; 30; 31; 32; 33; 34; 38; 39; 40; 41; 42; 67; 68; 69; 70; 71; 72; 73; 74; 75; 95; 96; 97; 98; 99; 100; 101; 102; 103; 111; 112; 113; 114; 115; 116; 117; 121; 122; 123; 129; 130; 131; 132; 133; 134; 135; 136; 137; 138; 139; 140; 141; 142; 143; 144; 145; 146; 147; 148; 149; 150; 151; 152; 175; 176; 177; 178; 179; 180; 181; 182; 183; 184; 185; 186; 233; 234; 235; 236; 237; 238; 239; 240; 285; 286; 287; 288; 289; 362; 363; 364; 365; 366; 367; 368; 391; 392; 393; 402; 403; 404; 405; 406; 407; 408; 409; 410; 411; 457; 458; 459; 475; 476; 477; 478; 479; 515; 516; 517; 518; 519; 528; 529; 530; 536; 537; 538; 550; 551; 552; 553; 554; 564; 565; 566; 572; 573; 574; 575; 576; 619; 620; 621; 622; 623; 624; 625; 626; 627; 628; 629; 630; 631; 632; 633; 634; 635; 636; 637; 638; 639; 640; 647; 648; 649; 678; 679; 680; 681; 682; 683; 684; 685; 686; 692; 693; 694; 695; 696; 697; 698; 699; 700; 701; 702; 703; 704; 705; 706; 707; 708; 709; 720; 721; 722; 723; 724; 747; 748; 749; 796; 797; 798; 799; 800; 818; 819; 820; 821; 822; 823; 824; 825; 826; 827; 828; 829; 830; 831; 907; 908; 909; 910; 911; 912; 913; 914; 915; 916; 952; 953; 954; 955; 956; 1010; |

TABLE 1-continued

| Tissue | Phenotype Category | Phenotype | Phenotype Description | Applications | Ceres ID | SEQ ID NO |
|---|---|---|---|---|---|---|
| | | | | | 21068; ANNOT 1463333; ANNOT 1505772; ANNOT 1495675; ANNOT 1469576; ANNOT 1505772; ANNOT 1442758; ANNOT 1442758; CLONE 23518; ANNOT 1475658; ANNOT 1449267; ANNOT 1449267; ANNOT 1507191; ANNOT 1475658; CLONE 23523; ANNOT 1453919; ANNOT 1453919; CLONE 25172; ANNOT 1457346; ANNOT 1457346; ANNOT 1541170; CLONE 26542; ANNOT 1475323; ANNOT 1475323; ANNOT 1538272; CLONE 26825; ANNOT 1513438; ANNOT 1513438; ANNOT 1460167; ANNOT 1460167; CLONE 26907; ANNOT 1484074; ANNOT 1484074; ANNOT 1440016; ANNOT 1474847; ANNOT 1518242; CLONE 27460; ANNOT 1474847; ANNOT 1474847; ANNOT 1507835; ANNOT 1507835; CLONE 31014; ANNOT 1527449; ANNOT 1527449; ANNOT 1484207; CLONE 32348; ANNOT 1470719; ANNOT 1470719; ANNOT 1543728; ANNOT 1482066; ANNOT 1482066; CLONE 32361; ANNOT 1471776; ANNOT 1471776; ANNOT 1445033; ANNOT 1445033; CLONE 32548; ANNOT 1450324; ANNOT 1450324; ANNOT 1460836; CLONE 32615; ANNOT 1471372; ANNOT 1471372; CLONE 32737; ANNOT 1536373; ANNOT 1482905; ANNOT 1482905; CLONE 32751; ANNOT 1451171; CLONE 32753; ANNOT 1480607; ANNOT 1480607; ANNOT 1472242; ANNOT 1472242; CLONE 32791; ANNOT 1540248; ANNOT 1540248; CLONE 33482; ANNOT 1497019; ANNOT 1497019; CLONE 33554; ANNOT 1445599; ANNOT 1445599; ANNOT 1471882; ANNOT 1471882; ANNOT 1452398; ANNOT 1452398; ANNOT 1443041; ANNOT 1443041; ANNOT 1452397; ANNOT 1505498; ANNOT 1505498; ANNOT 1505497; ANNOT 1505497; ANNOT 1443040; ANNOT 1443040; ANNOT 1495964; ANNOT 1495964; ANNOT 1498580; ANNOT 1498580; ANNOT 1466060; ANNOT 1466060; CLONE 34151; ANNOT 1473827; ANNOT 1473827; ANNOT 1473827; ANNOT 1468614; ANNOT 1468614; CLONE 34167; ANNOT 1538733; ANNOT 1538733; ANNOT 1499810; ANNOT 1499810; ANNOT 1485323; ANNOT 1485323; ANNOT 1485323; CLONE 34385; ANNOT 1445331; ANNOT 1445331; ANNOT 1498316; ANNOT 1498316; CLONE 34552; ANNOT 1516449; ANNOT 1516449; ANNOT 1512976; ANNOT 1512976; CLONE 34635; ANNOT 1487773; ANNOT 1487773; ANNOT 1457333; ANNOT 1457333; ANNOT 1442634; ANNOT 1442634; CLONE 36818; ANNOT 1471507; ANNOT 1471507; ANNOT 1444893; ANNOT 1444893; ANNOT 1458642; ANNOT 1458642; ANNOT 1522497; ANNOT 1522497; ANNOT 1469105; ANNOT 1469105; ANNOT 1484993; ANNOT 1484993; CLONE 36891; ANNOT 1480518; ANNOT 1480518; ANNOT 1442194; ANNOT 1442194; ANNOT 1454127; ANNOT 1454127; ANNOT 1461716; ANNOT 1461716; ANNOT 1440277; ANNOT 1440277; ANNOT 1461415; ANNOT 1461415; ANNOT 1461414; ANNOT 1461414; ANNOT 1447424; ANNOT 1447424; ANNOT 1528127; ANNOT 1528127; ANNOT 1438717; ANNOT 1438717; ANNOT 1440276; ANNOT 1440276; ANNOT 1442556; ANNOT 1442556; ANNOT 1452873; ANNOT 1452873; ANNOT 1453483; ANNOT 1453483; ANNOT 1473384; ANNOT 1473384; ANNOT 1473708; ANNOT 1438698; ANNOT 1475808; ANNOT 1474708; ANNOT 1474708; ANNOT 1438698; ANNOT 1526083; ANNOT 1526083; ANNOT 1498856; ANNOT 1498856; CLONE 36904; ANNOT 1445872; ANNOT 1445872; ANNOT 1472663; ANNOT 1472663; CLONE 37217; ANNOT 1465580; ANNOT 1465580; ANNOT 1472014; ANNOT 1472014; ANNOT 1445195; ANNOT 1445195; CLONE 37298; ANNOT 1453650; ANNOT 1453650; CLONE 37298; ANNOT 1476538; ANNOT 1476538; ANNOT 1493576; ANNOT 1493576; CLONE 37589; ANNOT 1440727; ANNOT 1440727; CLONE 37658; ANNOT 1497485; ANNOT 1497485; CLONE 37663; ANNOT 37658; ANNOT | 1011; 1012; 1013; 1014; 1030; 1031; 1032; 1033; 1034; 1043; 1044; 1045; 1046; 1047; 1048; 1049; 1055; 1056; 1057; 1058; 1059; 1185; 1186; 1187; 1188; 1189; 1219; 1220; 1221; 1222; 1223; 1224; 1225; 1226; 1227; 1228; 1229; 1230; 1231; 1232; 1233; 1234; 1235; 1239; 1240; 1241; 1242; 1243; 1244; 1245; 1246; 1247; 1248; 1249; 1250; 1251; 1252; 1253; 1254; 1255; 1256; 1257; 1279; 1280; 1281; 1287; 1288; 1289; 1290; 1291; 1292; 1293; 1294; 1295; 1296; 1297; 1298; 1299; 1300; 1301; 1302; 1303; 1304; 1305; 1306; 1307; 1308; 1309; 1338; 1339; 1340; 1341; 1342; 1343; 1344; 1345; 1346; 1347; 1348; 1349; 1364; 1365; 1366; 1367; 1368; 1406; 1407; 1408; 1409; 1410; 1416; 1417; 1418; 1419; 1420; 1421; 1422; 1505; 1506; 1507; 1508; 1509; 1510; 1511; 1512; 1513; 1514; 1515; 1516; 1517; 1548; 1549; 1550; 1551; 1552; 1553; 1554; 1555; 1556; 1557; 1558; 1559; 1560; 1561; 1562; 1563; 1564; 1565; 1566; 1567; 1568; 1569; 1570; 1571; 1572; 1573; 1574; 1575; 1576; 1577; 1578; 1579; 1580; 1581; 1582; 1583; 1584; 1585; 1586; 1587; 1588; 1589; 1590; 1591; 1592; 1593; 1610; 1611; 1612; 1613; 1614; 1615; 1616; 1622; 1623; 1624; 1625; 1626; 1627; 1628; 1629; 1651; 1652; 1653; 1654; 1655; 1656; 1657; 1658; 1659; |

TABLE 1-continued

| Tissue | Phenotype Category | Phenotype | Phenotype Description | Applications | Ceres ID | SEQ ID NO |
|---|---|---|---|---|---|---|
| | | | | | 1447659; ANNOT 1447659; ANNOT 1438478; CLONE 38101; ANNOT 1454656; ANNOT 1454656; ANNOT 1528263; ANNOT 1458103; ANNOT 1458103; ANNOT 1464899; ANNOT 1482966; ANNOT 1482966; ANNOT 1441039; ANNOT 1520449; ANNOT 1520449; CLONE 38419; ANNOT 1542971; ANNOT 1521332; ANNOT 1521332; ANNOT 1467961; ANNOT 1467961; CLONE 38690; ANNOT 1525183; ANNOT 1525183; CLONE 38785; ANNOT 1461193; ANNOT 1461193; ANNOT 1514466; ANNOT 1514466; CLONE 39286; ANNOT 1447961; ANNOT 1447961; ANNOT 1490936; ANNOT 1499936; CLONE 40508; ANNOT 1453626; ANNOT 1453626; CLONE 40729; ANNOT 1481678; ANNOT 1481678; CLONE 40766; ANNOT 1450499; ANNOT 1450499; CLONE 41306; ANNOT 1475806; ANNOT 1475806; ANNOT 1454125; ANNOT 1454125; CLONE 41439; CLONE 4214l; ANNOT 1473839; ANNOT 1473839; CLONE 92670; ANNOT 1531919; ANNOT 1531919; CLONE 95135; ANNOT 1527449; ANNOT 1527449; ANNOT 1537653; ANNOT 1537653; ANNOT 1473733; ANNOT 1468537; ANNOT 1468537; CLONE 97434; ANNOT 1488311; ANNOT 1518776; ANNOT 1518776; CLONE 97480; ANNOT 1493111; ANNOT 1493111; CLONE 98855; ANNOT 1460836; ANNOT 1460836; ANNOT 1450324; ANNOT 1450324; CLONE 99657; ANNOT 1461858; ANNOT 1461858; ANNOT 1461858; ANNOT 1440018; ANNOT 1440018; ANNOT 1440018; ANNOT 1440019; ANNOT 1511305; ANNOT 1511305; ANNOT 1511305; ANNOT 1464927; ANNOT 1527449; ANNOT 1464927; ANNOT 1464927; CLONE 100465; ANNOT 1466439; ANNOT 1466439; ANNOT 1448977; ANNOT 1448977; ANNOT 1519767; ANNOT 1519767; ANNOT 1501982; ANNOT 1501982; CLONE 107731; ANNOT 1480518; ANNOT 1480518; ANNOT 1442194; ANNOT 1442194; ANNOT 1454127; ANNOT 1454127; ANNOT 1461414; ANNOT 1461414; ANNOT 1447424; ANNOT 1447424; ANNOT 1452873; ANNOT 1452873; ANNOT 1474708; ANNOT 1474708; CLONE 108056; ANNOT 1464935; ANNOT 1464935; ANNOT 1458064; ANNOT 1458064; ANNOT 1511298; ANNOT 1511298; ANNOT 1511298; ANNOT 1458065; ANNOT 1458065; ANNOT 1511299; ANNOT 1511299; CLONE 110454; CLONE 111209; ANNOT 1494507; ANNOT 1494507; CLONE 112288; ANNOT 1517215; ANNOT 1517215; CLONE 114466; ANNOT 1479643; ANNOT 1479643; ANNOT 1486882; ANNOT 1486882; CLONE 116257; ANNOT 1520806; ANNOT 1520806; ANNOT 1473089; ANNOT 1473089; ANNOT 1500150; CLONE 117895; ANNOT 1448592; ANNOT 1448592; ANNOT 148943; ANNOT 1448594; CLONE 1448594; CLONE 119256; ANNOT 1469636; ANNOT 1469636; ANNOT 1479002; CLONE 119598; ANNOT 1497424; ANNOT 1497424; ANNOT 1497424; ANNOT 1471357; ANNOT 1471357; CLONE 122353; ANNOT 1472265; ANNOT 1472265; CLONE 141805; ANNOT 1497485; ANNOT 1497485; CLONE 141890; ANNOT 1494533; ANNOT 1494533; ANNOT 1493111; ANNOT 1466313; ANNOT 1466313; CLONE 147358; ANNOT 1493111; ANNOT 1461452; ANNOT 1461452; CLONE 148680; ANNOT 1522509; ANNOT 1522509; CLONE 148943; ANNOT 1472949; ANNOT 1472949; CLONE 149380; ANNOT 1461440; ANNOT 1461440; ANNOT 1461430; ANNOT 1461430; ANNOT 1461427; ANNOT 1461427; ANNOT 1440253; ANNOT 1440253; CLONE 151087; ANNOT 1504145; ANNOT 1504145; ANNOT 1451079; ANNOT 1451079; ANNOT 1451079; CLONE 157058; ANNOT 1528285; ANNOT 1528285; ANNOT 1454671; ANNOT 1454671; CLONE 157547; ANNOT 1473898; ANNOT 1473898; CLONE 158333; ANNOT 1466505; ANNOT 1466505; ANNOT 1449026; CLONE 205648; ANNOT 1456842; ANNOT 1456842; ANNOT 1456842; ANNOT 1504224; ANNOT 1504224; CLONE 227651; ANNOT | 1660; 1661; 1682; 1683;<br>1684; 1685; 1686; 1687;<br>1688; 1689; 1690; 1691;<br>1692; 1693; 1694; 1695;<br>1696; 1747; 1748; 1749;<br>1750; 1751; 1752; 1753;<br>1774; 1775; 1776; 1796;<br>1797; 1798; 1799; 1800;<br>1838; 1839; 1840; 1841;<br>1842; 1912; 1913; 1914;<br>1930; 1931; 1932; 1933;<br>1934; 1935; 1976; 1977;<br>1978; 1979; 1980; 1998;<br>2015; 2016; 2017; 2061;<br>2062; 2063; 2076; 2077;<br>2078; 2079; 2080; 2081;<br>2082; 2083; 2084; 2103;<br>2104; 2105; 2106; 2107;<br>2108; 2109; 2110; 2118;<br>2119; 2120; 2121; 2122;<br>2142; 2143; 2144; 2145;<br>2146; 2147; 2148; 2149;<br>2150; 2151; 2152; 2153;<br>2154; 2155; 2156; 2157;<br>2158; 2159; 2160; 2196;<br>2197; 2198; 2199; 2200;<br>2201; 2202; 2203; 2204;<br>2263; 2264; 2265; 2266;<br>2267; 2268; 2269; 2270;<br>2271; 2272; 2273; 2274;<br>2275; 2276; 2277; 2281;<br>2282; 2283; 2284; 2285;<br>2286; 2287; 2288; 2289;<br>2290; 2291; 2313; 2314;<br>2315; 2316; 2327; 2328;<br>2329; 2345; 2346; 2347;<br>2348; 2349; 2394; 2395;<br>2396; 2397; 2398; 2399;<br>2400; 2412; 2413; 2414;<br>2415; 2416; 2451; 2452;<br>2453; 2454; 2455; 2456;<br>2457; 2458; 2459; 2460;<br>2481; 2482; 2483; 2517;<br>2518; 2519; 2523; 2524;<br>2525; 2526; 2527; 2528;<br>2529; 2530; 2531; 2532;<br>2540; 2541; 2542; 2543;<br>2544; 2545; 2546; 2547;<br>2548; 2549; 2550; 2551;<br>2552; 2553; 2554; 2560; |

TABLE 1-continued

| Tissue | Phenotype Category | Phenotype | Phenotype Description | Applications | Ceres ID | SEQ ID NO |
|---|---|---|---|---|---|---|
| | | | | | 1474222; ANNOT 1474222; ANNOT 1468994; ANNOT 1468994; ANNOT 1497043; ANNOT 1497043; CLONE 262460; ANNOT 1530053; ANNOT 1530053; ANNOT 1493414; ANNOT 1493414; CLONE 463203; ANNOT 1511505; ANNOT 1511505; CLONE 482122; ANNOT 1438776; ANNOT 1438776; CLONE 534397; ANNOT 1453458; ANNOT 1453458; ANNOT 1489056; ANNOT 1489056; ANNOT 1442794; ANNOT 1442794; ANNOT 1495713; ANNOT 1495713; ANNOT 1442797; ANNOT 1442797; ANNOT 1468612; ANNOT 1468612; ANNOT 1460503; ANNOT 1460503; ANNOT 1488307; ANNOT 1488307; ANNOT 1440343; ANNOT 1440343; ANNOT 1493212; ANNOT 1493212; CLONE 536457; ANNOT 1490030; ANNOT 1490030; ANNOT 1493787; ANNOT 1493787; CLONE 536796; ANNOT 1484779; ANNOT 1484779; ANNOT 1538185; ANNOT 1538185; ANNOT 1455109; ANNOT 1455109; ANNOT 1477384; ANNOT 1477384; CLONE 572121; ANNOT 1477450; ANNOT 1477450; CLONE 641355; ANNOT 1463335; ANNOT 1463334; ANNOT 1463334; ANNOT 1452665; ANNOT 1452665; CLONE 660003; ANNOT 1508184; ANNOT 1508184; ANNOT 1528645; ANNOT 1528645; CLONE 664365; ANNOT 1463333; ANNOT 1463333; ANNOT 1505772; ANNOT 1505772; ANNOT 1478872; ANNOT 1478872; ANNOT 1442758; ANNOT 1442758; ANNOT 1495675; ANNOT 1495675; ANNOT 1469576; ANNOT 1469576; ANNOT 1452666; ANNOT 1452666; ANNOT 1452668; ANNOT 1452668; ANNOT 1442757; ANNOT 1442757; CLONE 708342; ANNOT 1538185; ANNOT 1538185; CLONE 965175; ANNOT 1479013; ANNOT 1479013; CLONE 1001432; ANNOT 1475043; ANNOT 1475043; ANNOT 1454586; ANNOT 1454586; ANNOT 1507756; ANNOT 1507756; ANNOT 1469708; ANNOT 1469708; CLONE 1002819; ANNOT 1474290; ANNOT 1474290; ANNOT 1522314; ANNOT 1522314; ANNOT 1497147; ANNOT 1497147; ANNOT 1471045; ANNOT 1471045; CLONE 1006934; ANNOT 1532963; ANNOT 1532963; CLONE 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1479711; ANNOT 1440649; ANNOT 1440649; ANNOT 1464547; ANNOT 1464547; ANNOT 1454104; ANNOT 1454104; CLONE 1043081; ANNOT 1478584; ANNOT 1478584; ANNOT 1455564; ANNOT 1455564; ANNOT 1508764; ANNOT 1508764; ANNOT 1477651; ANNOT 1477651; ANNOT 1487130; ANNOT 1487130; CDNA 23495481; ANNOT 1485271; ANNOT 1485271; ANNOT 1447245; ANNOT 1447245; CDNA 23498145; ANNOT 1482362; ANNOT 1482362; ANNOT 1489077; ANNOT 1489077; CDNA 23507479; ANNOT 1510416; ANNOT 1510416; ANNOT 1541253; ANNOT 1541253; CDNA 23518705; ANNOT 1463957; ANNOT 1463957; ANNOT 1458961; ANNOT 1458961; CDNA 23530811; ANNOT 1453922; ANNOT 1453922; CDNA 23545147; ANNOT 1443044; ANNOT 1443044; CDNA 3607011; ANNOT 1442604; ANNOT 1442604; ANNOT 1442612; ANNOT 1442612; ANNOT 1442608; ANNOT 1442608; ANNOT 1452827; ANNOT 1452827; CDNA 3650272; CDNA 3650177; CDNA 3650475; ANNOT 1497025; ANNOT 1497025; CDNA 3651022; ANNOT 1473760; CDNA 3651290; ANNOT 1471370; ANNOT 1471370; ANNOT 1473760; ANNOT 1444471; ANNOT 1444471; ANNOT 1491278; ANNOT 1491278; ANNOT 1447690; ANNOT 1447690; CDNA 36529808; ANNOT 1440346; ANNOT 1440346; ANNOT 1457794; ANNOT 1457794; CDNA 36534269; ANNOT 1524172; ANNOT 1524172; CDNA 36534713; ANNOT 1514007; ANNOT 1514007; ANNOT 1460742; ANNOT 1460742; CDNA 36535718; ANNOT 1451133; ANNOT 1451133; ANNOT 1456774; ANNOT 1456774; CDNA 36560639; ANNOT 1437702; ANNOT 1437702; ANNOT 1444156; ANNOT 1444156; CDNA 36571789; CDNA 36575796; ANNOT 1486224; ANNOT 1486224; ANNOT 1497097; ANNOT 1497097; ANNOT 1444021; ANNOT 1444021; CDNA 36579424; ANNOT 1455663; ANNOT | 2561; 2562; 2563; 2564; 2588; 2589; 2590; 2591; 2592; 2593; 2594; 2595; 2611; 2612; 2613; 2614; 2615; 2625; 2626; 2627; 2628; 2629; 2683; 2684; 2685; 2686; 2687; 2688; 2689; 2774; 2775; 2776; 2777; 2778; 3003; 3004; 3005; 3049; 3050; 3051; 3109; 3110; 3111; 3112; 3113; 3114; 3115; 3116; 3117; 3118; 3119; 3120; 3121; 3122; 3123; 3124; 3125; 3126; 3127; 3128; 3129; 3130; 3131; 3132; 3133; 3134; 3154; 3155; 3156; 3157; 3158; 3159; 3160; 3161; 3162; 3252; 3253; 3254; 3304; 3305; 3306; 3307; 3308; 3309; 3310; 3314; 3315; 3316; 3317; 3318; 3319; 3320; 3321; 3322; 3323; 3324; 3325; 3326; 3327; 3328; 3329; 3330; 3331; 3332; 3333; 3334; 3335; 3336; 3337; 3361; 3362; 3363; 3388; 3389; 3390; 3419; 3420; 3421; 3422; 3423; 3424; 3425; 3426; 3427; 3428; 3429; 3430; 3431; 3432; 3433; 3434; 3435; 3436; 3437; 3438; 3439; 3440; 3441; 3442; 3443; 3444; 3445; 3446; 3447; 3448; 3449; 3450; 3451; 3452; 3453; 3454; 3455; 3456; 3481; 3482; 3483; 3484; 3485; 3486; 3487; 3488; 3489; 3490; 3491; 3622; 3623; 3624; 3625; 3626; 3641; 3642; 3643; 3644; 3645; 3704; 3705; 3706; 3707; 3708; 3748; 3749; 3750; 3751; 3752; 3787; 3788; 3789; 3813; 3814; 3815; 3875; 3876; 3877; 3878; 3879; 3880; 3881; 3882; 3883; 3889; |

TABLE 1-continued

| Tissue | Phenotype Category | Phenotype | Phenotype Description | Applications | Ceres ID | SEQ ID NO |
|---|---|---|---|---|---|---|
| | | | | | 1455663; ANNOT 1438024; ANNOT 1438024; ANNOT 1448068; ANNOT 1448068; CDNA 3695523; ANNOT 1451434; ANNOT 1451434; CDNA 3697835; ANNOT 1461440; ANNOT 1461440; ANNOT 1461427; ANNOT 1461427; ANNOT 1461430; ANNOT 1461430; ANNOT 1440253; ANNOT 1440253; CDNA 3679029; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; ANNOT 1461475; | 3890; 3891; 3892; 3893; 3894; 3895; 3896; 3897; 3898; 3899; 3900; 3901; 3902; 3903; 3904; 3920; 3921; 3922; 3938; 3939; 3940; 3941; 3942; 3943; 3944; 3945; 3946; 3947; 3956; 3957; 3958; 3959; 3960; 4005; 4006; 4007; 4043; 4044; 4045; 4046; 4047; 4053; 4054; 4055; 4056; 4057; 4063; 4064; 4065; 4066; 4067; 4068; 4069; 4070; 4071; 4072; 4073; 4074; 4075; 4076; 4077; 4078; 4079; 4080; 4081; 4082; 4083; 4084; 4085; 4086; 4087; 4088; 4089; 4090; 4091; 4092; 4093; 4094; 4095; 4096; 4097; 4098; 4099; 4100; 4101; 4102; 4103; 4104; 4105; 4106; 4107; 4108; 4109; 4110; 4111; 4112; 4113; 4114; 4115; 4116; 4117; 4118; 4119; 4120; 4121; 4122; 4123; 4124; 4125; 4126; 4127; 4128; 4129; 4130; 4131; 4132; 4133; 4134; 4135; 4136; 4137; 4138; 4139; 4140; 4141; 4142; 4143; 4144; 4145; 4146; 4147; 4148; 4149; 4150; 4151; 4152; 4153; 4154; 4155; 4156; 4157; 4158; 4159; 4160; 4161; 4162; 4163; 4164; 4165; 4166; 4167; 4168; 4169; 4170; 4171; 4172; 4173; 4174; 4175; 4176; 4177; 4178; 4179; 4180; 4181; 4182; 4183; 4184; 4185; 4186. |
| WHOLE PLANT | Development | Late Senescence | The plant senesces significantly late copared to wild-type. | Useful for delaying senescence | CLONE 13263; ANNOT 1470919; ANNOT 1470919; CLONE 13757; ANNOT 1471425; ANNOT 1471425; CLONE 32152; ANNOT 1450535; ANNOT 1450535; ANNOT 1513913; ANNOT 1513913; ANNOT 1460651; ANNOT 1460651; ANNOT 1442535; ANNOT 1442535; ANNOT 1452888; ANNOT 1452888; ANNOT 1487705; ANNOT 1487705; CLONE 33559; ANNOT 1481146; ANNOT 1481146; ANNOT 1481150; ANNOT 1481150; ANNOT 1481138; ANNOT 1481138; ANNOT 1485824; ANNOT 1485824; ANNOT 1534622; ANNOT 1534622; CLONE 40729; ANNOT | 536; 537; 538; 564; 565; 566; 1206; 1207; 1208; 1209; 1210; 1211; 1212; 1213; 1214; 1215; 1216; 1217; 1218; 1310; 1311; 1312; 1313; 1314; 1315; 1316; 1317; 1318; 1319; |

| Tissue | Phenotype Category | Phenotype | Phenotype Description | Applications | Ceres ID | SEQ ID NO |
|---|---|---|---|---|---|---|
| | | | | | 1481678; ANNOT 1481678; CLONE 97480; ANNOT 1493111; ANNOT 1493111; CLONE 99298; ANNOT 1473029; ANNOT 1467502; ANNOT 1467502; CLONE 99657; ANNOT 1461858; ANNOT 1461858; ANNOT 1461858; ANNOT 1440018; ANNOT 1440018; ANNOT 1440018; ANNOT 1440019; ANNOT 1440019; ANNOT 1511305; ANNOT 1511305; ANNOT 1511305; ANNOT 1464927; ANNOT 1464927; CLONE 100245; ANNOT 1535451; ANNOT 1535451; ANNOT 1152285; ANNOT 1532285; ANNOT 148024I; ANNOT 148024I; ANNOT 1446025; CLONE 101798; ANNOT 1449432; ANNOT 1449432; CLONE 106301; CDNA 2350510З; ANNOT 1449431; ANNOT 1502439; ANNOT 1502439; ANNOT 1491278; ANNOT 1491278; ANNOT 1447690; ANNOT 1447690; ANNOT 1490915; ANNOT 1490915; ANNOT 1500987; ANNOT 1500987; | 1320; 1930; 1931; 1932; 2108; 2109; 2110; 2130; 2131; 2132; 2133; 2134; 2142; 2143; 2144; 2145; 2146; 2147; 2148; 2149; 2150; 2151; 2152; 2153; 2154; 2155; 2156; 2157; 2158; 2159; 2160; 2182; 2183; 2184; 2185; 2186; 2187; 2188; 2189; 2190; 2219; 2220; 2221; 2222; 2223; 2224; 2225; 2262; 3687; 3688; 3689; 3690; 3691; 3692; 3693; 3694; 3695; |
| WHOLE PLANT | Nitrogen use | Low Nitrate | The plants are tolerant to low nitrogen/nitrate conditions compared to control. | Useful for making plants tolerant to low nitrogen | CLONE 18152; ANNOT 1448104; ANNOT 1448104; ANNOT 1483641; CLONE 599633; ANNOT 1449885; CDNA 23522373; ANNOT 1538994; ANNOT 1538994; ANNOT 1447080; ANNOT 1447080; CDNA 36529494; | 710; 711; 712; 713; 714; 3270; 3271; 3272; 3761; 3762; 3763; 3764; 3765; 3919; |
| WHOLE PLANT | Nitrogen use | No Nitrogen | The plants have increased vigor under no nitrogen conditions compared to control. | Useful for making plants tolerant to low nitrogen | CLONE 116356; ANNOT 1467190; CLONE 123228; ANNOT 1533417; ANNOT 1533417; ANNOT 1470723; | 2401; 2402; 2403; 2487; 2488; 2489; 2490; 2491; |
| WHOLE PLANT | Nitrogen use, Phosphate use | No N, No PO4 | The plants are tolerant to no nitrogen and no phosphate growth media. | Useful for making plants tolerant to low nitrogen/low phosphate | CLONE 585; ANNOT 1447138; ANNOT 1469376; ANNOT 1469376; ANNOT 1475299; ANNOT 1475299; | 18; 19; 20; 21; 22; 23; 24; |
| WHOLE PLANT | Nitrogen use, Stress tolerance | LNABA | The plants are tolerant to low nitrogen conditions and high ABA concentrations. | Useful for making plants tolerant to low nitrogen and drought conditions | CLONE 38286; ANNOT 1459467; ANNOT 1459467; ANNOT 1516688; ANNOT 1516688; ANNOT 1488767; ANNOT 1488767; ANNOT 1463396; ANNOT 1463396; ANNOT 1495750; ANNOT 1495750; ANNOT 1452612; ANNOT 1452612; ANNOT 1442831; ANNOT 1442831; | 1717; 1718; 1719; 1720; 1721; 1722; 1723; 1724; 1725; 1726; 1727; 1728; 1729; 1730; 1731; |
| WHOLE PLANT | Nutrient uptake | MSX | The plants are tolerant to nitrogen assimilation inhibitor, low nitrogen conditions and have seed nitrogen accumulation. | Useful for making plants tolerant to low nitrogen | CLONE 6288; ANNOT 1442129; ANNOT 1442129; ANNOT 1467192; ANNOT 1467192; CLONE 8184; ANNOT 1485684; ANNOT 1485684; ANNOT 1447192; ANNOT 1447192; CLONE 13625; ANNOT 1455211; ANNOT 1455211; CLONE 15650; ANNOT 1513435; ANNOT 1513435; CLONE 20676; ANNOT 1444531; ANNOT 1444531; ANNOT 1467580; ANNOT 1467580; ANNOT 1450490; ANNOT 1450490; ANNOT 1472925; CLONE 21759; ANNOT 1472925; ANNOT 1460694; ANNOT 1460694; ANNOT 1452864; ANNOT 1452864; CLONE 26838; ANNOT 1452938; ANNOT 1452938; ANNOT 1442477; ANNOT 1442477; CLONE 29992; ANNOT 1494652; ANNOT 1494652; ANNOT 1459467; ANNOT 1459467; ANNOT 1488767; ANNOT 1488767; ANNOT 1463396; ANNOT 1463396; ANNOT 1516688; ANNOT 1516688; ANNOT 1495750; ANNOT 1495750; ANNOT | 280; 281; 282; 283; 284; 352; 353; 354; 355; 356; 544; 545; 546; 644; 645; 646; 801; 802; 803; 804; 805; 806; 807; 859; 860; 861; 862; 863; 864; 865; 1035; 1036; 1037; 1038; 1039; 1161; 1162; 1163; 1717; 1718; 1719; 1720; 1721; 1722; 1723; 1724; 1725; 1726; 1727; 1728; |

TABLE 1-continued

| Tissue | Phenotype Category | Phenotype | Phenotype Description | Applications | Ceres ID | SEQ ID NO |
|---|---|---|---|---|---|---|
| | | | | | 1452612; ANNOT 1452612; ANNOT 1442831; CLONE 38584; ANNOT 1485549; ANNOT 1485549; ANNOT 1447057; CLONE 38891; ANNOT 1440360; ANNOT 1514613; ANNOT CLONE 41359; ANNOT 1520442; CLONE 41471; ANNOT 1515268; ANNOT 1515268; ANNOT 1461975; ANNOT 1449897; ANNOT 1449897; ANNOT 1439694; ANNOT 1519353; ANNOT 1519353; ANNOT 1466018; CLONE 118640; ANNOT 1479513; ANNOT 1479513; ANNOT 1471879; ANNOT 1471879; CLONE 545780; CLONE 561791; ANNOT 1486447; ANNOT 2702830; ANNOT 1516968; ANNOT 1516968; ANNOT 1520085; CDNA 4811190; ANNOT 1482936; ANNOT 1482936; | 1729; 1730; 1731; 1761; 1762; 1763; 1764; 1765; 1806; 1807; 1808; 1809; 1810; 1995; 1996; 1997; 2002; 2003; 2004; 2005; 2006; 2007; 2008; 2009; 2010; 2011; 2012; 2013; 2014; 2426; 2427; 2428; 2638; 2639; 2640; 3196; 3224; 3225; 3226; 3492; 3493; 3494; 3495; 3496; 3511; 3512; 3513; |
| WHOLE SEEDLING | Photosynthetic capacity | Dark Green | The plant is visibly darker green. | Useful for increasing chlorophyll and photosynthetic capacity | CLONE 38370; ANNOT 1471869; ANNOT 1471869; ANNOT 1448032; ANNOT 1448031; ANNOT 1448031; ANNOT 1438060; ANNOT 1438061; ANNOT 1438061; ANNOT 1448030; ANNOT 1437831; ANNOT 1437831; | 1732; 1733; 1734; 1735; 1736; 1737; 1738; 1739; 1740; 1741; 1742; 1743; 1744; 1745; 1746; |
| WHOLE PLANT | Photosynthetic capacity | Dark Green | The plant is abnormally dark green. | Useful for increasing chlorophyll and photosynthetic capacity | CLONE 907; ANNOT 1502138; ANNOT 1449135; ANNOT 1449135; ANNOT 1502138; ANNOT 1453081; ANNOT 1442349; CLONE 1241; ANNOT 1453081; ANNOT 1442349; ANNOT 1442349; CLONE 1496; ANNOT 1490668; ANNOT 1474027; ANNOT 1474027; ANNOT 1497865; ANNOT 1471512; ANNOT 1471512; ANNOT 1443061; ANNOT 1443061; ANNOT 1504203; ANNOT 1505468; ANNOT 1452369; ANNOT 1452369; CLONE 1610; ANNOT 1454586; ANNOT 1454586; ANNOT 1475043; ANNOT 1475043; ANNOT 1507756; ANNOT 1469708; ANNOT 1469708; CLONE 2403; ANNOT 1509972; ANNOT 1509972; ANNOT 1504203; ANNOT 1504203; ANNOT 1443061; ANNOT 1452369; ANNOT 1452369; ANNOT CLONE 2561; ANNOT 1450958; ANNOT 1450958; ANNOT 1456475; ANNOT 1456475; ANNOT 1446945; ANNOT 1446945; CLONE 3000; ANNOT 1518918; ANNOT 1518918; ANNOT 1535677; ANNOT 1535677; ANNOT 1482181; ANNOT 1482181; CLONE 3006; ANNOT 1472173; ANNOT 1472173; CLONE 3036; ANNOT 1456840; ANNOT 1456840; CLONE 3363; ANNOT 1445515; ANNOT 1445515; ANNOT 1461861; ANNOT 1461861; ANNOT 1449363; ANNOT 1449363; ANNOT 1465198; ANNOT 1465198; ANNOT 1518517; ANNOT 1518517; CLONE 3542; ANNOT 1471301; ANNOT 1471301; CLONE 3858; ANNOT 1459068; ANNOT 1459068; CLONE 5597; ANNOT 1507708; ANNOT 1507708; ANNOT 1475094; ANNOT 1475094; CLONE 6387; ANNOT 1509111; ANNOT 1509111; ANNOT 1541620; ANNOT 1541620; CLONE 6411; ANNOT 1505322; ANNOT 1505322; ANNOT 1496110; ANNOT 1496110; ANNOT 1496111; CLONE 7191; ANNOT 1493787; ANNOT 1493787; CLONE 8254; ANNOT 1543042; ANNOT 1543042; ANNOT 1489655; ANNOT 1489655; CLONE 8265; ANNOT 1438919; ANNOT 1438919; ANNOT 1499398; ANNOT 1499398; ANNOT 1446419; ANNOT 1446419; CLONE 8877; ANNOT 1507340; ANNOT 1507340; ANNOT 1529361; ANNOT 1529361; CLONE 8916; ANNOT 1462804; ANNOT 1462804; CLONE 9683; ANNOT 1471514; ANNOT 1471514; CLONE 9897; ANNOT 1445849; ANNOT 1445849; ANNOT 1500561; ANNOT 1500561; ANNOT 1464458; ANNOT 1464458; ANNOT 1467184; ANNOT 1467184; CLONE 11854; ANNOT CLONE 10879; ANNOT 1506763; ANNOT 1506763; ANNOT 1453614; ANNOT 1453614; CLONE 12250; ANNOT 1497150; ANNOT 1497150; ANNOT 1524446; ANNOT 1524446; CLONE | 30; 31; 32; 33; 34; 38; 39; 40; 41; 42; 50; 51; 52; 53; 54; 55; 56; 57; 58; 59; 60; 61; 62; 63; 64; 65; 66; 67; 68; 69; 70; 71; 72; 73; 74; 75; 95; 96; 97; 98; 99; 100; 101; 102; 103; 104; 105; 106; 107; 108; 109; 110; 111; 112; 113; 114; 115; 116; 117; 118; 119; 120; 121; 122; 123; 129; 130; 131; 132; 133; 134; 135; 136; 137; 138; 139; 145; 146; 147; 175; 176; 177; 233; 234; 235; 236; 237; 285; 286; 287; 288; 289; 293; 294; 295; 296; 297; 298; 299; 317; 318; 319; 357; 358; 359; 360; 361; 362; 363; 364; 365; 366; 367; 368; 383; 384; 385; 386; 387; 388; 389; 390; 402; 403; 404; 405; 406; 407; 408; 409; 410; 411; 437; 438; 439; 475; 476; 477; 478; 479; 510; 511; 512; 513; 514; 536; 537; 538; 555; 556; 557; 558; 559; 560; 561; 562; 563; 564; 565; 566; 572; 573; 574; 575; 576; 619; 620; |

TABLE 1-continued

| Tissue | Phenotype Category | Phenotype | Phenotype Description | Applications | Ceres ID | SEQ ID NO |
|---|---|---|---|---|---|---|
| | | | | | 13263; ANNOT 1470919; ANNOT 1442604; CLONE 13745; ANNOT 1442604; ANNOT 1442608; ANNOT 1442612; ANNOT 1442608; ANNOT 1452827; ANNOT 1452827; CLONE 13757; ANNOT 1471425; ANNOT 1471425; CLONE 13800; ANNOT 1458335; ANNOT 1458335; ANNOT 1464663; ANNOT 1464663; CLONE 14583; ANNOT 1530256; ANNOT 1530256; ANNOT 1476783; ANNOT 1476783; ANNOT 1503166; ANNOT 1503166; CLONE 16461; ANNOT 1479013; ANNOT 1479013; CLONE 17632; ANNOT 1474847; ANNOT 1474847; ANNOT 1474847; ANNOT 1507835; CLONE 1776l; ANNOT 1481206; ANNOT 1481206; ANNOT 1534689; ANNOT 1534689; CLONE 17912; ANNOT 1514378; ANNOT 1514378; ANNOT 1494118; ANNOT 1494118; CLONE 19116; ANNOT 1467522; ANNOT 1467522; ANNOT 1526421; ANNOT 1526421; CLONE 19188; CLONE 19188; ANNOT 1445089; ANNOT 1445089; CLONE 19486; ANNOT 1452204; ANNOT 1452204; ANNOT 1443204; ANNOT 1443204; CLONE 19510; ANNOT 1501412; ANNOT 1501412; ANNOT 1490383; ANNOT 1490383; ANNOT 1448419; ANNOT 1448419; CLONE 19657; ANNOT 1456256; ANNOT 1456256; ANNOT 1503828; ANNOT 1503828; ANNOT 1450752; ANNOT 1450752; CLONE 20045; ANNOT 1519797; ANNOT 1519797; CLONE 21068; ANNOT 1463333; ANNOT 1463333; ANNOT 1505772; ANNOT 1505772; ANNOT 1495675; ANNOT 1495675; ANNOT 1469576; ANNOT 1469576; ANNOT 1442758; ANNOT 1442758; CLONE 23322; ANNOT 1512337; ANNOT 1512337; ANNOT 1517094; ANNOT 1517094; CLONE 23518; ANNOT 1475658; ANNOT 1475658; ANNOT 1449267; ANNOT 1449267; ANNOT 1507191; ANNOT 1507191; CLONE 23523; ANNOT 1453919; ANNOT 1453919; CLONE 25538; ANNOT 1480776; ANNOT 1480776; CLONE 2607; CLONE 25607; ANNOT 1450220; ANNOT 1450220; CLONE 25758; ANNOT 1473748; ANNOT 1473748; CLONE 25886; ANNOT 1446650; ANNOT 1446650; ANNOT 1439514; ANNOT 1439514; ANNOT 1477202; ANNOT 1477202; ANNOT 1455325; ANNOT 1455325; CLONE 26560; ANNOT 1536088; ANNOT 1536088; ANNOT 1482610; ANNOT 1482610; CLONE 26637; ANNOT 1451045; ANNOT 1451045; ANNOT 1451045; CLONE 26655; ANNOT 1477170; ANNOT 1477170; ANNOT 1508498; ANNOT 1508498; ANNOT 1530647; ANNOT 1530647; CLONE 26825; ANNOT 1513438; ANNOT 1513438; ANNOT 1460167; ANNOT 1460167; CLONE 27460; ANNOT 1474847; ANNOT 1474847; ANNOT 1507835; ANNOT 1507835; CLONE 27464; ANNOT 1453044; ANNOT 1453044; ANNOT 1451171; ANNOT 1451171; CLONE 28033; ANNOT 1459086; ANNOT 1459086; CLONE 28602; ANNOT 1461728; ANNOT 1461728; ANNOT 1488330; ANNOT 1488330; ANNOT 1460480; ANNOT 1460480; ANNOT 1461614; ANNOT 1461614; ANNOT 1479711; ANNOT 1479711; ANNOT 1479712; ANNOT 1479712; ANNOT 1488329; ANNOT 1488329; ANNOT 1460481; ANNOT 1460481; ANNOT 1461613; ANNOT 1461613; ANNOT 1458198; ANNOT 1458198; ANNOT 1483327; ANNOT 1483327; CLONE 30759; ANNOT 1520359; ANNOT 1520359; ANNOT 1494753; ANNOT 1494753; ANNOT 1441875; ANNOT 1441875; ANNOT 1467006; ANNOT 1467006; ANNOT 1441867; ANNOT 1441867; ANNOT 1441871; ANNOT 1441871; ANNOT 1441864; ANNOT 1441864; ANNOT 1441868; ANNOT 1441868; ANNOT 1441859; ANNOT 1441859; ANNOT 1467009; ANNOT 1467009; CLONE 31014; ANNOT 1527449; ANNOT 1527449; ANNOT 1527449; ANNOT 1484207; ANNOT 1484207; CLONE 32348; ANNOT 1470719; ANNOT 1470719; ANNOT 1470719; ANNOT 1543728; ANNOT 1543728; ANNOT 1482066; ANNOT 1482066; CLONE 32361; ANNOT 1471776; ANNOT 1471776; ANNOT 1445033; ANNOT 1445033; CLONE 32548; ANNOT 1450324; ANNOT 1450324; ANNOT 1460836; ANNOT 1460836; ANNOT 32615; ANNOT 1471372; ANNOT 1471372; ANNOT 32737; ANNOT 1536373; ANNOT 1536373; ANNOT 1482905; ANNOT | 621; 622; 623; 624; 625; 647; 648; 649; 695; 696; 697; 698; 699; 700; 701; 702; 703; 704; 705; 706; 707; 708; 709; 735; 736; 737; 738; 739; 747; 748; 749; 767; 768; 769; 770; 771; 772; 773; 774; 775; 776; 777; 778; 789; 790; 791; 792; 793; 794; 795; 818; 819; 820; 821; 822; 823; 824; 825; 826; 827; 828; 829; 830; 831; 897; 898; 899; 900; 901; 907; 908; 909; 910; 911; 912; 913; 914; 915; 916; 967; 968; 969; 970; 971; 972; 973; 974; 975; 986; 987; 988; 989; 990; 991; 992; 993; 994; 1015; 1016; 1017; 1018; 1019; 1020; 1021; 1022; 1023; 1024; 1025; 1026; 1027; 1028; 1029; 1030; 1031; 1032; 1033; 1034; 1055; 1056; 1057; 1058; 1059; 1060; 1061; 1062; 1063; 1064; 1085; 1086; 1087; 1099; 1100; 1101; 1102; 1103; 1104; 1105; 1106; 1107; 1108; 1109; 1110; 1111; 1112; 1113; 1114; 1115; 1116; 1117; 1118; 1119; 1120; 1121; 1164; 1165; 1166; 1167; 1168; 1169; 1170; 1171; 1172; 1173; 1174; 1175; 1176; 1177; 1178; 1179; 1180; 1181; 1182; 1183; 1184; 1185; 1186; 1187; 1188; 1189; 1219; 1220; 1221; 1222; 1223; 1224; 1225; 1226; 1227; 1228; 1229; 1230; 1231; 1232; 1233; 1234; 1235; 1239; 1240; 1241; 1242; 1243; 1244; 1245; 1246; 1247; 1248; 1249; 1250; 1251; 1252; 1253; 1254; 1279; 1280; 1281; 1287; 1288; 1289; 1290; |

TABLE 1-continued

| Tissue | Phenotype Category | Phenotype | Phenotype Description | Applications | Ceres ID | SEQ ID NO |
|---|---|---|---|---|---|---|
| | | | | | 1482905; CLONE 32751; ANNOT 1451143; ANNOT 1451171; CLONE 32753; ANNOT 1480607; ANNOT 1472242; CLONE 33482; ANNOT 1499019; ANNOT 1499019; CLONE 33554; ANNOT 1445599; ANNOT 1445599; ANNOT 1471882; ANNOT 1471882; ANNOT 1452398; ANNOT 1452398; ANNOT 1443041; ANNOT 1443041; ANNOT 1452397; ANNOT 1452397; ANNOT 1505498; ANNOT 1505498; ANNOT 1505497; ANNOT 1505497; ANNOT 1443040; ANNOT 1443040; ANNOT 1495964; ANNOT 1498580; ANNOT 1498580; ANNOT 1466060; CLONE 34167; ANNOT 1538733; ANNOT 1538733; ANNOT 1499810; ANNOT 1485323; ANNOT 1485323; CLONE 34385; ANNOT 1445331; ANNOT 1445331; ANNOT 1498316; ANNOT 1498316; CLONE 34412; ANNOT 1449739; ANNOT 1449739; ANNOT 1449738; ANNOT 1449738; ANNOT 1458830; CLONE 34549; ANNOT 1442496; ANNOT 1442496; CLONE 34635; ANNOT 1487773; ANNOT 1487773; ANNOT 1457333; ANNOT 1457333; ANNOT 1442634; ANNOT 1442634; CLONE 35015; ANNOT 1438730; ANNOT 1438730; CLONE 35493; ANNOT 1457751; ANNOT 1457751; ANNOT 1518757; ANNOT 1518757; CLONE 1465420; ANNOT 1465420; CLONE 35999; ANNOT 1515818; ANNOT 1515818; CLONE 36904; ANNOT 1526083; ANNOT 1526083; ANNOT 1498856; ANNOT 1498856; ANNOT 1445872; ANNOT 1445872; ANNOT 1472663; ANNOT 1472663; CLONE 37217; ANNOT 1465580; ANNOT 1465580; ANNOT 1472014; ANNOT 1472014; ANNOT 1445195; ANNOT 1445195; CLONE 37229; ANNOT 1485157; ANNOT 1485157; ANNOT 1476218; ANNOT 1476218; CLONE 37288; ANNOT 1453650; ANNOT 1453650; CLONE 37298; ANNOT 1476538; ANNOT 1476538; ANNOT 1493576; ANNOT 1493576; CLONE 37493; ANNOT 1494370; ANNOT 1494370; ANNOT 1441478; ANNOT 1441478; CLONE 37543; ANNOT 1539972; ANNOT 1539972; ANNOT 1486562; ANNOT 1486562; ANNOT 1496735; ANNOT 1496735; ANNOT 1443794; ANNOT 1443794; CLONE 37658; ANNOT 1497485; ANNOT 1497485; CLONE 37663; ANNOT 1447659; ANNOT 1447659; ANNOT 1438478; ANNOT 1438478; CLONE 38101; ANNOT 1454656; ANNOT 1454656; ANNOT 1528263; ANNOT 1528263; ANNOT 1458103; ANNOT 1458103; ANNOT 1464899; ANNOT 1464899; ANNOT 1482966; ANNOT 1482966; ANNOT 1441039; ANNOT 1441039; ANNOT 1520449; ANNOT 1520449; CLONE 38105; ANNOT 1473032; ANNOT 1473032; ANNOT 1467499; ANNOT 1467499; ANNOT 1526442; ANNOT 1526442; CLONE 38214; ANNOT 1466779; ANNOT 1466779; ANNOT 1465769; ANNOT 1465769; ANNOT 1538318; ANNOT 1538318; CLONE 38277; ANNOT 1512884; ANNOT 1512884; ANNOT 1538419; ANNOT 1538419; ANNOT 1542971; ANNOT 1542971; ANNOT 1521332; ANNOT 1521332; ANNOT 1467961; ANNOT 1467961; CLONE 38690; ANNOT 1525183; ANNOT 1525183; CLONE 39286; ANNOT 1447961; ANNOT 1447961; ANNOT 1490936; ANNOT 1490936; CLONE 39740; ANNOT 1483180; ANNOT 1483180; ANNOT 1480950; ANNOT 1480950; CLONE 40508; ANNOT 1453626; ANNOT 1453626; CLONE 40538; ANNOT 1452757; ANNOT 1452757; CLONE 40729; ANNOT 1481678; ANNOT 1481678; CLONE 41320; ANNOT 1488507; ANNOT 1488507; ANNOT 1554929; ANNOT 1554929; ANNOT 1460282; ANNOT 1460282; CLONE 1516613; ANNOT 1516613; ANNOT 1513097; ANNOT 1513097; ANNOT 1463324; ANNOT 1463324; CLONE 41439; CLONE 41446; ANNOT 1469832; ANNOT 1469832; CLONE 42336; ANNOT 1455510; ANNOT 1455510; ANNOT 1538733; CLONE 42533; ANNOT 1499810; ANNOT 1499810; ANNOT 1485323; ANNOT 1485323; ANNOT 1462354; ANNOT 1462354; CLONE 42955; ANNOT CLONE 42925; ANNOT 1505155; ANNOT 1505155; CLONE 93867; ANNOT 1474944; ANNOT 1474944; | 1291; 1292; 1293; 1294; 1295; 1296; 1297; 1298; 1299; 1300; 1301; 1302; 1303; 1304; 1305; 1306; 1307; 1308; 1309; 1343; 1344; 1345; 1346; 1347; 1348; 1349; 1364; 1365; 1366; 1367; 1368; 1376; 1377; 1378; 1379; 1380; 1381; 1382; 1403; 1404; 1405; 1416; 1417; 1418; 1419; 1420; 1421; 1422; 1438; 1439; 1440; 1460; 1461; 1462; 1463; 1464; 1465; 1466; 1487; 1488; 1489; 1585; 1586; 1587; 1588; 1589; 1590; 1591; 1592; 1593; 1610; 1611; 1612; 1613; 1614; 1615; 1616; 1617; 1618; 1619; 1620; 1621; 1622; 1623; 1624; 1625; 1626; 1627; 1628; 1629; 1637; 1638; 1639; 1640; 1641; 1642; 1643; 1644; 1645; 1646; 1647; 1648; 1649; 1650; 1654; 1655; 1656; 1657; 1658; 1659; 1660; 1661; 1682; 1683; 1684; 1685; 1686; 1687; 1688; 1689; 1690; 1691; 1692; 1693; 1694; 1695; 1696; 1697; 1698; 1699; 1700; 1701; 1702; 1703; 1707; 1708; 1709; 1710; 1711; 1712; 1713; 1714; 1715; 1716; 1747; 1748; 1749; 1750; 1751; 1752; 1753; 1774; 1775; 1776; 1838; 1839; 1840; 1841; 1842; 1877; 1878; 1879; 1880; 1881; 1912; 1913; 1914; 1915; 1916; 1917; 1930; 1931; 1932; 1981; 1982; 1983; 1984; 1985; 1986; 1987; 1988; 1989; 1990; 1991; 1992; 1993; 1994; 1998; 1999; 2000; 2001; 2018; 2019; 2020; 2030; 2031; 2032; 2033; 2034; 2035; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1506849; ANNOT 1506849; ANNOT 1492957; ANNOT 1492957; CLONE 95135; ANNOT 1527449; ANNOT 1527449; ANNOT 1537653; ANNOT 1537653; ANNOT 1473733; ANNOT 1473733; ANNOT 1468537; ANNOT 1468537; CLONE 95453; ANNOT 1460836; ANNOT 1460836; ANNOT 1450324; ANNOT 1450324; CLONE 95677; ANNOT 1459723; ANNOT 1459723; ANNOT 1516455; ANNOT 1516455; ANNOT 1516455; CLONE 96020; ANNOT 1450365; ANNOT 1450365; ANNOT 1460794; ANNOT 1460794; CLONE 97415; ANNOT 1481701; ANNOT 1481701; CLONE 98855; ANNOT 1460836; ANNOT 1460836; ANNOT 1450324; ANNOT 1450324; ANNOT CLONE 100465; ANNOT 1466439; ANNOT 1466439; ANNOT 1448977; ANNOT 1448977; ANNOT 1519767; ANNOT 1519767; ANNOT 1501982; ANNOT 1501982; ANNOT CLONE 103581; ANNOT 1486398; ANNOT 1486398; ANNOT 1496840; ANNOT 1496840; CLONE 104929; ANNOT 1449020; ANNOT 1449020; CLONE 105554; ANNOT 1451783; ANNOT 1451783; CLONE 107731; ANNOT 1480518; ANNOT 1480518; ANNOT 1442194; ANNOT 1442194; ANNOT 1454127; ANNOT 1454127; ANNOT 1461414; ANNOT 1461414; ANNOT 1447424; ANNOT 1447424; ANNOT 1452873; ANNOT 1452873; ANNOT 1474708; ANNOT 1474708; CLONE 110454; CLONE 111209; ANNOT 1494507; ANNOT 1494507; CLONE 113990; ANNOT 1438327; ANNOT 1438327; ANNOT 1447769; ANNOT 1447769; CLONE 114602; ANNOT 1450785; ANNOT 1450785; ANNOT 1456283; ANNOT 1456283; ANNOT 1460638; ANNOT 1460638; ANNOT 1513900; ANNOT 1513900; ANNOT 1540271; ANNOT 1540271; CLONE 115946; ANNOT 1458342; ANNOT 1458342; CLONE 115975; ANNOT 1507138; ANNOT 1507138; CLONE 116257; ANNOT 1520806; ANNOT 1520806; ANNOT 1473089; ANNOT 1473089; ANNOT 1500150; ANNOT 1500150; CLONE 117369; ANNOT 1499284; ANNOT 1499284; ANNOT 1481671; ANNOT 1481671; CLONE 117895; ANNOT 1448592; ANNOT 1448592; ANNOT 1448594; ANNOT 1448594; CLONE 118337; ANNOT 1454773; ANNOT 1454773; ANNOT 1511811; ANNOT 1511811; ANNOT 1478364; ANNOT 1478364; ANNOT 1464394; ANNOT 1464394; CLONE 119256; ANNOT 1469636; ANNOT 1469636; ANNOT 1479002; ANNOT 1479002; CLONE 141890; ANNOT 1494533; ANNOT 1494533; ANNOT 1494533; ANNOT 1466313; ANNOT 1466313; CLONE 147358; ANNOT 1493111; ANNOT 1493111; ANNOT 1493111; ANNOT 1461452; ANNOT 1461452; CLONE 150912; ANNOT 1533910; ANNOT 1533910; ANNOT 1480439; ANNOT 1480439; CLONE 152141; ANNOT 1439403; ANNOT 1439403; CLONE 157547; ANNOT 1513900; ANNOT 1540271; ANNOT 1473898; CLONE 157730; ANNOT 1532681; ANNOT 1532681; ANNOT 1469739; ANNOT 1469739; CLONE 158333; ANNOT 1466505; ANNOT 1466505; ANNOT 1449026; ANNOT 1449026; CLONE 205648; ANNOT 1456842; ANNOT 1456842; ANNOT 1504224; ANNOT 1504224; CLONE 226818; ANNOT 1503617; ANNOT 1503617; ANNOT 1450560; ANNOT 1450560; ANNOT 1460622; ANNOT 1460622; CLONE 264705; ANNOT 1485750; ANNOT 1485750; ANNOT 1440730; ANNOT 1440730; ANNOT 1440730; CLONE 382267; ANNOT 1456223; ANNOT 1456223; ANNOT 1467304; ANNOT 1467304; ANNOT 1467304; CLONE 463203; ANNOT 1511505; ANNOT 1511505; CLONE 464504; ANNOT 1438401; ANNOT 1438401; CLONE 482122; ANNOT 1438776; ANNOT 1438776; CLONE 534397; ANNOT 1453458; ANNOT 1453458; ANNOT 1489056; ANNOT 1489056; ANNOT 1442794; ANNOT 1442794; ANNOT 1495713; ANNOT 1495713; ANNOT 1495713; ANNOT 1442797; ANNOT 1442797; ANNOT 1468612; ANNOT 1468612; ANNOT 1468612; ANNOT 1460503; ANNOT 1460503; ANNOT 1488307; ANNOT 1488307; CLONE 627596; ANNOT 1440343; ANNOT 1440343; ANNOT 1493212; ANNOT 1493212; CLONE 641355; ANNOT 1500987; ANNOT 1500987; ANNOT 1490915; ANNOT 1490915; CLONE 641355; ANNOT 1463335; ANNOT 1463335; ANNOT 1463334; ANNOT 1463334; ANNOT 1452665; ANNOT 1452665; CLONE 660003; ANNOT 1508184; | 2036; 2045; 2046; 2047; 2048; 2049; 2050; 2064; 2065; 2066; 2067; 2068; 2069; 2070; 2076; 2077; 2078; 2079; 2080; 2081; 2082; 2083; 2084; 2085; 2086; 2087; 2088; 2089; 2090; 2091; 2092; 2093; 2094; 2095; 2096; 2097; 2098; 2099; 2100; 2101; 2102; 2118; 2119; 2120; 2121; 2122; 2196; 2197; 2198; 2199; 2200; 2201; 2202; 2203; 2204; 2232; 2233; 2234; 2235; 2236; 2237; 2238; 2239; 2247; 2248; 2249; 2263; 2264; 2265; 2266; 2267; 2268; 2269; 2270; 2271; 2272; 2273; 2274; 2275; 2276; 2277; 2313; 2314; 2315; 2316; 2340; 2341; 2342; 2343; 2344; 2350; 2351; 2352; 2353; 2354; 2355; 2356; 2357; 2358; 2359; 2360; 2370; 2371; 2372; 2373; 2374; 2375; 2394; 2395; 2396; 2397; 2398; 2399; 2400; 2407; 2408; 2409; 2410; 2411; 2412; 2413; 2414; 2415; 2416; 2417; 2418; 2419; 2420; 2421; 2422; 2423; 2424; 2425; 2451; 2452; 2453; 2454; 2455; 2523; 2524; 2525; 2526; 2527; 2528; 2529; 2530; 2531; 2532; 2555; 2556; 2557; 2558; 2559; 2568; 2569; 2570; 2593; 2594; 2595; 2601; 2602; 2603; 2604; 2605; 2611; 2612; 2613; 2614; 2615; 2625; 2626; 2627; 2628; 2629; 2676; 2677; 2678; 2679; 2680; 2681; 2682; 2779; 2780; 2781; 2782; 2783; 2986; 2987; 2988; 2989; 2990; 3003; 3004; 3005; 3006; 3007; 3008; 3049; 3050; 3051; |

TABLE 1-continued

| Tissue | Phenotype Category | Phenotype | Phenotype Description | Applications | Ceres ID | SEQ ID NO |
|---|---|---|---|---|---|---|
| | | | | | ANNOT 1508184; ANNOT 1528645; CLONE 664365; ANNOT 1463333; ANNOT 1478872; ANNOT 1505772; ANNOT 1478872; ANNOT 1478872; ANNOT 1442758; ANNOT 1442758; ANNOT 1495675; ANNOT 1495675; ANNOT 1469576; ANNOT 1452666; ANNOT 1452666; ANNOT 1452668; ANNOT 1442757; ANNOT 1442757; CLONE 965175; ANNOT 1479013; CLONE 1001432; ANNOT 1475043; ANNOT 1475043; ANNOT 1454586; ANNOT 1507756; ANNOT 1507756; ANNOT 1469708; CLONE 1006934; ANNOT 1532963; ANNOT 1532963; CLONE 1007549; ANNOT 1458198; ANNOT 1458198; ANNOT 1439989; ANNOT 1439989; ANNOT 1464789; ANNOT 1461728; ANNOT 1461728; ANNOT 1479711; ANNOT 1440649; ANNOT 1440649; ANNOT 1464547; ANNOT 1454104; ANNOT 1454104; CLONE 1011386; ANNOT 1531134; ANNOT 1508758; ANNOT 1508758; CLONE 1011537; ANNOT 1473879; ANNOT 1468666; ANNOT 1468666; ANNOT 1438163; CLONE 1043081; ANNOT 1478584; ANNOT 1455564; ANNOT 1508764; ANNOT 1508764; ANNOT 1508764; ANNOT 1477651; ANNOT 1487130; ANNOT 1487130; CDNA 12672729; ANNOT 1500350; CDNA 23494432; CDNA 23495481; ANNOT 1485271; ANNOT 1447245; ANNOT 1447245; CDNA 23498145; ANNOT 1482362; ANNOT 1489077; ANNOT 1489077; ANNOT 1510416; ANNOT 1510416; ANNOT 1541253; CDNA 23518705; ANNOT 1463957; ANNOT 1463957; ANNOT 1458961; CDNA 23530811; ANNOT 1453922; CDNA 23507011; ANNOT 1442604; ANNOT 1442612; ANNOT 1442608; ANNOT 1442612; ANNOT 1452827; CDNA 36512904; ANNOT 1471370; ANNOT 1444471; ANNOT 1491278; ANNOT 1491278; ANNOT 1447690; CDNA 36514446; ANNOT 1475322; ANNOT 1447690; ANNOT 1457794; ANNOT 1449892; CDNA 36695523; CDNA 36534269; CDNA 36545977; ANNOT 1449892; ANNOT . 1447690; ANNOT 1451434; ANNOT . 1491278; ANNOT . 1447690; ANNOT . 1500987; ANNOT . 1500987; ANNOT . 1490915; ANNOT . 1490915; | 3109; 3110; 3111; 3112; 3113; 3114; 3115; 3116; 3117; 3118; 3119; 3120; 3121; 3122; 3123; 3124; 3125; 3126; 3127; 3128; 3129; 3299; 3300; 3301; 3302; 3303; 3304; 3305; 3306; 3307; 3308; 3309; 3310; 3314; 3315; 3316; 3317; 3318; 3319; 3320; 3321; 3322; 3323; 3324; 3325; 3326; 3327; 3328; 3329; 3330; 3331; 3332; 3333; 3334; 3335; 3336; 3337; 3388; 3389; 3390; 3419; 3420; 3421; 3422; 3423; 3424; 3425; 3426; 3427; 3437; 3438; 3439; 3440; 3441; 3442; 3443; 3444; 3445; 3446; 3447; 3448; 3449; 3450; 3451; 3452; 3453; 3454; 3455; 3456; 3462; 3463; 3464; 3465; 3466; 3467; 3468; 3469; 3470; 3471; 3472; 3473; 3481; 3482; 3483; 3484; 3485; 3486; 3487; 3488; 3489; 3490; 3491; 3517; 3518; 3519; 3621; 3622; 3623; 3624; 3625; 3626; 3641; 3642; 3643; 3644; 3645; 3687; 3704; 3705; 3706; 3707; 3708; 3748; 3749; 3750; 3751; 3752; 3787; 3788; 3789; 3875; 3876; 3877; 3878; 3879; 3880; 3881; 3882; 3883; 3896; 3897; 3898; 3899; 3900; 3901; 3902; 3903; 3904; 3905; 3906; 3907; 3938; 3939; 3940; 3941; 3942; 3984; 3985; 3986; 4070; 4071; 4072; 3688; 3689; 3690; 3691; 3692; 3693; 3694; 3695; |
| ROSETTE LEAVES | Shade | Long Petioles | The leaf petioles are abnormally long. | Useful for making plants that grow better in shade | CLONE 11854; ANNOT 1506763; ANNOT 1453614; ANNOT 1453614; CLONE 13757; ANNOT 1471425; ANNOT 1471425; CLONE 27460; ANNOT 1474847; ANNOT 1474847; ANNOT 1507835; ANNOT 1507835; CLONE 35999; ANNOT 1515818; ANNOT 1515818; CLONE 38690; ANNOT 1525183; ANNOT 1525183; CLONE 151087; ANNOT 1504145; ANNOT 1504145; ANNOT | 475; 476; 477; 478; 479; 564; 565; 566; 1055; 1056; 1057; 1058; 1059; 1487; 1488; 1489; 1774; 1775; 1776; 2560; 2561; |

TABLE 1-continued

| Tissue | Phenotype Category | Phenotype | Phenotype Description | Applications | Ceres ID | SEQ ID NO |
|---|---|---|---|---|---|---|
| | | | | | 1451079; ANNOT 1451079; CLONE 158833; ANNOT 1466505; ANNOT 1449026; ANNOT 1449026; CLONE 225200; ANNOT 1471976; ANNOT 1471976; ANNOT 1465507; ANNOT 1465507; CLONE 641355; ANNOT 1463335; ANNOT 1463335; ANNOT 1463334; ANNOT 1463334; ANNOT 1452665; ANNOT 1452665; CDNA 23507479; ANNOT 1510416; ANNOT 1541253; ANNOT 1541253; CDNA 3651789; ANNOT 1444156; ANNOT 1497097; ANNOT 1497097; | 2562; 2563; 2564; 2611; 2612; 2613; 2614; 2615; 2655; 2656; 2657; 2658; 2659; 3304; 3305; 3306; 3307; 3308; 3309; 3310; 3704; 3705; 3706; 3707; 3708; 3893; 3894; 3895; 4043; 4044; 4045; 4046; 4047; |
| ROSETTE LEAVES | Shade | Varying Petiole Lengths | the leaf petioles vary in length throughout the rosette | Useful for making plants that grow better in shade | CLONE 20945; ANNOT 1519797; ANNOT 1519797; CLONE 38419; ANNOT 1542971; ANNOT 1542971; ANNOT 1521332; ANNOT 1521332; ANNOT 1467961; ANNOT 1467961; | 818; 819; 820; 1747; 1748; 1749; 1750; 1751; 1752; 1753; |
| WHOLE PLANT | Stress tolerance | ABA | The plants are tolerant to ABA/drought and/or other stresses | Useful for making plants with enhanced tolerance to drought | CLONE 2083; ANNOT 1441581; ANNOT 1441581; CLONE 5132; ANNOT 1465660; ANNOT 1465660; CLONE 6637; ANNOT 1456291; ANNOT 1456291; ANNOT 1450794; ANNOT 1450794; CLONE 7713; ANNOT 1470658; ANNOT 1470658; ANNOT 1480027; ANNOT 1480027; CLONE 10044; ANNOT 1510467; ANNOT 1510467; ANNOT 1457266; ANNOT 1457266; ANNOT 1457267; ANNOT 1457267; CLONE 10987; ANNOT 1454090; ANNOT 1454090; ANNOT 1475712; ANNOT 1475712; CLONE 11496; ANNOT 1520074; ANNOT 1520074; CLONE 11830; ANNOT 1472114; ANNOT 1472114; ANNOT 1525524; ANNOT 1525524; ANNOT 1453309; ANNOT 1453309; CLONE 13704; ANNOT 1481636; ANNOT 1481636; ANNOT 1461019; ANNOT 1461019; ANNOT 1496766; ANNOT 1496766; CLONE 22551; ANNOT 1443824; ANNOT 1443824; ANNOT 1486521; ANNOT 1486521; ANNOT 1465987; ANNOT 1465987; ANNOT 1451283; ANNOT 1451283; CLONE 29678; ANNOT 1487885; ANNOT 1487885; ANNOT 1457156; ANNOT 1457156; ANNOT 1441125; ANNOT 1441125; ANNOT 1494024; ANNOT 1494024; CLONE 25200; ANNOT 1511048; ANNOT 1511048; CLONE 26006; ANNOT 1457048; ANNOT 1457048; ANNOT 1510252; ANNOT 1510252; ANNOT 1451281; ANNOT 1451281; ANNOT 1451282; ANNOT 1451282; ANNOT 1504349; ANNOT 1504349; CLONE 34358; ANNOT 1452837; ANNOT 1452837; ANNOT 1442590; ANNOT 1442590; ANNOT 1450457; ANNOT 1450457; ANNOT 1460721; ANNOT 1460721; CLONE 37952; ANNOT 1438071; ANNOT 1438071; ANNOT 1448019; ANNOT 1448019; ANNOT 1498609; ANNOT 1498609; ANNOT 1472308; ANNOT 1472308; CLONE 38206; ANNOT 1525715; ANNOT 1525715; ANNOT 1543295; ANNOT 1543295; ANNOT 1445629; ANNOT 1445629; CLONE 99920; ANNOT 1446695; ANNOT 1446695; ANNOT 1481700; ANNOT 1481700; CLONE 111694; ANNOT 1468539; ANNOT 1468539; ANNOT 1492884; ANNOT 1492884; ANNOT 1527153; ANNOT 1527153; CLONE 120982; ANNOT 1515144; ANNOT 1515144; ANNOT 1487614; ANNOT 1487614; CLONE 529835; ANNOT 1541881; ANNOT 1541881; ANNOT 1488468; ANNOT 1488468; ANNOT 1475186; ANNOT 1475186; ANNOT 1437875; ANNOT 1437875; ANNOT 1476056; ANNOT 1476056; ANNOT 1454958; ANNOT 1454958; ANNOT 1454260; ANNOT 1454260; CDNA 23510894; ANNOT 1467221; ANNOT 1467221; ANNOT 1442171; ANNOT 1442171; CDNA 23519977; ANNOT 1459840; ANNOT 1459840; | 87; 88; 89; 220; 221; 222; 312; 313; 314; 315; 316; 328; 329; 330; 331; 332; 412; 413; 414; 415; 416; 417; 418; 440; 441; 442; 443; 444; 460; 461; 462; 463; 464; 465; 466; 467; 468; 469; 547; 548; 549; 884; 885; 886; 887; 888; 889; 890; 891; 892; 893; 894; 895; 896; 957; 958; 959; 995; 996; 997; 998; 999; 1000; 1001; 1002; 1003; 1004; 1005; 1006; 1007; 1008; 1009; 1156; 1157; 1158; 1159; 1160; 1355; 1356; 1357; 1358; 1359; 1360; 1361; 1362; 1363; 1669; 1670; 1671; 1672; 1673; 1674; 1675; 1676; 1677; 1678; 1679; 1680; 1681; 1704; 1705; 1706; 2168; 2169; 2170; 2171; 2172; 2322; 2323; 2324; 2325; 2326; 2475; 2476; 2477; 2478; 2479; 3052; 3053; 3054; 3055; 3056; 3057; 3058; 3059; 3060; 3061; 3062; 3063; 3064; 3065; 3066; 3067; 3068; 3712; 3713; 3714; 3715; 3716; 3753; 3754; 3755; |
| WHOLE PLANT | Stress tolerance | Cold Germination | The plant germinate better at cold temperatures | Useful for making plants with increased tolerance to | CLONE 2403; ANNOT 1509972; ANNOT 1504203; ANNOT 1504203; ANNOT 1443061; ANNOT 1443061; ANNOT 1452369; ANNOT 1452369; CLONE 4524; ANNOT 1442935; ANNOT 1442935; CLONE 10072; ANNOT 1458457; ANNOT 1458457; ANNOT 1464514; ANNOT 1464514; ANNOT 1493574; | 95; 96; 97; 98; 99; 100; 101; 102; 103; 204; 205; 206; 419; 420; 421; 422; 423; 424; 425; 426; 427; |

TABLE 1-continued

| Tissue | Phenotype Category | Phenotype | Phenotype Description | Applications | Ceres ID | SEQ ID NO |
|---|---|---|---|---|---|---|
| | | | compared to control. | cold stress | ANNOT 1493574; ANNOT 1527203; CLONE 17081; ANNOT 1481199; ANNOT 1481199; ANNOT 1543087; ANNOT 1489696; ANNOT 1489696; CLONE 33559; ANNOT 1481146; ANNOT 1481146; ANNOT 1481150; ANNOT 1481150; ANNOT 1481138; ANNOT 1485824; ANNOT 1485824; ANNOT 1534622; CLONE 271922; ANNOT 1485385; ANNOT 1485385; ANNOT 1486234; CDNA 36553419; ANNOT 1459723; ANNOT 1459723; ANNOT 1516455; ANNOT 1516455; | 663; 664; 665; 666; 667; 668; 669; 1310; 1311; 1312; 1313; 1314; 1315; 1316; 1317; 1318; 1319; 1320; 2816; 2817; 2818; 2819; 2820; 3995; 3996; 3997; 3998; 3999; |
| ROSETTE LEAVES | Stress tolerance | Glossy | The leaves are shiny/glossy in appearance | Useful for making plants with enhanced abiotic stress tolerance | CLONE 12272; CLONE 12993; ANNOT 1506387; ANNOT 1474522; ANNOT 1474522; CLONE 12993; ANNOT 1479464; ANNOT 1479464; CLONE 14583; ANNOT 1530256; ANNOT 1530256; ANNOT 1476783; ANNOT 1476783; ANNOT 1503166; ANNOT 1503166; CLONE 35742; ANNOT 1478035; ANNOT 1478035; CLONE 38277; ANNOT 1512884; ANNOT 1512884; ANNOT 41446; ANNOT 1469832; ANNOT 1469832; CLONE 205648; ANNOT 1456842; ANNOT 1456842; ANNOT 1504224; ANNOT 1504224; CLONE 641355; ANNOT 1463355; ANNOT 1463335; ANNOT 1463334; ANNOT 1463334; ANNOT 1452665; ANNOT 1452665; CLONE 664365; ANNOT 1463333; ANNOT 1463333; ANNOT 1505772; ANNOT 1505772; ANNOT 1478872; ANNOT 1478872; ANNOT 1442758; ANNOT 1442758; ANNOT 1495675; ANNOT 1495675; ANNOT 1452666; ANNOT 1452666; ANNOT 1469576; ANNOT 1469576; ANNOT 1442757; ANNOT 1442757; ANNOT 1452668; ANNOT 1452668; ANNOT 1478584; ANNOT 1478584; ANNOT 1455564; ANNOT 1455564; ANNOT 1508764; ANNOT 1508764; ANNOT 1477651; ANNOT 1477651; ANNOT 1487130; CDNA 36512904; ANNOT 1471370; ANNOT 1471370; ANNOT 1444471; ANNOT 1491278; ANNOT 1491278; ANNOT 1447690; ANNOT 1447690; | 515; 516; 517; 518; 519; 520; 521; 522; 619; 620; 621; 622; 623; 624; 625; 1481; 1482; 1483; 1714; 1715; 1716; 1999; 2000; 2001; 2625; 2626; 2627; 2628; 2629; 3304; 3305; 3306; 3307; 3308; 3309; 3310; 3319; 3320; 3321; 3322; 3323; 3324; 3325; 3326; 3327; 3328; 3329; 3330; 3331; 3332; 3333; 3334; 3335; 3336; 3337; 3481; 3482; 3483; 3484; 3485; 3486; 3487; 3488; 3489; 3490; 3491; 3896; 3897; 3898; 3899; 3900; 3901; 3902; 3903; 3904; |
| CAULINE LEAVES | Stress tolerance | Glossy | The leaves are shiny/glossy in appearance. | Useful for making plants with enhanced abiotic stress tolerance | CLONE 12993; ANNOT 1479464; ANNOT 1479464 | 520; 521; 522; |
| WHOLE PLANT | Stress tolerance | Heat | The plants have enhanced thermotolerance. | Useful for making plants with enhanced tolerance to heat | CLONE 125039; ANNOT 1514426; ANNOT 1514426; | 2504; 2505; 2506; |
| WHOLE PLANT | Stress tolerance | High Sucrose | Plants are tolerant to high sucrose conditions | Useful for making plants with enhanced tolerance to drought | CLONE 19512; ANNOT 1515042; ANNOT 1515042; ANNOT 1492757; CLONE 256433; ANNOT 1529361; ANNOT 1492757; ANNOT 1507347; ANNOT 1475918; ANNOT 1507347; ANNOT 1507347; ANNOT 1454201; ANNOT 1454201; CDNA 2702830; ANNOT 1516968; ANNOT 1516968; ANNOT 1520085; ANNOT 1520085; | 779; 780; 781; 782; 783; 2738; 2739; 2740; 2741; 2742; 2743; 2744; 3492; 3493; 3494; 3495; 3496; |
| WHOLE PLANT | Stress tolerance | Mannitol | The plants are tolerant to mannitol, and possibly drought stress. | Useful for making plants with enhanced tolerance to drought | CLONE 1994; ANNOT 1506401; CLONE 8877; ANNOT 1507340; ANNOT 1507340; ANNOT 1529361; CLONE 10987; ANNOT 1454090; ANNOT 1454090; ANNOT 1475712; CLONE 11830; ANNOT 1472114; ANNOT 1472114; ANNOT 1525524; ANNOT 1525524; ANNOT 1453309; CLONE 26006; ANNOT 1457048; ANNOT 1457048; ANNOT 1510252; ANNOT 1510252; ANNOT 1451281; ANNOT 1451281; ANNOT 1451282; ANNOT 1451282; ANNOT 1504349; ANNOT 1465987; ANNOT 1465987; ANNOT 1451283; CLONE 29675; ANNOT 1461449; ANNOT 1461449; ANNOT 1440240; ANNOT 1440240; ANNOT 1519418; ANNOT 1519418; ANNOT 1448924; CLONE | 81; 82; 83; 383; 384; 385; 386; 387; 440; 441; 442; 443; 444; 463; 464; 465; 466; 467; 468; 469; 995; 996; 997; 998; 999; 1000; 1001; 1002; 1003; 1004; 1005; 1006; 1007; 1008; 1009; 1151; 1152; 1153; 1154; 1155; 1518; 1519; 1520; 1521; 1522; |

TABLE 1-continued

| Tissue | Phenotype Category | Phenotype | Phenotype Description | Applications | Ceres ID | SEQ ID NO |
|---|---|---|---|---|---|---|
| | | | | | 36681; ANNOT 1527156; ANNOT 1512959; ANNOT 1463128; ANNOT 1468540; ANNOT 1440644; ANNOT 1440644; ANNOT 1493523; CLONE 99920; ANNOT 1446695; ANNOT 1446695; ANNOT 1481700; ANNOT 1467221; ANNOT 1442171; ANNOT 23510894; ANNOT 1467221; ANNOT 1459840; CDNA 23519977; ANNOT 1459840; CDNA 23555942; ANNOT 1473401; ANNOT 1473401; | 1523; 1524; 1525; 1526; 1527; 1528; 1529; 1530; 1531; 1532; 1533; 1534; 1535; 2168; 2169; 2170; 2171; 2172; 3712; 3713; 3714; 3715; 3716; 3753; 3754; 3755; 3829; 3830; 3831; |
| WHOLE PLANT | Stress tolerance | PEG | The plants are tolerant to PEG/drought stress. | Useful for making plants with increased tolerance to drought | CLONE 10044; ANNOT 1510467; ANNOT 1457266; ANNOT 1457267; ANNOT 1457267; CLONE 10987; ANNOT 1454090; ANNOT 1454090; ANNOT 1475712; ANNOT 1475712; ANNOT 11830; ANNOT 1472114; ANNOT 1525524; ANNOT 1525524; ANNOT 1453309; ANNOT 1453309; CLONE 26006; ANNOT 1457048; ANNOT 1457048; ANNOT 1510252; ANNOT 1510252; ANNOT 1451281; ANNOT 1451281; ANNOT 1451282; ANNOT 1451282; ANNOT 1504349; ANNOT 1504349; ANNOT 1465987; ANNOT 1465987; ANNOT 1451283; ANNOT 1451283; CLONE 35220; ANNOT 1444404; ANNOT 1444404; ANNOT 1471304; ANNOT 1471304; ANNOT 1497357; ANNOT 1497357; CLONE 256804; ANNOT 1461811; ANNOT 1461811; ANNOT 1439959; ANNOT 1439959; ANNOT 1535293; ANNOT 1535293; ANNOT 1481806; ANNOT 1481806; ANNOT 1503112; ANNOT 1503112; ANNOT 1516877; ANNOT 1516877; ANNOT 1506920; ANNOT 1506920; ANNOT 1453775; ANNOT 1453775; ANNOT 1478539; ANNOT 1478539; ANNOT 1515247; ANNOT 1515247; ANNOT 1536456; ANNOT 1536456; ANNOT 1451195; ANNOT 1451195; ANNOT 1482990; ANNOT 1482990; ANNOT 1461956; ANNOT 1461956; ANNOT 1451956; CLONE 280039; ANNOT 1494544; ANNOT 1494544; ANNOT 1437855; ANNOT 1437855; ANNOT 1448245; ANNOT 1448245; CLONE 299144; ANNOT 1443651; ANNOT 1443651; CLONE 543549; ANNOT 1529916; ANNOT 1529916; ANNOT 1440973; ANNOT 1440973; ANNOT 1520978; ANNOT 1520978; ANNOT 1472957; ANNOT 1472957; ANNOT 1476456; ANNOT 1476456; CDNA 23510894; ANNOT 1467221; ANNOT 1467221; ANNOT 1442171; ANNOT 1442171; ANNOT 1459840; ANNOT 1459840; CDNA 23555942; ANNOT 1473401; ANNOT 1473401; | 412; 413; 414; 415; 416; 417; 418; 440; 441; 442; 443; 444; 463; 464; 465; 466; 467; 468; 469; 995; 996; 997; 998; 999; 1000; 1001; 1002; 1003; 1004; 1005; 1006; 1007; 1008; 1009; 1448; 1449; 1450; 1451; 1452; 1453; 1454; 2745; 2746; 2747; 2748; 2749; 2750; 2751; 2752; 2753; 2754; 2755; 2756; 2757; 2758; 2759; 2760; 2761; 2762; 2763; 2764; 2765; 2766; 2767; 2768; 2769; 2770; 2771; 2772; 2773; 2826; 2827; 2828; 2829; 2830; 2831; 2832; 2874; 2875; 2876; 3178; 3179; 3180; 3181; 3182; 3183; 3184; 3185; 3186; 3187; 3188; 3712; 3713; 3714; 3715; 3716; 3753; 3754; 3755; 3829; 3830; 3831; |
| WHOLE PLANT | Stress tolerance | Soil Drought | The plants have increased tolerance to soil drought | Useful for making plants with increased tolerance to drought | CLONE 8381; ANNOT 1462544; ANNOT 1462544; CLONE 26006; ANNOT 1457048; ANNOT 1457048; ANNOT 1510252; ANNOT 1510252; ANNOT 1451281; ANNOT 1451281; ANNOT 1451282; ANNOT 1451282; ANNOT 1504349; ANNOT 1504349; ANNOT 1465987; ANNOT 1465987; ANNOT 1451283; ANNOT 1451283; ANNOT 1446695; ANNOT 1481700; ANNOT 1481700; CLONE 99920; ANNOT 1446695; ANNOT 1481700; | 369; 370; 371; 995; 996; 997; 998; 999; 1000; 1001; 1002; 1003; 1004; 1005; 1006; 1007; 1008; 1009; 2168; 2169; 2170; 2171; 2172; |
| WHOLE PLANT | Stress tolerance, Phosphate use | pH (high) | The plants are tolerant to high pH, and low phosphate conditions. | Useful for making plants tolerant to high pH or low phosphate | CLONE 11830; ANNOT 1472114; ANNOT 1472114; ANNOT 1525524; ANNOT 1525524; ANNOT 1453309; ANNOT 1453309; CLONE 17250; ANNOT 1450185; ANNOT 1450185; CLONE 26006; ANNOT 1457048; ANNOT 1457048; ANNOT 1510252; ANNOT 1510252; ANNOT 1451281; ANNOT 1451281; ANNOT 1451282; ANNOT 1451282; ANNOT 1504349; ANNOT 1504349; ANNOT 1465987; ANNOT 1465987; ANNOT 1451283; ANNOT 1451283; CLONE 34035; ANNOT 1525523; ANNOT 1525523; ANNOT 1525524; ANNOT 1472113; ANNOT 1472113; CLONE 38286; ANNOT 1459467; ANNOT 1459467; ANNOT 1516688; ANNOT 1516688; ANNOT 1488767; ANNOT 1488767; ANNOT 1463396; ANNOT 1463396; ANNOT 1495750; ANNOT 1495750; ANNOT 1452612; ANNOT 1452612; ANNOT 1442831; ANNOT 1442831; CLONE 39890; ANNOT 1511886; ANNOT 1511886; ANNOT 1517635; ANNOT 1517635; ANNOT | 463; 464; 465; 466; 467; 468; 469; 670; 671; 672; 995; 996; 997; 998; 999; 1000; 1001; 1002; 1003; 1004; 1005; 1006; 1007; 1008; 1009; 1328; 1329; 1330; 1331; 1332; 1717; 1718; 1719; 1720; 1721; 1722; 1723; 1724; 1725; 1726; 1727; 1728; 1729; 1730; 1731; 1882; 1883; |

TABLE 1-continued

| Tissue | Phenotype Category | Phenotype | Phenotype Description | Applications | Ceres ID | SEQ ID NO |
|---|---|---|---|---|---|---|
| | | | | | 1517635; CLONE 40781; ANNOT 1440480; ANNOT 1440480; CLONE 116356; ANNOT 1467190; CLONE 126592; ANNOT 1474017; ANNOT 1474017; ANNOT 1468796; ANNOT 1468796; | 1884; 1885; 1886; 1936; 1937; 1938; 2401; 2402; 2403; 2512; 2513; 2514; 2515; 2516; |
| INFLORESCENCE | Vigor | Strong | The primary inflorescence appears significantly stronger, whether by thickness or rigidity | Useful for making stronger plants | CLONE 314; ANNOT 1543129; ANNOT 1543129; CLONE 4067; ANNOT 1514362; ANNOT 1514362; ANNOT 1494090; ANNOT 1494090; CLONE 5597; ANNOT 1507708; ANNOT 1507708; ANNOT 1475094; ANNOT 1475094; CLONE 8265; ANNOT 1438919; ANNOT 1438919; ANNOT 1499398; ANNOT 1499398; ANNOT 1446419; ANNOT 1446419; CLONE 8458; ANNOT 1454042; ANNOT 1454042; CLONE 10879; ANNOT 1467184; ANNOT 1467184; CLONE 12993; ANNOT 1479464; ANNOT 1479464; CLONE 17356; ANNOT 1478584; ANNOT 1478584; ANNOT 1487130; CLONE 19116; ANNOT 1467522; ANNOT 1467522; ANNOT 1526421; ANNOT 1526421; CLONE 23322; ANNOT 1512337; ANNOT 1512337; ANNOT 1517094; ANNOT 1517094; CLONE 25886; ANNOT 1446650; ANNOT 1446650; ANNOT 1439514; ANNOT 1439514; ANNOT 1477202; ANNOT 1477202; ANNOT 1455325; ANNOT 1455325; CLONE 37288; ANNOT 1453650; ANNOT 1453650; CLONE 38697; ANNOT 1470862; ANNOT 1470862; ANNOT 1443740; ANNOT 1443740; ANNOT 1461162; ANNOT 1461162; ANNOT 1526959; ANNOT 1526959; ANNOT 1468331; ANNOT 1468331; CLONE 40538; ANNOT 1452757; ANNOT 1452757; ANNOT 1475806; ANNOT 1475806; ANNOT 1475806; ANNOT 1454125; ANNOT 1454125; CLONE 98855; ANNOT 1460836; ANNOT 1460836; ANNOT 1450324; ANNOT 1450324; CLONE 116257; ANNOT 1520806; ANNOT 1520806; ANNOT 1473089; ANNOT 1473089; ANNOT 1500150; ANNOT 1500150; CLONE 118648; ANNOT 1510664; ANNOT 1510664; ANNOT 1457458; ANNOT 1457458; ANNOT 1443693; ANNOT 1443693; ANNOT 1496628; ANNOT 1496628; ANNOT 1451509; ANNOT 1451509; ANNOT 1540402; ANNOT 1540402; ANNOT 1487005; ANNOT 1487005; CLONE 119925; ANNOT 1473490; ANNOT 1473490; ANNOT 1526901; ANNOT 1526901; CLONE 148680; ANNOT 1522509; ANNOT 1522509; CLONE 150912; ANNOT 1533910; ANNOT 1480439; ANNOT 1480439; CLONE 156655; ANNOT 1441740; ANNOT 1441740; CLONE 158702; ANNOT 1501773; ANNOT 1501773; CLONE 566317; ANNOT 1489585; ANNOT 1489585; ANNOT 1467905; ANNOT 1467905; ANNOT 1517371; ANNOT 1517371; ANNOT 1512104; ANNOT 1512104; ANNOT 1458837; ANNOT 1458837; CLONE 627596; ANNOT 1500987; ANNOT 1500987; ANNOT 1490915; ANNOT 1490915; CLONE 1001432; ANNOT 1475043; ANNOT 1475043; ANNOT 1454586; ANNOT 1454586; ANNOT 1507756; ANNOT 1507756; ANNOT 1469708; CLONE 1002819; ANNOT 1474290; ANNOT 1474290; ANNOT 1522314; ANNOT 1522314; ANNOT 1497147; ANNOT 1497147; ANNOT 1471045; ANNOT 1471045; CLONE 1007549; ANNOT 1458198; ANNOT 1458198; ANNOT 1439989; ANNOT 1439989; ANNOT 1464789; ANNOT 1464789; ANNOT 1461728; ANNOT 1461728; ANNOT 1479711; ANNOT 1479711; ANNOT 1440649; ANNOT 1440649; ANNOT 1464547; ANNOT 1464547; ANNOT 1471370; ANNOT 1471370; ANNOT 1454104; CDNA 23505103; CDNA 36512904; ANNOT 1491278; ANNOT 1491278; ANNOT 1444471; ANNOT 1444471; ANNOT 1447690; ANNOT 1447690; ANNOT 1447690; ANNOT . 1491278; ANNOT . 1500987; ANNOT . 1500987; ANNOT . 1491278; ANNOT . 1490915; ANNOT . 1490915; | 9; 10; 11; 196; 197; 198; 199; 200; 233; 234; 235; 236; 237; 362; 363; 364; 365; 366; 367; 368; 372; 373; 374; 437; 438; 439; 520; 521; 522; 673; 674; 675; 676; 677; 735; 736; 737; 738; 739; 897; 898; 899; 900; 901; 986; 987; 988; 989; 990; 991; 992; 993; 994; 1622; 1623; 1624; 1777; 1778; 1779; 1780; 1781; 1782; 1783; 1784; 1785; 1786; 1787; 1915; 1916; 1917; 1976; 1977; 1978; 1979; 1980; 2118; 2119; 2120; 2121; 2122; 2394; 2395; 2396; 2397; 2398; 2399; 2400; 2429; 2430; 2431; 2432; 2433; 2434; 2435; 2436; 2437; 2438; 2439; 2440; 2441; 2442; 2443; 2461; 2462; 2463; 2464; 2465; 2540; 2541; 2542; 2555; 2556; 2557; 2558; 2559; 2580; 2581; 2582; 2616; 2617; 2618; 3241; 3242; 3243; 3244; 3245; 3246; 3247; 3248; 3249; 3250; 3251; 3299; 3300; 3301; 3302; 3303; 3419; 3420; 3421; 3422; 3423; 3424; 3425; 3426; 3427; 3428; 3429; 3430; 3431; 3432; 3433; 3434; 3435; 3436; 3440; 3441; 3442; 3443; 3444; 3445; 3446; 3447; 3448; 3449; 3450; 3451; 3452; 3453; 3454; 3455; 3456; 3687; 3896; 3897; 3898; 3899; 3900; 3901; 3902; 3903; 3904; 3688; 3689; 3690; 3691; 3692; 3693; 3694; 3695; |

TABLE 1-continued

| Tissue | Phenotype Category | Phenotype | Phenotype Description | Applications | Ceres ID | SEQ ID NO |
|---|---|---|---|---|---|---|
| INFLORESCENCE | Vigor | Weak | The primary inflorescence appears significantly weaker, whether by thickness or rigidity. | Useful for making stronger plants | CLONE 5055; ANNOT 1438157; ANNOT 1500936; ANNOT 1500936; CLONE 8254; ANNOT 1543042; ANNOT 1489655; | 215; 216; 217; 218; 219; 357; 358; 359; 360; 361; |
| | | | | | ANNOT 1489655; CLONE 10879; ANNOT 1467184; CLONE 1489655; | 437; 438; 439; 507; 508; |
| | | | | | 12071; ANNOT 1466704; ANNOT 1466704; CLONE 13625; ANNOT 1455211; | 509; 544; 545; 546; 917; |
| | | | | | ANNOT 1455211; CLONE 23556; ANNOT 1519418; ANNOT 1448924; | 918; 919; 920; 921; 922; |
| | | | | | 1448924; ANNOT 1448924; ANNOT 1482978; ANNOT 1448490; | 923; 924; 925; 926; 927; |
| | | | | | ANNOT 1448490; ANNOT 1477878; ANNOT 1477878; CLONE 26907; ANNOT | 1043; 1044; 1045; 1046; |
| | | | | | 1484074; ANNOT 1484074; ANNOT 1440016; ANNOT 1518242; | 1047; 1048; 1049; 1255; |
| | | | | | ANNOT 1518242; CLONE 32791; ANNOT 1540248; ANNOT 1540248; CLONE | 1256; 1257; 1476; 1477; |
| | | | | | 35733; ANNOT 1486258; ANNOT 1486258; ANNOT 1443988; ANNOT 1443988; | 1478; 1479; 1480; 1732; |
| | | | | | CLONE 38370; ANNOT 1471869; ANNOT 1471869; ANNOT 1448032; ANNOT | 1733; 1734; 1735; 1736; |
| | | | | | 1448032; ANNOT 1448031; ANNOT 1448031; ANNOT 1438060; ANNOT 1438060; | 1737; 1738; 1739; 1740; |
| | | | | | ANNOT 1438061; ANNOT 1438061; ANNOT 1448030; ANNOT 1448030; ANNOT | 1741; 1742; 1743; 1744; |
| | | | | | 1437831; CLONE 40436; ANNOT 1441645; ANNOT 1441645; | 1745; 1746; 1904; 1905; |
| | | | | | CLONE 40729; ANNOT 1481678; ANNOT 1481678; CLONE 92670; ANNOT | 1906; 1930; 1931; 1932; |
| | | | | | 1531919; ANNOT 1531919; CLONE 95453; ANNOT 1460836; ANNOT 1460836; | 2061; 2062; 2063; 2085; |
| | | | | | ANNOT 1459723; ANNOT 1450324; ANNOT 1450324; CLONE 95677; ANNOT 1459723; ANNOT | 2086; 2087; 2088; 2089; |
| | | | | | 1459723; ANNOT 1516455; ANNOT 1516455; CLONE 100465; ANNOT 1466439; | 2090; 2091; 2092; 2093; |
| | | | | | ANNOT 1466439; ANNOT 1466439; ANNOT 1448977; ANNOT 1519767; ANNOT | 2094; 2196; 2197; 2198; |
| | | | | | 1519767; ANNOT 1501982; ANNOT 1501982; CLONE 147358; ANNOT 1493111; ANNOT 1493111; ANNOT 1461452; ANNOT 1461452; CLONE 149380; ANNOT 1461440; ANNOT 1461440; ANNOT 1461430; ANNOT 1461430; ANNOT 1461427; ANNOT 1461427; ANNOT 1440253; ANNOT 1440253; CLONE 267657; ANNOT 1471473; ANNOT 1471473; ANNOT 1444931; ANNOT 1444931; CLONE 480332; ANNOT 1511016; ANNOT 1511016; ANNOT 1518556; ANNOT 1518556; ANNOT 1457793; ANNOT 1457793; ANNOT 1465233; ANNOT 1465233; CLONE 563522; ANNOT 1460321; ANNOT 1460321; ANNOT 1508144; ANNOT 1508144; ANNOT 1541886; ANNOT 1541886; ANNOT 1475178; ANNOT 1475178; CDNA 23505182; ANNOT 1525474; ANNOT 1525474; CDNA 2350747; ANNOT 1510416; ANNOT 1510416; ANNOT 1541253; ANNOT 1541253; CDNA 36554381; ANNOT 1523115; ANNOT 1523115; ANNOT 1479243; ANNOT 1479243; | 2199; 2200; 2201; 2202; 2203; 2204; 2528; 2529; 2530; 2531; 2532; 2546; 2547; 2548; 2549; 2550; 2551; 2552; 2553; 2554; 2801; 2802; 2803; 2804; 2805; 3034; 3035; 3036; 3037; 3038; 3039; 3040; 3041; 3042; 3227; 3228; 3229; 3230; 3231; 3232; 3233; 3234; 3235; 3696; 3697; 3698; 3704; 3705; 3706; 3707; 3708; 4000; 4001; 4002; 4003; 4004; |

From the disclosure of Table 1 and the Sequence Listing, it can be seen that the nucleotides and polypeptides of the inventions are useful, depending upon the respective individual sequence, to make plants with one or more altered characteristics in traits such as appearance, architecture, biomass, composition, confinement, development, nitrogen use, nutrient uptake, phosphate use, photosynthetic capacity, shade avoidance, stress tolerance, vigor, flowering time and yield.

Nucleotides and polypeptides that are useful for modulating plant characteristics in traits such as appearance include those that have been given the designation Appearance in the Category column of Table 1. Nucleotides and polypeptides that have been given the Appearance designation include those that are able to confer one or more of the following phenotypes, relative to wild-type control, when mis-expressed in plants: altered leaf shape; altered leaf structure; altered leaf color; increased or decreased leaf size; altered flower shape; altered flower structure; increased or decreased flower size. Altering plant appearance through genetic technologies is valuable for making ornamental plants, increasing plant biomass produced per acre of arable land, increasing crop yield per acre of arable land, and for other agricultural and/or horticultural purposes.

Nucleotides and polypeptides that are useful for modulating plant characteristics in traits such as plant architecture include those that have been given the designation Architecture in the Category column of Table 1. Nucleotides and polypeptides that have been given the Architecture designation include those that are able to confer one or more of the following phenotypes, relative to wild-type control, when mis-expressed in plants: altered branching angle; increased or decreased number of branches; increased or decreased number of leaves per branch; altered leaf angle (relative to the horizontal plane); increased or decreased internode length. Altering plant architecture through genetic technologies is valuable for increasing plant biomass produced per acre of arable land, increasing crop yield per acre of arable land, improving harvesting efficiency, making ornamental plants, and for other agricultural and/or horticultural purposes.

Nucleotides and polypeptides that are useful for modulating plant characteristics in traits such as plant biomass include those that have been given the designation Biomass in the Category column of Table 1. Nucleotides and polypeptides that have been given the Biomass designation include those that are able to confer one or more of the following phenotypes, relative to wild-type control, when mis-expressed in plants: increased or decreased plant size; increased or decreased plant height; increased or decreased leaf size; altered leaf shape; altered leaf structure; increased or decreased number of leaves; increased or decreased organ size; altered organ shape; increased or decreased organ number; increased or decreased branching length; increased or decreased branch number; increased or decreased apical dominance; and increased or decreased hypocotyls length. Altering plant biomass is valuable for increasing plant biomass produced per acre of arable land, increasing crop yield per acre of arable land, utilizing plants as chemical factories to produce valuable pharmaceutical compounds, developing a genetic confinement system designed to reduce or prevent gene flow from transgenic pants to commercial crops and wild-type counterparts, making ornamental plants, and for other agricultural and/or horticultural purposes.

Nucleotides and polypeptides that are useful for modulating plant characteristics in traits such as the composition of a plant, plant material, plant tissue, plant cell and seed from a plant include those that have been given the designation Composition in the Category column of Table 1. Nucleotides and polypeptides that have been given the Composition designation include those that are able to confer one or more of the following phenotypes, relative to wild-type control, when mis-expressed in plants: increased or decreased carbon content; increased or decreased plant nitrogen content; altered color (indicative of change(s) to the chemical composition); altered metabolic profile, increased or decreased starch content, increased or decreased fiber content; increased or decreased amount of a valuable compound (e.g. increased alkaloids and/or terpenoids); increased or decreased number of trichomes; increased or decreased cotyledon size; increased or decreased cotyledon number; altered cotyledon shape; increased or decreased fruit size; increased or decreased fruit length; altered fruit shape; increased or decreased seed size; and altered seed shape; altered seed color (indicative of altered chemical composition); and having activated expression of a gene operably linked to an alkaloid or terpenoid related regulatory region or promoter. Altering characteristics such as the composition of a plant, plant organ, plant tissue and plant cell is valuable for improving the nutritional value of crops, improving the composition of plants to be used as bio-fuels, utilizing plants as chemical factories by increasing the content of valuable pharmaceutical compounds, producing plants with increased tolerance to abiotic or biotic stress, developing a genetic confinement system designed to reduce or prevent gene flow from transgenic pants to commercial crops and wild-type counterparts, making ornamental plants, and for other agricultural and/or horticultural purposes.

Nucleotides and polypeptides that are useful for modulating plant characteristics in traits such as sterility, lethality and viability have been given the designation Confinement in the Category column of Table 1. Nucleotides and polypeptides that have been given the Confinement designation include those that are able to confer one or more of the following phenotypes, relative to wild-type control, when mis-expressed in plants: increased or decreased number of floral organs; alter floral organ type; reduced fertility; sterility, including female-sterility and/or male-sterility; alter how leaves emerge from the meristem; low/no seed germination; and reduced plant viability (e.g. albino plants and plants with vitrified leaves). The ability to modulate sterility, lethality, and/or viability is important in developing a genetic confinement system designed to reduce or prevent gene flow from transgenic pants to commercial crops and wild-type counterparts, making ornamental plants; and for other agricultural and/or horticultural purposes. Nucleotides and polynucleotides useful for developing a genetic confinement system can be utilized by procedures known to those skilled in the art, such as in US2005/0257293 A1, hereby incorporated by reference.

Nucleotides and polypeptides that are useful for modulating plant characteristics in traits such as plant development include those that have been given the designation Development in the Category column of Table 1. Nucleotides and polypeptides that have been given the Development designation include those that are able to confer one or more of the following phenotypes, relative to wild-type control, when mis-expressed in plants: increased or decreased time to bolting; increased or decreased time to harvesting; increased or decreased time to senesces; and increased or decreased time to flowering. Altering plant development through genetic technologies is valuable for increasing yearly plant biomass production per year per acre of arable land; increasing yearly crop yield per acre of arable land, developing a genetic confinement system designed to reduce or prevent gene flow from transgenic pants to commercial crops and wild-type counterparts, making ornamental plants, and for other agricultural and/or horticultural purposes.

Nucleotides and polypeptides that are useful for modulating plant characteristics in traits such as phosphate use include those that have been given the designation Phosphate use in the Category column of Table 1. Nucleotides and polypeptides that have been given the Phosphate use designation include those that are able to confer one or more of the following phenotypes, relative to wild-type control, when mis-expressed in plants: increased or decreased tolerance to low phosphate conditions; increased or decreased tolerance to no phosphate conditions, and increased or decreased tolerance to high pH conditions. Altering characteristics such as phosphate use through genetic technologies is valuable for producing crop plants with increased tolerance to phosphate limiting conditions, using traditionally un-arable land to grow crop plants with increased tolerance to phosphate limiting conditions, developing a genetic confinement system designed to reduce or prevent gene flow from transgenic pants to commercial crops and wild-type counterparts, and for other agricultural and/or horticultural purposes.

Nucleotides and polypeptides that are useful for modulating plant characteristics in traits such as shade avoidance and shade tolerance include those that have been given the designation Shade in the Category column of Table 1. Nucleotides and polypeptides that have been given the Shade designation include those that are able to confer one or more of the following phenotypes, relative to wild-type control, when mis-expressed in plants: increased or decreased vigor in the dark; increased or decreased seedling vigor under low light conditions; increased or decreased plant vigor under low light conditions; increased or decreased leaf length; altered leaf shape; altered leaf structure, and increased or decreased cotyledon length. Altering characteristics such as shade avoidance and shade tolerance through genetic technologies is valuable for producing plants with tolerance to light limiting conditions, increasing plant biomass produced per acre of arable land, increasing crop production per acre of arable land, developing a genetic confinement system designed to reduce or prevent gene flow from transgenic pants to commercial crops and wild-type counterparts, making ornamental plants, and for other agricultural and/or horticultural purposes.

Nucleotides and polypeptides that are useful for modulating plant characteristics in traits such as nitrogen use include those that have been given the designation Nitrogen use in the Category column of Table 1. Nucleotides and polypeptides that have been given the Nitrogen use designation include those that are able to confer one or more of the following phenotypes, relative to wild-type control, when mis-expressed in plants: increased or decreased tolerance to low nitrogen conditions and surrogate low nitrogen conditions (e.g. exposure to an effective amount of MSX); increased or decreased tolerance to no nitrogen conditions; increased tolerance to high nitrogen conditions. Altering nitrogen use through genetic technologies is valuable for producing plants with increased tolerance to high or low nitrogen conditions, decreasing the amount of fertilizers used in crop production, using traditionally un-arable land to grow crop plants with increased tolerance to high or low nitrogen conditions, developing a genetic confinement system designed to reduce or prevent gene flow from transgenic pants to commercial crops and wild-type counterparts, and for other agricultural and/or horticultural purposes.

Nucleotides and polypeptides that are useful for modulating plant characteristics in traits such as nutrient uptake include those that have been given the designation Nutrient uptake in the Category column of Table 1. Nucleotides and polypeptides that have been given the Nutrient uptake designation include those that are able to confer one or more of the following phenotypes, relative to wild-type control, when mis-expressed in plants: increased or decreased lateral root length under high nitrogen conditions; increased or decreased lateral root length under low nitrogen conditions; increased or decreased lateral root length; increased or decreased number of lateral roots; increased or decreased root hair length; increased or decreased number of root hairs; increased or decreased primary root length(s); increased or decreased thickness of primary root(s); increased or decreased number of primary roots; altered root architecture; altered root growth pattern; and increased or decreased root mass. Altering nutrient uptake through genetic technologies is valuable for producing plants which are more efficient in gathering nutrients from the environment, using traditionally un-arable land to grow crop plants which are more efficient in gathering nutrients from the environment, decreasing the amount of fertilizers used for crop production, increasing plant biomass production per acre or arable land, increasing crop yield per acre of arable land, developing a genetic confinement system designed to reduce or prevent gene flow from transgenic pants to commercial crops and wild-type counterparts, making ornamental plants, and for other agricultural and/or horticultural purposes.

Nucleotides and polypeptides that are useful for modulating plant characteristics in traits such as photosynthetic capacity include those that have been given the designation Photosynthetic capacity in the Category column of Table 1. Nucleotides and polypeptides that have been given the Photosynthetic capacity designation include those that are able to confer one or more of the following phenotypes, relative to wild-type control, when mis-expressed in plants: darker green or lighter green plants (indicative of a higher or lower chlorophyll content respectively); and increased or decreased chlorophyll content. Altering photosynthetic capacity through genetic technologies is valuable for increasing plant biomass produced per acre of arable land, increasing crop yield per acre of arable land, developing a genetic confinement system designed to reduce or prevent gene flow from transgenic pants to commercial crops and wild-type counterparts, and for other agricultural and/or horticultural purposes.

Nucleotides and polypeptides that are useful for modulating plant characteristics in traits such as abiotic stress tolerance include those that have been given the designation Stress tolerance in the Category column of Table 1. Nucleotides and polypeptides that have been given the Stress tolerance designation include those that are able to confer one or more of the following phenotypes, relative to wild-type control, when mis-expressed in plants: increased or decreased tolerance to drought and/or surrogate drought conditions (e.g. exposure to effective amounts of ABA, PEG, mannitol or sucrose); increased or decreased tolerance to low temperature conditions; increased or decreased tolerance to high temperature conditions; increased or decreased salt tolerance; increased or decreased tolerance to oxidative stressors and/or surrogate oxidative stressors (e.g. exposure to an effective amount of arginine or salicylic acid); and having leaves with shiny or dull appearance (indicative of altered wax composition and/or content). Altering abiotic stress tolerance through genetic technologies is valuable for farmers seeking to minimize economic losses due to drought, cold, heat, flooding and oxidative stressors; producing crop plants with increased tolerance to abiotic stressors; using traditionally un-arable land to grow crop plants with increased tolerance to abiotic stressors; developing a genetic confinement system designed to reduce or prevent gene flow from transgenic pants to commercial crops and wild-type counterparts; making ornamental plants; and for other agricultural and/or horticultural purposes.

Nucleotides and polypeptides that are useful for modulating plant characteristics in traits such as vigor include those that have been given the designation Vigor in the Category column of Table 1. Nucleotides and polypeptides that have been given the Vigor designation include those that are able to confer one or more of the following phenotypes, relative to wild-type control, when mis-expressed in plants: increased or decreased thickness of the primary inflorescence; and increased or decreased rigidity of the primary inflorescence. Altering vigor through genetic technologies is valuable for using traditionally un-arable land to grow crop plants which are more tolerant to biotic and/or abiotic stressors; developing a genetic confinement system designed to reduce or prevent gene flow from transgenic pants to commercial crops and wild-type counterparts, and for other agricultural and/or horticultural purposes.

Nucleotides and polypeptides that are useful for modulating plant characteristics in traits such as yield include those that have been given the designation Yield in the Category column of Table 1. Nucleotides and polypeptides that have been given the Yield designation include those that are able to confer one or more of the following phenotypes, relative to wild-type control, when mis-expressed in plants: increased or decreased fruit size; increased or decreased fruit length; increased or decreased fruit number; altered fruit shape; increased or decreased seed size; and alter seed shape. The ability to maximize plant yield through genetic technologies is valuable for increasing crop yield per acre of arable land; increasing plant biomass production per acre of arable land, using plants as chemical factories by increasing the content of valuable pharmaceutical compounds (e.g. increased alkaloids and/or terpenoids), developing a genetic confinement system designed to reduce or prevent gene flow from transgenic pants to commercial crops and wild-type counterparts, making ornamental plants and for other agricultural and/or horticultural purposes.

The phenotypes disclosed in Table 1 can be modulated by controlling the expression of nucleic acid sequences and polypeptide sequences that confer phenotype(s) when mis-expressed in plants. Modulation of a phenotype can also be achieved by inhibiting the expression of nucleic acid sequences and polypeptide sequences that confer phenotype(s) when mis-expressed in plants. A phenotype resulting from the expression of a nucleic acid sequence and/or polypeptide sequence can be modulated (e.g. increase or decrease of an observable/measurable phenotypic change in relation to wild-type control) using recombinant-DNA methods, as discussed in previous paragraphs.

According to another aspect, the nucleotide sequences of the invention encode polypeptides that can be utilized as herbicide targets, those useful in the screening of new herbicide compounds. Thus, the proteins encoded by the nucleotide sequences provide the bases for assays designed to easily and rapidly identify novel herbicides.

According to yet another aspect, the present invention provides a method of identifying a herbicidal compound, comprising: (a) combining a polypeptide comprising an amino acid sequence at least 85% identical to an amino acid sequence selected from the group consisting of the polypeptides described in the sequence listing with a compound to be tested for the ability to inhibit the activity of said polypeptide, under conditions conducive to inhibition; (b) selecting a compound identified in (a) that inhibits the activity of said polypeptide; (c) applying a compound selected in (b) to a plant to test for herbicidal activity; (d) selecting a compound identified in (c) that has herbicidal activity. The polypeptide can alternatively comprise an amino acid sequence at least 90%, or at least 95%, or at least 99% identical to an amino acid sequence selected from the group consisting of the polypeptides in the sequence listing. The present invention also provides a method for killing or inhibiting the growth or viability of a plant, comprising applying to the plant a herbicidal compound identified according to this method.

The Sequence Listing sets forth the polypeptide and polynucleotide sequences of the invention, including functional homologs/orthologs of specific query sequences.

The Sequence Listing indicates which of the functional homologs/orthologs are associated with each query sequence. The sequence listing also presents other information for each of the functional homologs, such as the % identity of the homolog relative to the query/Lead sequence, the corresponding E-value, the plant species for the homolog, the Sequence ID No. in the Sequence Listing.

The present invention further encompasses nucleotides that encode the above described polypeptides, as well as the complements thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981)*Adv. App. Math.* 2:482.
(9) Needleman and Wunsch (1970) *J. Mol. Biol.* 48:443.
(10) Pearson and Lipman (1988) *Proc. Natl. Acad. Sci.* (*USA*) 85: 2444.
(11) Yamauchi et al. (1996) *Plant Mol. Biol.* 30:321-9.
(12) Xu et al. (1995) *Plant Mol. Biol.* 27:237.
(13) Yamamoto et al. (1991) *Plant Cell* 3:371.
(14) P. Tijessen, Hybridization with Nucleic Acid Probes In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., Molecular Cloning: A Laboratory Manual, Second Edition, Cold Spring Harbor Laboratory Press, 1989, New York.
(17) Shizuya et al. (1992) *Proc. Natl. Acad. Sci. USA*, 89: 8794-8797.
(18) Hamilton et al. (1996) *Proc. Natl. Acad. Sci. USA*, 93: 9975-9979.
(19) Burke et al. (1987) *Science,* 236:806-812.
(20) Sternberg N. et al. (1990) *Proc Natl Acad Sci USA.,* 87:103-7.
(21) Bradshaw et al. (1995) *Nucl Acids Res*, 23: 4850-4856.
(22) Frischauf et al. (1983) *J. Mol Biol,* 170: 827-842.

(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.,* 22:421.
(29) Christou (1995) *Euphytica*, v. 85, n. 1-3:13-27.
(30) Newell (2000)
(31) Griesbach (1987) *Plant Sci.* 50:69-77.
(32) Fromm et al. (1985) *Proc. Natl. Acad. Sci. USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: iotechnology, A Multi-Volume Comprehensive treatise (H. J. Rehm, G. Reed, A. Püler, P. Stadler, eds., Vol. 2, 627-659, VCH Weinheim-New York-Basel-Cambridge).
(36) *Crit. Rev. Plant. Sci.* 4:146.
(37) Fromm et al. (1990) *Biotechnology* 8:833-844.
(38) Cho et al. (2000) *Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), Genetically Engineered Viruses (C. J. A. Ring and E. D. Blair, Eds). Pp. 59-99, BIOS Scientific Publishers, Ltd. Oxford, UK.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07989676B2). An electronic copy of the "Sequence Listing" will also be available from the USPTO upon request and payment of the fee set forth in 37 CFR 1.19(b)(3).

The invention claimed is:

1. A vector, comprising:
(a) a first nucleic acid molecule comprising a plant regulatory region; and
(b) a second nucleic acid molecule comprising a nucleotide sequence that encodes a polypeptide having at least 95% sequence identity to SEQ ID NO:997 or a nucleotide sequence having at least 95% identity to SEQ ID NO:996, wherein said first and second nucleic acid molecules are operably linked and wherein said regulatory region is heterologous to said second nucleic acid molecule and is selected from the group consisting of YP0092 (SEQ ID NO:4146), PT0676 (SEQ ID NO:4120), PT0708 (SEQ ID NO:4125), PT0613 (SEQ ID NO:4113), PT0672 (SEQ ID NO:4119), PT0678 (SEQ ID NO:4121), PT0688 (SEQ ID NO:4123), PT0837 (SEQ ID NO:4132), the napin promoter, the Arcelin-5 promoter, the phaseolin gene promoter, the soybean trypsin inhibitor promoter, the ACP promoter, the stearoyl-ACP desaturase gene, the soybean α subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-I promoter, the beta-amylase gene promoter, the barley hordein gene promoter, p326 (SEQ ID NO:4184), YP0144 (SEQ ID NO:4163), YP0190 (SEQ ID NO:4167), p13879 (SEQ ID NO:4183), YP0050 (SEQ ID NO:4143), p32449 (SEQ ID NO:4185), 21876 (SEQ ID NO:4109), YP0158 (SEQ ID NO:4165), YP0214 (SEQ ID NO:4169), YP0380 (SEQ ID NO:4178), PT0848 (SEQ ID NO:4134), PT0633 (SEQ ID NO:4172), the cauliflower mosaic virus (CaMV) 35S promoter, the mannopine synthase (MAS) promoter, the 1' promoter from the T-DNA of *Agrobacterium tumefaeiens*, the 2' promoter from the T-DNA of *Agrobacterium tumefaciens*, the figwort mosaic virus 34S promoter, an actin promoter, the rice aetin promoter, a ubiquitin promoter, the maize ubiquitin-1 promoter, a ribulose-1,5-bisphosphate carboxylase (RbcS) promoters, the RbcS promoter from eastern larch (Larix laricina), the pine cab6 promoter, the Cab-1 gene promoter from wheat, the CAB-1 promoter from spinach, the cab1R promoter from rice, the pyruvate orthophosphate dikinase (PPDK) promoter from corn, the tobacco Lhcb1*2 promoter, the *Arabidopsis thaliana* SUC2 sucrose-H+symporter promoter and thylakoid membrane protein promoters from spinach (psaD, psaF, psaE, PC, FNR, atpC, atpD, cab, rbcS, PT0535 (SEQ ID NO:4111), PT0668 (SEQ ID NO:4110), PT0886 (SEQ ID NO:4137), PR0924 (SEQ ID NO:4192), YP0380 (SEQ ID NO:4178) and PT0585 (SEQ ID NO:4112).

2. A method of modulating leaf development, leaf morphology, drought tolerance, phosphate use or nutrient uptake in a plant, said method comprising introducing into a plant cell an exogenous nucleic acid molecule, said exogenous nucleic acid molecule comprising a regulatory region operably linked to a nucleotide sequence encoding a polypeptide having an amino acid sequence with at least 95 percent sequence identity to SEQ ID NO:997, wherein a plant produced from said plant cell has a modulated leaf development, leaf morphology, drought tolerance, phosphate use or nutrient uptake as compared to a control plant that does not comprise said nucleic acid.

3. The method of claim 2, wherein said nucleotide sequence encodes SEQ ID NO:997.

4. A plant cell comprising an exogenous nucleic acid molecule which comprises a regulatory region and a coding region, wherein said regulatory region and said coding region are operably linked, and wherein said coding region encodes a polypeptide having at least 95 percent sequence identity with SEQ ID NO:997 and wherein said regulatory and coding regions are operably linked, and wherein a plant produced from said plant cell has modulated leaf development, leaf morphology, drought tolerance, phosphate use or nutrient uptake as compared to a control plant that does not comprise said nucleic acid.

5. The plant cell of claim 4, wherein said coding region encodes the polypeptide of SEQ ID NO:997.

6. A transgenic plant comprising the plant cell of claim 4 or 5.

7. The transgenic plant of claim 6, wherein said plant is a species selected from the group consisting of *Panicum virgatum* (switchgrass), *Sorghum bicolor* (sorghum, sudangrass), *Miscanthus giganteus* (miseanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago saliva* (alfalfa), *Beta vulgaris* (sugarbeet), or *Pennisetum glaucum* (pearl millet).

8. Seed of the transgenic plant according to claim 6 or 7, wherein said seed contains said exogenous nucleic acid.

9. A food or feed product comprising vegetative tissue from the transgenic plant according to claim 6 or 7, wherein said food or feed product contains said exogenous nucleic acid.

10. A method of producing a transgenic plant having modified leaf development, leaf morphology, drought tolerance, phosphate use or nutrient uptake, said method comprising growing a plant cell comprising an exogenous nucleic acid molecule which comprises a regulatory region and a coding region, wherein said regulatory and coding regions are operably linked, and wherein said coding region encodes a polypeptide having at least 95 percent sequence identity to SEQ ID NO:997, wherein a plant produced from said plant cell has a modified leaf development, leaf morphology, drought tolerance, phosphate use or nutrient uptake as compared to a control plant that does not comprise said nucleic acid.

11. The method of producing a transgenic plant of claim 10, wherein said coding region encodes the polypeptide SEQ ID NO:997.

12. A method of modulating leaf development, leaf morphology, drought tolerance, phosphate use or nutrient uptake in a plant, said method comprising introducing into a plant cell an exogenous nucleic acid molecule, said exogenous nucleic acid molecule comprising a regulatory region and a coding region, wherein said regulatory and coding regions are operably linked, and wherein said coding region encodes a polypeptide with an amino acid sequence that has at least 95 percent sequence identity with SEQ ID NO:997, and wherein a tissue of a plant produced from said plant cell has modified leaf development, leaf morphology, drought tolerance, phosphate use or nutrient uptake as compared to a control plant that does not comprise said nucleic acid.

13. The method of modulating leaf development, leaf morphology, drought tolerance, phosphate use or nutrient uptake in the plant of claim 12, wherein said coding region encodes the polypeptide of SEQ ID NO:997.

* * * * *